US012290562B2

(12) United States Patent
Kawaoka et al.

(10) Patent No.: US 12,290,562 B2
(45) Date of Patent: May 6, 2025

(54) RECOMBINANT MULTIVALENT INFLUENZA VIRUSES

(71) Applicant: Wisconsin Alumni Research Foundation (WARF), Madison, WI (US)

(72) Inventors: Yoshihiro Kawaoka, Middleton, WI (US); Gabriele Neumann, Madison, WI (US)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 0 days.

(21) Appl. No.: 17/212,836

(22) Filed: Mar. 25, 2021

(65) Prior Publication Data

US 2021/0299249 A1 Sep. 30, 2021

Related U.S. Application Data

(60) Provisional application No. 62/994,738, filed on Mar. 25, 2020.

(51) Int. Cl.

| | |
|---|---|
| ***A61K 39/295*** | (2006.01) |
| ***A61K 39/145*** | (2006.01) |
| ***A61K 39/215*** | (2006.01) |
| ***A61P 31/14*** | (2006.01) |
| ***A61P 31/16*** | (2006.01) |
| ***C07K 14/005*** | (2006.01) |
| ***C12N 7/00*** | (2006.01) |
| *A61K 39/00* | (2006.01) |

(52) U.S. Cl.

CPC .......... *A61K 39/295* (2013.01); *A61K 39/145* (2013.01); *A61K 39/215* (2013.01); *A61P 31/14* (2018.01); *A61P 31/16* (2018.01); *C07K 14/005* (2013.01); *C12N 7/00* (2013.01); *A61K 2039/5254* (2013.01); *A61K 2039/5256* (2013.01); *A61K 2039/55* (2013.01); *A61K 2039/70* (2013.01); *C07K 2319/03* (2013.01); *C12N 2760/16121* (2013.01); *C12N 2760/16122* (2013.01); *C12N 2760/16134* (2013.01); *C12N 2760/16171* (2013.01); *C12N 2770/18021* (2013.01); *C12N 2770/18022* (2013.01); *C12N 2770/18034* (2013.01); *C12N 2770/18071* (2013.01)

(58) Field of Classification Search

None

See application file for complete search history.

(56) References Cited

U.S. PATENT DOCUMENTS 4,071,618 A 1/1978 Konobe et al.
4,659,569 A 4/1987 Mitsuhashi et al.
5,166,057 A 11/1992 Palese et al.
5,578,473 A 11/1996 Palese et al.
5,716,821 A 2/1998 Wertz et al.
5,750,394 A 5/1998 Palese et al.
5,786,199 A 7/1998 Palese
5,789,229 A 8/1998 Wertz et al.
5,820,871 A 10/1998 Palese et al.
5,840,520 A 11/1998 Clarke et al.
5,854,037 A 12/1998 Palese et al.
5,948,410 A 9/1999 Van Scharrenburg et al.
5,994,526 A 11/1999 Meulewaeter et al.
6,001,634 A 12/1999 Palese et al.
6,033,886 A 3/2000 Conzelmann
6,037,348 A 3/2000 Colacino et al.
6,146,642 A 11/2000 Garcia-Sastre et al.
6,169,175 B1 1/2001 Frace et al.
6,194,546 B1 2/2001 Newton et al.
6,270,958 B1 8/2001 Olivo et al.
6,271,011 B1 8/2001 Lee et al.
6,358,733 B1 3/2002 Motwani et al.
6,455,298 B1 9/2002 Groner et al.
6,544,785 B1 4/2003 Palese et al.
6,656,720 B2 12/2003 Groner et al.
6,825,036 B2 11/2004 Makizumi et al.
6,843,996 B1 1/2005 Parkin et al.
6,872,395 B2 3/2005 Kawaoka
6,890,710 B1 5/2005 Palese et al.
6,951,752 B2 10/2005 Reiter et al.
6,951,754 B2 10/2005 Hoffmann
6,974,695 B2 12/2005 Vogels et al.
7,037,707 B2 5/2006 Webster et al.
7,176,021 B2 2/2007 Kawaoka (Continued)

FOREIGN PATENT DOCUMENTS

AU 2012204138 B2 5/2014
AU 2014202470 11/2016

(Continued)

OTHER PUBLICATIONS

GenBank Accessions QHU79173, surface glycoprotein [Severe acute respiratory syndrome coronavirus 2], (Mar. 17, 2020).*
GenBank Accessions QHO62107, surface glycoprotein [Severe acute respiratory syndrome coronavirus 2], (Feb. 11, 2020).*
"International Application Serial No. PCT/US2021/024200, International Search Report mailed Jul. 16, 2021", 6 pgs.
"International Application Serial No. PCT/US2021/024200, Written Opinion mailed Jul. 16, 2021", 6 pgs.

(Continued)

*Primary Examiner* — Benjamin P Blumel
(74) *Attorney, Agent, or Firm* — Schwegman Lundberg & Woessner, P.A.

(57) ABSTRACT

The invention provides a composition useful to prepare influenza vaccine viruses, e.g., in the absence of helper virus, which includes internal viral segments from an influenza virus vaccine strain or isolate, e.g., one that is safe in humans, for instance, one that does not result in significant disease, and encodes a heterologous antigen.

16 Claims, 58 Drawing Sheets

Specification includes a Sequence Listing.

(56) References Cited

U.S. PATENT DOCUMENTS

| | | | |
|---|---|---|---|
| 7,211,378 | B2 | 5/2007 | Kawaoka et al. |
| 7,226,774 | B2 | 6/2007 | Kawaoka |
| 7,312,064 | B2 | 12/2007 | Hoffmann |
| 7,335,356 | B2 | 2/2008 | Hart et al. |
| 7,507,411 | B2 | 3/2009 | Zhou et al. |
| 7,566,458 | B2 | 7/2009 | Yang et al. |
| 7,585,657 | B2 | 9/2009 | Kawaoka |
| 7,588,769 | B2 | 9/2009 | Kawaoka |
| 7,601,356 | B2 | 10/2009 | Jin et al. |
| 7,670,837 | B2 | 3/2010 | Schwartz |
| 7,682,618 | B2 | 3/2010 | Bavari et al. |
| 7,723,094 | B2 | 5/2010 | Kawaoka et al. |
| 7,833,788 | B2 | 11/2010 | Pau et al. |
| 7,883,844 | B2 | 2/2011 | Nouchi et al. |
| 7,955,833 | B2 | 6/2011 | Reiter et al. |
| 7,959,930 | B2 | 6/2011 | De Wit et al. |
| 7,968,101 | B2 | 6/2011 | Kawaoka et al. |
| 7,972,843 | B2 | 7/2011 | Hoffmann |
| 7,993,924 | B2 | 8/2011 | Billeter et al. |
| 8,012,736 | B2 | 9/2011 | Hoffman et al. |
| 8,043,856 | B2 | 10/2011 | Kawaoka et al. |
| 8,048,430 | B2 | 11/2011 | Yang et al. |
| 8,057,806 | B2 | 11/2011 | Kawaoka et al. |
| 8,093,033 | B2 | 1/2012 | Kemble et al. |
| 8,114,415 | B2 | 2/2012 | Hoffmann et al. |
| 8,119,337 | B2 | 2/2012 | Gregersen |
| 8,119,388 | B2 | 2/2012 | Schwartz et al. |
| 8,298,805 | B2 | 10/2012 | Kawaoka |
| 8,309,099 | B2 | 11/2012 | Hoffmann |
| 8,354,114 | B2 | 1/2013 | Lu et al. |
| 8,357,376 | B2 | 1/2013 | Liu et al. |
| 8,409,843 | B2 | 4/2013 | Kemble et al. |
| 8,460,914 | B2 | 6/2013 | Gregersen |
| 8,465,960 | B2 | 6/2013 | Kawaoka et al. |
| 8,475,806 | B2 | 7/2013 | Kawaoka |
| 8,507,247 | B2 | 8/2013 | Kawaoka et al. |
| 8,524,497 | B2 | 9/2013 | Reiter et al. |
| 8,546,123 | B2 | 10/2013 | Lewis |
| 8,574,591 | B2 | 11/2013 | Hoffmann et al. |
| 8,574,593 | B2 | 11/2013 | Yang et al. |
| 8,580,277 | B2 | 11/2013 | Yang et al. |
| 8,591,914 | B2 | 11/2013 | Yang et al. |
| 8,597,661 | B2 | 12/2013 | Kawaoka et al. |
| 8,679,819 | B2 | 3/2014 | Kawaoka |
| 8,877,209 | B2 | 11/2014 | Kawaoka et al. |
| 8,900,595 | B2 | 12/2014 | Kawaoka et al. |
| 9,101,653 | B2 | 8/2015 | Kawaoka et al. |
| 9,109,013 | B2 | 8/2015 | Kawaoka et al. |
| 9,222,118 | B2 | 12/2015 | Kawaoka et al. |
| 9,254,318 | B2 | 2/2016 | Kawaoka et al. |
| 9,284,533 | B2 | 3/2016 | Bilsel et al. |
| 9,474,798 | B2 | 10/2016 | Watanabe et al. |
| 9,757,446 | B2 | 9/2017 | LeFebvre et al. |
| 9,890,363 | B2 | 2/2018 | Kawaoka |
| 9,926,535 | B2 | 3/2018 | Kawaoka et al. |
| 9,950,057 | B2 | 4/2018 | Kawaoka et al. |
| 10,053,671 | B2 | 8/2018 | Kawaoka et al. |
| 10,059,925 | B2 | 8/2018 | Kawaoka et al. |
| 10,119,124 | B2 | 11/2018 | Watanabe et al. |
| 10,130,697 | B2 | 11/2018 | Watanabe |
| 10,172,934 | B2 | 1/2019 | Kawaoka et al. |
| 10,246,686 | B2 | 4/2019 | Kawaoka et al. |
| 10,358,630 | B2 | 7/2019 | Kawaoka et al. |
| 10,494,613 | B2 | 12/2019 | Kawaoka et al. |
| 10,513,692 | B2 | 12/2019 | Kawaoka et al. |
| 10,633,422 | B2 | 4/2020 | Kawaoka et al. |
| 10,808,229 | B2 | 10/2020 | Kawaoka et al. |
| 11,007,262 | B2 | 5/2021 | Watanabe et al. |
| 11,046,934 | B2 | 6/2021 | Kawaoka et al. |
| 11,180,737 | B2 | 11/2021 | Kawaoka et al. |
| 11,197,925 | B2 | 12/2021 | Kawaoka et al. |
| 11,197,926 | B2 | 12/2021 | Kawaoka et al. |
| 11,241,492 | B2 | 2/2022 | Kawaoka et al. |
| 11,384,339 | B2 | 7/2022 | Kawaoka et al. |
| 11,389,523 | B2 | 7/2022 | Kawaoka et al. |
| 11,390,649 | B2 | 7/2022 | Kawaoka et al. |
| 11,739,303 | B2 | 8/2023 | Kawaoka et al. |
| 11,802,273 | B2 | 10/2023 | Kawaoka et al. |
| 11,807,872 | B2 | 11/2023 | Kawaoka et al. |
| 11,851,648 | B2 | 12/2023 | Kawaoka et al. |
| 12,076,387 | B2 | 9/2024 | Watanabe et al. |
| 12,122,807 | B2 | 10/2024 | Kawaoka et al. |
| 12,144,857 | B2 | 11/2024 | Kawaoka et al. |
| 2002/0010143 | A1 | 1/2002 | Barbosa et al. |
| 2002/0164770 | A1 | 11/2002 | Hoffmann |
| 2002/0197705 | A1 | 12/2002 | Kawaoka |
| 2003/0035814 | A1 | 2/2003 | Kawaoka et al. |
| 2003/0044962 | A1 | 3/2003 | Makizumi et al. |
| 2003/0073223 | A1 | 4/2003 | Groner et al. |
| 2003/0119183 | A1 | 6/2003 | Groner |
| 2003/0194694 | A1 | 10/2003 | Kawaoka |
| 2003/0215794 | A1 | 11/2003 | Kawaoka et al. |
| 2004/0002061 | A1 | 1/2004 | Kawaoka |
| 2004/0029251 | A1 | 2/2004 | Hoffman et al. |
| 2004/0057967 | A1 | 3/2004 | Bavari et al. |
| 2004/0063141 | A1 | 4/2004 | Lok |
| 2004/0077086 | A1 | 4/2004 | Reiter et al. |
| 2004/0132164 | A1 | 7/2004 | Doyle et al. |
| 2004/0142322 | A1 | 7/2004 | Malcolm et al. |
| 2004/0219170 | A1 | 11/2004 | Kawaoka |
| 2004/0241139 | A1 | 12/2004 | Hobom et al. |
| 2004/0242518 | A1 | 12/2004 | Chen et al. |
| 2005/0003349 | A1 | 1/2005 | Kawaoka |
| 2005/0037487 | A1 | 2/2005 | Kawaoka et al. |
| 2005/0095583 | A1 | 5/2005 | Pekosz et al. |
| 2005/0118140 | A1 | 6/2005 | Vorlop et al. |
| 2005/0158342 | A1 | 7/2005 | Kemble et al. |
| 2005/0186563 | A1 | 8/2005 | Hoffmann |
| 2005/0202553 | A1 | 9/2005 | Groner et al. |
| 2005/0232950 | A1 | 10/2005 | Kawaoka |
| 2005/0266023 | A1 | 12/2005 | Bavari et al. |
| 2005/0266026 | A1 | 12/2005 | Hoffmann et al. |
| 2006/0057116 | A1 | 3/2006 | Kawaoka et al. |
| 2006/0088909 | A1 | 4/2006 | Compans |
| 2006/0099609 | A1 | 5/2006 | Bavari et al. |
| 2006/0134138 | A1 | 6/2006 | Kawaoka et al. |
| 2006/0166321 | A1 | 7/2006 | Kawaoka et al. |
| 2006/0188977 | A1 | 8/2006 | Schwartz et al. |
| 2006/0216702 | A1 | 9/2006 | Compans et al. |
| 2006/0240515 | A1* | 10/2006 | Dimitrov ............... C07K 16/10 435/325 |
| 2006/0246092 | A1 | 11/2006 | Neirynck et al. |
| 2007/0141699 | A1 | 6/2007 | Kawaoka |
| 2007/0231348 | A1 | 10/2007 | Kawaoka et al. |
| 2008/0009031 | A1 | 1/2008 | Kawaoka |
| 2008/0187557 | A1 | 8/2008 | Sambhara |
| 2008/0233560 | A1 | 9/2008 | Hoffmann |
| 2008/0254067 | A1 | 10/2008 | Trepanier et al. |
| 2008/0274141 | A1 | 11/2008 | Groner et al. |
| 2008/0292658 | A1 | 11/2008 | De Wit et al. |
| 2008/0293040 | A1 | 11/2008 | Kawaoka et al. |
| 2008/0311148 | A1 | 12/2008 | Hoffmann |
| 2008/0311149 | A1 | 12/2008 | Hoffmann |
| 2009/0017444 | A1 | 1/2009 | Kawaoka et al. |
| 2009/0047728 | A1 | 2/2009 | Kawaoka et al. |
| 2009/0074812 | A1 | 3/2009 | Watanabe et al. |
| 2009/0081252 | A1 | 3/2009 | Gregersen |
| 2009/0181446 | A1 | 7/2009 | Nouchi et al. |
| 2009/0311669 | A1 | 12/2009 | Kawaoka |
| 2009/0324640 | A1 | 12/2009 | Kawaoka et al. |
| 2010/0021499 | A1 | 1/2010 | Bilsel et al. |
| 2010/0080825 | A1 | 4/2010 | Kawaoka et al. |
| 2010/0112000 | A1 | 5/2010 | Schwartz |
| 2010/0183671 | A1 | 7/2010 | Gregersen et al. |
| 2010/0247572 | A1 | 9/2010 | Kawaoka |
| 2010/0267116 | A1 | 10/2010 | Kawaoka et al. |
| 2011/0020374 | A1 | 1/2011 | Frazer |
| 2011/0027314 | A1 | 2/2011 | Broeker |
| 2011/0045022 | A1 | 2/2011 | Tsai |
| 2011/0081373 | A1 | 4/2011 | Kawaoka et al. |
| 2011/0110978 | A1 | 5/2011 | Kawaoka et al. |
| 2011/0159031 | A1 | 6/2011 | Falkner et al. |
| 2011/0236417 | A1 | 9/2011 | Watanabe et al. |
| 2011/0263554 | A1 | 10/2011 | Kawaoka et al. |

(56) References Cited

U.S. PATENT DOCUMENTS

| | | | | |
|---|---|---|---|---|
| 2011/0300604 | A1 | 12/2011 | Kawaoka et al. | |
| 2012/0020997 | A1 | 1/2012 | Hoffman et al. | |
| 2012/0034600 | A1 | 2/2012 | Gregersen | |
| 2012/0058124 | A1 | 3/2012 | Kurosawa et al. | |
| 2012/0115206 | A1 | 5/2012 | Schwartz et al. | |
| 2012/0156241 | A1 | 6/2012 | De Wit et al. | |
| 2012/0207785 | A1 | 8/2012 | Fabry et al. | |
| 2012/0251568 | A1* | 10/2012 | Garcia-Sastre | C07K 14/005 435/235.1 |
| 2013/0095135 | A1 | 4/2013 | Collignon et al. | |
| 2013/0183741 | A1 | 7/2013 | Park et al. | |
| 2013/0230552 | A1* | 9/2013 | Kawaoka | A61P 31/16 435/325 |
| 2013/0243744 | A1 | 9/2013 | Betenbaugh | |
| 2013/0315929 | A1 | 11/2013 | Bock | |
| 2013/0316434 | A1 | 11/2013 | Reiter et al. | |
| 2014/0227310 | A1 | 8/2014 | Li et al. | |
| 2015/0017205 | A1 | 1/2015 | Kawaoka et al. | |
| 2015/0166967 | A1 | 6/2015 | Kawaoka et al. | |
| 2015/0307851 | A1 | 10/2015 | Kawaoka et al. | |
| 2015/0368621 | A1 | 12/2015 | Kawaoka et al. | |
| 2016/0024193 | A1 | 1/2016 | Ayalon et al. | |
| 2016/0024479 | A1 | 1/2016 | Kawaoka et al. | |
| 2016/0115518 | A1 | 4/2016 | Kawaoka et al. | |
| 2016/0208223 | A1 | 7/2016 | Kawaoka et al. | |
| 2016/0215040 | A1 | 7/2016 | Kyratsous et al. | |
| 2016/0355790 | A1 | 12/2016 | Kawaoka et al. | |
| 2017/0058265 | A1 | 3/2017 | Kawaoka et al. | |
| 2017/0067029 | A1 | 3/2017 | Kawaoka et al. | |
| 2017/0096645 | A1 | 4/2017 | Watanabe et al. | |
| 2017/0097334 | A1 | 4/2017 | Kawaoka et al. | |
| 2017/0121391 | A1 | 5/2017 | Kawaoka et al. | |
| 2017/0258888 | A1 | 9/2017 | Kawaoka | |
| 2017/0298120 | A1 | 10/2017 | Sasisekharan | |
| 2017/0354730 | A1 | 12/2017 | Kawaoka et al. | |
| 2018/0245054 | A1 | 8/2018 | Kawaoka et al. | |
| 2018/0273588 | A1 | 9/2018 | Kawaoka et al. | |
| 2018/0340152 | A1 | 11/2018 | Kawaoka et al. | |
| 2019/0032023 | A1 | 1/2019 | Kawaoka et al. | |
| 2019/0048324 | A1 | 2/2019 | Kawaoka et al. | |
| 2019/0117759 | A1 | 4/2019 | Wantanabe et al. | |
| 2019/0167781 | A1 | 6/2019 | Kawaoka et al. | |
| 2020/0188506 | A1 | 6/2020 | Kawaoka et al. | |
| 2020/0237899 | A1 | 7/2020 | Kawaoka et al. | |
| 2020/0263142 | A1 | 8/2020 | Kawaoka et al. | |
| 2020/0263143 | A1 | 8/2020 | Kawaoka et al. | |
| 2020/0291384 | A1 | 9/2020 | Kawaoka et al. | |
| 2021/0061862 | A1 | 3/2021 | Kawaoka et al. | |
| 2021/0102178 | A1 | 4/2021 | Kawaoka et al. | |
| 2021/0121545 | A1 | 4/2021 | Knoll et al. | |
| 2021/0228708 | A1* | 7/2021 | Smith | A61K 39/12 |
| 2021/0246432 | A1 | 8/2021 | Kawaoka et al. | |
| 2021/0252130 | A1 | 8/2021 | Watanabe et al. | |
| 2021/0290754 | A1 | 9/2021 | Kawaoka et al. | |
| 2022/0025339 | A1 | 1/2022 | Kawaoka et al. | |
| 2022/0202926 | A1 | 6/2022 | Kawaoka et al. | |
| 2022/0202927 | A1 | 6/2022 | Kawaoka et al. | |
| 2022/0241396 | A1 | 8/2022 | Kawaoka et al. | |
| 2023/0321217 | A1 | 10/2023 | Kawaoka et al. | |
| 2023/0346911 | A1 | 11/2023 | Kawaoka et al. | |
| 2023/0348864 | A1 | 11/2023 | Kawaoka et al. | |
| 2024/0010995 | A1 | 1/2024 | Kawaoka et al. | |
| 2024/0076632 | A1 | 3/2024 | Kawaoka et al. | |
| 2024/0238403 | A1 | 7/2024 | Kawaoka et al. | |
| 2024/0318167 | A1 | 9/2024 | Kawaoka et al. | |

FOREIGN PATENT DOCUMENTS

| | | | |
|---|---|---|---|
| AU | 2014290203 | B2 | 12/2020 |
| AU | 2017221444 | B2 | 11/2021 |
| BR | PI0410702 | B1 | 4/2022 |
| CA | 2379012 | A1 | 1/2001 |
| CA | 2816242 | C | 1/2019 |
| CA | 2525953 | | 10/2023 |
| CN | 1826407 | A | 8/2006 |
| CN | 101472941 | A | 7/2009 |
| CN | 101613678 | A | 12/2009 |
| CN | 1826407 | B | 9/2013 |
| CN | 105296356 | A | 2/2016 |
| CN | 106661569 | A | 5/2017 |
| CN | 103540614 | B | 2/2018 |
| CN | 109477074 | A | 3/2019 |
| CN | 113874496 | A | 12/2021 |
| CN | 114929269 | A | 8/2022 |
| CN | 109477074 | B | 1/2023 |
| EP | 0687471 | A1 | 12/1995 |
| EP | 0700991 | A1 | 3/1996 |
| EP | 0702085 | A1 | 3/1996 |
| EP | 0704533 | A1 | 4/1996 |
| EP | 1201760 | A1 | 5/2002 |
| EP | 2010557 | B1 | 2/2014 |
| EP | 1572910 | B1 | 12/2015 |
| EP | 1631663 | B1 | 8/2016 |
| EP | 2747778 | B1 | 12/2017 |
| EP | 3009507 | B1 | 6/2020 |
| EP | 2493912 | B1 | 7/2020 |
| EP | 3022296 | B1 | 12/2022 |
| IL | 171831 | A | 5/2015 |
| JP | 07-203958 | | 8/1995 |
| JP | H08510749 | A | 11/1996 |
| JP | H10500113 | A | 1/1998 |
| JP | 2002536992 | A | 11/2002 |
| JP | 2003528570 | A | 9/2003 |
| JP | 2004500842 | A | 1/2004 |
| JP | 2004531232 | A | 10/2004 |
| JP | 2005523698 | A | 8/2005 |
| JP | 2005245302 | A | 9/2005 |
| JP | 2005535288 | A | 11/2005 |
| JP | 2006525815 | A | 11/2006 |
| JP | 2007518395 | A | 7/2007 |
| JP | 2007525175 | A | 9/2007 |
| JP | 2007259758 | | 10/2007 |
| JP | 2007529997 | A | 11/2007 |
| JP | 2008500041 | | 1/2008 |
| JP | 2008512443 | | 4/2008 |
| JP | 2008520248 | A | 6/2008 |
| JP | 2009511084 | A | 3/2009 |
| JP | 2009514850 | A | 4/2009 |
| JP | 2009523252 | A | 6/2009 |
| JP | 2009532352 | A | 9/2009 |
| JP | 2009539965 | A | 11/2009 |
| JP | 2010530248 | A | 9/2010 |
| JP | 2011530295 | A | 12/2011 |
| JP | 4927290 | | 5/2012 |
| JP | 4927290 | B2 | 5/2012 |
| JP | 2013507990 | A | 3/2013 |
| JP | 2013511280 | A | 4/2013 |
| JP | 2013518059 | | 5/2013 |
| JP | 2014039551 | A | 3/2014 |
| JP | 2014131516 | A | 7/2014 |
| JP | 2015501141 | | 1/2015 |
| JP | 2016500007 | A | 1/2016 |
| JP | 2016521553 | A | 7/2016 |
| JP | 2016144463 | A | 8/2016 |
| JP | 2016524915 | A | 8/2016 |
| JP | 2016169225 | A | 9/2016 |
| JP | 2017506903 | A | 3/2017 |
| JP | 2017527557 | A | 9/2017 |
| JP | 2017197555 | A | 11/2017 |
| JP | 2018064493 | A | 4/2018 |
| JP | 6352974 | B2 | 6/2018 |
| JP | 6375329 | B2 | 7/2018 |
| JP | 2019510481 | A | 4/2019 |
| JP | 2019171818 | A | 10/2019 |
| JP | 2020010711 | A | 1/2020 |
| JP | 2020114250 | A | 7/2020 |
| JP | 2021036878 | A | 3/2021 |
| JP | 2021500891 | A | 4/2021 |
| JP | 2015536228 | A | 12/2021 |
| JP | 2021184761 | A | 12/2021 |
| JP | 2021533157 | A | 12/2021 |
| JP | 2022066209 | A | 4/2022 |
| JP | 2022522112 | A | 4/2022 |

(56) References Cited

FOREIGN PATENT DOCUMENTS

| | | | |
|---|---|---|---|
| JP | 2022527235 | A | 6/2022 |
| JP | 2022172369 | A | 11/2022 |
| JP | 2022551805 | A | 12/2022 |
| JP | 2023011603 | A | 1/2023 |
| JP | 7244455 | B2 | 3/2023 |
| JP | 2023511444 | A | 3/2023 |
| JP | 7297832 | | 6/2023 |
| JP | 2023109845 | | 8/2023 |
| JP | 2024028825 | | 3/2024 |
| JP | 2024091645 | A | 7/2024 |
| JP | 7575012 | B2 | 10/2024 |
| JP | 2024161055 | | 11/2024 |
| KR | 101113432 | B1 | 2/2012 |
| MX | 285206 | | 3/2011 |
| NO | 341506 | | 11/2017 |
| WO | WO-9610631 | A1 | 4/1996 |
| WO | WO-9610632 | A1 | 4/1996 |
| WO | WO-9640955 | A1 | 12/1996 |
| WO | WO-9737000 | A1 | 10/1997 |
| WO | WO-9802530 | A1 | 1/1998 |
| WO | WO-9848834 | A1 | 11/1998 |
| WO | WO-9853078 | A1 | 11/1998 |
| WO | WO-9928445 | A1 | 6/1999 |
| WO | WO-0053786 | A1 | 9/2000 |
| WO | WO-0060050 | A2 | 10/2000 |
| WO | WO-2000060050 | A2 | 10/2000 |
| WO | WO-0060050 | A3 | 1/2001 |
| WO | WO-2001004333 | A1 | 1/2001 |
| WO | WO-2001025462 | A1 | 4/2001 |
| WO | WO-0179273 | A2 | 10/2001 |
| WO | WO-2001079273 | A2 | 10/2001 |
| WO | WO-0183794 | A2 | 11/2001 |
| WO | WO-2001083794 | A2 | 11/2001 |
| WO | WO-2007146057 | A2 | 12/2001 |
| WO | WO-0210143 | A1 | 1/2002 |
| WO | WO-02064757 | A2 | 8/2002 |
| WO | WO-02074795 | A2 | 9/2002 |
| WO | WO-03068923 | A2 | 8/2003 |
| WO | WO-2003068923 | A2 | 8/2003 |
| WO | WO-03076462 | A1 | 9/2003 |
| WO | WO-2003080846 | A1 | 10/2003 |
| WO | WO-03091401 | A2 | 11/2003 |
| WO | WO-2003091401 | A2 | 11/2003 |
| WO | WO-2004094466 | A2 | 11/2004 |
| WO | WO-04112831 | A2 | 12/2004 |
| WO | WO-2004112831 | A2 | 12/2004 |
| WO | WO-2004112831 | A3 | 12/2004 |
| WO | WO-05028658 | A2 | 3/2005 |
| WO | WO-05028658 | A3 | 3/2005 |
| WO | WO-2005026658 | A2 | 3/2005 |
| WO | WO-2005062820 | A2 | 7/2005 |
| WO | WO-2006051069 | A2 | 5/2006 |
| WO | WO-2007044024 | A2 | 4/2007 |
| WO | WO-2007044024 | A3 | 4/2007 |
| WO | WO-2007126810 | A2 | 11/2007 |
| WO | WO-2007126810 | A3 | 11/2007 |
| WO | WO-2007146057 | A3 | 12/2007 |
| WO | WO-08156681 | A3 | 12/2008 |
| WO | WO-200815678 | A2 | 12/2008 |
| WO | WO-2008147496 | A2 | 12/2008 |
| WO | WO-2008147496 | A3 | 12/2008 |
| WO | WO-2008156681 | A2 | 12/2008 |
| WO | WO-2008156778 | A3 | 12/2008 |
| WO | WO-2008157583 | A1 | 12/2008 |
| WO | WO-09008921 | A3 | 1/2009 |
| WO | WO-09008921 | A9 | 1/2009 |
| WO | WO-2009007244 | A2 | 1/2009 |
| WO | WO-2009008921 | A2 | 1/2009 |
| WO | WO-2009014919 | A2 | 1/2009 |
| WO | WO-2008156778 | A9 | 2/2009 |
| WO | WO-09128867 | A2 | 10/2009 |
| WO | WO-2009152181 | A1 | 12/2009 |
| WO | WO-2009128867 | A3 | 3/2010 |
| WO | WO-2010053573 | A2 | 5/2010 |
| WO | WO-2010053473 | A3 | 7/2010 |
| WO | WO-2011/014645 | A1 | 2/2011 |
| WO | 2011063308 | | 5/2011 |
| WO | WO-2011056591 | A1 | 5/2011 |
| WO | WO-2011087839 | A1 | 7/2011 |
| WO | WO-2011126370 | A1 | 10/2011 |
| WO | WO-2011130627 | A2 | 10/2011 |
| WO | WO-2012045882 | A2 | 4/2012 |
| WO | WO-2012177924 | A2 | 12/2012 |
| WO | WO-2013032942 | A1 | 3/2013 |
| WO | WO-2013032942 | A9 | 3/2013 |
| WO | WO-2013034069 | A1 | 3/2013 |
| WO | WO-2013087945 | A2 | 6/2013 |
| WO | WO-2013148302 | A1 | 10/2013 |
| WO | WO-2014195920 | A2 | 12/2014 |
| WO | WO-2015009743 | A1 | 1/2015 |
| WO | WO-2015/142671 | A2 | 9/2015 |
| WO | WO-2015134488 | A1 | 9/2015 |
| WO | WO-2015196150 | A2 | 12/2015 |
| WO | WO-2015196150 | A3 | 12/2015 |
| WO | WO-2016144933 | A1 | 9/2016 |
| WO | WO-2016207853 | A2 | 12/2016 |
| WO | WO-2017007839 | A1 | 1/2017 |
| WO | WO-2017040203 | A1 | 3/2017 |
| WO | WO-2017136575 | A1 | 8/2017 |
| WO | WO-2017143236 | A1 | 8/2017 |
| WO | WO-2019084310 | A1 | 5/2019 |
| WO | WO-2019241579 | A1 | 12/2019 |
| WO | WO-2020033527 | A2 | 2/2020 |
| WO | WO-2020041311 | A1 | 2/2020 |
| WO | 2020061443 | | 3/2020 |
| WO | WO-2020/033527 | A3 | 3/2020 |
| WO | WO-2020163804 | A1 | 8/2020 |
| WO | WO-2020167432 | A2 | 8/2020 |
| WO | WO-2020223699 | A1 | 11/2020 |
| WO | WO-2020167432 | A3 | 12/2020 |
| WO | WO-2020264141 | A1 | 12/2020 |
| WO | WO-2021041624 | A2 | 3/2021 |
| WO | WO-2021041624 | A3 | 5/2021 |
| WO | WO-2021150874 | A1 | 7/2021 |
| WO | WO-2021195410 | A1 | 9/2021 |
| WO | WO-2021242597 | A1 | 12/2021 |
| WO | 2022245888 | | 11/2022 |
| WO | 2023125889 | | 7/2023 |
| WO | 2023164556 | | 10/2023 |
| WO | 2024015510 | | 1/2024 |
| WO | WO-2024197167 | A1 | 9/2024 |

OTHER PUBLICATIONS

Halstead, Scott B,, et al., "Dengue Antibody-Dependent Enhancement: Knowns and Unknowns", Microbiology Spectrum, 2(6), (2014), 1-18.
Huisman, W., et al., "Vaccine-induced enhancement of viral infections", Vaccine, 27(4), (2009), 505-512.
Smatti, Maria K., et al., "Viral-Induced Enhanced Disease Illness", Front Microbiol, vol. 9: Article 2991, (Dec. 2018), 1-19.
Takada, Ayato, et al., "Antibody-dependent enhancement of viral infection: molecular mechanisms and in vivo implications", Rev Med Virol, 13(6), (2003), 387-398.
Takada, Ayato, et al., "Epitopes Required for Antibody-Dependent Enhancement of Ebola Virus Infection", J Infect Dis, 196 (Suppl 2), (2007), S347-S356.
Takada, Ayato, et al., "Infectivity-Enhancing Antibodies to Ebola Virus Glycoprotein", Journal of Virology, 75(5), (2001), 2324-2330.
Wan, Yushun, et al., "Molecular mechanism for Antibody-Dependent Enhancement of Coronavirus EntrM", Journal of Virology, 94(5): e02015-19, (2019), 1-15.
Wang, Sheng-Fan, et al., "Antibody-dependent SARS coronavirus infection is mediated by antibodies against spike proteins", Biochem Biophys Res Commun, 451, (2014), 208-214.
Wanitchang, Asawin, et al., "Characterization of influenza A virus pseudotyped with the spike protein of porcine epidemic diarrhea virus", Archives of Virology, 163(12), (2018), 3255-3264.
Yip, Ming S., et al., "Antibody-dependent infection of human macrophages by severe acute respiratory syndrome", Virology Journal, 11: 82, (2014), 11 pgs.

(56) References Cited

OTHER PUBLICATIONS

"International Application Serial No. PCT/US2021/024200, International Preliminary Report jon Patentability mailed Oct. 6, 2022", 8 pgs.
U.S. Appl. No. 17/835,830, filed Jun. 8, 2022, Influenza Viruses With Mutant PB2 Gene Segment as Live Attenuated Vaccines.
U.S. Appl. No. 14/332,121 U.S. Pat. No. 9,950,057, filed Jul. 15, 2014, High Titer Recombinant Influenza Viruses With Enhanced Replication in MDCK or Vero Cells or Eggs.
U.S. Appl. No. 15/593,039 U.S. Pat. No. 10,172,934, filed May 11, 2017, High Titer Recombinant Influenza Viruses With Enhanced Replication in MDCK or Vero Cells or Eggs.
U.S. Appl. No. 16/178,323, filed Nov. 1, 2018, High Titer Recombinant Influenza Viruses With Enhanced Replication in MDCK or Vero Cells or Eggs.
U.S. Appl. No. 14/745,236 U.S. Pat. No. 10,053,671, filed Jun. 19, 2015, Mutations That Confer Genetic Stability to Additional Genes in Influenza Viruses.
U.S. Appl. No. 15/966,092 U.S. Pat. No. 11,046,934, filed Apr. 30, 2018, Mutations That Confer Genetic Stability to Additional Genes in Influenza Viruses.
U.S. Appl. No. 17/352,845, filed Jun. 21, 2021, Mutations That Confer Genetic Stability to Additional Genes in Influenza Viruses.
U.S. Appl. No. 15/204,381, filed Jul. 7, 2016, Potent Glycoprotein Antibody as a Therapeutic Against Ebola Virus.
U.S. Appl. No. 15/170,556 U.S. Pat. No. 10,633,422, filed Jun. 1, 2016, Influenza Virus Replication by Inhibiting Microrna LEC7C Binding to Influenza Viral CRNA and MRNA.
U.S. Appl. No. 15/203,581 U.S. Pat. No. 9,890,363, filed Jul. 6, 2016, Influenza Virus Replication for Vaccine Development.
U.S. Appl. No. 15/865,364 U.S. Pat. No. 10,246,686, filed Jan. 9, 2018, Influenza Virus Replication for Vaccine Development.
U.S. Appl. No. 16/284,020, filed Feb. 25, 2019, Influenza Virus Replication for Vaccine Development.
U.S. Appl. No. 15/247,006 U.S. Pat. No. 10,494,613, filed Aug. 25, 2016, Generation of Influenza Viruses From Virus-Like Particles.
U.S. Appl. No. 16/547,262 U.S. Pat. No. 11,180,737, filed Aug. 21, 2019, Generation of Infectious Influenza Viruses From Virus-Like Particles.
U.S. Appl. No. 15/436,245 U.S. Pat. No. 11,197,925, filed Feb. 17, 2017, Influenza B Virus Replication for Vaccine Development.
U.S. Appl. No. 17/546,835, filed Dec. 9, 2021, Influenza B Virus Replication for Vaccine Development.
U.S. Appl. No. 16/170,321 U.S. Pat. No. 11,197,926, filed Oct. 25, 2018, Recombinant Influenza Viruses With Stabilized HA for Replication in Eggs.
U.S. Appl. No. 17/546,967, filed Dec. 9, 2021, Recombinant Influenza Viruses With Stabilized HA for Replication in Eggs.
U.S. Appl. No. 17/266,049, filed Feb. 4, 2021, Recombinant Biologically Contained Filovirus Vaccine.
U.S. Appl. No. 16/545,761 U.S. Pat. No. 11,389,523, filed Aug. 20, 2019, Vectors for Eliciting Immune Responses to Non-Dominant Epitopes in the Hemagglutinin (HA) Protein.
U.S. Appl. No. 17/813,178, filed Jul. 18, 2022, Vectors for Eliciting Immune Responses to Non-Dominant Epitopes in the Hemagglutinin (HA) Protein.
U.S. Appl. No. 16/785,449, filed Feb. 7, 2020, Humanized Cell Line.
U.S. Appl. No. 16/865,194 U.S. Pat. No. 11,390,649, filed May 1, 2020, Influenza Virus Replication for Vaccine Development.
U.S. Appl. No. 17/813,200, filed Jul. 18, 2022, Influenza Virus Replication for Vaccine Development.
U.S. Appl. No. 16/749,910 U.S. Pat. No. 11,241,492, filed Jan. 22, 2020, Mutations That Confer Genetic Stability to Genes in Influenza Viruses.
U.S. Appl. No. 17/578,939, filed Jan. 19, 2022, Mutations That Confer Genetic Stability to Genes in Influenza Viruses.
U.S. Appl. No. 17/004,583, filed Aug. 27, 2020, Recombinant Influenza Viruses With Stabilized HA for Replication in Eggs.
U.S. Appl. No. 17/155,625, filed Jan. 22, 2021, Recombinant Influenza Viruses With Stabilize NA.
U.S. Appl. No. 17/936,194, filed Sep. 28, 2022, Compositions Comprising Complexes Displaying Antigens and Methods of Using the Compositions.
U.S. Appl. No. 18/173,535, filed Feb. 23, 2023, Broadly Protective Influenza B Virus Vaccines.
Result 1, NCBI Blast nucleotide search of SEQ ID No. 3, database "nr"; Result 4, NCBI Blast nucleotide search of SEQ ID No. 4, database "nr", (Jul. 22, 2006), 11 pgs.
Result 2, NCBI Blast nucleotide search of SEQ ID No. 5, database "nr"; Result 4, NCBI Blast nucleotide search of SEQ ID No. 6, database "nr", (Jul. 22, 2006), 6 pgs.
Results 1, NCBI Blast nucleotide search of SEQ ID No. 7, database "nr"; Result 1, NCBI Blast nucleotide search of SEQ ID No. 8, database "nr", (Jul. 23, 2006), 8 pgs.
Result 17, NCBI Blast nucleotide search of SEQ ID No. 2, database "nr", (Jul. 18, 2006), 3 pgs.
Result 7, NCBI Blast nucleotide search of SEQ ID: 1, database "nr", (Jul. 18, 2006), 3 pgs.
FLUMISTTM Package Insert Template, [Online]. Retrieved from the Internet: http://www.fda.gov/downloads/BiologicsBLoodVaccines!Vaccines/ApprovedProducts/UCM294307.pdf, (Mar. 1, 2012), 26 pgs.
"1.A.32 The Type B Influenza Virus NB Channel (NB-C) Family", Transport Protein Database, (University of California, San Diego, The Sailer Laboratory Bioinformatics Group) [online}. http://www.web.archive.org/web/200301311055254/http://tcdb.ucsd.edu/tcdb/tcfamilybrowse.php?tcname=1.A.32, (Archived Jan. 31, 2003), 1 pg.
"U.S. Appl. No. 10/855,975 Response filed Aug. 28, 2007 to Final Office Action mailed Jun. 28, 2007", 16 pgs.
"2018-19 ACIP Background—Immunogenicity, Efficacy, and Effectiveness of Influenza Vaccines", [online]. [archived on Dec. 3, 2018]. Retrieved from the Internet: <URL: https://web.archive.org/web/20181203190316/https://www.cdc.gov/flu/professionals/acip/2018-2019/background/immunogenicity.htm>, (updated Aug. 23, 2018), 5 pgs.
Final O.A Jun. 28, 2007, 5 pgs.
"Application Serial No. 04809419.7, Office Action Mailed Sep. 9, 2009", 3 pgs.
"U.S. Appl. No. 09/834,095, Advisory Action mailed Jan. 8, 2004", 3 pgs.
"U.S. Appl. No. 09/834,095, Final Office Action mailed Aug. 26, 2003", 12 pgs.
"U.S. Appl. No. 09/834,095, Non-Final Office Action mailed Nov. 4, 2002", 12 pgs.
"U.S. Appl. No. 09/834,095, Notice of Allowance mailed Sep. 27, 2004", 13 pgs.
"U.S. Appl. No. 09/834,095, Office Action mailed Apr. 20, 2004", 11 pgs.
"U.S. Appl. No. 09/834,095, Response filed Feb. 4, 2003 to Office Action mailed Nov. 4, 2002", 14 pgs.
"U.S. Appl. No. 09/834,095, Response filed Jun. 12, 2003 to Restriction Requirement mailed Apr. 22, 2003", 2 pgs.
"U.S. Appl. No. 09/834,095, Response filed Jun. 18, 2004 to Office Action mailed Apr. 20, 2004", 11 pgs.
"U.S. Appl. No. 09/834,095, Response filed Aug. 1, 2002 to Restriction Requirement mailed Jul. 1, 2002". 3 pgs.
"U.S. Appl. No. 09/834,095, Response filed Nov. 26, 2003 to Final Office Action mailed Aug. 26, 2003", 10 pgs.
"U.S. Appl. No. 09/834,095, Restriction Requirement mailed Apr. 22, 2003", 5 pgs.
"U.S. Appl. No. 09/834,095, Restriction Requirement mailed Jul. 1, 2002", 9 pgs.
"U.S. Appl. No. 09/834,095, Supplemental Amendment filed Aug. 4, 2004", 7 pgs.
"U.S. Appl. No. 10/081,170, Advisory Action mailed Sep. 27, 2004", 3 pgs.
"U.S. Appl. No. 10/081,170, Final Office Action mailed Apr. 12, 2006", 7 pgs.
"U.S. Appl. No. 10/081,170, Final Office Action mailed Jul. 13, 2004", 8 pgs.

(56) References Cited

OTHER PUBLICATIONS

"U.S. Appl. No. 10/081,170, Non Final Office Action mailed Jan. 15, 2004", 9 pgs.
"U.S. Appl. No. 10/081,170, Non Final Office Action mailed Feb. 8, 2005", 9 pgs.
"U.S. Appl. No. 10/081,170, Non Final Office Action mailed Aug. 24, 2005", 9 pgs.
"U.S. Appl. No. 10/081,170, Notice of Allowance mailed Sep. 18, 2006", 8 pgs.
"U.S. Appl. No. 10/081,170, Preliminary Amendment filed May 20, 2003", 2 pgs.
"U.S. Appl. No. 10/081,170, Preliminary Amendment filed Jun. 6, 2002", 1 pg.
"U.S. Appl. No. 10/081,170, Response filed Jan. 24, 2006 to Non Final Office Action mailed Aug. 24, 2005", 11 pgs.
"U.S. Appl. No. 10/081,170, Response filed Apr. 12, 2004 to Non Final Office Action mailed Jan. 15, 2004", 12 pgs.
"U.S. Appl. No. 10/081,170, Response filed Jun. 8, 2005 to Non Final Office Action mailed Feb. 8, 2005", 11 pgs.
"U.S. Appl. No. 10/081,170, Response filed Aug. 17, 2006 to Final Office Action mailed Apr. 12, 2006", 9 pgs.
"U.S. Appl. No. 10/081,170, Response filed Sep. 13, 2004 to Final Office Action mailed Jul. 13, 2004", 10 pgs.
"U.S. Appl. No. 10/081,170, Response filed Oct. 10, 2003 to Restriction Requirement mailed Sep. 10, 2003", 3 pgs.
"U.S. Appl. No. 10/081,170, Restriction Requirement mailed Sep. 10, 2003", 4 pgs.
"U.S. Appl. No. 10/353,856, Final Office Action mailed Jun. 1, 2006", 10 pgs.
"U.S. Appl. No. 10/353,856, Non-Final Office Action mailed Sep. 30, 2005", 9 pgs.
"U.S. Appl. No. 10/353,856, Non-Final Office Action mailed Dec. 16, 2004", 11 pgs.
"U.S. Appl. No. 10/353,856, Notice of Allowance mailed Oct. 18, 2006", 9 pgs.
"U.S. Appl. No. 10/353,856, Preliminary Amendment filed May 20, 2003", 2 pgs.
"U.S. Appl. No. 10/353,856, PTO Response to 312 Amendment mailed Mar. 8, 2007", 2 pgs.
"U.S. Appl. No. 10/353,856, Response filed Feb. 28, 2006 to Non-Final Office Action mailed Sep. 30, 2005", 10 pgs.
"U.S. Appl. No. 10/353,856, Response filed Apr. 7, 2005 to Non-Final Office Action mailed Dec. 16, 2004", 10 pgs.
"U.S. Appl. No. 10/353,856, Response filed Aug. 17, 2006 to Final Office Action mailed Jun. 1, 2006", 11 pgs.
"U.S. Appl. No. 10/353,856, Response filed Oct. 8, 2004 to Restriction Requirement mailed Sep. 10, 2004", 2 pgs.
"U.S. Appl. No. 10/353,856, Restriction Requirement mailed Sep. 10, 2004", 5 pgs.
"U.S. Appl. No. 10/353,856, Supplemental Amendment filed Jan. 9, 2007", 4 pgs.
"U.S. Appl. No. 10/353,856, Supplemental Preliminary Amendment filed Jun. 23, 2003", 4 pgs.
"U.S. Appl. No. 10/827,995, Final Office Action mailed Nov. 15, 2006", 10 pgs.
"U.S. Appl. No. 10/827,995, Non-Final Office Action mailed Jun. 2, 2006", 15 pgs.
"U.S. Appl. No. 10/827,995, Non-Final Office Action mailed Oct. 25, 2007", 7 pgs.
"U.S. Appl. No. 10/827,995, Notice of Allowance mailed Feb. 17, 2009", 9 pgs.
"U.S. Appl. No. 10/827,995, Notice of Allowance mailed Jul. 2, 2008", 9 pgs.
"U.S. Appl. No. 10/827,995, Notice of Allowance mailed Oct. 17, 2008", 7 pgs.
"U.S. Appl. No. 10/827,995, Notice of Non-Compliant Amendment Jul. 25, 2007", 4 pgs.
"U.S. Appl. No. 10/827,995, Proposed Examiner's Amendment mailed Jun. 5, 2008", 6 pgs.
"U.S. Appl. No. 10/827,995, Response filed Mar. 3, 2008 to Office Action mailed Oct. 25, 2007", 10 pgs.
"U.S. Appl. No. 10/827,995, Response filed May 14, 2007 Final Office Action mailed Nov. 15, 2006", 16 pgs.
"U.S. Appl. No. 10/827,995, Response filed Aug. 13, 2007 to Notice of Non-Compliant Amendment Jul. 25, 2007", 16 pgs.
"U.S. Appl. No. 10/827,995, Response filed Aug. 17, 2006 Non-Final Office Action mailed Jun. 2, 2006", 15 pgs.
"U.S. Appl. No. 10/855,875 , Response filed May 17, 2012 to Non Final Office Action mailed Mar. 15, 2012", 15 pgs.
"U.S. Appl. No. 10/855,875, Final Office Action mailed Mar. 11, 2008", FOAR, 20 Pgs.
"U.S. Appl. No. 10/855,875, Final Office Action mailed Aug. 2, 2006", 34 pgs.
"U.S. Appl. No. 10/855,875, Final Office Action mailed Dec. 10, 2010", 15 pgs.
"U.S. Appl. No. 10/855,875, Non Final Office Action mailed Mar. 15, 2012", 15 pgs.
"U.S. Appl. No. 10/855,875, Non-Final Office Action mailed Feb. 19, 2010", 7 pgs.
"U.S. Appl. No. 10/855,875, Non-Final Office Action mailed May 3, 2007", 13 pgs.
"U.S. Appl. No. 10/855,875, Non-Final Office Action mailed Aug. 7, 2009", 32 pgs.
"U.S. Appl. No. 10/855,875, Non-Final Office Action mailed Nov. 6, 2008", 12 pgs.
"U.S. Appl. No. 10/855,875, Non-Final Office Action mailed Nov. 30, 2005", 13 pgs.
"U.S. Appl. No. 10/855,875, Notice of Allowance mailed Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action mailed Aug. 2, 2007". 14 pgs.
"U.S. Appl. No. 10/855,875, Response filed Mar. 18, 2011 to Final Office Action mailed Dec. 10, 2010", 15 pgs.
"U.S. Appl. No. 10/855,875, Response filed Aug. 17, 2010 to Non Final Office Action mailed Feb. 19, 2010", 20 pgs.
"U.S. Appl. No. 10/855,875, Response filed Dec. 7, 2009 to Non Final Office Action mailed Aug. 7, 2009", 15 pgs.
"U.S. Appl. No. 10/855,875, Response filed Mar. 31, 2009 to Non Final Office Action mailed Nov. 6, 2008", 14 pgs.
"U.S. Appl. No. 10/855,875, Response filed May 1, 2006 Non-Final Office Action mailed Nov. 30, 2005", 13 pgs.
"U.S. Appl. No. 10/855,875, Response filed Aug. 18, 2008 to final Office Action mailed Mar. 11, 2008", 15 pgs.
"U.S. Appl. No. 10/855,875, Response filed Sep. 20, 2005 to Restriction Requirement mailed Jul. 26, 2005", 4 pgs.
"U.S. Appl. No. 10/855,875, Restriction Requirement mailed Dec. 23, 2011", 9 pgs.
"U.S. Appl. No. 10/855,875, Restriction Requirement mailed Jul. 26, 2005", 9 pgs.
"U.S. Appl. No. 10/855,975, Advisory Action mailed Sep. 6, 2006", 3 pgs.
"U.S. Appl. No. 10/855,975, Advisory Action mailed Sep. 13, 2007", 3 pgs.
"U.S. Appl. No. 10/855,975, Advisory Action mailed Dec. 24, 2008", 4 pgs.
"U.S. Appl. No. 10/855,975, Final Office Action mailed May 17, 2006", 7 pgs.
"U.S. Appl. No. 10/855,975, Final Office Action mailed Jun. 28, 2007", 7 pgs.
"U.S. Appl. No. 10/855,975, Final Office Action mailed Aug. 7, 2008", 5 pgs.
"U.S. Appl. No. 10/855,975, Non-Final Office Action mailed Jan. 4, 2008", 10 pgs.
"U.S. Appl. No. 10/855,975, Non-Final Office Action mailed Jan. 19, 2007", 7 pgs.
"U.S. Appl. No. 10/855,975, Non-Final Office Action mailed May 29, 2009", 5 pgs.
"U.S. Appl. No. 10/855,975, Non-Final Office Action mailed Nov. 30, 2005", 11 pgs.

(56) References Cited

OTHER PUBLICATIONS

"U.S. Appl. No. 10/855,975, Notice of Allowance mailed Dec. 16, 2009", 19 pgs.
"U.S. Appl. No. 10/855,975, Response filed Jan. 29, 2009 to Advisory Action mailed Dec. 24, 2008", 15 pgs.
"U.S. Appl. No. 10/855,975, Response filed Feb. 28, 2006 to Non-Final Office Action mailed Nov. 30, 2005", 15 pgs.
"U.S. Appl. No. 10/855,975, Response filed Apr. 3, 2008 to Non Final Office Action mailed Jan. 4, 2008", 16 pgs.
"U.S. Appl. No. 10/855,975, Response filed Apr. 19, 2007 to Non-Final Office Action mailed Jan. 19, 2007", 16 pgs.
"U.S. Appl. No. 10/855,975, Response filed Aug. 13, 2009 to Non Final Office Action mailed May 29, 2009", 19 pgs.
"U.S. Appl. No. 10/855,975, Response filed Aug. 17, 2006 to Final Office Action mailed May 17, 2006", 13 pgs.
"U.S. Appl. No. 10/855,975, Response filed Aug. 28, 2007 to Final Office Action mailed Jun. 28, 2007", 15 pgs.
"U.S. Appl. No. 10/855,975, Response filed Sep. 28, 2005 to Restriction Requirement mailed Jul. 12, 2005", 3 pgs.
"U.S. Appl. No. 10/855,975, Response filed Dec. 11, 2008 to Final Office Action mailed Aug. 7, 2008", 14 pgs.
"U.S. Appl. No. 10/855,975, Restriction Requirement mailed Jul. 12, 2005", 8 pgs.
"U.S. Appl. No. 10/855,875, Response filed Nov. 2, 2007 to Office Action mailed May 3, 2007", 16 pgs.
"U.S. Appl. No. 11/043,768 Non-Final Office Action mailed Sep. 27, 2010", 8 pgs.
"U.S. Appl. No. 11/043,768, Final Office Action mailed Jun. 27, 2008", 8 pgs.
"U.S. Appl. No. 11/043,768, Non-Final Office Action mailed Feb. 23, 2010", 6 pgs.
"U.S. Appl. No. 11/043,768, Non-Final Office Action mailed Feb. 23, 2009", 7 pgs.
"U.S. Appl. No. 11/043,768, Non-Final Office Action mailed Nov. 28, 2007", 9 pgs.
"U.S. Appl. No. 11/043,768, Notice of Allowance mailed Jun. 29, 2011", 12 pgs.
"U.S. Appl. No. 11/043,768, Response filed May 2, 2011 to Final Office Action mailed Feb. 3, 2011", 11 pgs.
"U.S. Appl. No. 11/043,768, Response filed Jun. 15, 2010 to Non Final Office Action mailed Feb. 23, 2010", 9 pgs.
"U.S. Appl. No. 11/043,768, Response filed Jun. 23, 2009 to Non-Final Office Action mailed Feb. 23, 2009", 9 pgs.
"U.S. Appl. No. 11/043,768, Response filed Sep. 13, 2007 to Restriction Requirement mailed Mar. 13, 2007" 10 pgs.
"U.S. Appl. No. 11/043,768, Response filed Oct. 26, 2010 to Non Final Office Action mailed Sep. 27, 2010", 11 pgs.
"U.S. Appl. No. 11/043,768, Response filed Dec. 12, 2008 to Final Office Action mailed Jun. 27, 2008", 9 pgs.
"U.S. Appl. No. 11/043,768, Response filed Mar. 10, 2008 to Office Action mailed Nov. 28, 2007", 12 pgs.
"U.S. Appl. No. 11/043,768, Restriction Requirement mailed Mar. 13, 2007", 9 pgs.
"U.S. Appl. No. 11/043,786, Final Office Action mailed Feb. 3, 2011", 10 pgs.
"U.S. Appl. No. 11/283,498, Non Final Office Action mailed Sep. 3, 2009", 5 pgs.
"U.S. Appl. No. 11/283,498, Non Final Office Action mailed Jul. 9, 2007", 7 pgs.
"U.S. Appl. No. 11/283,498, Non-Final Office Action mailed Jan. 23, 2008", 20 pgs.
"U.S. Appl. No. 11/283,498, Non-Final Office Action mailed Apr. 29, 2010", 10 pgs.
"U.S. Appl. No. 11/283,498, Notice of Allowance mailed Feb. 23, 2011", 9 pgs.
"U.S. Appl. No. 11/283,498, Response filed Jan. 4, 2010 to Non Final Office Action mailed Sep. 3, 2009", 12 pgs.
"U.S. Appl. No. 11/283,498, Response filed Oct. 28, 2010 to Non Final Office Action mailed Apr. 29, 2010", 13 pgs.
"U.S. Appl. No. 11/283,498, Response filed Nov. 7, 2007 to Office Action mailed Jul. 9, 2007", 17 pgs.
"U.S. Appl. No. 11/283,498, Response filed Apr. 16, 2007 to Restriction Requirement mailed Oct. 16, 2006". 17 pgs.
"U.S. Appl. No. 11/283,498, Response filed Jul. 22, 2008 to Non Final Office Action mailed Jan. 23, 2008", 12 pgs.
"U.S. Appl. No. 11/283,498, Restriction Requirement mailed Oct. 16, 2006", 6 pgs.
"U.S. Appl. No. 11/283,498, Supplemental Amendment Response to Non Final Office Action mailed Oct. 28, 2010", 11 pgs.
"U.S. Appl. No. 11/509,249, Final Office Action mailed Jun. 12, 2008", 5 pgs.
"U.S. Appl. No. 11/509,249, Non Final Office Action with Restriction Requirement mailed Aug. 24, 2007", 8 pgs.
"U.S. Appl. No. 11/509,249, Notice of Allowance mailed Apr. 9, 2009", 7 pgs.
"U.S. Appl. No. 11/509,249, Notice of Allowance mailed Nov. 17, 2008", 4 pgs.
"U.S. Appl. No. 11/509,249, Response filed Feb. 20, 2008 to Non Final Office Action mailed Aug. 24, 2007", 11 pgs.
"U.S. Appl. No. 11/509,249, Response filed Oct. 6, 2008 to Office Action mailed Jun. 12, 2008", 11 pgs.
"U.S. Appl. No. 11/644,179 , Response filed Oct. 21, 2013 to Final Office Action mailed May 21, 2013", 8 pgs.
"U.S. Appl. No. 11/644,179, Final Office Action mailed May 21, 2013", 11 pgs.
"U.S. Appl. No. 11/644,179, Final Office Action mailed Jul. 2, 2010", 8 pgs.
"U.S. Appl. No. 11/644,179, Non Final Office Action mailed Nov. 29, 2012", 19 pgs.
"U.S. Appl. No. 11/644,179, Non Final Office Action mailed Dec. 8, 2009", 7 pgs.
"U.S. Appl. No. 11/644,179, Notice of Allowance mailed Nov. 1, 2013", 11 pgs.
"U.S. Appl. No. 11/644,179, Preliminary Amendment filed Dec. 22, 2006", 5 pgs.
"U.S. Appl. No. 11/644,179, Response filed Jan. 30, 2008 to Restriction Requirement mailed Oct. 30, 2007", 5 pgs.
"U.S. Appl. No. 11/644,179, Response filed Apr. 8, 2010 to Non Final Office Action mailed Dec. 8, 2009", 8 pgs.
"U.S. Appl. No. 11/644,179, Response filed Aug. 17, 2010 to Final Office Action mailed Jul. 2, 2010", 8 pgs.
"U.S. Appl. No. 11/644,179, Restriction Requirement mailed Oct. 30, 2007", 7 pgs.
"U.S. Appl. No. 11/644,179, Supplemental Preliminary Amendment filed Feb. 6, 2008", 6 pgs.
"U.S. Appl. No. 11/644,179. Response filed Feb. 20, 2013 to Non Final Office Action mailed Nov. 29, 2012", 10 pgs.
"U.S. Appl. No. 11/654,863 Final Office Action mailed Jul. 17, 2017", 11 pgs.
"U.S. Appl. No. 11/654,863 Restriction Requirement mailed Sep. 3, 2010", 5 pgs.
"U.S. Appl. No. 11/654,863, Appeal Brief filed Apr. 30, 2014", 22 pgs.
"U.S. Appl. No. 11/654,863, Appeal Decision mailed Aug. 3, 2016", 11 pgs.
"U.S. Appl. No. 11/654,863, Decision on Pre-Appeal Brief Request mailed Dec. 5, 2013", 2 pgs.
"U.S. Appl. No. 11/654,863, Declaration of Dr. Heinz Feldmann dated Jan. 9, 2018". 2 pgs.
"U.S. Appl. No. 11/654,863, Declaration of Yoshihiro Kawaoka dated Apr. 18, 2012", 2 pgs.
"U.S. Appl. No. 11/654,863, Examiner's Answer to Appeal Brief mailed Jun. 18, 2014", 10 pgs.
"U.S. Appl. No. 11/654,863, Final Office Action mailed Jul. 11, 2013", 9 pgs.
"U.S. Appl. No. 11/654,863, Final Office Action mailed Sep. 12, 2018", 12 pgs.
"U.S. Appl. No. 11/654,863, Final Office Action mailed Oct. 25, 2011", 9 pgs.
"U.S. Appl. No. 11/654,863, Non Final Office Action mailed Feb. 11, 2013", 10 pgs.

(56) References Cited

OTHER PUBLICATIONS

"U.S. Appl. No. 11/654,863, Non Final Office Action mailed Mar. 29, 2018", 12 pgs.
"U.S. Appl. No. 11/654,863, Non Final Office Action mailed Jun. 27, 2011", 9 pgs.
"U.S. Appl. No. 11/654,863, Non Final Office Action mailed Dec. 2, 2010", 8 pgs.
"U.S. Appl. No. 11/654,863, Non Final Office Action mailed Dec. 21, 2016", 14 pgs.
"U.S. Appl. No. 11/654,863, Pre-Appeal Brief Request filed Nov. 11, 2013", 5 pgs.
"U.S. Appl. No. 11/654,863, Preliminary Amendment filed May 7, 2007", 15 pgs.
"U.S. Appl. No. 11/654,863, Reply Brief filed Aug. 18, 2014", 6 pgs.
"U.S. Appl. No. 11/654,863, Response filed Jan. 17, 2018 to Final Office Action mailed Jul. 17, 2017", 9 pgs.
"U.S. Appl. No. 11/654,863, Response filed Apr. 18, 2012 to Final Office Action mailed Oct. 25, 2011", 8 pgs.
"U.S. Appl. No. 11/654,863, Response filed Jun. 2, 2011 to Non Final Office Action mailed Dec. 2, 2010", 6 pgs.
"U.S. Appl. No. 11/654,863, Response filed Jun. 7, 2013 to Non Final Office Action mailed Feb. 11, 2013", 10 pgs.
"U.S. Appl. No. 11/654,863, Response filed Jun. 21, 2017 to Non Final Office Action mailed Dec. 21, 2016", 11 pgs.
"U.S. Appl. No. 11/654,863, Response filed Jul. 9, 2018 to Non Final Office Action mailed Mar. 29, 2018", 10 pgs.
"U.S. Appl. No. 11/654,863, Response filed Sep. 28, 2010 to Restriction Requirement mailed Sep. 3, 2010", 6 pgs.
"U.S. Appl. No. 11/654,863, Response filed Oct. 6, 2011 to Non Final Office Action mailed Jun. 27, 2011", 9 pgs.
"U.S. Appl. No. 11/729,557, Advisory Action mailed May 9, 2011", 3 pgs.
"U.S. Appl. No. 11/729,557, Advisory Action mailed Dec. 24, 2014", 3 pgs.
"U.S. Appl. No. 11/729,557, Final Office Action mailed Feb. 2, 2011", 14 pgs.
"U.S. Appl. No. 11/729,557, Final Office Action mailed Aug. 20, 2009", 13 Pgs.
"U.S. Appl. No. 11/729,557, Final Office Action mailed Sep. 12, 2014", 14 pgs.
"U.S. Appl. No. 11/729,557, Non Final Office Action mailed Feb. 18, 2015", 13 pgs.
"U.S. Appl. No. 11/729,557, Non Final Office Action mailed Feb. 26, 2014", 16 pgs.
"U.S. Appl. No. 11/729,557, Non-Final Office Action mailed Jan. 30, 2009", 20 pgs.
"U.S. Appl. No. 11/729,557, Non-Final Office Action mailed Feb. 22, 2010", 16 pgs.
"U.S. Appl. No. 11/729,557, Non-Final Office Action mailed Aug. 23, 2010", 15 pgs.
"U.S. Appl. No. 11/729,557, Notice of Allowance mailed Sep. 30, 2015", 11 pgs.
"U.S. Appl. No. 11/729,557, Respons filed Jun. 22, 2010 to Non Final Office Action mailed Feb. 22, 2010", 33 pgs.
"U.S. Appl. No. 11/729,557, Response filed Apr. 27, 2011 to Final Office Action mailed Feb. 2, 2011". 14 pgs.
"U.S. Appl. No. 11/729,557, Response filed Apr. 30, 2009 to Non Final Office Action mailed Jan. 30, 2009", 18 pgs.
"U.S. Appl. No. 11/729,557, Response filed May 22, 2014 to Non Final Office Action mailed Feb. 26, 2014", 13 pgs.
"U.S. Appl. No. 11/729,557, Response filed May 28, 2008 to Restriction Requirement mailed Nov. 28, 2007", 13 pgs.
"U.S. Appl. No. 11/729,557, Response filed Jun. 22, 2010 to Non Final Office Action mailed Feb. 22, 2010", 16 pgs.
"U.S. Appl. No. 11/729,557, Response filed Jun. 22, 2015 to non Final Office Action mailed Feb. 18, 2015", 13 pgs.
"U.S. Appl. No. 11/729,557, Response filed Oct. 28, 2010 to Non Final Office Action mailed Aug. 23, 2010", 13 pgs.
"U.S. Appl. No. 11/729,557, Response filed Dec. 1, 2009 to Final Office Action mailed Aug. 26, 2009", 16 pgs.
"U.S. Appl. No. 11/729,557, Response filed Dec. 11, 2014 to Final Office Action mailed Sep. 12, 2014", 15 pgs.
"U.S. Appl. No. 11/729,557, Restriction Requirement mailed Nov. 28, 2007", 9 pgs.
"U.S. Appl. No. 11/810,956, Final Office Action mailed Mar. 22, 2010", 8 pgs.
"U.S. Appl. No. 11/810,956, Non-Final Office Action mailed Aug. 11, 2009", 9 pgs.
"U.S. Appl. No. 11/810,956, Response filed Jan. 11, 2010 to Non Final Office Action mailed Aug. 11, 2009", 8 pgs.
"U.S. Appl. No. 11/810,956, Response filed Apr. 23, 2009 to Restriction Requirement mailed Mar. 23, 2009", 6 pgs.
"U.S. Appl. No. 11/810,956, Restriction Requirement mailed Mar. 23, 2009", 6 pgs.
"U.S. Appl. No. 12/058,389, Advisory Action mailed Jan. 2, 2013", 2 pgs.
"U.S. Appl. No. 12/058,389, Final Office Action mailed Jan. 22, 2010", 8 pgs.
"U.S. Appl. No. 12/058,389, Final Office Action mailed Nov. 14, 2012", 7 pgs.
"U.S. Appl. No. 12/058,389, Non Final Office Action mailed Aug. 10, 2012", 5 pgs.
"U.S. Appl. No. 12/058,389, Non Final Office Action mailed Dec. 8, 2011", 8 pgs.
"U.S. Appl. No. 12/058,389, Non-Final Office Action mailed Apr. 13, 2009", 12 pgs.
"U.S. Appl. No. 12/058,389, Notice of Allowability mailed Mar. 22, 2013", 8 pgs.
"U.S. Appl. No. 12/058,389, Notice of Allowance mailed Feb. 20, 2013", 9 pgs.
"U.S. Appl. No. 12/058,389, Preliminary Amendment filed Jun. 23, 2008", 7 pgs.
"U.S. Appl. No. 12/058,389, Respnse filed Nov. 6, 2012 to Non Final Office Action mailed Aug. 10, 2012", 7 pgs.
"U.S. Appl. No. 12/058,389, Response filed Feb. 6, 2009 to Restriction Requirement mailed Dec. 3, 2008", 7 pgs.
"U.S. Appl. No. 12/058,389, Response filed Apr. 10, 2012 to Non Final Office Action mailed Dec. 8, 2011", 7 pgs.
"U.S. Appl. No. 12/058,389, Response filed Jun. 16, 2010 to Final Office Action mailed Jan. 22, 2010". 6 pgs.
"U.S. Appl. No. 12/058,389, Response filed Oct. 13, 2009 to Non Final Office Action mailed Apr. 13, 2009", 9 pgs.
"U.S. Appl. No. 12/058,389, Response filed Dec. 18, 2012 to Non Final Office Action mailed Nov. 14, 2012", 7 pgs.
"U.S. Appl. No. 12/058,389, Restriction Requirement mailed Dec. 3, 2008", 7 pgs.
"U.S. Appl. No. 12/113,690, Final Office Action mailed Apr. 15, 2011", 10 pgs.
"U.S. Appl. No. 12/113,690, Non-Final Office Action mailed Nov. 10, 2010", 11 pgs.
"U.S. Appl. No. 12/113,690, Notice of Allowability mailed Aug. 19, 2013", 9 pgs.
"U.S. Appl. No. 12/113,690, Notice of Allowance mailed Jul. 18, 2013", 14 pgs.
"U.S. Appl. No. 12/113,690, Preliminary Amendment filed Jul. 31, 2008", 14 pgs.
"U.S. Appl. No. 12/113,690, Response filed Jun. 23, 2011 to Final Office Action mailed Apr. 15, 2011", 17 pgs.
"U.S. Appl. No. 12/113,690, Response filed Aug. 5, 2010 to Restriction Requirement mailed Apr. 6, 2010", 14 pgs.
"U.S. Appl. No. 12/113,690, Response filed Dec. 22, 2010 to Non Final Office Action mailed Nov. 10, 2010", 19 pgs.
"U.S. Appl. No. 12/113,690, Restriction Requirement mailed Apr. 6, 2010", 10 pgs.
"U.S. Appl. No. 12/139,183, Non Final Office Action mailed Jan. 6, 2011", 12 pgs.
"U.S. Appl. No. 12/139,183, Non-Final Office Action mailed Jan. 4, 2010", 6 pgs.
"U.S. Appl. No. 12/139,183, Non-Final Office Action mailed Jul. 13, 2010", 15 pgs.

(56) References Cited

OTHER PUBLICATIONS

"U.S. Appl. No. 12/139,183, Notice of Allowance mailed Jun. 27, 2011", 11 pgs.
"U.S. Appl. No. 12/139,183, Preliminary Amendment filed Sep. 11, 2008", 17 pgs.
"U.S. Appl. No. 12/139,183, Response filed Mar. 22, 2011 to Non Final Office Action mailed Jan. 6, 2011", 21 pgs.
"U.S. Appl. No. 12/139,183, Response filed Apr. 12, 2010 to Non Final Office Action mailed Jan. 4, 2010", 17 pgs.
"U.S. Appl. No. 12/139,183, Response filed Aug. 18, 2009 to Restriction Requirement mailed Jul. 24, 2009", 16 pgs.
"U.S. Appl. No. 12/139,183, Response filed Sep. 21, 2010 to Non Final Office Action mailed Jul. 13, 2010", 21 pgs.
"U.S. Appl. No. 12/139,183, Restriction Requirement mailed Jul. 24, 2009", 12 pgs.
"U.S. Appl. No. 12/214,414, Advisory Action mailed Feb. 2, 2016", 5 pgs.
"U.S. Appl. No. 12/214,414, Advisory Action mailed Apr. 15, 2015", 6 pgs.
"U.S. Appl. No. 12/214,414, Advisory Action mailed Oct. 21, 2011", 5 pgs.
"U.S. Appl. No. 12/214,414, Examiner Interview Summary mailed Dec. 11, 2015", 3 pgs.
"U.S. Appl. No. 12/214,414, Final Office Action mailed Jan. 20, 2015", 28 pgs.
"U.S. Appl. No. 12/214,414, Final Office Action mailed Aug. 2, 2011", 7 pgs.
"U.S. Appl. No. 12/214,414, Final Office Action mailed Nov. 18, 2015", 17 pgs.
"U.S. Appl. No. 12/214,414, Non Final Office Action mailed Jun. 12, 2014", 28 pgs.
"U.S. Appl. No. 12/214,414, Non Final Office Action mailed Dec. 10, 2010", 6 pgs.
"U.S. Appl. No. 12/214,414, Non-Final Office Action mailed Mar. 2, 2010", 9 pgs.
"U.S. Appl. No. 12/214,414, Notice of Allowance mailed Jun. 7, 2016", 18 pgs.
"U.S. Appl. No. 12/214,414, Response filed Jan. 19, 2016 to Final Office Action mailed Nov. 18, 2015", 14 pgs.
"U.S. Appl. No. 12/214,414, Response filed Feb. 18, 2016 to Final Office Action mailed Nov. 18, 2015", 14 pgs.
"U.S. Appl. No. 12/214,414, Response filed Mar. 26, 2015 to Final Office Action mailed Jan. 20, 2015", 13 pgs.
"U.S. Appl. No. 12/214,414, Response filed May 3, 2011 to Non Final Office Action mailed Dec. 10, 2010", 12 pgs.
"U.S. Appl. No. 12/214,414, Response filed Jul. 20, 2015 to Advisory Action mailed Apr. 15, 2015", 14 pgs.
"U.S. Appl. No. 12/214,414, Response filed Aug. 31, 2010 to Non Final Office Action mailed Mar. 2, 2010", 11 pgs.
"U.S. Appl. No. 12/214,414, Response filed Oct. 3, 2011 to Non Final Office Action mailed Aug. 2, 2011", 9 pgs.
"U.S. Appl. No. 12/214,414, Response filed Oct. 14, 2014 to Non Final Office Action mailed Jun. 12, 2014", 16 pgs.
"U.S. Appl. No. 12/214,414, Response filed Dec. 21, 2011 to Advisory Action mailed Oct. 21, 2011", 10 pgs.
"U.S. Appl. No. 12/245,296, Final Office Action mailed Jul. 11, 2013", 15 pgs.
"U.S. Appl. No. 12/245,296, Final Office Action mailed Dec. 17, 2010", 16 pgs.
"U.S. Appl. No. 12/245,296, Non Final Office Action mailed Mar. 25, 2013", 14 pgs.
"U.S. Appl. No. 12/245,296, Non-Final Office Action mailed Jun. 1, 2010", 13 pgs.
"U.S. Appl. No. 12/245,296, Notice of Allowance mailed Aug. 1, 2014", 10 pgs.
"U.S. Appl. No. 12/245,296, Preliminary Amendment mailed Jan. 28, 2009", 14 pgs.
"U.S. Appl. No. 12/245,296, Response filed Jan. 8, 2013 to Final Office Action mailed Jul. 11, 2013", 10 pgs.
"U.S. Appl. No. 12/245,296, Response filed Apr. 8, 2010 to Restriction Requirement mailed Mar. 9, 2010", 6 pgs.
"U.S. Appl. No. 12/245,296, Response filed May 17, 2011 to Final Office Action mailed Dec. 17, 2010", 10 pgs.
"U.S. Appl. No. 12/245,296, Response filed Jun. 7, 2013 to Non Final Office Action mailed Mar. 25, 2013", 9 pgs.
"U.S. Appl. No. 12/245,296, Response filed Oct. 1, 2010 to Non Final Office Action mailed Jun. 1, 2010", 12 pgs.
"U.S. Appl. No. 12/245,296, Restriction Requirement mailed Mar. 9, 2010", 6 pgs.
"U.S. Appl. No. 12/467,492, Restriction Requirement mailed Nov. 22, 2010", 6 pgs.
"U.S. Appl. No. 12/470,287 , Response filed Jan. 23, 2012 to Non Final Office Action mailed Jul. 22, 2011", 13 pgs.
"U.S. Appl. No. 12/470,287 , Response filed May 31, 2012 to Final Office Action mailed Apr. 3, 2012", 14 pgs.
"U.S. Appl. No. 12/470,287, Corrected Notice of Allowability mailed Sep. 11, 2012", 2 gs.
"U.S. Appl. No. 12/470,287, Final Office Action mailed Apr. 3, 2012", 7 pgs.
"U.S. Appl. No. 12/470,287, Non Final Office Action mailed Jul. 22, 2011", 9 pgs.
"U.S. Appl. No. 12/470,287, Notice of Allowance mailed Jun. 19, 2012", 5 pgs.
"U.S. Appl. No. 12/470,287, Response filed Apr. 28, 2011 to Restriction Requirement mailed Dec. 29, 2010", 8 pgs.
"U.S. Appl. No. 12/470,287, Restriction Requirement mailed Dec. 29, 2010", 6 pgs.
"U.S. Appl. No. 12/854,578 , Response filed Oct. 1, 2012 to Non Final Office Action mailed Jun. 29, 2012", 10 pgs.
"U.S. Appl. No. 12/854,578, Final Office Action mailed Nov. 29, 2012", 8 pgs.
"U.S. Appl. No. 12/854,578, Non Final Office Action mailed Jun. 29, 2012", 8 pgs.
"U.S. Appl. No. 12/854,578, Notice of Allowance mailed Apr. 10, 2013", 6 pgs.
"U.S. Appl. No. 12/854,578, PTO Response to 312 Amendment mailed Jul. 18, 2013", 2 pgs.
"U.S. Appl. No. 12/854,578, Response filed Feb. 28, 2013 to Final Office Action mailed Nov. 29, 2012", 8 pgs.
"U.S. Appl. No. 12/854,578, Restriction Requirement mailed Apr. 6, 2012", 6 pgs.
"U.S. Appl. No. 12/912,411, Advisory Action mailed Feb. 5, 2014", 3 pgs.
"U.S. Appl. No. 12/912,411, Examiner Interview Summary mailed Feb. 11, 2014", 2 pgs.
"U.S. Appl. No. 12/912,411, Final Office Action mailed Jan. 14, 2015", 10 pgs.
"U.S. Appl. No. 12/912,411, Final Office Action mailed Oct. 25, 2013", 11 pgs.
"U.S. Appl. No. 12/912,411, Non Final Office Action mailed Jun. 7, 2013", 8 pgs.
"U.S. Appl. No. 12/912,411, Non Final Office Action mailed Sep. 24, 2014", 11 pgs.
"U.S. Appl. No. 12/912,411, Notice of Allowability mailed May 20, 2015", 7 pgs.
"U.S. Appl. No. 12/912,411, Notice of Allowance mailed Apr. 8, 2015", 11 pgs.
"U.S. Appl. No. 12/912,411, Response filed Jan. 27, 2014 to Final Office Action mailed Oct. 25, 2013", 11 pgs.
"U.S. Appl. No. 12/912,411, Response filed Feb. 18, 2013 to Restriction Requirement mailed Oct. 17, 2012", 9 pgs.
"U.S. Appl. No. 12/912,411, Response filed Feb. 25, 2014 to Final Office Action mailed Oct. 25, 2013". 11 pgs.
"U.S. Appl. No. 12/912,411, Response filed Mar. 16, 2015 to Final Office Action mailed Jan. 14, 2015", 9 pgs.
"U.S. Appl. No. 12/912,411, Response filed Oct. 7, 2013 to Non Final Office Action mailed Jun. 7, 2013", 10 pgs.
"U.S. Appl. No. 12/912,411, Response filed Dec. 31, 2014 to Non Final Office Action mailed Sep. 24, 2014", 12 pgs.
"U.S. Appl. No. 12/912,411, Restriction Requirement mailed Oct. 17, 2012", 9 pgs.

(56) References Cited

OTHER PUBLICATIONS

"U.S. Appl. No. 13/070,110 Response filed Feb. 14, 2017 to Final Office Action mailed Sep. 14, 2016", 8 pgs.
"U.S. Appl. No. 13/070,110, Advisory Action mailed Mar. 3, 2017", 5 pgs.
"U.S. Appl. No. 13/070,110, Examiner Interview Summary mailed Jan. 16, 2018", 3 pgs.
"U.S. Appl. No. 13/070,110, Final Office Action malled Apr. 3, 2015", 18 pgs.
"U.S. Appl. No. 13/070,110, Final Office Action mailed Jun. 12, 2013", 7 pgs.
"U.S. Appl. No. 13/070,110, Final Office Action mailed Sep. 14, 2016", 12 pgs.
"U.S. Appl. No. 13/070,110, Non Final Office Action mailed Jul. 21, 2017", 14 pgs.
"U.S. Appl. No. 13/070,110, Non Final Office Action mailed Oct. 2, 2014", 24 pgs.
"U.S. Appl. No. 13/070,110, Non Final Office Action mailed Dec. 11, 2015", 19 pgs.
"U.S. Appl. No. 13/070,110, Non Final Office Action mailed Dec. 21, 2012", 7 pgs.
"U.S. Appl. No. 13/070,110, Notice of Allowance mailed Mar. 26, 2018", 6 pgs.
"U.S. Appl. No. 13/070,110, Notice of Allowance mailed Jul. 20, 2018", 7 pgs.
"U.S. Appl. No. 13/070,110, Preliminary Amendment filed Jun. 6, 2011", 4 pgs.
"U.S. Appl. No. 13/070,110, PTO Response to Rule 312 Communication mailed Aug. 15, 2018", 2 pgs.
"U.S. Appl. No. 13/070,110, Response filed Jan. 22, 2018 to Non Final Office Action mailed Jul. 21, 2017", 10 pgs.
"U.S. Appl. No. 13/070,110, Response filed Mar. 22, 2013 to Non Final Office Action mailed Dec. 21, 2012", 8 pgs.
"U.S. Appl. No. 13/070,110, Response filed May 27, 2016 to Non Final Office Action mailed Dec. 11, 2015", 13 pgs.
"U.S. Appl. No. 13/070,110, Response filed Jun. 20, 2017 to Advisory Action mailed Mar. 3, 2017", 13 pgs.
"U.S. Appl. No. 13/070,110, Response filed Sep. 3, 2014 to Restriction Requirement mailed Jul. 8, 2014", 7 pgs.
"U.S. Appl. No. 13/070,110, Response filed Oct. 2, 2015 to Final Office Action mailed Apr. 3, 2015", 11 pgs.
"U.S. Appl. No. 13/070,110, Response filed Nov. 12, 2013 to Final Office Action mailed Jun. 12, 2013", 9 pgs.
"U.S. Appl. No. 13/070,110, Response filed Dec. 30, 2014 to Non Final Office Action mailed Oct. 2, 2014", 13 pgs.
"U.S. Appl. No. 13/070,110, Restriction Requirement mailed Jul. 8, 2014", 7 pgs.
"U.S. Appl. No. 13/113,244, Final Office Action mailed Feb. 27, 2014", 8 pgs.
"U.S. Appl. No. 13/113,244, Non Final Office Action mailed Jul. 5, 2013", 6 pgs.
"U.S. Appl. No. 13/113,244, Non Final Office Action mailed Oct. 1, 2012", 7 pgs.
"U.S. Appl. No. 13/113,244, Notice of Allowance malled Jun. 30, 2014", 9 pgs.
"U.S. Appl. No. 13/113,244, Preliminary Amendment filed Aug. 11, 2011", 4 pgs.
"U.S. Appl. No. 13/113,244, Response filed Jan. 30, 2012 to Restriction Requirement mailed Oct. 31, 2011", 10 pgs.
"U.S. Appl. No. 13/113,244, Response filed Feb. 20, 2013 to Non Final Office Action mailed Oct. 1, 2012", 12 pgs.
"U.S. Appl. No. 13/113,244, Response filed Jun. 13, 2014 to Final Office Action mailed Feb. 27, 2014", 6 pgs.
"U.S. Appl. No. 13/113,244, Response filed Oct. 31, 2013 to Non Final Office Action mailed Jul. 5, 2013", 12 pgs.
"U.S. Appl. No. 13/113,244, Restriction Requirement mailed Oct. 31, 2011", 8 pgs.
"U.S. Appl. No. 13/127,951, Advisory Action mailed Jul. 16, 2014", 3 pgs.
"U.S. Appl. No. 13/127,951, Final Office Action mailed Apr. 9, 2014", 23 pgs.
"U.S. Appl. No. 13/127,951, Non Final Office Action mailed Sep. 26, 2013", 18 pgs.
"U.S. Appl. No. 13/127,951, Notice of Allowance mailed Jul. 20, 2015", 7 pgs.
"U.S. Appl. No. 13/127,951, Preliminary Amendment filed May 5, 2011", 7 pgs.
"U.S. Appl. No. 13/127,951, PTO Response to Rule 312 Communication mailed Oct. 23, 2015", 2 pgs.
"U.S. Appl. No. 13/127,951, Response filed Mar. 18, 2014 to Non Final Office Action nailed Sep. 26, 2013", 14 pgs.
"U.S. Appl. No. 13/127,951, Response filed Jul. 7, 2014 to Final Office Action mailed Apr. 9, 2014", 10 pgs.
"U.S. Appl. No. 13/127,951, Response filed Aug. 30, 2013 to Restriction Requirement mailed Apr. 30, 2013", Aug. 30, 2013.
"U.S. Appl. No. 13/127,951, Response filed Oct. 9, 2014 to Advisory Action mailed Jul. 16, 2014". 10 pgs.
"U.S. Appl. No. 13/127,951, Restriction Requirement mailed Apr. 30, 2013", 15 pgs.
"U.S. Appl. No. 13/594,611, Final Office Action mailed Aug. 15, 2014", 7 pgs.
"U.S. Appl. No. 13/594,611, Non Final Office Action mailed Apr. 24, 2014", 9 pgs.
"U.S. Appl. No. 13/594,611, Notice of Allowance mailed Jan. 13, 2015", 7 pgs.
"U.S. Appl. No. 13/594,611, PTO Response to Rule 312 Communication mailed Apr. 16, 2015", 2 pgs.
"U.S. Appl. No. 13/594,611, Response filed Feb. 25, 2014 to Restriction Requirement mailed Jan. 27, 2014", 8 pgs.
"U.S. Appl. No. 13/594,611, Response filed Jul. 7, 2014 to Non Final Office Action mailed Apr. 24, 2014", 9 pgs.
"U.S. Appl. No. 13/594,611, Response filed Dec. 15, 2014 to Final Office Action mailed Aug. 15, 2014", 10 pgs.
"U.S. Appl. No. 13/594,611, Restriction Requirement mailed Jan. 27, 2014", 8 pgs.
"U.S. Appl. No. 14/332,121, Non Final Office Action mailed May 16, 2016", 9 pgs.
"U.S. Appl. No. 14/332,121, Notice of Allowance mailed Feb. 15, 2017", 10 pgs.
"U.S. Appl. No. 14/332,121, Notice of Allowance mailed Jun. 15, 2017", 8 pgs.
"U.S. Appl. No. 14/332,121, Notice of Allowance mailed Oct. 11, 2017", 8 pgs.
"U.S. Appl. No. 14/332,121, Preliminary Amendment filed Sep. 30, 2014", 5 pgs.
"U.S. Appl. No. 14/332,121, Response filed Jan. 29, 2016 to Restriction Requirement mailed Jul. 30, 2015", 9 pgs.
"U.S. Appl. No. 14/332,121, Response filed Sep. 7, 2017 to Notice of Allowability mailed Jun. 15, 2017", 8 pgs.
"U.S. Appl. No. 14/332,121, Response filed Oct. 11, 2016 to Non Final Office Action mailed May 16, 2016", 9 pgs.
"U.S. Appl. No. 14/332,121, Restriction Requirement mailed Jul. 30, 2015", 9 pgs.
"U.S. Appl. No. 14/332,121, Supplemental Amendment filed Jan. 23, 2017", 10 pgs.
"U.S. Appl. No. 14/528,997, Advisory Action mailed Aug. 9, 2017", 3 pgs.
"U.S. Appl. No. 14/528,997, Final Office Action mailed Feb. 10, 2017", 9 pgs.
"U.S. Appl. No. 14/528,997, Non Final Office Action mailed Jun. 16, 2016", 12 pgs.
"U.S. Appl. No. 14/528,997, Non Final Office Action mailed Jun. 29, 2018", 7 pgs.
"U.S. Appl. No. 14/528,997, Notice of Allowance mailed Mar. 8, 2019", 7 pgs.
"U.S. Appl. No. 14/528,997, PTO Response to Rule 312 Communication mailed Jun. 19, 2019", 2 pgs.
"U.S. Appl. No. 14/528,997, Response filed Mar. 16, 2016 to Restriction Requirement mailed Sep. 16, 2015", 11 pgs.
"U.S. Appl. No. 14/528,997, Response filed Jul. 27, 2017 to Final Office Action mailed Feb. 10, 2017", 11 pgs.

(56) References Cited

OTHER PUBLICATIONS

"U.S. Appl. No. 14/528,997, Response filed Oct. 10, 2016 to Non Final Office Action mailed Jun. 16, 2016", 12 pgs.
"U.S. Appl. No. 14/528,997, Response filed Nov. 16, 2018 to Non Final Office Action mailed Jun. 29, 2018", 11 pgs.
"U.S. Appl. No. 14/528,997, Restriction Requirement mailed Sep. 16, 2015", 8 pgs.
"U.S. Appl. No. 14/699,213, Advisory Action mailed Mar. 7, 2018", 3 pgs.
"U.S. Appl. No. 14/699,213, Final Office Action mailed Dec. 1, 2017", 11 pgs.
"U.S. Appl. No. 14/699,213, Non Final Office Action mailed Jun. 2, 2017", 12 pgs.
"U.S. Appl. No. 14/699,213, Non-Final Office Action mailed Jan. 11, 2019", 10 pgs.
"U.S. Appl. No. 14/699,213, Notice of Allowance mailed Jul. 30, 2019", 8 pgs.
"U.S. Appl. No. 14/699,213, Preliminary Amendment filed Apr. 30, 2015", 8 pgs.
"U.S. Appl. No. 14/699,213, PTO Response to Rule 312 Communication mailed Nov. 19, 2019", 2 pgs.
"U.S. Appl. No. 14/699,213, Response filed Feb. 15, 2017 to Restriction Requirement mailed Aug. 15, 2016", 9 pgs.
"U.S. Appl. No. 14/699,213, Response filed Feb. 27, 2018 to Final Office Action mailed Dec. 1, 2017", 34 pgs.
"U.S. Appl. No. 14/699,213, Response filed Aug. 22, 2017 to Non Final Office Action mailed Jun. 2, 2017", 12 pgs.
"U.S. Appl. No. 14/699,213, Response filed Apr. 11, 2019 to Non-Final Office Action mailed Jan. 11, 2019", 13 pgs.
"U.S. Appl. No. 14/699,213, Restriction Requirement mailed Aug. 15, 2016", 10 pgs.
"U.S. Appl. No. 14/745,236, Advisory Action mailed Nov. 15, 2017", 2 pgs.
"U.S. Appl. No. 14/745,236, Final Office Action mailed Aug. 25, 2017", 16 pgs.
"U.S. Appl. No. 14/745,236, Non Final Office Action mailed Feb. 2, 2017", 14 pgs.
"U.S. Appl. No. 14/745,236, Notice of Allowability mailed Jul. 5, 2018", 4 pgs.
"U.S. Appl. No. 14/745,236, Notice of Allowance mailed Feb. 5, 2018", 9 pgs.
"U.S. Appl. No. 14/745,236, PTO Response to Rule 312 Communication mailed Jul. 10, 2018", 2 pgs.
"U.S. Appl. No. 14/745,236, Response filed May 2, 2017 to Non Final Office Action mailed Feb. 2, 2017", 10 pgs.
"U.S. Appl. No. 14/745,236, Response filed Nov. 6, 2017 to Final Office Action mailed Aug. 25, 2017", 12 pgs.
"U.S. Appl. No. 14/745,236, Response filed Dec. 14, 2017 to Final Office Action mailed Aug. 25, 2017", 12 pgs.
"U.S. Appl. No. 14/745,236, Response filed Dec. 23, 2016 to Restriction Requirement mailed Sep. 23, 2016", 8 pgs.
"U.S. Appl. No. 14/745,236, Restriction Requirement mailed Sep. 23, 2016", 8 pgs.
"U.S. Appl. No. 14/816,807, Non Final Office Action mailed Oct. 3, 2017", 7 pgs.
"U.S. Appl. No. 14/816,807, Notice of Allowance mailed Apr. 20, 2018", 8 pgs.
"U.S. Appl. No. 14/816,807, Preliminary Amendment filed Aug. 11, 2015", 8 pgs.
"U.S. Appl. No. 14/816,807, PTO Response to Rule 312 Communication mailed Jul. 6, 2018", 2 pgs.
"U.S. Appl. No. 14/816,807, Response filed Jan. 3, 2018 to Non Final Office Action mailed Oct. 3, 2017", 8 pgs.
"U.S. Appl. No. 14/816,807, Response filed May 1, 2017 to Restriction Requirement mailed Nov. 1, 2016", 9 pgs.
"U.S. Appl. No. 14/816,807, Restriction Requirement mailed Nov. 1, 2016", 8 pgs.
"U.S. Appl. No. 14/919,431, Preliminary Amendment filed Jan. 4, 2016", 8 pgs.
"U.S. Appl. No. 15/000,851, Non Final Office Action mailed Jan. 26, 2017", 15 pgs.
"U.S. Appl. No. 15/000,851, Notice of Allowance mailed Nov. 8, 2017", 9 pgs.
"U.S. Appl. No. 15/000,851, Preliminary Amendment filed Feb. 3, 2016", 3 pgs.
"U.S. Appl. No. 15/000,851, Response filed Jul. 26, 2017 to Non Final Office Action mailed Jan. 26, 2017", 16 pgs.
"U.S. Appl. No. 15/000,851, Response filed Oct. 12, 2016 to Restriction Requirement mailed May 12, 2016", 11 pgs.
"U.S. Appl. No. 15/000,851, Restriction Requirement mailed May 12, 2016", 6 pgs.
"U.S. Appl. No. 15/000,851, Supplemental Amendment filed Apr. 4, 2016", 10 pgs.
"U.S. Appl. No. 15/170,556, Final Office Action mailed Jul. 30, 2019", 6 pgs.
"U.S. Appl. No. 15/170,556, Non Final Office Action mailed Feb. 8, 2019", 11 pgs.
"U.S. Appl. No. 15/170,556, Non Final Office Action mailed Jul. 27, 2018", 10 pgs.
"U.S. Appl. No. 15/170,556, Notice of Allowability mailed Jan. 29, 2020", 4 pgs.
"U.S. Appl. No. 15/170,556, Notice of Allowance mailed Nov. 27, 2019", 8 pgs.
"U.S. Appl. No. 15/170,556, Preliminary Amendment filed Aug. 22, 2016", 9 pgs.
"U.S. Appl. No. 15/170,556, Response filed Apr. 5, 2018 to Restriction Requirement mailed Feb. 16, 2018", 8 pgs.
"U.S. Appl. No. 15/170,556, Response filed Oct. 29, 2018 to Non Final Office Action mailed Jul. 27, 2018", 9 pgs.
"U.S. Appl. No. 15/170,556, Response filed Nov. 18, 2019 to Final Office Action mailed Jul. 30, 2019", 8 pgs.
"U.S. Appl. No. 15/170,556, Response filed Apr. 15, 2019 to Non Final Office Action mailed Feb. 8, 2019", 9 pgs.
"U.S. Appl. No. 15/170,556, Restriction Requirement mailed Feb. 16, 2018", 7 pgs.
"U.S. Appl. No. 15/170,556. PTO Response to Rule 312 Communication mailed Apr. 3, 2020", 2 pgs.
"U.S. Appl. No. 15/203,581, Examiners Interview Summary mailed Sep. 11, 2017", 1 pg.
"U.S. Appl. No. 15/203,581, Notice of Allowance mailed Sep. 11, 2017", 12 pgs.
"U.S. Appl. No. 15/203,581, Preliminary Amendment filed Sep. 22, 2016", 4 pgs.
"U.S. Appl. No. 15/203,581, PTO Response to Rule 312 Communication mailed Dec. 27, 2017", 2 pgs.
"U.S. Appl. No. 15/203,581, Response filed Aug. 15, 2017 to Restriction Requirement mailed Jun. 16, 2017", 8 pgs.
"U.S. Appl. No. 15/203,581, Restriction Requirement mailed Jun. 16, 2017", 8 pgs.
"U.S. Appl. No. 15/204,381, Advisory Action mailed Feb. 7, 2019", 3 pgs.
"U.S. Appl. No. 15/204,381, Advisory Action mailed Aug. 25, 2020", 3 pgs.
"U.S. Appl. No. 15/204,381, Final Office Action mailed Feb. 27, 2020", 21 pgs.
"U.S. Appl. No. 15/204,381, Final Office Action mailed Jul. 9, 2021", 14 pgs.
"U.S. Appl. No. 15/204,381, Final Office Action mailed Sep. 21, 2018", 10 pgs.
"U.S. Appl. No. 15/204,381, Non Final Office Action mailed Feb. 23, 2018", 10 pgs.
"U.S. Appl. No. 15/204,381, Non Final Office Action mailed Jun. 13, 2019", 23 pgs.
"U.S. Appl. No. 15/204,381, Non Final Office Action mailed Oct. 6, 2020", 15 pgs.
"U.S. Appl. No. 15/204,381, Preliminary Amendment filed Oct. 25, 2016", 74 pgs.
"U.S. Appl. No. 15/204,381, Response filed Jan. 2, 2019 to Final Office Action mailed Sep. 21, 2018". 6 pgs.
"U.S. Appl. No. 15/204,381, Response filed Jan. 19, 2018 to Restriction Requirement mailed Oct. 13, 2017", 6 pgs.

(56) References Cited

OTHER PUBLICATIONS

"U.S. Appl. No. 15/204,381, Response filed Apr. 6, 2021 to Non Final Office Action mailed Oct. 6, 2020", 12 pgs.
"U.S. Appl. No. 15/204,381, Response filed May 30, 2018 to Non Final Office Action mailed Feb. 23, 2018", 9 pgs.
"U.S. Appl. No. 15/204,381, Response filed Jul. 27, 2020 to Final Office Action mailed Feb. 27, 2020". 11 pgs.
"U.S. Appl. No. 15/204,381, Response filed Aug. 27, 2020 to Advisory Action mailed Aug. 25, 2020", 2 pgs.
"U.S. Appl. No. 15/204,381, Response Filed Nov. 14, 2019 to Non Final Office Action mailed Jun. 13, 2019", 9 pgs.
"U.S. Appl. No. 15/204,381, Response Filed Mar. 21, 2019 to Advisory Action mailed Feb. 7, 2019", 7 pgs.
"U.S. Appl. No. 15/204,381, Restriction Requirement mailed Oct. 13, 2017", 10 pgs.
"U.S. Appl. No. 15/227,147, Preliminary Amendment filed Oct. 10, 2016", 7 pgs.
"U.S. Appl. No. 15/227,147, Restriction Requirement mailed Jan. 19, 2017", 14 pgs.
"U.S. Appl. No. 15/247,006 Response filed Jun. 4, 2019 to Final Office Action mailed Feb. 4, 2019", 7 pgs.
"U.S. Appl. No. 15/247,006, Examiner Interview Summary mailed Nov. 27, 2017", 4 pgs.
"U.S. Appl. No. 15/247,006, Final Office Action mailed Feb. 4, 2019", 8 pgs.
"U.S. Appl. No. 15/247,006, Non Final Office Action mailed Apr. 20, 2018", 7 pgs.
"U.S. Appl. No. 15/247,006, Non Final Office Action mailed Sep. 8, 2017", 8 pgs.
"U.S. Appl. No. 15/247,006, Notice of Allowance mailed Jun. 24, 2019", 7 pgs.
"U.S. Appl. No. 15/247,006, Notice of Allowance mailed Oct. 8, 2019", 7 pgs.
"U.S. Appl. No. 15/247,006, Preliminary Amendment filed Nov. 22, 2016", 3 pgs.
"U.S. Appl. No. 15/247,006, Response filed May 3, 2017 to Restriction Requirement mailed Mar. 17, 2017", 12 pgs.
"U.S. Appl. No. 15/247,006, Response filed Oct. 22, 2018 to Non Final Office Action mailed Apr. 20, 2018", 14 pgs.
"U.S. Appl. No. 15/247,006, Response filed Dec. 7, 2017 to Non Final Office Action mailed Sep. 8, 2017", 13 pgs.
"U.S. Appl. No. 15/247,006, Restriction Requirement mailed Mar. 17, 2017", 9 pgs.
"U.S. Appl. No. 15/292,595, Non Final Office Action mailed Sep. 25, 2017", 13 pgs.
"U.S. Appl. No. 15/292,595, Notice of Allowance mailed Feb. 28, 2018", 9 pgs.
"U.S. Appl. No. 15/292,595, Notice of Allowance mailed Jun. 20, 2018", 9 pgs.
"U.S. Appl. No. 15/292,595, Preliminary Amendment filed Dec. 27, 2016", 5 pgs.
"U.S. Appl. No. 15/292,595, Response filed Dec. 22, 2017 to Non Final Office Action mailed Sep. 25, 2017", 9 pgs.
"U.S. Appl. No. 15/436,245, Corrected Notice of Allowability mailed Nov. 10, 2021", 2 pgs.
"U.S. Appl. No. 15/436,245, Final Office Action mailed Mar. 24, 2021", 9 pgs.
"U.S. Appl. No. 15/436,245, Final Office Action mailed Nov. 18, 2019", 9 pgs.
"U.S. Appl. No. 15/436,245, Non Final Office Action mailed Apr. 19, 2019", 9 pgs.
"U.S. Appl. No. 15/436,245, Non Final Office Action mailed Sep. 4, 2020", 9 pgs.
"U.S. Appl. No. 15/436,245, Notice of Allowance mailed Aug. 3, 2021", 9 pgs.
"U.S. Appl. No. 15/436,245, Preliminary Amendment filed May 5, 2017", 3 pgs.
"U.S. Appl. No. 15/436,245, PTO Response to Rule 312 Communication mailed Oct. 27, 2021", 2 pgs.
"U.S. Appl. No. 15/436,245, Response filed Apr. 27, 2020 to Final Office Action mailed Nov. 18, 2019", 10 pgs.
"U.S. Appl. No. 15/436,245, Response filed Jun. 24, 2021 to Final Office Action mailed Mar. 24, 2021", 11 pgs.
"U.S. Appl. No. 15/436,245, Response filed Dec. 4, 2020 to Non Final Office Action mailed Sep. 4, 2020", 12 pgs.
"U.S. Appl. No. 15/436,245, Response filed Jul. 29, 2019 to Non-Final Office Action mailed Apr. 19, 2019", 11 pgs.
"U.S. Appl. No. 15/436,245, Restriction Requirement mailed Oct. 11, 2018", 9 pgs.
"U.S. Appl. No. 15/436,245, Supplemental Amendment filed Jul. 19, 2021", 10 pgs.
"U.S. Appl. No. 15/593,039, Non Final Office Action mailed Feb. 6, 2018", 8 pgs.
"U.S. Appl. No. 15/593,039, Notice of Allowance mailed Jul. 11, 2018", 5 pgs.
"U.S. Appl. No. 15/593,039, Preliminary Amendment filed Jul. 25, 2017", 7 pgs.
"U.S. Appl. No. 15/593,039, PTO Response to Rule 312 Communication mailed Oct. 9, 2018", 2 pgs.
"U.S. Appl. No. 15/593,039, Response filed Apr. 30, 2018 to Non Final Office Action mailed Feb. 4, 2018", 8 pgs.
"U.S. Appl. No. 15/593,039, Response filed Dec. 18, 2017 to Restriction Requirement mailed Oct. 18, 2017", 8 pgs.
"U.S. Appl. No. 15/593,039, Restriction Requirement mailed Oct. 18, 2017", 6 pgs.
"U.S. Appl. No. 15/593,039, Supplemental Preliminary Amendment filed Jul. 26, 2017", 4 pgs.
"U.S. Appl. No. 15/865,364, Notice of Allowance mailed Nov. 15, 2018", 7 pgs.
"U.S. Appl. No. 15/865,364, Preliminary Amendment filed Apr. 10, 2018", 10 pgs.
"U.S. Appl. No. 15/905,454, Preliminary Amendment filed Nov. 2, 2018", 5 pgs.
"U.S. Appl. No. 15/905,454, Restriction Requirement mailed Jan. 3, 2019", 6 pgs.
"U.S. Appl. No. 15/915,486 Supplemental Preliminary Amendment Filed Mar. 12, 2019", 5 pgs.
"U.S. Appl. No. 15/915,486, Advisory Action mailed Jun. 28, 2021", 7 pgs.
"U.S. Appl. No. 15/915,486, Advisory Action mailed Jul. 13, 2020", 3 pgs.
"U.S. Appl. No. 15/915,486, Final Office Action mailed Jan. 11, 2022", 9 pgs.
"U.S. Appl. No. 15/915,486, Final Office Action mailed Jan. 27, 2020", 8 pgs.
"U.S. Appl. No. 15/915,486, Final Office Action mailed Feb. 1, 2021", 8 pgs.
"U.S. Appl. No. 15/915,486, Non Final Office Action mailed Sep. 2, 2021", 8 pgs.
"U.S. Appl. No. 15/915,486, Non Final Office Action mailed Sep. 15, 2020", 10 pgs.
"U.S. Appl. No. 15/915,486, Non Final Office Action mailed Oct. 24, 2019", 10 pgs.
"U.S. Appl. No. 15/915,486, Response filed Jan. 3, 2020 to Non Final Office Action mailed Oct. 24, 2019", 8 pgs.
"U.S. Appl. No. 15/915,486, Response filed Jun. 1, 2021 to Final Office Action mailed Feb. 1, 2021", 10 pgs.
"U.S. Appl. No. 15/915,486, Response filed Jun. 23, 2020 to Final Office Action mailed Jan. 27, 2020", 7 pgs.
"U.S. Appl. No. 15/915,486, Response filed Jul. 27, 2021 to Advisory Action mailed Jun. 28, 2021", 10 pgs.
"U.S. Appl. No. 15/915,486, Response filed Nov. 30, 2021 to Non Final Office Action mailed Sep. 2, 2021", 6 pgs.
"U.S. Appl. No. 15/915,486, Response filed Dec. 21, 2020 to Non Final Office Action mailed Sep. 15, 2020", 7 pgs.
"U.S. Appl. No. 15/915,486, Restriction Requirement mailed Aug. 5, 2019", 9 pgs.
"U.S. Appl. No. 15/966,092, Interview Summary mailed Mar. 2, 2021", 2 pgs.
"U.S. Appl. No. 15/966,092, Non Final Office Action mailed Jun. 26, 2020", 22 pgs.

(56) References Cited

OTHER PUBLICATIONS

"U.S. Appl. No. 15/966,092, Notice of Allowance mailed Feb. 11, 2021", 5 pgs.
"U.S. Appl. No. 15/966,092, Response filed Oct. 26, 2020 to Non Final Office Action mailed Jun. 26, 2020", 9 pgs.
"U.S. Appl. No. 16/046,250, Non Final Office Action mailed Mar. 6, 2020", 10 pgs.
"U.S. Appl. No. 16/046,250, Notice of Allowance mailed Jun. 15, 2020", 9 pgs.
"U.S. Appl. No. 16/046,250, Response filed Jun. 3, 2020 to Non Final Office Action mailed Mar. 6, 2020", 10 pgs.
"U.S. Appl. No. 16/046,250, Response filed Oct. 25, 2019 to Restriction Requirement mailed Jul. 25, 2019", 9 pgs.
"U.S. Appl. No. 16/046,250, Restriction Requirement mailed Jul. 25, 2019", 7 pgs.
"U.S. Appl. No. 16/170,321, Advisory Action mailed Feb. 23, 2021", 3 pgs.
"U.S. Appl. No. 16/170,321, Corrected Notice of Allowability mailed Sep. 29, 2021", 2 pgs.
"U.S. Appl. No. 16/170,321, Final Office Action mailed Dec. 14, 2020", 13 pgs.
"U.S. Appl. No. 16/170,321, Non Final Office Action mailed Apr. 13, 2020", 13 pgs.
"U.S. Appl. No. 16/170,321, Notice of Allowance mailed Aug. 4, 2021", 10 pgs.
"U.S. Appl. No. 16/170,321, PTO Response to Rule 312 Communication mailed Sep. 1, 2021", 2 pgs.
"U.S. Appl. No. 16/170,321, Response filed Jan. 24, 2020 to Restriction Requirement mailed Nov. 27, 2019", 9 pgs.
"U.S. Appl. No. 16/170,321, Response filed Jan. 26, 2021 to Final Office Action mailed Dec. 14, 2020", 9 pgs.
"U.S. Appl. No. 16/170,321, Response filed Mar. 9, 2021 to Advisory Action mailed Feb. 23, 2021", 9 pgs.
"U.S. Appl. No. 16/170,321, Response filed Sep. 11, 2020 to Non Final Office Action mailed Apr. 13, 2020", 9 pgs.
"U.S. Appl. No. 16/170,321, Restriction Requirement mailed Nov. 27, 2019", 10 pgs.
"U.S. Appl. No. 16/173,605 Preliminary Amendment Filed Nov. 18, 2019", 5 pgs.
"U.S. Appl. No. 16/173,605, Final Office Action mailed Jul. 27, 2020", 7 pgs.
"U.S. Appl. No. 16/173,605, Non Final Office Action mailed Mar. 13, 2020", 10 pgs.
"U.S. Appl. No. 16/173,605, Notice of Allowance mailed Jan. 13, 2021", 6 pgs.
"U.S. Appl. No. 16/173,605, Response filed Jul. 13, 2020 to Non Final Office Action mailed Mar. 13, 2020", 13 pgs.
"U.S. Appl. No. 16/173,605, Response filed Dec. 21, 2020 to Final Office Action mailed Jul. 27, 2020", 7 pgs.
"U.S. Appl. No. 16/545,761, Final Office Action mailed Oct. 20, 2021", 10 pgs.
"U.S. Appl. No. 16/545,761, Non Final Office Action mailed Feb. 11, 2021", 12 pgs.
"U.S. Appl. No. 16/545,761, Notice of Allowance mailed Mar. 9, 2022", 6 pgs.
"U.S. Appl. No. 16/545,761, Preliminary Amendment filed Feb. 7, 2020", 9 pgs.
"U.S. Appl. No. 16/545,761, PTO Response to Rule 312 Communication mailed May 13, 2022", 2 pgs.
"U.S. Appl. No. 16/545,761, Response filed Feb. 16, 2022 to Final Office Action mailed Oct. 20, 2021", 10 pgs.
"U.S. Appl. No. 16/545,761, Response filed Jun. 30, 2021 to Non Final Office Action mailed Feb. 11, 2021", 13 pgs.
"U.S. Appl. No. 16/547,262, Non Final Office Action mailed Mar. 31, 2021", 13 pgs.
"U.S. Appl. No. 16/547,262, Notice of Allowance mailed Jul. 22, 2021", 7 pgs.
"U.S. Appl. No. 16/547,262, Response filed Jun. 30, 2021 to Non Final Office Action mailed Mar. 31, 2021", 12 pgs.
"U.S. Appl. No. 16/547,262, Response filed Dec. 17, 2020 to Restriction Requirement mailed Jul. 17, 2020", 12 pgs.
"U.S. Appl. No. 16/547,262, Restriction Requirement mailed Jul. 17, 2020", 6 pgs.
"U.S. Appl. No. 16/694,748, Non Final Office Action mailed Nov. 9, 2021", 6 pgs.
"U.S. Appl. No. 16/694,748, Notice of Allowance mailed Mar. 3, 2022", 9 pgs.
"U.S. Appl. No. 16/694,748, Preliminary Amendment filed May 8, 2020", 7 pgs.
"U.S. Appl. No. 16/694,748, Response filed Feb. 9, 2022 to Non Final Office Action mailed Nov. 9, 2021", 7 pgs.
"U.S. Appl. No. 16/694,748, Response filed Jul. 27, 2021 to Restriction Requirement mailed Jan. 27, 2021", 8 pgs.
"U.S. Appl. No. 16/694,748, Restriction Requirement mailed Jan. 27, 2021", 9 pgs.
"U.S. Appl. No. 16/749,910, Notice of Allowance mailed Sep. 22, 2021", 10 pgs.
"U.S. Appl. No. 16/749,910, Response filed Jun. 17, 2021 to Restriction Requirement mailed Apr. 19, 2021", 11 pgs.
"U.S. Appl. No. 16/749,910, Restriction Requirement mailed Apr. 19, 2021", 9 pgs.
"U.S. Appl. No. 16/785,449, Final Office Action mailed Mar. 18, 2022", 12 pgs.
"U.S. Appl. No. 16/785,449, Non Final Office Action mailed Jul. 21, 2021", 9 pgs.
"U.S. Appl. No. 16/785,449, Non Final Office Action mailed Sep. 22, 2022", 13 pgs.
"U.S. Appl. No. 16/785,449, Response filed Jan. 20, 2023 to Non Final Office Action mailed Sep. 22, 2022", 8 pgs.
"U.S. Appl. No. 16/785,449, Response filed Jun. 27, 2022 to Final Office Action mailed Mar. 18, 2022", 7 pgs.
"U.S. Appl. No. 16/785,449, Response filed Jul. 2, 2021 to Restriction Requirement mailed Jun. 21, 2021", 6 pgs.
"U.S. Appl. No. 16/785,449, Response filed Dec. 17, 2021 to Non Final Office Action mailed Jul. 21, 2021", 8 pgs.
"U.S. Appl. No. 16/785,449, Restriction Requirement mailed Jun. 21, 2021", 8 pgs.
"U.S. Appl. No. 16/785,449, Final Office Action mailed Mar. 22, 2023", 16 pgs.
"U.S. Appl. No. 16/865,194, Notice of Allowance mailed Mar. 3, 2022", 9 pgs.
"U.S. Appl. No. 16/865,194, Response filed Dec. 20, 2021 to Restriction Requirement mailed Oct. 20, 2021", 11 pgs.
"U.S. Appl. No. 16/865,194, Restriction Requirement mailed Oct. 20, 2021", 7 pgs.
"U.S. Appl. No. 17/004,583, 312 Amendment filed Mar. 16, 2023", 7 pgs.
"U.S. Appl. No. 17/004,583, Advisory Action mailed Aug. 30, 2022", 2 pgs.
"U.S. Appl. No. 17/004,583, Final Office Action mailed Jun. 9, 2022", 6 pgs.
"U.S. Appl. No. 17/004,583, Non Final Office Action mailed Feb. 24, 2022", 5 pgs.
"U.S. Appl. No. 17/004,583, Non Final Office Action mailed Sep. 29, 2022", 8 pgs.
"U.S. Appl. No. 17/004,583, Notice of Allowability mailed Feb. 10, 2023", 4 pgs.
"U.S. Appl. No. 17/004,583, Notice of Allowance mailed Feb. 1, 2023", 10 pgs.
"U.S. Appl. No. 17/004,583, Notice of Allowance mailed May 15, 2023", 7 pgs.
"U.S. Appl. No. 17/004,583, Preliminary Amendment filed Dec. 21, 2020", 6 pgs.
"U.S. Appl. No. 17/004,583, PTO Response to Rule 312 Communication mailed Feb. 23, 2023", 4 pgs.
"U.S. Appl. No. 17/004,583, PTO Response to Rule 312 Communication mailed Apr. 6, 2023", 3 pgs.
"U.S. Appl. No. 17/004,583, Response filed Jan. 31, 2022 to Restriction Requirement mailed Nov. 24, 2021", 7 pgs.
"U.S. Appl. No. 17/004,583, Response filed May 24, 2022 to Non Final Office Action mailed Feb. 24, 2022", 9 pgs.

(56) References Cited

OTHER PUBLICATIONS

"U.S. Appl. No. 17/004,583, Response filed Aug. 9, 2022 to Final Office Action mailed Jun. 9, 2022", 9 pgs.
"U.S. Appl. No. 17/004,583, Response filed Sep. 8, 2022 to Advisory Action mailed Aug. 30, 2022", 15 pgs.
"U.S. Appl. No. 17/004,583, Response filed Dec. 29, 2022 to Non Final Office Action mailed Sep. 29, 2022", 8 pgs.
"U.S. Appl. No. 17/004,583, Restriction Requirement mailed Nov. 24, 2021", 10 pgs.
"U.S. Appl. No. 17/004,583, Supplemental Amendment filed Mar. 28, 2023", 6 pgs.
"U.S. Appl. No. 17/155,625, Advisory Action mailed Jan. 20, 2023", 3 pgs.
"U.S. Appl. No. 17/155,625, Final Office Action mailed Sep. 28, 2022", 18 pgs.
"U.S. Appl. No. 17/155,625, Non Final Office Action mailed May 26, 2022", 10 pgs.
"U.S. Appl. No. 17/155,625, Notice of Allowance mailed Apr. 12, 2023", 11 pgs.
"U.S. Appl. No. 17/155,625, Response filed Feb. 28, 2023 to Advisory Action mailed Jan. 20, 2023", 8 pgs.
"U.S. Appl. No. 17/155,625, Response filed May 2, 2022 to Restriction Requirement mailed Mar. 3, 2022", 7 pgs.
"U.S. Appl. No. 17/155,625, Response filed Aug. 29, 2022 to Non Final Office Action mailed May 26, 2022", 8 pgs.
"U.S. Appl. No. 17/155,625, Response filed Dec. 28, 2022 to Final Office Action mailed Sep. 28, 2022", 8 pgs.
"U.S. Appl. No. 17/155,625, Restriction Requirement mailed Mar. 3, 2022", 9 pgs.
"U.S. Appl. No. 17/229,001, Preliminary Amendment filed Apr. 26, 2021", 7 pgs.
"U.S. Appl. No. 17/266,049, Non Final Office Action mailed Mar. 14, 2023", 12 pgs.
"U.S. Appl. No. 17/352,845, Non Final Office Action mailed Dec. 16, 2022", 15 pgs.
"U.S. Appl. No. 17/352,845, Response filed May 16, 2023 to Non Final Office Action mailed Dec. 16, 2022", 8 pgs.
"U.S. Appl. No. 17/578,939, Non Final Office Action mailed Apr. 21, 2023", 5 pgs.
"U.S. Appl. No. 17/578,939, Preliminary Amendment filed Apr. 14, 2022", 9 pgs.
"U.S. Appl. No. 17/813,178, Preliminary Amendment filed Jan. 18, 2023", 7 pgs.
"U.S. Appl. No. 17/813,200, Preliminary Amendment filed Mar. 7, 2023", 10 pgs.
"U.S. Appl. No. 14/528,997, Preliminary Amendment filed Dec. 8, 2014", 3 pgs.
"U.S. Appl. No. 14/919,431, Restriction Requirement mailed Feb. 3, 2016", 18 pgs.
"Australian Application Serial No. 2001255336, Examiner's First Report mailed Feb. 16, 2005", 2 pgs.
"Australian Application Serial No. 2001255336, Response filed Aug. 23, 2005 to Examiner's First Report dated Feb. 16, 2005", 10 pgs.
"Australian Application Serial No. 2003219745, Examiner's First Report mailed Feb. 14, 2007", 2 pgs.
"Australian Application Serial No. 2003219745, Response filed Mar. 14, 2008 to Examiner's First Report mailed Feb. 14, 2007", 24 pgs.
"Australian Application Serial No. 2004249133, First Examiner's Report mailed May 5, 2008", 4 pgs.
"Australian Application Serial No. 2004249133, Response filed Mar. 30, 2009 to First Examiner's Report mailed May 5, 2008", 30 pgs.
"Australian Application Serial No. 2004274860, Office Action mailed May 21, 2008", 2 pgs.
"Australian Application Serial No. 2007245192, Office Action mailed Aug. 25, 2011", 2 pgs.
"Australian Application Serial No. 2007245192, Response filed Feb. 28, 2012 to Office Action mailed Aug. 25, 2011", 22 pgs.
"Australian Application Serial No. 2008203186, First Examiner Report mailed Jan. 28, 2011", 2 pgs.
"Australian Application Serial No. 2008203186, Office Action Received mailed Sep. 16, 2010", 1 page.
"Australian Application Serial No. 2008203186, Response filed Mar. 28, 2011 to First Examiner Report mailed Jan. 28, 2011", 53 pgs.
"Australian Application Serial No. 2008203186, Response filed Aug. 29, 2011 to Official Action dated Apr. 13, 2011", 20 pgs.
"Australian Application Serial No. 2012204138, First Examiner Report mailed Jul. 16, 2013", 4 pgs.
"Australian Application Serial No. 2012204138, Response filed Dec. 24, 2013 to First Examiner Report mailed Jul. 16, 2013", 21 pgs.
"Australian Application Serial No. 2014202470, First Examiner Report mailed Jul. 20, 2015", 2 pgs.
"Australian Application Serial No. 2014202470, Response filed Jul. 4, 2016 to Subsequent Examiners Report mailed Feb. 1, 2016", 3 pgs.
"Australian Application Serial No. 2014202470, Response filed Jul. 20, 2016 to Subsequent Examiners Report mailed Jul. 19, 2016", 15 pgs.
"Australian Application Serial No. 2014202470, Response filed Dec. 1, 2015 to First Examiner Report mailed Jul. 20, 2015", 22 pgs.
"Australian Application Serial No. 2014202470, Subsequent Examiners Report mailed Feb. 1, 2016", 2 pgs.
"Australian Application Serial No. 2014202470, Subsequent Examiners Report mailed Jul. 19, 2016", 3 pgs.
"Australian Application Serial No. 2014290203, First Examination Report mailed Oct. 10, 2019", 4 pgs.
"Australian Application Serial No. 2014290203, Response filed Mar. 13, 2020 to First Examination Report mallled Oct. 10, 2019", 16 pgs.
"Australian Application Serial No. 2014290203, Response filed Jun. 24, 2020 to Subsequent Examiners Report mailed Mar. 23, 2020", 16 pgs.
"Australian Application Serial No. 2014290203, Response filed Sep. 29, 2020 to Subsequent Examiners Report mailed Jul. 21, 2020", 25 pgs.
"Australian Application Serial No. 2014290203, Response filed Dec. 9, 2020 to Subsequent Examiners Report mailed Oct. 6, 2020", 14 pgs.
"Australian Application Serial No. 2014290203, Subsequent Examiners Report mailed Mar. 23, 2020", 6 pgs.
"Australian Application Serial No. 2014290203, Subsequent Examiners Report mailed Jul. 21, 2020", 5 pgs.
"Australian Application Serial No. 2014290203, Subsequent Examiners Report mailed Oct. 6, 2020", 4 pgs.
"Australian Application Serial No. 2017221444, First Examination Report mailed Jul. 8, 2020", 6 pgs.
"Australian Application Serial No. 2017221444, Fourth Examiners Report mailed Jun. 29, 2021", 3 pgs.
"Australian Application Serial No. 2017221444, Response filed Jan. 25, 2021 to Subsequent Examiners Report mailed Nov. 27, 2020", 18 pgs.
"Australian Application Serial No. 2017221444, Response filed Jun. 2, 2021 to Subsequent Examiners Report mailed Feb. 24, 2021", 20 pgs.
"Australian Application Serial No. 2017221444, Response filed Jul. 6, 2021 to Fourth Examiners Report mailed Jun. 29, 2021", 7 pgs.
"Australian Application Serial No. 2017221444, Response filed Nov. 13, 2020 to First Examination Report mailed Jul. 8, 2020", 13 pgs.
"Australian Application Serial No. 2017221444, Subsequent Examiners Report mailed Feb. 24, 2021", 4 pgs.
"Australian Application Serial No. 2017221444, Subsequent Examiners Report mailed Nov. 27, 2020", 4 pgs.
"Australian Application Serial No. 2021201844, First Examination Report filed Sep. 29, 2022", 3 pgs.
"Australian Application Serial No. 2021201844, Response filed Feb. 3, 2023 to First Examination Report filed Sep. 29, 2022", Claims not amended in response filed, 4 pgs.

(56) References Cited

OTHER PUBLICATIONS

"Australian Application Serial No. 2021201844, Voluntary Amendment filed Dec. 6, 2021", 17 pgs.
"Australian Application Serial No. 2021204721, First Examination Report mailed Mar. 16, 2023", 6 pgs.
"Australian Application Serial No. 2008203186, Subsequent Examiner Report mailed Apr. 13, 2011", 2 pgs.
"Avian Inluenza", Queensland Government—Department of Primary Industries, (Observed Feb. 22, 2003), 2 pgs.
"Avian Inluenza", http://www.iah.bbsrc.ac.uk/reports/1997/ainf.html, (Observed Feb. 22, 2003), 2 pgs.
"Brazil Application Serial No. PI 0410702-0, Office Action mailed Oct. 6, 2020", (w/ English Translation), 9 pgs.
"Brazil Application Serial No. PI 0410702-0, Response filed Dec. 14, 2020 to Office Action mailed Oct. 6, 2020", (w/ English Translation of Claims), 42 pgs.
"Brazil Application Serial No. PI0307679-2, Office Action mailed May 16, 2017", 2 pgs.
"Brazil Application Serial No. PI0307679-2, Response filed Jul. 13, 2017 to Office Action mailed May 16, 2017", 9 pgs.
"Brazilian Application Serial No. PI 0307679-2, Office Action published in Patent Gazette No. 1871 of Nov. 14, 2006", 2 pgs.
"Brazilian Application Serial No. PI 0307679-2, Petition filed Jan. 10, 2007 in response to publication dated Nov. 14, 2006", 6 pgs.
"Brazilian Application Serial No. PI 0410702-0, Office Action mailed Nov. 1, 2019", (w/ English Translation), 6 pgs.
"Brazilian Application Serial No. PI 0410702-0, Response filed Feb. 6, 2020 to Office Action mailed Nov. 1, 2019", (w/ English Translation of Claims), 92 pgs.
"Brazilian Application Serial No. PI0307679-2, Final Office Action mailed Jul. 7, 2020", w/o English Translation, 6 pgs.
"Brazilian Application Serial No. PI0307679-2, Office Action mailed May 13, 2019", (w/ English Translation), 17 pgs.
"Brazilian Application Serial No. PI0307679-2, Office Action mailed Oct. 3, 2019", (w/ English Translation), 6 pgs.
"Brazilian Application Serial No. PI0307679-2, Office Action mailed Dec. 20, 2016", 2 pgs.
"Brazilian Application Serial No. PI0307679-2, Response filed Feb. 1, 2017 to Office Action mailed Dec. 20, 2016", 6 pgs.
"Brazilian Application Serial No. PI0307679-2, Response filed Aug. 16, 2019 to Office Action mailed May 13, 2019", (w/ English Translation of Claims), 29 pgs.
"Brazilian Application Serial No. PI0307679-2, Response filed Dec. 11, 2019 to Office Action mailed Oct. 3, 2019", w/ English Claims, 59 pgs.
"Brazilian Application Serial No. PI0410702-0, Office Action mailed Feb. 23, 2012", w/ English Translation, 4 pgs.
"Brazilian Application Serial No. PI0410702-0, Office Action mailed Apr. 1, 2020", (w/ English Summary), 6 pgs.
"Brazilian Application Serial No. PI0410702-0, Response filed May 7, 2012 to Office Action mailed Feb. 23, 2012", w/ English Claims, 11 pgs.
"Brazilian Application Serial No. PI0410702-0, Response filed Aug. 28, 2020 to Office Action mailed Apr. 1, 2020", (w/ English Translation of Claims), 86 pgs.
"Canadian Application Serial No. 11/509,249, Response filed May 16, 2011 to Office Acttion mailed Nov. 18, 2010", 15 pgs.
"Canadian Application Serial No. 2,406,180, Office Action mailed Sep. 9, 2008", 5 pgs.
"Canadian Application Serial No. 2,406,180, Office Action mailed Nov. 10, 2011", 3 pgs.
"Canadian Application Serial No. 2,406,180, Office Action mailed Nov. 23, 2009", 3 pgs.
"Canadian Application Serial No. 2,406,180, Office Action mailed Dec. 10, 2010", 2 Pgs.
"Canadian Application Serial No. 2,406,180, Response filed Jan. 26, 2009 to Official Action mailed Sep. 9, 2008", 22 pgs.
"Canadian Application Serial No. 2,406,180, Response filed May 7, 2012 to Office Action mailed Nov. 10, 2011", 11 pgs.
"Canadian Application Serial No. 2,406,180, Response filed May 21, 2010 to Office action mailed Nov. 23, 2009", 13 pgs.
"Canadian Application Serial No. 2,406,180, Response filed Jun. 14, 2011 to Office Action mailed Dec. 10, 2010", 10 pgs.
"Canadian Application Serial No. 2,406,180, Response mailed Jun. 10, 2011 to Office Action mailed Dec. 10, 2010", 10 pgs.
"Canadian Application Serial No. 2,492,097, Office Action mailed Jan. 10, 2012", 4 pgs.
"Canadian Application Serial No. 2,492,097, Office Action mailed Apr. 24, 2008", 3 pgs.
"Canadian Application Serial No. 2,492,097, Office Action mailed Jul. 31, 2009", 3 pgs.
"Canadian Application Serial No. 2,492,097, Response filed Jan. 29, 2010 to Office Action mailed Jul. 31, 2009", 13 pgs.
"Canadian Application Serial No. 2,492,097, Response filed May 2, 2012 to Office Action mailed Jan. 10, 2012", 12 pgs.
"Canadian Application Serial No. 2,492,097, Response filed Oct. 23, 2008 to Office Action mailed Apr. 24, 2008", 14 pgs.
"Canadian Application Serial No. 2,522,081, Amendment After Allowance filed Aug. 10, 2012", 3 pgs.
"Canadian Application Serial No. 2,522,081, Office Action filed Nov. 18, 2011", 11 pgs.
"Canadian Application Serial No. 2,522,081, Office Action mailed Jun. 6, 2011", 2 pgs.
"Canadian Application Serial No. 2,522,081, Office Action mailed Aug. 30, 2010", 2 pgs.
"Canadian Application Serial No. 2,522,081, Office Action mailed Oct. 8, 2009", 6 pgs.
"Canadian Application Serial No. 2,522,081, Response filed Feb. 28, 2011 to Office Action mailed Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,522,081, Response filed Nov. 18, 2011 to Office Action mailed Jun. 6, 2011", 11 pgs.
"Canadian Application Serial No. 2,525,953, Amendment and Response filed Feb. 1, 2017 to Office Action mailed Aug. 1, 2016", 28 pgs.
"Canadian Application Serial No. 2,525,953, Non Final Office Action mailed Mar. 30, 2022", 4 pgs.
"Canadian Application Serial No. 2,525,953, Office Action mailed Jan. 21, 2016", 6 pgs.
"Canadian Application Serial No. 2,525,953, Office Action mailed Jan. 29, 2020", 4 pgs.
"Canadian Application Serial No. 2,525,953, Office Action mailed Apr. 28, 2021", 7 pgs.
"Canadian Application Serial No. 2,525,953, Office Action mailed Jul. 31, 2012", 4 pgs.
"Canadian Application Serial No. 2,525,953, Office Action mailed Aug. 1, 2016", 6 pgs.
"Canadian Application Serial No. 2,525,953, Office Action mailed Aug. 16, 2013", 3 pgs.
"Canadian Application Serial No. 2,525,953, Office Action mailed Oct. 3, 2017", 4 pgs.
"Canadian Application Serial No. 2,525,953, Office Action mailed Nov. 2, 2018", 6 pgs.
"Canadian Application Serial No. 2,525,953, Office Action mailed Nov. 6, 2014", 3 pgs.
"Canadian Application Serial No. 2,525,953, Office Action mailed Jun. 22, 2011", 4 pgs.
"Canadian Application Serial No. 2,525,953, Response filed Jan. 31, 2013 to Office Action mailed Jul. 31, 2012", 11 pgs.
"Canadian Application Serial No. 2,525,953, Response filed Feb. 1, 2017 to Office Action mailed Aug. 1, 2016", 28 pgs.
"Canadian Application Serial No. 2,525,953, Response filed Feb. 14, 2014 to Office Action mailed Aug. 16, 2013", 16 pgs.
"Canadian Application Serial No. 2,525,953, Response filed Apr. 3, 2018 to Office Action mailed Oct. 3, 2017", 46 pgs.
"Canadian Application Serial No. 2,525,953, Response filed May 1, 2015 to Office Action mailed Nov. 6, 2014", 23 pgs.
"Canadian Application Serial No. 2,525,953, Response filed May 2, 2019 to Office Action mailed Nov. 2, 2018", 31 pgs.
"Canadian Application Serial No. 2,525,953, Response filed May 25, 2020 to Office Action mailed Jan. 29, 2020", 35 pgs.

(56) References Cited

OTHER PUBLICATIONS

"Canadian Application Serial No. 2,525,953, Response filed Jul. 11, 2016 to Office Action mailed Jan. 21, 2016", 21 pgs.
"Canadian Application Serial No. 2,525,953, Response filed Aug. 26, 2021 to Office Action mailed Apr. 28, 2021", 16 pgs.
"Canadian Application Serial No. 2,525,953, Response filed Dec. 22, 2011 to Office Action mailed Jun. 22, 2011", 17 pgs.
"Canadian Application Serial No. 2,647,985 , Response filed Sep. 30, 2013 to Office Action mailed May 15, 2013", 20 pgs.
"Canadian Application Serial No. 2,647,985, Office Action mailed May 15, 2013", 3 pgs.
"Canadian Application Serial No. 2,816,242, Office Action mailed Jun. 16, 2014", 3 pgs.
"Canadian Application Serial No. 2,816,242, Office Action mailed Jul. 12, 2017", 4 pgs.
"Canadian Application Serial No. 2,816,242, Office Action mailed Sep. 16, 2016", 4 pgs.
"Canadian Application Serial No. 2,816,242, Office Action mailed Oct. 5, 2015", 6 pgs.
"Canadian Application Serial No. 2,816,242, Response filed Jan. 3, 2018 to Office Action mailed Jul. 12, 2017", 13 pgs.
"Canadian Application Serial No. 2,816,242, Response filed Mar. 10, 2017 to Office Action mailed Sep. 16, 2016", 18 pgs.
"Canadian Application Serial No. 2,816,242, Response filed Apr. 5, 2016 to Office Action mailed Oct. 5, 2015", 13 pgs.
"Canadian Application Serial No. 2,816,242, Response filed Dec. 16, 2014 to Office Action mailed Jun. 16, 2014", 9 pgs.
"Canadian Application Serial No. 2492097, Office Action mailed Nov. 18, 2010", 4 pgs.
"Canadian Application Serial No. 3,014,435, Office Action mailed Oct. 26, 2021", 4 pgs.
"Canadian Application Serial No. 3,014,435, Office Action mailed Nov. 6, 2020", 5 pgs.
"Canadian Application Serial No. 3,014,435, Office Action mailed Nov. 13, 2019", 4 pgs.
"Canadian Application Serial No. 3,014,435, Response filed Feb. 25, 2022 to Office Action mailed Oct. 26, 2021", 15 pgs.
"Canadian Application Serial No. 3,014,435, Response filed Mar. 5, 2021 to Office Action mailed Nov. 6, 2020", 20 pgs.
"Canadian Application Serial No. 3,014,435, Response filed Mar. 13, 2020 to Office Action mailed Nov. 13, 2019", 18 pgs.
"Chinese Application Serial No. 202080048487.4, Voluntary Amendment filed Dec. 5, 2022", w/ English Claims, 33 pgs.
"Chinese Application Serial No. 03808356.6, Office Action mailed Sep. 5, 2008", (English Translation), 6 pgs.
"Chinese Application Serial No. 03808356.6, Office Action received Jul. 1, 2011", (w/ English Translation of Office Action), 8 pgs.
"Chinese Application Serial No. 03808356.6, Reexamination Notice mailed Nov. 26, 2012", (w/ English Translation), 9 pgs.
"Chinese Application Serial No. 03808356.6, Response filed Mar. 11, 2013 to Office Action mailed Nov. 26, 2012", (w/ English Translation of Amended Claims), 9 pgs.
"Chinese Application Serial No. 03808356.6, Response filed Mar. 16, 2009 to Office Action mailed Sep. 5, 2008", (w/ English Translation of Claims), 8 pgs.
"Chinese Application Serial No. 03808356.6, Response filed Oct. 14, 2011 to Office Action mailed Jul. 1, 2011", (w/ English Translation of Amended Claims), 25 pgs.
"Chinese Application Serial No. 200480017037, First Office Action dated May 25, 2007", (w/ English Translation), 10 pgs.
"Chinese Application Serial No. 200480017037, Response filed Oct. 30, 2007 to First Office Action dated May 25, 2007", (w/ English Translation of Claims), 26 pgs.
"Chinese Application Serial No. 200480017037.X, Response filed May 14, 2010 to Third Office Action mailed Mar. 1, 2010", (w/ English Translation of Claims), 16 pgs.
"Chinese Application Serial No. 200480017037.X, Response filed Aug. 4, 2009 to Second Office Action mailed Mar. 20, 2009", (w/ English Translation of Amended Claims), 15 pgs.
"Chinese Application Serial No. 200480017037.X, Second Office Action mailed Mar. 20, 2009", (English Translation), 7 pgs.
"Chinese Application Serial No. 200480017037.X, Third Office Action mailed Mar. 1, 2010", (w/ English Translation), 9 pgs.
"Chinese Application Serial No. 200480021259.9 Office Action Sep. 11, 2009", (English Translation), 7 pgs.
"Chinese Application Serial No. 200480021259.9 Response filed Aug. 20, 2010 to Office Acton mailed May 6, 2010", (w/ English Translation of Claims), 26 pgs.
"Chinese Application Serial No. 200480021259.9, First Office Action issued on Aug. 24, 2007", (w/ English Translation), 9 pgs.
"Chinese Application Serial No. 200480021259.9, Notice of Reexamination mailed Jul. 3, 2012", (w/ English Translation), 10 pgs.
"Chinese Application Serial No. 200480021259.9, Office Action mailed Jan. 11, 2011", (w/ English Translation), 15 pgs.
"Chinese Application Serial No. 200480021259.9, Office Action mailed May 6, 2010", (w/ English Translation), 12 pgs.
"Chinese Application Serial No. 200480021259.9, Office Action mailed Jul. 3, 2012", (w/ English Translation), 10 pgs.
"Chinese Application Serial No. 200480021259.9, Reexamination Decision mailed Mar. 25, 2013", (w/ English Translation), 17 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Offiice Action issued on Aug. 24, 2007", (w/ English Translation of Claims), 13 pgs.
"Chinese Application Serial No. 200480021259.9, Response filed Oct. 16, 2012 to Office Action mailed Jul. 3, 2012", (w/ English Translation of Claims), 13 pgs.
"Chinese Application Serial No. 200480022014, First Office Action mailed Aug. 24, 2007", w/English Translation, 6 pgs.
"Chinese Application Serial No. 200580046922.5, Office Action mailed Jul. 24, 2009", 12 pgs.
"Chinese Application Serial No. 200780020095.1, Decision on Rejection mailed Jul. 22, 2013", (w/ English Translation), 11 pgs.
"Chinese Application Serial No. 200780020095.1, First Office Action mailed Jun. 24, 2011", (w/ English Translation), 13 pgs.
"Chinese Application Serial No. 200780020095.1, Office Action mailed Jan. 29, 2013", (w/ English Translation), 10 pgs.
"Chinese Application Serial No. 200780020095.1, Office Action mailed Mar. 5, 2015", (w/ English Translation), 12 pgs.
"Chinese Application Serial No. 200780020095.1, Office Action mailed Apr. 26, 2016", (w/ English Summary), 4 pgs.
"Chinese Application Serial No. 200780020095.1, Office Action mailed May 3, 2012", (w/ English Translation), 10 pgs.
"Chinese Application Serial No. 200780020095.1, Office Action mailed Nov. 2, 2016", (w/ English Translation), 11 pgs.
"Chinese Application Serial No. 200780020095.1, Response filed Jan. 6, 2017 to Office Action mailed Nov. 2, 2016", (w/ English Translation of Claims), 15 pgs.
"Chinese Application Serial No. 200780020095.1, Response filed Jun. 9, 2013 to Office Action mailed Jan. 29, 2013", (w/ English Translation of Claims), 10 pgs.
"Chinese Application Serial No. 200780020095.1, Response filed Jun. 23, 2015 to Office Action mailed Mar. 5, 2015", (w/ English Translation of Claims), 16 pgs.
"Chinese Application Serial No. 200780020095.1, Response filed Jun. 30, 2016 to Office Action mailed Apr. 26, 2016", (w/ English Translation of Claims), 22 pgs.
"Chinese Application Serial No. 200780020095.1, Response filed Sep. 17, 2012 to Office Action mailed May 3, 2012", (w/ English Translation of Claims), 17 pgs.
"Chinese Application Serial No. 200780020095.1, Response filed Nov. 5, 2013 to to Decision on Rejection mailed Jul. 22, 2013", (w/ English Translation of Claims), 12 pgs.
"Chinese Application Serial No. 200780020095.1, Response filed Nov. 8, 2011 to Office Action mailed Jun. 24, 2011", (w/ English Translation of Amended Claims), 20 pgs.
"Chinese Application Serial No. 201310400039.8, Notice of Reexamination mailed Aug. 26, 2016", (w/ English Translation), 7 pgs.
"Chinese Application Serial No. 201310400039.8, Office Action mailed Feb. 12, 2015", (w/ English Translation), 10 pgs.

(56) References Cited

OTHER PUBLICATIONS

"Chinese Application Serial No. 201310400039.8, Office Action mailed Feb. 15, 2016", (w/ English Translation), 12 pgs.
"Chinese Application Serial No. 201310400039.8, Office Action mailed Apr. 1, 2017", (English Translation), 10 pgs.
"Chinese Application Serial No. 201310400039.8, Office Action mailed Aug. 7, 2015", (w/ English Translation), 10 pgs.
"Chinese Application Serial No. 201310400039.8, Office Action mailed Aug. 21, 2014", (w/ English Translation), 13 pgs.
"Chinese Application Serial No. 201310400039.8, Office Action Response mailed Jun. 16, 2017", W / English Claims, 8 pgs.
"Chinese Application Serial No. 201310400039.8, Response filed Jan. 4, 2015 to Office Action mailed Aug. 21, 2014", (w/ English Translation of Claims), 10 pgs.
"Chinese Application Serial No. 201310400039.8, Response filed Apr. 27, 2015 to Office Action mailed Feb. 12, 2015", (w/ English Translation of Claims), 16 pgs.
"Chinese Application Serial No. 201310400039.8, Response filed Jun. 1, 2016 to Office Action mailed Feb. 15, 2016", (w/ English Translation of Claims), 9 pgs.
"Chinese Application Serial No. 201310400039.8, Response filed Oct. 10, 2016 to Notice of Reexamination mailed Aug. 26, 2016", (w/ English Translation of Claims), 12 pgs.
"Chinese Application Serial No. 201310400039.8, Response filed Oct. 20, 2015 to Office Action mailed Aug. 7, 2015", (w/ English Translation of Claims), 11 pgs.
"Chinese Application Serial No. 201310400039.8, Response filed Aug. 14, 2017 to Office Action Response mailed Jun. 16, 2017", W/ English Claims, 11 pgs.
"Chinese Application Serial No. 201310400039.8, Response filed Aug. 7, 2017 to Office Action Response mailed Jun. 16, 2017", W/ English Claims, 10 pgs.
"Chinese Application Serial No. 201780024821.0, Office Action mailed Jun. 15, 2022", (w/ English Translation), 6 pgs.
"Chinese Application Serial No. 201780024821.0, Office Action mailed Nov. 30, 2021", (w/ English Translation), 21 pgs.
"Chinese Application Serial No. 201780024821.0, Response filed Apr. 12, 2022 to Office Action mailed Nov. 30, 2021", (w/ English Translation of Claims). 17 pgs.
"Chinese Application Serial No. 201780024821.0, Response filed Aug. 30, 2022 to Office Action mailed Jun. 15, 2022", w/ English Claims, 18 pgs.
"Chinese Application Serial No. 201780024821.0, Response to Examiner Telephone Interview filed Sep. 26, 2022", w/ English Claims, 10 pgs.
"Chinese Application Serial No. 202080048487.4, Notification to Make Rectification mailed Jan. 18, 2022", w/o English Translation, 1 pg.
"Chinese Application Serial No. 202080048487.4, Notification to Make Rectification mailed May 26, 2022", w/o English translation, 1 pg.
"Chinese Application Serial No. 200480021259.9, Office Action mailed May 8, 2009", (w/ English Translation), 6 pgs.
"Confirmed Cases of Avian Influenza A(H5N1)", World Health Organization, (Jan. 28, 2004), 1 pg.
"Declaration of Anne Koch Ballard dated Oct. 6, 2011", 1 pg.
"Eurasian Application No. 200501890, Notice of Allowance mailed Jun. 23, 2009", 1 pg.
"Eurasian Application Serial No. 200501890, Office Action mailed Mar. 23, 2007", (w English Translation), 2 pgs.
"Eurasian Application Serial No. 200501890, Office Action mailed Sep. 4, 2008", (English Translation), 1 pg.
"Eurasian Application Serial No. 200501890, Office Action mailed Dec. 17, 2007", (w/ English Translation), 6 pgs.
"Eurasian Application Serial No. 200501890, Response filed Mar. 26, 2008 to Office Action mailed Dec. 17, 2007", (w/ English Translation of Claims), 15 pgs.
"Eurasian Application Serial No. 200501890, Response filed Jun. 14, 2007 to Office Action mailed Mar. 23, 2007", (w/ English Translation of Claims), 11 pgs.
"Eurasian Application Serial No. 200501890, Response filed Dec. 17, 2008 to Office Action mailed Sep. 4, 2008", (w/ English Translation of Claims), 14 pgs.
"Eurasian Application Serial No. 200701097, Office Action mailed Sep. 4, 2008", OAR-MISC, 2 pgs.
"Eurasion Application Serial No. 200701097, Office Action mailed Jun. 16, 2009", 3 pgs.
"European Application 04750333.9, Communication dated Oct. 12, 2006", 6 pgs.
"European Application 04750333.9, Communication dated Dec. 8, 2006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication Oct. 12, 2006", 4 pgs.
"European Application Serial 17709236.8 , Response filed Apr. 26, 2019 to Communication Pursuant to Rules 161 (1) and 162 EPC mailed Oct. 19, 2018", 9 pgs.
"European Application Serial No. 21705801.5, Response to Communication pursuant to Rules 161 and 162 filed Mar. 28, 2023", 13 pgs.
"European Application Serial No. 03716017.3, Office Action mailed Aug. 23, 2012", 4 pgs.
"European Application Serial No. 01928486.8 Office Action mailed Oct. 1, 2009", 2 pgs.
"European Application Serial No. 01928486.8, Communication dated Aug. 10, 2007", 3 pgs.
"European Application Serial No. 01928486.8, Communication dated Sep. 20, 2005", 4 pgs.
"European Application Serial No. 01928486.8, Office Action mailed Feb. 19, 2009", 3 pgs.
"European Application Serial No. 01928486.8, Response filed Jan. 30, 2006 to Communication dated Sep. 20, 2005", 9 pgs.
"European Application Serial No. 01928486.8, Response filed Aug. 28, 2009 to Communication mailed Feb. 19, 2009", 5 pgs.
"European Application Serial No. 01928486.8, Response filed Jan. 21, 2008 to Communication dated Aug. 10, 2007", 11 pgs.
"European Application Serial No. 01928486.8, Response filed Dec. 9, 2009 to Office Action mailed Oct. 1, 2009", 11 pgs.
"European Application Serial No. 02724994.5, Office Action mailed Mar. 27, 2009", 2 pgs.
"European Application Serial No. 03716017.3, Communication and Supplementary European Search Report mailed Jan. 2, 2008", 8 pgs.
"European Application Serial No. 03716017.3, Communication mailed May 23, 2006", 3 pgs.
"European Application Serial No. 03716017.3, Communication mailed Jul. 26, 2006", 2 pgs.
"European Application Serial No. 03716017.3, Communication mailed Oct. 20, 2008", 7 pgs.
"European Application Serial No. 03716017.3, Further Written Submissions filed Mar. 19, 2015", 45 pgs.
"European Application Serial No. 03716017.3, Office Action mailed Jul. 27, 2010", 4 pgs.
"European Application Serial No. 03716017.3, Response filed Feb. 4, 2011 to Office Action mailed Jul. 27, 2010", 12 pgs.
"European Application Serial No. 03716017.3, Response filed Feb. 27, 2015 to Summons mailed Nov. 3, 2014", 29 pgs.
"European Application Serial No. 03716017.3, Response filed Mar. 4, 2013 to Examination Notification Art. 94(3) mailed Aug. 23, 2012", 19 pgs.
"European Application Serial No. 03716017.3, Response filed Mar. 24, 2015 to Office Action mailed Nov. 3, 2014", 38 pgs.
"European Application Serial No. 03716017.3, Response filed Jul. 28, 2006 to Communication mailed May 23, 2006", 5 pgs.
"European Application Serial No. 03716017.3, Response filed Aug. 19, 2009 to Communication mailed Oct. 20, 2008", 17 pgs.
"European Application Serial No. 03716017.3, Response filed Sep. 28, 2015", 13 pgs.
"European Application Serial No. 03716017.3, Result of Consultation mailed Mar. 17, 2015", 5 pgs.

(56) References Cited

OTHER PUBLICATIONS

"European Application Serial No. 03716017.3, Summons to Attend Oral proceedings mailed Nov. 3, 2014", 5 pgs.
"European Application Serial No. 04750333.9, Office Action mailed Jan. 22, 2009", 5 pgs.
"European Application Serial No. 04750333.9, Response filed Oct. 21, 2008 to Communication mailed Apr. 11, 2008", 15 pgs.
"European Application Serial No. 04750333.9, Response filed Nov. 17, 2009 to Communication mailed Jan. 22, 2009", 17 pgs.
"European Application Serial No. 04750333.9, Summons to Attend Oral Proceedings mailed Aug. 3, 2011", 13 pgs.
"European Application Serial No. 04776133.3, Communication mailed Mar. 30, 2006", 3 pgs.
"European Application Serial No. 04776133.3, Examination Notification Art. 94(3) mailed Jul. 28, 2015", 4 pgs.
"European Application Serial No. 04776133.3, Examination Notification Art. 94(3) mailed Nov. 25, 2013", 5 pgs.
"European Application Serial No. 04776133.3, Office Action mailed Jan. 5, 2010", 4 pgs.
"European Application Serial No. 04776133.3, Response filed Jan. 25, 2007 to Communication mailed Mar. 30, 2006", 20 pgs.
"European Application Serial No. 04776133.3, Response filed Apr. 30, 2014 to Examination Notification Art. 94(3) mailed Nov. 25, 2013", 12 pgs.
"European Application Serial No. 04776133.3, Response filed Jul. 15, 2010 to Office Action mailed Jan. 5, 2010", 9 pgs.
"European Application Serial No. 04776133.3, Response filed Sep. 18, 2015 to Examination Notification Art. 94(3) mailed Jul. 28, 2015", 47 pgs.
"European Application Serial No. 04809419.7, Communication mailed Apr. 3, 2007", 3 pgs.
"European Application Serial No. 04809419.7, Response filed Oct. 19, 2007 to Communication mailed Apr. 3, 2007", 20 pgs.
"European Application Serial No. 07754132.4, Office Action mailed Apr. 28, 2009", 4 pgs.
"European Application Serial No. 07754132.4, Office Action mailed Sep. 5, 2011", 5 pgs.
"European Application Serial No. 07754132.4, Office Action mailed Nov. 2, 2012", 4 pgs.
"European Application Serial No. 07754132.4, Response filed Feb. 5, 2010 to Office Action mailed Apr. 28, 2009", 15 pgs.
"European Application Serial No. 07754132.4, Response filed Mar. 15, 2012 to Office Action mailed Sep. 5, 2011", 21 pgs.
"European Application Serial No. 07754132.4, Response filed May 10, 2013 to Office Action mailed Nov. 2, 2012", 14 pgs.
"European Application Serial No. 07754132.4, Response filed Jun. 26, 2013", 8 pgs.
"European Application Serial No. 10777154.5, Communication Pursuant to Article 94(3) EPC mailed Apr. 4, 2018", 7 pgs.
"European Application Serial No. 10777154.5, Communication Pursuant to Article 94(3) EPC mailed Jun. 11, 2019", 3 pgs.
"European Application Serial No. 10777154.5, Communication Pursuant to Article 94(3) EPC mailed Oct. 12, 2017", 7 pgs.
"European Application Serial No. 10777154.5, Examination Notification Art. 94(3) mailed Oct. 6, 2014", 7 pgs.
"European Application Serial No. 10777154.5, Office Action mailed May 2, 2016", 6 pgs.
"European Application Serial No. 10777154.5, Office Action mailed Jul. 4, 2012", 2 pgs.
"European Application Serial No. 10777154.5, Response field May 13, 2019 to Summons to Attend Oral Proceedings mailed Jan. 7, 2019", 35 pgs.
"European Application Serial No. 10777154.5, Response field Jun. 4, 2019 to Summons to Attend Oral Proceedings mailed Jan. 7, 2019", 9 pgs.
"European Application Serial No. 10777154.5, Response filed Jan. 14, 2013 to Office Action mailed Jul. 4, 2012", 12 pgs.
"European Application Serial No. 10777154.5, Response filed Feb. 21, 2018 to Communication Pursuant to Article 94(3) EPC mailed Oct. 12, 2017", 12 pgs.
"European Application Serial No. 10777154.5, Response filed Jul. 29, 2019 to Communication Pursuant to Article 94(3) EPC mailed Jun. 11, 2019", 57 pgs.
"European Application Serial No. 10777154.5, Response filed Sep. 7, 2018 to Communication Pursuant to Article 94(3) EPC mailed Apr. 4, 2018", 18 pgs.
"European Application Serial No. 10777154.5, Response filed Sep. 8, 2016 to Office Action mailed May 2, 2016", 69 pgs.
"European Application Serial No. 10777154.5, Summons to Attend Oral Proceedings mailed Jan. 7, 2019", 5 pgs.
"European Application Serial No. 12761841.1, Communication pursuant to Article 94(3) EPC mailed Dec. 23, 2016", 6 pgs.
"European Application Serial No. 12761841.1, Response filed Feb. 23, 2017 to Communication pursuant to Article 94(3) EPC mailed Dec. 23, 2016", 9 pgs.
"European Application Serial No. 12761841.1, Voluntary Amendment filed Dec. 1, 2014", 5 pgs.
"European Application Serial No. 14745060.5, Communication Pursuant to Article 94(3) EPC mailed Feb. 6, 2018", 5 pgs.
"European Application Serial No. 14745060.5, Communication Pursuant to Article 94(3) EPC mailed Mar. 12, 2020", 4 pgs.
"European Application Serial No. 14745060.5, Communication Pursuant to Article 94(3) EPC mailed Jul. 18, 2019", 5 pgs.
"European Application Serial No. 14745060.5, Communication Pursuant to Article 94(3) EPC mailed Sep. 15, 2021", 4 pgs.
"European Application Serial No. 14745060.5, Communication Pursuant to Article 94(3) EPC mailed Sep. 18, 2018", 4 pgs.
"European Application Serial No. 14745060.5, Communication Pursuant to Article 94(3) EPC mailed Nov. 9, 2020", 4 pgs.
"European Application Serial No. 14745060.5, Office Action mailed Feb. 23, 2016", 2 pgs.
"European Application Serial No. 14745060.5, Response filed Jan. 5, 2022 to Communication Pursuant to Article 94(3) EPC mailed Sep. 15, 2021", 78 pgs.
"European Application Serial No. 14745060.5, Response filed Jan. 28, 2020 to Communication Pursuant to Article 94(3) EPC mailed Jul. 18, 2019", 9 pgs.
"European Application Serial No. 14745060.5, Response filed Mar. 27, 2019 to Communication Pursuant to Article 94(3) EPC mailed Sep. 18, 2018", 13 pgs.
"European Application Serial No. 14745060.5, Response filed May 12, 2021 to Communication Pursuant to Article 94(3) EPC mailed Nov. 9, 2020", 12 pgs.
"European Application Serial No. 14745060.5, Response filed Jun. 15, 2018 to Communication Pursuant to Article 94(3) EPC mailed Feb. 6, 2018", 14 pgs.
"European Application Serial No. 14745060.5, Response filed Jul. 17, 2020 to Communication Pursuant to Article 94(3) EPC mailed Mar. 12, 2020", 52 pgs.
"European Application Serial No. 14745060.5, Response filed Dec. 22, 2016 to Communication pursuant to Rules 161(1) and 162 EPC mailed Feb. 23, 2016", 6 pgs.
"European Application Serial No. 15197386.4, Communication Pursuant to Article 94(3) EPC mailed Feb. 21, 2018", 5 pgs.
"European Application Serial No. 15197386.4, Communication Pursuant to Article 94(3) EPC mailed Apr. 21, 2017", 5 pgs.
"European Application Serial No. 15197386.4, Communication Pursuant to Article 94(3) EPC mailed Jun. 19, 2019", 4 pgs.
"European Application Serial No. 15197386.4, extended European Search Report mailed Feb. 26, 2016", 11 pgs.
"European Application Serial No. 15197386.4, Response filed Jul. 3, 2018 to Communication Pursuant to Article 94(3) EPC mailed Feb. 21, 2018", 7 pgs.
"European Application Serial No. 15197386.4, Response filed Aug. 27, 2019 to Communication Pursuant to Article 94(3) EPC mailed Jun. 19, 2019", 61 pgs.
"European Application Serial No. 15197386.4, Response filed Oct. 20, 2016 to Extended European Search Report mailed Feb. 26, 2016", 4 pgs.
"European Application Serial No. 15197386.4, Response filed Oct. 31, 2017 to Communication Pursuant to Article 94(3) EPC mailed Apr. 21, 2017", 5 pgs.

(56) References Cited

OTHER PUBLICATIONS

"European Application Serial No. 16778485.9, Communication Pursuant to Article 94(3) EPC mailed Feb. 18, 2022", 4 pgs.
"European Application Serial No. 16778485.9, Communication Pursuant to Article 94(3) EPC mailed May 25, 2020", 5 pgs.
"European Application Serial No. 16778485.9, Communication Pursuant to Article 94(3) EPC mailed Aug. 22, 2019", 5 pgs.
"European Application Serial No. 16778485.9, Office Action mailed Apr. 30, 2018", 3 pgs.
"European Application Serial No. 16778485.9, Response filed Aug. 9, 2022 to Communication Pursuant to Article 94(3) EPC mailed Feb. 18, 2022", 14 pgs.
"European Application Serial No. 16778485.9, Response filed Oct. 5, 2020 to Communication Pursuant to Article 94(3) EPC mailed May 25, 2020", 14 pgs.
"European Application Serial No. 16778485.9, Response filed Nov. 8, 2018 to Office Action mailed Apr. 30, 2018", 18 pgs.
"European Application Serial No. 16778485.9, Response filed Dec. 19, 2019 to Communication Pursuant to Article 94(3) EPC mailed Aug. 22, 2019", 20 pgs.
"European Application Serial No. 17709236.8, Communication Pursuant to Article 94(3) EPC mailed Jun. 8, 2022", 6 pgs.
"European Application Serial No. 17709236.8, Communication Pursuant to Article 94(3) EPC mailed Jul. 6, 2021", 10 pgs.
"European Application Serial No. 17709236.8, Response filed Jan. 17, 2022 to Communication Pursuant to Article 94(3) EPC mailed Jul. 6, 2021", 13 pgs.
"European Application Serial No. 17709236.8, Response filed Oct. 11, 2022 to Communication Pursuant to Article 94(3) EPC mailed Jun. 8, 2022", 65 pgs.
"European Application Serial No. 18800815.5, Response to Communication pursuant to Rules 161(1) and 162 EPC filed Dec. 15, 2020", 14 pgs.
"European Application Serial No. 19778696.5, Response to Communication persuant to Rules 161 and 162 filed Oct. 15, 2021", 39 pgs.
"European Application Serial No. 20714015.3, Response to Communication persuant to Rules 161 and 162 filed Apr. 7, 2022", 10 pgs.
"European Application Serial No. 20731609.2, Response to Communication persuant to Rules 161 and 162 filed Mar. 16, 2022", 17 pgs.
"European Application Serial No. 20768781.5, Response to Communication pursuant to Rules 161 and 162 filed Oct. 17, 2022", 17 pgs.
"Evaluation of Medicines for human Use", EMEA/CPMP/BWP/2289/01, London the European Agency for the Evaluation of Medicinal Products, Committee for Proprietary Medicinal Products (CPMP), (Feb. 20, 2003), 14.
"FLUZONE Influenza Virus Vaccine", Sanofi Aventis Pasteur, Swiftwater, (Jul. 2005), 12 pgs.
"Gen Bank Accession AFP82914", matrix protein 1 [Influenza A virus (A/reassortant/IVR-148(Brisbane/59/2007×Texas/1/1977) (H1N1)] (2012), 2 pgs.
"Gen Bank Accession JX414012", Influenza A virus (A/reassortant/IVR-148(Brisbane/59/2007×Texas/Jan. 1977)(H1 N1)) segment 7 matrix protein 2 (M2) and matrix protein 1 (M1) genes, complete cds, (2012), 2 pgs.
"Genbank", CY002484.1, (2005), 2 pgs.
"Genbank Accession # AAA43733, Neuraminidase Protein of Influenza B/Beijing/1/87 virus,", (1993), 4 pg.
"Genbank Accession # AAU94753, Neuraminidase Protein of Influenza B/Aichi/5/88 virus,", (2004), 7 pgs.
"Genbank Accession # ABA02233, Neuraminidase Protein of Influenza B/Perth/211/2001 virus", (2006), 3 pgs.
"Genbank Accession #,", neuraminidase influenza virus B/memphis/20/96,, (1999), 3 pgs.
"GFP antibody (ab6556) datasheet", (r) abcam. [online]. [retrieved on Dec. 5, 2004]. Retrieved from the Internet: <URL: http://www.abcam.com/index.html?datasheet=6556>, (2004), 5 pgs.
"Hemagglutinin [Influenza A virus (A/swine/France/WVL13/1995(H1N1))]", GenBank Accession# AC025026, (May 22, 2009), 1 pg.
"Hemagglutinin [Influenza B virus (B/Hong Kong/330/2001)]", GenBank ABL77178.1, 2006), 1 pg.
"https://www.abcam.com/gfp-antibody-ab6556", [online]. [accessed on Dec. 5, 2004]. Retrieved from the Internet: http://www.abcam.com/index.html?datasheet=6556, (Dec. 5, 2004), 5 pgs.
"Indian Application Serial No. 02082/KOLNP/2005, Examination Report mailed Mar. 17, 2008", 1 pg.
"Indian Application Serial No. 02082/KOLNP/2005, Examination Report mailed Dec. 26, 2007", 1 pg.
"Indian Application Serial No. 02082/KOLNP/2005, First Examination Report mailed Jan. 25, 2007", 9 pgs.
"Indian Application Serial No. 02082/KOLNP/2005, Response filed Jan. 22, 2008 to Examination Report mailed Dec. 28, 2007", 13 pgs.
"Indian Application Serial No. 02082/KOLNP/2005, Response filed Jun. 10, 2008 to Examination Report mailed Mar. 17, 2008", 3 pgs.
"Indian Application Serial No. 02082/KOLNP/2005, Response filed Nov. 19, 2007 to First Examination Report mailed Jan. 25, 2007", 26 pgs.
"Indian Application Serial No. 1026/KOLNP/2009, First Examiner Report mailed Mar. 13, 2014", 2 pgs.
"Indian Application Serial No. 2272/KOLNP/2005, First Examination Report mailed Mar. 17, 2008", 10 pgs.
"Indian Application Serial No. 2272/KOLNP/2005, Response filed Mar. 16, 2009 to Subsequent Examination Report mailed Mar. 6, 2009", 12 pgs.
"Indian Application Serial No. 2272/KOLNP/2005, Response filed Oct. 11, 2008 to First Examination Report mailed Mar. 17, 2008", 27 pgs.
"Indian Application Serial No. 2272/KOLNP/2005, Subsequent Examination Report mailed Mar. 6, 2009", 1 pg.
"Indian Application Serial No. 2388/KOLNP/2005, First Examination Report mailed Mar. 28, 2007", 10 pgs.
"Influenza B/Ann Arbor/1/66 (cold-adapted) nonstructural protein (seg 8) RNA, complete cds", GenBank Accession M20224, (Aug. 2, 1993), 2 pgs.
"Influenza B/lee/40, neuraminidase & nb (seg 6) rna", Database EM_VI E.B.I. Hinxton U.K., (Jun. 13, 1985), 10 pgs.
"Influenza virus A/CHR/ 157/83 genomic RNA for haemagglutinin", (2012), 2 pgs.
"International Application No. PCT/US2004/016680, International Search Report", (Feb. 2, 2005), 7 pgs.
"International Application Serial No. PCT/US2021/033365, International Search Report mailed Sep. 24, 2021", 6 pgs.
"International Application Serial No. PCT/US2021/033365, Written Opinion mailed Sep. 24, 2021", 6 pgs.
"International Application Serial No. PCT/US01/11963, Amendment filed Sep. 9, 2002 to Written Opinion dated Aug. 7, 2002", 12 pgs.
"International Application Serial No. PCT/US01/11963, International Preliminary Examination Report mailed Oct. 15, 2002", 13 pgs.
"International Application Serial No. PCT/US01/11963, International Search Report mailed May 7, 2002", 5 pgs.
"International Application Serial No. PCT/US01/11963, Written Opinion mailed Jun. 14, 2002", 2 pgs.
"International Application Serial No. PCT/US01/11963, Written Opinion mailed Aug. 7, 2002", 6 pgs.
"International Application Serial No. PCT/US02/05455, International Preliminary Examination Report dated Aug. 17, 2004", 4 pgs.
"International Application Serial No. PCT/US02/05455, International Search Report mailed Mar. 25, 2003", 3 pgs.
"International Application Serial No. PCT/US03/04233, International Search Report mailed Dec. 16, 2005", 7 pgs.
"International Application Serial No. PCT/US2004/012050, International Search Report mailed Feb. 2, 2005", 8 pgs.
"International Application Serial No. PCT/US2004/012050, Written Opinion mailed Feb. 2, 2005", 12 pgs.
"International Application Serial No. PCT/US2004/016649, International Preliminary Report on Patentability mailed Dec. 15, 2005", 7 pgs.

(56) References Cited

OTHER PUBLICATIONS

"International Application Serial No. PCT/US2004/016649, International Search Report mailed Apr. 18, 2005", 6 pgs.
"International Application Serial No. PCT/US2004/016680, International Preliminary Report on Patentability mailed Dec. 15, 2005", 11 pgs.
"International Application Serial No. PCT/US2005/041991, International Search Report mailed Jun. 4, 2007", 5 pgs.
"International Application Serial No. PCT/US2005/041991, Written Opinion mailed Jun. 4, 2007", 6 pgs.
"International Application Serial No. PCT/US2007/007562, International Preliminary Report on Patentability mailed Oct. 9, 2008", 5 pgs.
"International Application Serial No. PCT/US2007/007562, International Search Report mailed Jan. 14, 2008", 8 pgs.
"International Application Serial No. PCT/US2007/007562, Written Opinion mailed Jan. 14, 2008", 9 pgs.
"International Application Serial No. PCT/US2007/013407, International Search Report mailed Oct. 24, 2008", 10 pgs.
"International Application Serial No. PCT/US2007/013407, Written Opinion mailed Oct. 24, 2008", 14 pgs.
"International Application Serial No. PCT/US2008/004125, International Search Report mailed Feb. 20, 2009", 6 pgs.
"International Application Serial No. PCT/US2008/004125, Written Opinion mailed Feb. 20, 2009", 8 pgs.
"International Application Serial No. PCT/US2008/005641, International Preliminary Report on Patentability dated Nov. 10, 2009", 9 pgs.
"International Application Serial No. PCT/US2008/005641, International Search Report mailed Feb. 4, 2009", 6 pgs.
"International Application Serial No. PCT/US2008/005641, Written Opinion mailed Feb. 4, 2009", 8 pgs.
"International Application Serial No. PCT/US2008/007417, International Search Report mailed Jan. 30, 2009", 20 pgs.
"International Application Serial No. PCT/US2008/007417, Written Opinion mailed Jan. 30, 2009", 10 pgs.
"International Application Serial No. PCT/US2008/007582, International Preliminary Report on Patentability mailed Jan. 7, 2010", 9 pgs.
"International Application Serial No. PCT/US2008/007582, International Search Report and Written Opinion mailed Feb. 18, 2009", 16 pgs.
"International Application Serial No. PCT/US2009/000056, International Search Report mailed Feb. 9, 2010", 3 pgs.
"International Application Serial No. PCT/US2009/000056, Written Opinion mailed Feb. 9, 2010", 5 pgs.
"International Application Serial No. PCT/US2009/006019, International Preliminary Report on Patentability mailed May 19, 2011", 8 pgs.
"International Application Serial No. PCT/US2009/006019, Invitation to Pay Additional Fee mailed Apr. 6, 2010", 8 pgs.
"International Application Serial No. PCT/US2009/006019, Search Report mailed Jun. 10, 2010", 7 Pgs.
"International Application Serial No. PCT/US2009/006019, Written Opinion mailed Jun. 10, 2010", 6 pgs.
"International Application Serial No. PCT/US2010/054128, Preliminary Report on Patentability mailed May 10, 2012", 10 pgs.
"International Application Serial No. PCT/US2010/054128, Search Report mailed Feb. 23, 2011", 6 pgs.
"International Application Serial No. PCT/US2010/054128, Written Opinion mailed Feb. 23, 2011", 8 pgs.
"International Application Serial No. PCT/US2012/052368, International Preliminary Report on Patentability mailed Mar. 13, 2014", 8 pgs.
"International Application Serial No. PCT/US2012/052368, International Search Report mailed Dec. 3, 2012", 4 pgs.
"International Application Serial No. PCT/US2012/052368, Written Opinion mailed Dec. 3, 2012", 6 pgs.
"International Application Serial No. PCT/US2014/046731, International Preliminary Report on Patentability mailed Jan. 28, 2016", 12 pgs.
"International Application Serial No. PCT/US2014/046731, International Search Report mailed Nov. 25, 2014", 9 pgs.
"International Application Serial No. PCT/US2014/046731, Written Opinion mailed Nov. 25, 2014", 10 pgs.
"International Application Serial No. PCT/US2015/036803, International Preliminary Report on Patentability mailed Dec. 29, 2016", 10 pgs.
"International Application Serial No. PCT/US2015/036803, International Search Report mailed Dec. 11, 2015", 8 pgs.
"International Application Serial No. PCT/US2015/036803, Invitation to Pay Add'l Fees and Partial Search Rpt mailed Oct. 2, 2015", 8 pgs.
"International Application Serial No. PCT/US2015/036803, Written Opinion mailed Dec. 11, 2015", 8 pgs.
"International Application Serial No. PCT/US2016/041172, International Preliminary Report on Patentability mailed Jan. 18, 2018", 10 pgs.
"International Application Serial No. PCT/US2016/041172, International Search Report mailed Oct. 27, 2016", 6 pgs.
"International Application Serial No. PCT/US2016/041172, Written Opinion mailed Oct. 27, 2016", 8 pgs.
"International Application Serial No. PCT/US2016/048691, International Preliminary Report on Patentability mailed Mar. 15, 2018", 7 pgs.
"International Application Serial No. PCT/US2016/048691, International Search Report mailed Nov. 22, 2016", 7 pgs.
"International Application Serial No. PCT/US2016/048691, Written Opinion mailed Nov. 22, 2016" 6 pgs.
"International Application Serial No. PCT/US2017/018443, International Preliminary Report on Patentability mailed Aug. 30, 2018", 11 pgs.
"International Application Serial No. PCT/US2017/018443, International Search Report mailed May 22, 2017", 9 pgs.
"International Application Serial No. PCT/US2017/018443, Written Opinion mailed May 22, 2017", 9 pgs.
"International Application Serial No. PCT/US2018/057576, International Preliminary Report on Patentability mailed May 7, 2020", 12 pgs.
"International Application Serial No. PCT/US2018/057576, International Search Report mailed Mar. 25, 2019", 7 pgs.
"International Application Serial No. PCT/US2018/057576, Invitation to Pay Additional Fees and Partial Search Report mailed Jan. 31, 2019", 16 pgs.
"International Application Serial No. PCT/US2018/057576, Written Opinion mailed Mar. 25, 2019", 10 pgs.
"International Application Serial No. PCT/US2019/037084, International Preliminary Report on Patentability mailed Dec. 24, 2020", 12 pgs.
"International Application Serial No. PCT/US2019/037084, International Search Report mailed Nov. 14, 2019", 10 pgs.
"International Application Serial No. PCT/US2019/037084, Invitation to Pay Add'l Fees and Partial Search Report mailed Sep. 24, 2019", 10 pgs.
"International Application Serial No. PCT/US2019/037084, Written Opinion mailed Nov. 14, 2019", 10 pgs.
"International Application Serial No. PCT/US2019/045476, International Preliminary Report on Patentability mailed Feb. 18, 2021", 13 pgs.
"International Application Serial No. PCT/US2019/045476, International Search Report mailed Feb. 11, 2020", 8 pgs.
"International Application Serial No. PCT/US2019/045476, Invitation to Pay Additional Fees mailed Dec. 17, 2019", 14 pgs.
"International Application Serial No. PCT/US2019/045476, Written Opinion mailed Feb. 11, 2020", 13 pgs.
"International Application Serial No. PCT/US2019/047263, International Preliminary Report on Patentability mailed Mar. 4, 2021", 8 pgs.
"International Application Serial No. PCT/US2019/047263, International Search Report mailed Dec. 20, 2019", 5 pgs.
"International Application Serial No. PCT/US2019/047263, Written Opinion mailed Dec. 20, 2019", 6 pgs.
"International Application Serial No. PCT/US2020/014659, International Preliminary Report on Patentability mailed Aug. 5, 2021", 12 pgs.
"International Application Serial No. PCT/US2020/014659, International Search Report mailed Nov. 6, 2020", 7 pgs.

(56) References Cited

OTHER PUBLICATIONS

"International Application Serial No. PCT/US2020/014659, Invitation to Pay Additional Fees mailed Sep. 16, 2020", 11 pgs.
"International Application Serial No. PCT/US2020/014659, Written Opinion mailed Nov. 6, 2020", 10 pgs.
"International Application Serial No. PCT/US2020/017342, International Preliminary Report on Patentability mailed Aug. 19, 2021", 8 pgs.
"International Application Serial No. PCT/US2020/017342, International Search Report mailed Jun. 26, 2020", 6 pgs.
"International Application Serial No. PCT/US2020/017342, Written Opinion mailed Jun. 26, 2020", 6 pgs.
"International Application Serial No. PCT/US2020/031176, International Preliminary Report on Patentability mailed Nov. 11, 2021", 9 pgs.
"International Application Serial No. PCT/US2020/031176, International Search Report mailed Jul. 22, 2020", 6 pgs.
"International Application Serial No. PCT/US2020/031176, Written Opinion mailed Jul. 22, 2020", 7 pgs.
"International Application Serial No. PCT/US2020/048130, International Preliminary Report on Patentability mailed Mar. 10, 2022", 11 pgs.
"International Application Serial No. PCT/US2020/048130, International Search Report mailed Apr. 20, 2021", 9 pgs.
"International Application Serial No. PCT/US2020/048130, Invitation to Pay Additional Fees mailed Jan. 13, 2021", 7 pgs.
"International Application Serial No. PCT/US2020/048130, Written Opinion mailed Apr. 20, 2021", 9 pgs.
"International Application Serial No. PCT/US2021/014586, International Preliminary Report on Patentability mailed Aug. 4, 2022", 10 pgs.
"International Application Serial No. PCT/US2021/014586, International Search Report mailed May 20, 2021", 7 pgs.
"International Application Serial No. PCT/US2021/014586, Written Opinion mailed May 20, 2021", 8 pgs.
"International Application Serial No. PCT/US2021/033365, International Preliminary Report on Patentability mailed Dec. 8, 2022", 8 pgs.
"Israel Application Serial No. 163,546, Office Action mailed Nov. 12, 2009", w/English Translation, 1 pg.
"Israel Application Serial No. 163,546, Office Action mailed Dec. 26, 2007", w/English Translation, 1 pg.
"Israel Application Serial No. 163,546, Response filed May 9, 2008 to Office Action mailed Dec. 26, 2007", w/English Translation, 2 pgs.
"Israel Application Serial No. 163,546, Response filed Jun. 8, 2010 to Office Action mailed Nov. 12, 2009", w/English Claims, 3 pgs.
"Israel Application Serial No. 163,546, Response filed Aug. 16, 2009 to Substantive Examination Report mailed Feb. 23, 2009", w/English Claims, 4 pgs.
"Israel Application Serial No. 163,546, Response filed Oct. 20, 2010 to Office Action dated Jun. 8, 2010", w/English Claims, 8 pgs.
"Israel Application Serial No. 163,546, Response filed Nov. 27, 2008 to First Examination Report mailed Jul. 28, 2008", w/English Claims, 13 pgs.
"Israel Application Serial No. 163546, Office Action mailed Jun. 8, 2010", w/English Translation, 2 pgs.
"Israel Application Serial No. 183026, Office Action mailed Feb. 9, 2009", w/English Translation, 2 pgs.
"Israel Application Serial No. 238584, Office Action mailed Jul. 24, 2017", w/English Translation, 2 pgs.
"Israel Application Serial No. 238584, Response filed Nov. 21, 2017 to Office Action mailed Jul. 24, 2017", W/English Translation, 2 pgs.
"Israeli Application Serial No. 171831, Notification of Defects mailed Nov. 10, 2008", w/English Translation, 10 pgs.
"Israeli Application Serial No. 163,546, First Examination Report mailed Jul. 28, 2008", (English Translation), 2 pgs.
"Israeli Application Serial No. 163,546, Substantive Examination Report mailed Feb. 23, 2009", w/English Translation, 3 pgs.
"Israeli Application Serial No. 171372, Office Action mailed Feb. 21, 2010", w/English Translation, 2 pgs.
"Israeli Application Serial No. 171372, Office Action mailed Nov. 6, 2008", (Translation), 12 pgs.
"Israeli Application Serial No. 171372, Response filed Nov. 18, 2010 to Office Action mailed Feb. 21, 2010", w/English Translation, 19 pgs.
"Israeli Application Serial No. 171831, Office Action mailed Feb. 21, 2010", w/English Translation, 2 pgs.
"Israeli Application Serial No. 171831, Office Action mailed Apr. 18, 2012", (English Translation), 2 pgs.
"Israeli Application Serial No. 171831, Response filed Jan. 20, 2011 to Office Action mailed Feb. 21, 2010", w/English Translation, 18 pgs.
"Israeli Application Serial No. 171831, Response filed Jun. 24, 2009 to Notification of Defects mailed Nov. 10, 2008", w/English Claims, 10 pgs.
"Israeli Application Serial No. 171831, Response filed Nov. 6, 2012 to Office Action mailed Apr. 18, 1212", w/English Claims, 54 pgs.
"Israeli Application Serial No. 211324, Office Action mailed Sep. 18, 2014", w/English Translation, 5 pgs.
"Israeli Application Serial No. 211324, Office Action mailed Oct. 18, 2015", w/English Translation, 4 pgs.
"Israeli Application Serial No. 211324, Response filed Feb. 16, 2016 to Office Action mailed Oct 18, 2015", w/English Claims, 4 pgs.
"Israeli Application Serial No. 211324, Response filed Mar. 31, 2015 to Office Action mailed Sep. 8, 2014", w/English Translation, 21 pgs.
"Israeli Application Serial No. 238584, Notification of Defects in Patent Application mailed Jul. 21, 2019", (w/ English Translation), 5 pgs.
"Israeli Application Serial No. 238584, Office Action mailed Apr. 14, 2016", (English Translation), 3 pgs.
"Israeli Application Serial No. 238584, Office Action mailed Aug. 23, 2018", (w/ English Translation), 6 pgs.
"Israeli Application Serial No. 238584, Response filed Aug. 3, 2016 to Office Action mailed Apr. 14, 2016", (English Translation of Claims), 19 pgs.
"Israeli Application Serial No. 238584, Response filed Nov. 21, 2017 to Office Action mailed Jul. 24, 2017", (Translation), 2 pgs.
"Israeli Application Serial No. 238584, Response filed Nov. 21, 2019 to Notification of Defects in Patent Application mailed Jul. 21, 2019", (w/ English Translation of Claims), 6 pgs.
"Israeli Application Serial No. 238584, Response Filed Dec. 10, 2018 to Office Action mailed Aut. 23, 2018", (w/ English Translation of Claims), 10 pgs.
"Israeli Application Serial No. 171372, Office Action mailed Feb. 20, 2011", (Translation), 2 pgs.
"Japanese Application No. 2001-576868, Office Action mailed May 31, 2011", (w/ English Translation), 5 pgs.
"Japanese Application No. 2001-576868, Response filed Apr. 26, 2011 to Office Action mailed Nov. 2, 2010", (w/ Translation of Amended Claims), 14 pgs.
"Japanese Application Serial No. 2022-144599, Voluntary Amendment filed Nov. 9, 2022", w/ English Claims, 14 pgs.
"Japanese Application Serial No. 2022-544779, Voluntary Amendment filed Sep. 9, 2022", w/ English Claims, 8 pgs.
"Japanese Application Serial No. 2001-576868, Office Action mailed Nov. 2, 2010", w/ English (Translation), 10 pgs.
"Japanese Application Serial No. 2001-576868, Response filed Dec. 1, 2011 to Office Action mailed May 3, 2011", (w/ English Translation of Amended Claims), 37 pgs.
"Japanese Application Serial No. 2003-315106, Amended Claims filed Oct. 15, 2009 in Response to Office Action mailed Jun. 24, 2009", (English Translation), 6 pgs.
"Japanese Application Serial No. 2003-315106, Notice of Allowance mailed Jan. 5, 2010", (w/ English Translation), 5 pgs.
"Japanese Application Serial No. 2003-315106, Office Action malled Jun. 24, 2009", (w/ English Translation), 10 pgs.
"Japanese Application Serial No. 2003-568038, Amendment filed Aug. 19, 2005", (English Translation), 8 pgs.

(56) References Cited

OTHER PUBLICATIONS

"Japanese Application Serial No. 2003-568038, Notice of Allowance mailed Nov. 30, 2009", w/out English Translation, 3 pgs.
"Japanese Application Serial No. 2003-568038, Office Action mailed May 15, 2009", (w/ English Translation), 7 pgs.
"Japanese Application Serial No. 2003-568038, Office Action mailed Jul. 10, 2008", (w/ English Translation), 11 pgs.
"Japanese Application Serial No. 2003-568038, Office Action mailed Jul. 21, 2005", w/out English Translation, 3 pgs.
"Japanese Application Serial No. 2003-568038, Request for Examination filed Aug. 19, 2005 in Response to Official Action mailed Jul. 21, 2005", (w/ Partial English Translation of Specification), 8 pgs.
"Japanese Application Serial No. 2003-568038, Response filed Sep. 14, 2009 to Office Action mailed May 15, 2009", (w/ English Translation of Amended Claims), 10 pgs.
"Japanese Application Serial No. 2003-568038, Response filed Dec. 10, 2008 to Office Action mailed Jul. 10, 2008", (w/ English Translation of Amended Claims), 15 pgs.
"Japanese Application Serial No. 2006-513125, Office Action mailed Mar. 9, 2010", (English Translation), 11 pgs.
"Japanese Application Serial No. 2006-513125, Response filed Aug. 30, 2010 to Office Action mailed Mar. 9, 2010", (w/ English Translation of Amended Claims), 60 pgs.
"Japanese Application Serial No. 2006-533439, Decision of Final Rejection mailed Aug. 14, 2012", (w/ English Translation), 5 pgs.
"Japanese Application Serial No. 2006-533439, Office Action mailed Mar. 9, 2010", (w/ English Translations), 20 pgs.
"Japanese Application Serial No. 2006-533439, Office Action mailed Mar. 27, 2012", w/ English Translation, 8 pgs.
"Japanese Application Serial No. 2006-533439, Response filed May 21, 2012 to Office Action mailed Mar. 27, 2012", (w/ English Translation of Amended Claims), 19 pgs.
"Japanese Application Serial No. 2006-533439, Response filed Aug. 3, 2011 to Office Action mailed Feb. 15, 2011", (w/ English Translation of Amended Claims), 18 pgs.
"Japanese Application Serial No. 2006-533439,Office Action mailed Feb. 15, 2011", (w/ English Translation), 13 pgs.
"Japanese Application Serial No. 2006-533439; Office Action Response filed Jul. 9, 2010", (w/ English Translation of Claims), 25 pgs.
"Japanese Application Serial No. 2008-315106, Office Action mailed Jun. 24, 2009", (w/ English Translation), 10 pgs.
"Japanese Application Serial No. 2008-315106, Response filed Oct. 15, 2009 to Office Action mailed Jun. 24, 2009", w/English Translation, 103 pgs.
"Japanese Application Serial No. 2008-315106, Response filed Oct. 15, 2009 to Office Action mailed Jun. 24, 2009", (w/ English Translation of Amended Claims), 103 pgs.
"Japanese Application Serial No. 2008-315106, Response filed Dec. 3, 2009 to Office Action mailed Jun. 24, 2009", (w/ English Translation of Claims), 9 pgs.
"Japanese Application Serial No. 2009-238781, Office Action mailed Oct. 11, 2011", (w/ English Translation), 3 pgs.
"Japanese Application Serial No. 2009-502945, Examiners Decision of Final Refusal mailed Nov. 12, 2013", (w/ English Translation), 8 pgs.
"Japanese Application Serial No. 2009-502945, Office Action mailed Oct. 23, 2012", (w/ English Translation), 16 pgs.
"Japanese Application Serial No. 2009-502945, Response filed Apr. 10, 2013 to Office Action mailed Oct. 23, 2012", (w/ English Translation of Claims), 18 pgs.
"Japanese Application Serial No. 2011-111048, Office Action mailed Jun. 25, 2013", (w/ English Translation), 7 pgs.
"Japanese Application Serial No. 2011-111048, Office Action mailed Sep. 18, 2012", (w/ English Translation), 10 pga.
"Japanese Application Serial No. 2011-111048, Response filed Sep. 25, 2012 to Office Action mailed Jun. 25, 2013", (w/ English Translation of Amended Claims), 18 pgs.
"Japanese Application Serial No. 2011-111048. Response filed Mar. 15, 2013", (w/ Translation of Amended Claims), 14 pgs.
"Japanese Application Serial No. 2012-273898, Office Action mailed Jun. 10, 2014", (w/ English Translation), 7 pgs.
"Japanese Application Serial No. 2012-273898, Response filed Sep. 4, 2014 to Office Action mailed Jun. 10, 2014", W/ English Claims, 9 pgs.
"Japanese Application Serial No. 2012-536963, Amendment and Argument filed Jun. 26, 2015 to Office Action mailed Jan. 6, 2015", (w/ English Translation of Amended Claims), 12 pgs.
"Japanese Application Serial No. 2012-536963, Examiners Decision of Final Refusal mailed Nov. 17, 2015", (w/ English Translation), 8 pgs.
"Japanese Application Serial No. 2012-536963, Office Action mailed Jan. 6, 2015", (w/ English Translation), 14 pgs.
"Japanese Application Serial No. 2012-536963, Voluntary Amendment filed Jun. 27, 2012", (w/ English Translation of Amended Claims), 17 pgs.
"Japanese Application Serial No. 2013-198377, Office Action mailed Jan. 6, 2015", (w/ English Translation), 9 pgs.
"Japanese Application Serial No. 2014-049025 Response filed Sep. 4, 2015 to Office Action mailed Jun. 16, 2015", (w/ Amended Claims), 12 pgs.
"Japanese Application Serial No. 2014-049025, Examiners Decision of Final Refusal mailed Feb. 2, 2016", W/ English Translation, 5 pgs.
"Japanese Application Serial No. 2014-049025, Office Action mailed Jun. 16, 2015", (w/ English Translation), 6 pgs.
"Japanese Application Serial No. 2014-527339, Examiners Decision of Final Refusal mailed Feb. 7, 2017", (w/ English Translation), 5 pgs.
"Japanese Application Serial No. 2014-527339, Office Action mailed May 31, 2016", (w/ English Translation), 10 pgs.
"Japanese Application Serial No. 2014-527339, Response filed Sep. 16, 2016 to Office Action mailed May 31, 2016", (w/ English Translation of Amended Claims), 33 pgs.
"Japanese Application Serial No. 2016-053990, Office Action mailed Jun. 6, 2017", (w/ English Translation), 4 pgs.
"Japanese Application Serial No. 2016-053990, Response filed Dec. 6, 2017 to Office Action mailed Jun. 6, 2017", (w/ English Translation of Amended Claims), 14 pgs.
"Japanese Application Serial No. 2016-110879, Office Action mailed May 30, 2017", (w/ English Translation), 7 pgs.
"Japanese Application Serial No. 2016-110879, Response filed Nov. 30, 2017 to Office Action mailed May 30, 2017", (w/ English Translation of Claims), 25 pgs.
"Japanese Application Serial No. 2016-527046, Examiners Decision of Final Refusal mailed May 21, 2019", (w/ English Translation), 20 pgs.
"Japanese Application Serial No. 2016-527046, Reasons For Rejection mailed Aug. 14, 2018", (w/ English Translation), 14 pgs.
"Japanese Application Serial No. 2016-527046, Response Filed Dec. 4, 2018 to Reasons For Rejection mailed Aug. 14, 2018", (w/ English Translation of Amended Claims), 18 pgs.
"Japanese Application Serial No. 2017-111526, Office Action mailed May 14, 2019", (w/ English Translation), 6 pgs.
"Japanese Application Serial No. 2017-111526, Office Action mailed Jun. 26, 2018", (w/ English Translation), 5 pgs.
"Japanese Application Serial No. 2017-111526, Response Filed Dec. 21, 2018 to Office Action mailed Jun. 26, 2018", (w/ English Translation of Amended Claims), 7 pgs.
"Japanese Application Serial No. 2018-510751, Examiners Decision of Final Refusal mailed Dec. 17, 2019", w/ English Translation, 10 pgs.
"Japanese Application Serial No. 2018-510751, Notification of Reasons for Refusal mailed Mar. 13, 2019", (w/ English Translation), 14 pgs.
"Japanese Application Serial No. 2018-510751, Response filed Apr. 17, 2020 to Examiners Decision of Final Refusal mailed Dec. 17, 2019", w/ English Claims, 7 pgs.
"Japanese Application Serial No. 2018-510751, Response filed Aug. 9, 2019 to Notification of Reasons for Refusal mailed Mar. 13, 2019", (w/ English Translation of Claims), 24 pgs.

(56) References Cited

OTHER PUBLICATIONS

"Japanese Application Serial No. 2018-543688, Notification of Reasons for Rejection mailed Oct. 29, 2019", w/ English Translation, 14 pgs.
"Japanese Application Serial No. 2018-543688, Office Action mailed Jun. 30, 2020", w/ English translation, 11 pgs.
"Japanese Application Serial No. 2018-543688, Response filed Apr. 28, 2020 to Notification of Reasons for Rejection mailed Oct. 29, 2019", w/ English Claims, 12 pgs.
"Japanese Application Serial No. 2019-171818, Examiners Decision of Final Refusal mailed Oct. 5, 2021", (w/ English Translation), 15 pgs.
"Japanese Application Serial No. 2019-171818, Notification of Reasons for Rejection mailed Nov. 10, 2020", (w/ English Translation), 11 pgs.
"Japanese Application Serial No. 2019-171818, Preliminary Examination Report mailed May 10, 2022", (w/ English Translation), 2 pgs.
"Japanese Application Serial No. 2019-171818, Response filed Feb. 4, 2022 to Examiners Decision of Final Refusal mailed Oct. 5, 2021", (w/ English Translation of Claims), 21 pgs.
"Japanese Application Serial No. 2019-171818, Response filed May 10, 2021 to Notification of Reasons for Rejection mailed Nov. 10, 2020", (w/ English Translation of Claims), 12 pgs.
"Japanese Application Serial No. 2019-171818, Response filed Dec. 2, 2022 to Preliminary Examination Report mailed May 10, 2022", w/ English Claims, 44 pgs.
"Japanese Application Serial No. 2019-171818, Trial Brief filed Mar. 30, 2022", (w/ English Translation), 14 pgs.
"Japanese Application Serial No. 2020-073952, Examiners Decision of Final Refusal mailed Aug. 4, 2022", w/ English translation, 3 pgs.
"Japanese Application Serial No. 2020-073952, Final Notification of Reasons for Refusal mailed Jan. 25, 2022", w/ English Translation, 11 pgs.
"Japanese Application Serial No. 2020-073952, Notification of Reasons for Refusal mailed May 20, 2021", w/o English Translation, 2 pgs.
"Japanese Application Serial No. 2020-073952, Response filed Apr. 20, 2022 to Final Notification of Reasons for Refusal mailed Jan. 25, 2022", w/ English Claims, 40 pgs.
"Japanese Application Serial No. 2020-073952, Response filed Sep. 9, 2021 to Notification of Reasons for Refusal mailed May 20, 2021", w/ English Claims, 27 pgs.
"Japanese Application Serial No. 2020-073952, Response filed Dec. 2, 2022 to Examiners Decision of Final Refusal mailed Aug. 4, 2022", w/ English Claims, 36 pgs.
"Japanese Application Serial No. 2020-182549, Examiners Decision of Final Refusal mailed Jun. 7, 2022", (w/ English Translation), 11 pgs.
"Japanese Application Serial No. 2020-182549, Notification of Reasons for Refusal mailed Nov. 30, 2021", (w/ English Translation), 10 pgs.
"Japanese Application Serial No. 2020-182549, Preliminary Examination Report mailed Jan. 17, 2023", w/ English Translation, 3 pgs.
"Japanese Application Serial No. 2020-182549, Response filed Feb. 28, 2022 to Notification of Reasons for Refusal mailed Nov. 30, 2021", (w/ English Translation of Claims), 52 pgs.
"Japanese Application Serial No. 2020-182549, Response filed Oct. 6, 2022 to Examiners Decision of Final Refusal mailed Jun. 7, 2022", w/ English Claims, 21 pgs.
"Japanese Application Serial No. 2020-523276, Examiners Decision of Final Refusal mailed May 10, 2022", w/ English Translation, 13 pgs.
"Japanese Application Serial No. 2020-523276, Notification of Reasons for Refusal mailed Jul. 27, 2021", w/ English Translation, 12 pgs.
"Japanese Application Serial No. 2020-523276, Response filed Jan. 12, 2022 to Notification of Reasons for Refusal mailed Jul. 27, 2021", w/ English Claims, 27 pgs.
"Japanese Application Serial No. 2021-146743, Notification of Reasons for Rejection mailed Aug. 17, 2022", w/ English Translation, 3 pgs.
"Japanese Application Serial No. 2021-146743, Response filed Feb. 17, 2023 to Notification of Reasons for Rejection mailed Aug. 17, 2022", w/ English Claims, 34 pgs.
"Japanese Application Serial No. 2021-506434, Examiners Decision of Final Refusal mailed Jan. 10, 2023", w/ English Translation, 10 pgs.
"Japanese Application Serial No. 2021-506434, Notification of Reasons for Refusal mailed May 10, 2022", w/ English translation, 10 pgs.
"Japanese Application Serial No. 2021-506434, Response filed Feb. 18, 2022 to Office Action mailed Dec. 21, 2021", 135 pgs.
"Japanese Application Serial No. 2021-506434, Response filed Nov. 7, 2022 to Notification of Reasons for Refusal mailed May 10, 2022", w/ English Claims, 13 pgs.
"Japanese Application Serial No. 2021-509824, Voluntary Amendment filed Aug. 18, 2022", w/ English Claims, 39 pgs.
"Japanese Application Serial No. 2021-542525, Notification of Reasons for Refusal mailed Dec. 13, 2022", w/ English Translation, 14 pgs.
"Japanese Application Serial No. 2021-546853, Notification of Reasons for Refusal mailed Apr. 18, 2023", w/ English Translation, 11 pgs.
"Japanese Application Serial No. 2006-513125,Final Office Action mailed Jan. 18, 2011", (English Translation), 4 pgs.
"Korean Application Serial No. 10-2005-7020077, Response filed Apr. 28, 2008 to Examination Report mailed Dec. 28, 2007", (w/ English Translation of Revised Claims), 41 pgs.
"Korean Application Serial No. 10-2004-7012647, Office Action mailed Feb. 26, 2010", (w/ English Translation), 7 pgs.
"Korean Application Serial No. 10-2004-7012647, Response filed Jun. 10, 2010 to Office Action mailed Feb. 26, 2010", (w/ English Translation of Claims), 17 pgs.
"Korean Application Serial No. 10-2005-7020077, Examination Report mailed Dec. 28, 2007", (w/ English Translation), 8 pgs.
"Korean Application Serial No. 10-2005-7020077, Notice of Preliminary Rejection mailed Jun. 28, 2007", (w/ English Translation), 9 pgs.
"Korean Application Serial No. 10-2005-7020077, Response filed Aug. 28, 2007 to Notice of Preliminary Rejection mailed Jun. 28, 2007", (w/ English Translation), 40 pgs.
"Korean Application Serial No. 10-2005-7022564, Notice of Preliminary Rejection dated Jul. 25, 2007", W/ English Translation, 5 pgs.
"Korean Application Serial No. 10-2005-7022564, Office Action mailed Aug. 6, 2008", W/ English Translation, 4 pgs.
"Korean Application Serial No. 10-2005-7022564, Response and Amendment filed Dec. 29, 2008 to Office Action mailed Aug. 6, 2008", W/ English Translation, 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action mailed Aug. 6, 2008", (w/ English Translation of Claims), 16 pgs.
"Korean Application Serial No. 10-2010-7011520, Office Action mailed Jul. 20, 2010", (w/ English Translation), 6 pgs.
"Korean Application Serial No. 10-2010-7011520, Response filed Oct. 20, 2010 to Office Actiion mailed Jul. 20, 2010", (w/ English Translation of Amended Claims), 30 pgs.
"Korean Application Serial No. 10-2010-7011520, Amended Claims filed May 24, 2011 in Response to Office Action mailed Feb. 24, 2011", (English Translation of Amended Claims), 22 pgs.
"Korean Application Serial No. 10-2010-7011520, Office Action mailed Feb. 24, 2011", (w/ English Translation), 5 pgs.
"Mexican Application No. PA/a/2005/012712 Office Action mailed Jul. 21, 2009", (w/ English Translation), 9 pgs.
"Mexican Application Serial No. MX/a/2009/006341, Office Action mailed Mar. 29, 2012", (English Translation), 1 pg.

(56) References Cited

OTHER PUBLICATIONS

"Mexican Application Serial No. MX/a/2009/006341, Response filed Jun. 4, 2012 to Mar. 29, 2012", (w/ English Translation of Amended Claims), 16 pgs.
"Mexican Application Serial No. MX/a/2012/009249 Response filed Sep. 10, 2015 to Office Action mailed May 19, 2015", (w/ English Translation of Claims), 21 pgs.
"Mexican Application Serial No. MX/a/2012/009249, Office Action mailed Feb. 5, 2016", W/ English Claims, 2 pgs.
"Mexican Application Serial No. MX/a/2012/009249, Office Action mailed May 19, 2015", (English Translation), 1 pg.
"Mexican Application Serial No. MX/a/2012/009249, Response filed Mar. 29, 2016 to Office Action mailed Feb. 5, 2016", (English Translation of Claims), 18 pgs.
"Mexican Application Serial No. PA/a/2004/007914, Office Action mailed Feb. 14, 2008", (w/ English Translation), 3 pgs.
"Mexican Application Serial No. PA/a/2004/007914, Office Action mailed Feb. 22, 2008", (English Translation), 3 pgs.
"Mexican Application Serial No. PA/a/2004/007914, Response filed Jun. 11, 2008 to Office Action mailed Feb. 22, 2008", (w/ English Translation of Claims), 68 pgs.
"Mexican Application Serial No. PA/a/2005/011250, Office Action mailed Aug. 23, 2010", W/ English Translation, 4 pgs.
"Mexican Application Serial No. PA/a/2005/011250, Response Filed Dec. 20, 2010 to Office Action mailed Aug. 23, 2010", (w/ English Translation of Claims), 14 pgs.
"Mexican Application Serial No. PA/a/2005/012712 , Office Action Mailed Aug. 11, 2009", (English Translation), 5 pgs.
"Mexican Application Serial No. PA/a/2005/012712 , Response filed Sep. 28, 2009 to Office Action Mailed Jul. 21, 2009", (w/ English Translation of Claims), 24 pgs.
"Mexican Application Serial No. PA/a/2005/012712, Office Action mailed May 12, 2010", (w/ English Translation), 19 pgs.
"Mexican Application Serial No. PA/a/2005/012712, Office Action mailed Jun. 9, 2010", (w/ English Translation), 11 pgs.
"Mexican Application Serial No. PA/a/2005/012712, Office Action mailed Nov. 30, 2009", (w/ English Translation), 14 pgs.
"Mexican Application Serial No. PA/a/2005/012712, Official Action mailed Mar. 5, 2009", (English Translation), 2 pgs.
"Mexican Application Serial No. PA/a/2005/012712, Response filed Feb. 3, 2010 to Office Action mailed Nov. 30, 2009", (w/ English Translation of Amended Claims), 22 pgs.
"Mexican Application Serial No. PA/a/2005/012712, Response filed Sep. 27, 2010 to Office Action mailed May 12, 2010", (w/ English Translation of Claims). 19 pgs.
"Mexico Application Serial No. PA/a/2005/012712, Response filed Jun. 12, 2009 to Official Action mailed Mar. 5, 2009", (w/ English Translation of Claims), 11 pgs.
"Neuraminidase [Influenza A virus (A/Aichi/2/1968 (H3N2)]", GenBank: BAD16642.1, NCBI, [online]. Retrieved from the Internet: <URL: http://www.ncbi.nlm.nih.gov/protein/46401580>, (2008), 3 pgs.
"Neuraminidase [Influenza B virus]", GenBank: CAB71147.1, NCBI, [online]. Retrieved from the Internet: <URL: http://www.ncbi.nlm.nih.gov/protein/6851026>, (2005), 3 pgs.
"Neuraminidase, partial [Influenza A virus (A/swine/France/WVL13/1995(H1N1))]", GenBank Accession# AC025028, (May 22, 2009), 2 pgs.
"New Zealand Application Serial No. 542935, Examination Report dated Feb. 25, 2008", 2 pgs.
"New Zealand Application Serial No. 542935, Examination Report mailed Jun. 14, 2006", 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.
"New Zealand Application Serial No. 542935, Voluntary Amendments filed Sep. 12, 2007", 10 pgs.
"New Zealand Application Serial No. 543446, Examination Report mailed Feb. 29, 2008", 2 pgs.
"New Zealand Application Serial No. 543446, Examination Report mailed May 12, 2008", 1 pg.
"New Zealand Application Serial No. 543446, Response mailed Mar. 20, 2008 to Examination Report mailed Feb. 29, 2008", 2 pgs.
"New Zealand Application Serial No. 543587, Examination Report mailed Mar. 1, 2007", 1 pg.
"New Zealand Application Serial No. 543587, Examination Report mailed Jul. 7, 2006", 2 pgs.
"New Zealand Application Serial No. 543587, Response filed Aug. 7, 2007 to Examination Reports mailed Jul. 7, 2006 and Mar. 1, 2007", 24 pgs.
"New Zealand Application Serial No. 543587, Second Examination Report mailed Feb. 25, 2008", 2 pgs.
"New Zealand Application Serial No. 555245, First Examination Report mailed Aug. 26, 2008", 2 pgs.
"New Zealand Application Serial No. 555245, Subsequent Examiner Report mailed Jul. 3, 2009", 1 pg.
"Nonstructural protein 1 [influenza B virus (B/Hong Kong/330/2001)]", GenBank AAT69443.1, (2006), 1 pg.
"Norway Application Serial No. 20056074, Office Action mailed Jan. 17, 2017", (English Translation), 5 pgs.
"Norway Application Serial No. 20056074, Office Action mailed Apr. 25, 2017", (w English Translation), 3 pgs.
"Norway Application Serial No. 20056074, Office Action Response mailed Apr. 18, 2017", W/ English Claims, 27 Pgs.
"Norway Application Serial No. 20056074, Response filed Jul. 25, 2017 to Office Action mailed Apr. 25, 2017", (w/ English Translation of Amended Claims), 111 pgs.
"Nucleotide sequences of influenza virus segments 1 and 3 reveal mosaic structure of a small viral RNA segment", Database Uniprot, (Nov. 14, 2001), 2 pgs.
"Nucleotides Sequences of Influenza Virus Segments 1 and 3 Reveal Mosaic Structure of Small Viral RNA Segment", Database UniProt EBI / Accession No. NC_002023, (Jul. 10, 2008), 15 pgs.
"PCT Application Serial No. PCT/US2005/041991, International Preliminary Report on Patentability / Written Opinion mailed Jul. 19, 2007", 8 pgs.
"Polymerase acidic [influenza A virus (A/swine/Shizuoka/120/97(H3N2))]", GenBank AAO15329.1. (2003), 1 pg.
"polymerase PA [Influenza A virus (A/swine/Yangzhou/1/2008(H9N2))]", GenBank: ADK98493.1, [Online]. Retrieved from the Internet: <URL: https://www.ncbi.nlm.nih.gov/protein/ADK98493.1/>, 2 pgs.
"Polymerase PA [Influenza B virus (B/Hong Kong/330/2001)]", GenBank ABL7718 6 .1, (2006), 1 pg.
"Polymerase PB1 [Influenza B virus (B/Hong Kong/330/2001)]", GenBank ABL77187, (2006), 1 pg.
"Polymerase PB2 [Influenza B virus (B/Hong Kong/330/2001)] GenBank ABL77188.1", (2006), 1 pg.
"RecName: Full=Non-structural protein 1; Short=NS1; AllName: Full=NS1 B", GenPept Accesion P08013, NS1 of Influenza B strain B/Yamagata/1/73, (Dec. 9, 2015), 2 pgs.
"RNA World", http://faculty.uca.edu/~benw/biol4415/lecture10a/tsld003.htm, (Observed Feb. 25, 2003), 1 pg.
"Russian Federation Application No. 2005136233, Office Action mailed Dec. 25, 2007", 2 pgs.
"Russian Federation Application No. 2005136233, Response filed May 29, 2008 to Office Action mailed Dec. 25, 2007", (w/ Partial English Translation), 7 pgs.
"Russian Federation Application Serial No. 2005136233, First Office Action mailed Feb. 27, 2007", (w/ English Translation), 5 pgs.
"Russian Federation Application Serial No. 2005136233, Response filed Jun. 14, 2007 to First Office Action mailed Feb. 27, 2007", (English Translation of Claims), 6 pgs.
"Russian Federation Application Serial No. 2005136233, Response filed Nov. 20, 2007 to Office Action", (w/ English Translation of Amended Claims), 18 pgs.
"Singapore Application Serial No. 200507467-9, Invitation to Respond to Written Opinion mailed Jun. 19, 2007", 5 pgs.
"Singaporean Application Serial No. 200506858-0, Examination Report mailed Feb. 9, 2007", 4 pgs.

(56) References Cited

OTHER PUBLICATIONS

"Singaporean Application Serial No. 200506858-0, Response filed Dec. 22, 2006 to Written Opinion mailed Jul. 26, 2006", 18 pgs.
"Singaporean Application Serial No. 200506858-0, Written Opinion mailed Jul. 26, 2006", 8 pgs.
"Singaporean Application Serial No. 200507468-7, Examination Report mailed Mar. 19, 2008", 5 pgs.
"Singaporean Application Serial No. 200507468-7, Invitation to Respond to Written Opinion mailed Jun. 12, 2007", 6 pgs.
"Singaporean Application Serial No. 200507468-7, Response filed Nov. 7, 2007 to Invitation to Respond to Written Opinion mailed Jun. 12, 2007", 9 pgs.
"ST3GAL6 Gene ID: 478535", ncbi, nim, [Online]. Retrieved from the Internet: <URL: https://www.ncbi.nlm.nih.gov/gene/47853> Sep. 14, 2022, (Aug. 17, 2022), 14 pgs.
"The Influenza Virus: Structure and Replication", Rapid Reference to Influenza. Elsevier Ltd, [Online]. Retrieved from the Internet: http://www. rapidreferenceinfluenza.com/chapter/B978-0-7234-3433-7.50009-8/aim/influenza-virus-structure, (2006), 6 pgs.
"The Integral Membrane Proteins of Influenza A, B, and C Viruses", The Influenza Sequence Database, http://www.flu.lanl.gov/review/fluc.review2.html, (Observed Feb. 26, 2003), 1 pg.
"Ukrainese Application Serial No. 200512619, Response filed Jan. 21, 2010 to Office Action mailed Jun. 17, 2009", W/ English Claims, 14 pgs.
"Ukrainian Application Serial No. 200512619, Office Action mailed Feb. 27, 2009", (w/ English Translation), 21 pgs.
"Ukrainian Application Serial No. 200512619, Office Action mailed Jun. 17, 2009", (w/ English Translation), 4 pgs.
"Ukrainian Application Serial No. 200512619, Response filed Apr. 8, 2009 to Office Action mailed Feb. 27, 2009", (w/ English Translation of Claims), 9 pgs.
Abram, M. E, et al., "Nature, position, and frequency of mutations made in a single cycle of HIV-1 replication", J Virol., 84(19), (Oct. 2010), 9864-78.
Air, Gillian M., et al., "Antigenic, Sequence, and Crystal Variation in Influenza B Neuraminidase", Virology, 177(2), (1990), 578-587.
Air, Gillian M., et al., "Antigenic, Sequence, and Crystal Variation in Influenza B Neuraminidase", Virology vol. 177, (1990), 578-587.
Akarsu, H., et al., "Crystal structure of the M1 protein-binding domain of the influenza A virus nuclear export protein (NEP/NS2).", EMBO J., 22(18), (Sep. 15, 2003), 4646-55.
Albo, C., et al., "The 5' Ends of Thogoto Virus (Orthomyxoviridae) mRNAS Are Homogeneous in both Length and Sequence", Journal of Virology, 70(12), (1996), 9013-9017.
Alonso-Caplen, et al., "Efficient Transcription, Not Translation, Is Dependent on Adenovirus Tripartite Leader Sequences at Late Times of Infection", Journal of Virology, vol. 62, No. 5, 1606-1616, (1988), 11 pgs.
Author Unknown, "New Approaches to Influenza Vaccine", Medscape—Infections in Medicine, http://www.medscape.com/viewarticle/417404_3, (Observed Feb. 26, 2003), 4 pgs.
Avetisyan, G, et al., "Cell-mediated immune responses to influenza vaccination in healthy volunteers and allogeneic stem cell transplant recipients", Bone Marrow Transplant 411-415, (2005), 5 pgs.
Avilov, Sergiy V., et al., "Influenza A virus progeny vRNP trafficking in live infected cells studied with the virus-encoded fluorescently tagged PB2 protein", Vaccine, 30, (2012), 7411-7417.
Avilov, Sergiy V., et al., "Replication-Competent Influenza A Virus That Encodes a Split-Green Fluorescent Protein-Tagged PB2 Polymerase Subunit Allows", Journal of Virology, 86, (2012), 1433-1448.
Baez, M., et al., "Complete nucleotide sequence of the influenza A/PR/8/34 virus NS gene and comparison with the NS genes of the A/Udorn/72 and A/FPV/Rostock/34 strains", Nucleic Acids Research, 23(8), (1980), 5845-5858.
Bai, B., et al., "Virus-Like Particles of SARS-Like Coronavirus Formed by Membrane Proteins from Different Origins Demonstrate Stimulating Activity in Human Dendritic Cells", PloS One, 3(7): e2685, (2008), 1-12.
Bancroft, C. T, et al., "Evidence for segment-nonspecific packaging of the influenza a virus genome", J Virol., 76(14), (Jul. 2002), 7133-9.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Basler, C. F, et al., "Mutation of Neuraminidase Cysteine Residues Yields Temprature-Sensitive Influenza Viruses", Journal of Virology, 73(10), (Jun. 30, 1999), 8095-8103.
Beare, A. S., "Trials in Man With Live Recombinants Made From A/PR/8/34 (H0 N1) and Wild H3 N2 Influenza Viruses", The Lancet, 2(7938), (1975), 729-732.
Bedford, M. T, et al., "FBP WW domains and the Abl SH3 domain bind to a specific class of proline-rich ligands", EMBO J., 16(9), (May 1, 1997), 2376-83.
Betakova, T., et al., "The NB protein is an integral component of the membrane of influenza B virus.", J Gen Virol., 77 ( Pt 11), (Nov. 1996), 2689-94.
Biere, Barbara, et al., "Differentiation of Influenza B Virus Lineages Yamagata and Victoria by Real-Time PCR", Journal of Clinical Microbiology, vol. 48, No. 4 1425-1427, (2010), 3 pgs.
Bilsel, P., et al., "Mutations in the Cytoplasmic Tail of Influenza A Virus Neuraminidase Affect Incorporation into Virions", Journal of Virology, 67(11), (Nov. 30, 1993), 6762-6767.
Blount, K. F., et al., "The Hammerhead Ribozyme", Biochemical Society Transactions, 30(6), (2002), 1119-1122.
Bourmakina, S. V, et al., "Reverse genetics studies on the Filamentous morphology of influenza A Virus", Journal of General Virology (2003) 84,, (2003), 517-527.
Bowie, et al., "Deciphering the Message in Protein Sequences: Tolerance to Amino Acid Substitutions", Science, 247, (Mar. 1990), 1306-1310.
Bowie, J. U., et al., "Deciphering the Message in Protein Sequences: Tolerance to Amino Acid Substitutions", Science, 247(4948) 1306-1310, (1990), 5 pgs.
Boyer, J. C., et al., "Infectious transcripts and cDNA clones of RNA viruses", Virology, 198(2), (Feb. 1994), 415-426.
Bradfute, S. B., "The Early Clinical Development of Ebola Virus Treatments", Exp. Opin. Invest. Drugs 26(1):, (2017), 5 pgs.
Bradsher, K., "Cases of New Bird Flue in Hong Kong Prompt Worldwide Alerts", The New York Times web site, (Observed Feb. 22, 2003), 3 pgs.
Bradsher, K., "Man's Death of 'Bird Flu' in Hong Kong Raises Fears", The New York Times web site, (Observed Feb. 22, 2003), 3 pgs.
Brandli, A. W, et al., "A Polarized Epithelial Cell Mutant Deficient in Translocation of UDP-galactose into the Golgi Complex", Journal of Biological Chemistry, 263(31), (Nov. 5, 1988), 16283-16290.
Brands, R., et al., "Influvac: a Safe Madin Darby Canine Kidney (MDCK) Cell Culture-Based Influenza Vaccine", Dev. Biol. Stand., 98, (1999), 93-100.
Brassard, D.L., et al., "Influenza B virus NB glycoprotein is a component of the virion", Virol., 220(2), No Document, (1996), 350-360.
Bridgen, A., et al., "Rescue of a Segmented Negative-Strand RNA Virus Entirely From Cloned Complementary DNAs", Proc. Natl. Acad. Sci. USA, 93, (1996), 15400-15404.
Broecker, Felix, et al., "A mosaic hemagglutinin-based influenza virus vaccine candidate protects mice from challenge with divergent H3N2 strains", npj Vaccines (2019) 31, www.nature.com/npjvaccines Published in partnership with the Sealy Center for Vaccine Development, (Jul. 19, 2019), 9 pages.
Broecker, Felix, et al., "Extending the Stalk Enhances Inmunogenicity of the Influenza Virus Neuraminidase", Journal of Virology, 93(18), e00840-19, (Sep. 1, 2019), 1-12.
Broecker, Felix, et al., "Immunodominance of Antigenic Site B in the Hemagglutinin of the Current H3N2 In?uenza Virus in Humans and Mice", Journal of Virology, 92(20): e01100-18, (Oct. 2018), 1-13.
Brooke, C B, "Biological activities of 'noninfectious' influenza A virus particles", Future Virol 9(1) 41-51, (Jan. 2014), 16 pgs.

(56) References Cited

OTHER PUBLICATIONS

Brown, E. G., et al., “Genetic analysis of mouse-adapted influenza A virus identifies roles for the NA, PB1, and PB2 genes in virulence”, Virus Research, 61(1), (May 1999), 63-76.
Brown, TA, “Studying DNA”, Genomes—NCBI Bookshelf, Brown TA. Genomes. 2nd edition. Oxford: Wiley-Liss; 2002, (2002), 26 pgs.
Bruhl, P., et al., “Humoral and Cell-Mediated Immunity to Vero Cell-Derived Influenza Vaccine”, Vaccine, 19, (2001), 1149-1158.
Buchholz, U. J., et al., “Generation of Bovine Respiratory Syncytial Virus (BRSV) From cDNA: BRSV NS2 is Not Essential for Virus Replication in Tissue Culture, and the Human RSV Leader Region Acts as a Functional BRSV Genome Promoter”, Journal of Virology, 73(1), (1999), 251-259.
Bukreyev, A., et al., “Chimeric human parainfluenza virus bearing the Ebola virus glycoprotein as the sole surface protein is immunogenic and highly protective against Ebola virus challenge”, Virology, 383(2), (Abstract Only), (2009), 1 pg.
Bukreyev, A., et al., “Recovery of infectious respiratory syncytial virus expressing an additional, foreign gene”, Journal of Virology, 70(10), (Oct. 1996), 6634-6641.
Bullido, R., et al., “Influenza A Virus NEP (NS2 protein) Downregulates RNA Synthesis of Model Template RNAs”, Journal of Virology, 75(10), (May 2001), 4912-4917.
Bullido, R., et al., “Influenza A virus NEP(NS2 protein) downregulates RNA synthesis of model template RNAs”, Journal of Virology, vol. 75 4912-4917, (May 2001), 6 pgs.
Burmeister, W. P., et al., “The 2.2 a resolution crystal structure of influenza B neuraminidase and its complex with sialic acid”, The EMBO Journal, 11(1), (1992), 49-56.
Cannon, Joseph G., “Chapter Nineteen—Analog Design”, In: Burger’s Medicinal Chemistry and Drug Discovery, Fifth Edition, vol. I: Principles and Practice, Wiley-Interscience, (1995), 783-802.
Cao, S., et al., “Characterization of the Nucleocytoplasmic Shuttle of the Matrix Protein of Influenza B Virus”, Journal of Virology., 88(13), (Jul. 2014), 7464-7473.
Cardona, C. J., “Avian Influenza”, http://www.vetmed.ucdavis.edu/vetex/INF-PO_AvianinfluenzaFS.html, ((Observed Feb. 22, 2003), 3 pgs.
Castrucci, M. R, et al., “Attenuation of Influenza A Virus by Insertion of a Foreign Epitope into the Neuraminidase”, Journal of Virology, 66(8), (1992), 4647-4653.
Castrucci, M. R., et al., “Biologic Importance of Neuraminidase Stalk Length in Influenza A Virus”, Journal of Virology, 67(2), (1993), 759-764.
Castrucci, M. R, et al., “Protection against Lethal Lymphocytic Choriomeningitis Virus (LCMV) Infection by Immunization of Mice with an Influenza Virus Containing an LCMV Epitope Recognized by Cytotoxic T Lymphocytes”, Journal of Virology, 68(6), (1994), 3486-3490.
Castrucci, Maria R., et al., “Reverse genetics system for generation of an influenza A virus mutant containing a deletion of the carboxyl-terminal residue of M2 protein.”, J Virol., 69(5), (May 1995), 2725-8.
Catchpole, A P, et al., “Alternative base pairs attenuate influenza A virus when introduced into the duplex region of the conserved viral RNA promoter of either the NS or the PA gene”, Journal of General Virology, 84, (2003), 507-515.
Chan, Winnie, et al., “The cold adapted and temperature sensitive influenza A/Ann Arbor/6/60 virus, the master donor virus for live attenuated influenza vaccines, has multiple defects in replication at the restrictive temperature”, Virology, 380(2), (2008), 304-311.
Chang, M. W., et al., “Analysis of HIV Wild-Type and Mutant Structures via in Silico Docking against Diverse Ligand Libraries”, J. Chem. Inf. Model., 47(3), (2007), 1258-1262.
Chen, H, et al., “Generation and evaluation of a high-growth reassortant H9N2 influenza A virus as a pandemic vaccine candidate”, Vaccine, 21(17-18), (May 16, 2003), 1974-9.
Chen, Z., et al., “Influenza A Virus NS1 Protein Targets Poly(A)-Binding Protein II of the Cellular 3'-End Processing Machinery”, The EMBO Journal, 18(8), (1999), 2273-2283.
Chevalie, Christophe, et al., “PB1-F2 Influenza A Virus Protein Adopts a B-Sheet Conformation and Forms Amyloid Fibers in Membrane Environments”, The of Biological Chemistry, 285(17), (2010), 13233-13243.
Chiba, Shiho, et al., “Multivalent nanoparticle-based vaccines protect hamsters against SARS-CoV-2 after a single immunization”, Communications Biology, 4: 597, (2021), 1-9.
Cho, Alice, et al., “Implications of Broadly Neutralizing Antibodies in the Development of a Universal Influenza Vaccine”, Current Opinion in Virology, vol. 17 110-115, (Apr. 1, 2016), 6 pgs.
Chothia, Cyrus, et al., “Canonical Structures for the Hypervariable Regions of Immunoglobulins.”, J Mol Biol., 196(4), (1987), 901-917.
Chowrira, B M., et al., “In Vitro and in Vivo Comparision of Hammerhead, Hairpin, and Hepatitis Delta Virus Self-Processing Ribozyme Cassettes”, The Journal of Biological Chemistry, 269(41), (1994), 25856-25864.
Chung, C, et al., “Glycoengineering of Chinese Hamster Ovary Cells for Improving Biotherapeutics Efficacies”, A dissertation submitted to Johns Hopkins University in conformity with the requirements for the degree of Doctor of Philosophy, Retrieved from the Internet: <https://jscholarship.library.jhu.edu/handle/177>, (2016), 137 pgs.
Claas, E C. J., et al., “Human Influenza A H5N1 Virus Related to a Highly Pathogenic Avian Influenza Virus”, The Lancet, 351, (1998), 472-477.
Clarke, D. K., et al., “Rescue of Mumps Virus From cDNA”, Journal of Virology, 74(10), (2000), 4831-4838.
Cohen, Alexander A., et al., “Mosaic nanoparticles elicit cross-reactive immune responses to zoonotic coronaviruses in mice”, Science, 371(6530), and Supplementary Materials, (2021), 735-741 (30 pgs).
Coleman, P. M., et al., “Sequence and Structure Alignment of Paramyxovirus Hemagglutinin-Neuraminidase with Influenza Virus Neuraminidase”, Journal of Virology, 67(6), (1993), 2972-2980.
Collins, P. L., et al., “Chapter 41—Parainfluenza Viruses”, In: Fields Virology, edited by Fields, B. N., et al. (3rd Edition, 1996, Lippincott-Raven Publishers, Philadelphia, PA, 1205-1241.
Collins, P. L., et al., “Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D”, Proc. Natl. Acad. Sci. USA, 92, (1995), 11563-11567.
Collins, P. L., “Rescue of Synthetic Analogs of Respiratory Syncytial Virus Genomic RNA and Effect of Truncations and Mutations on the Expression of a Foreign Reporter Gene”, Proc. Natl. Acad. Sci. USA, 88, (1991), 9663-9667.
Conzelmann, K.-K., “Genetic Engineering of Animal RNA Viruses”, Trends in Microbiology, 4(10), (1996), 386-393.
Conzelmann, K.-K., “Genetic manipulation of non-segmented negative-strand RNA viruses”, Journal of General Virology, 77(Pt. 3), (Mar. 1996), 381-389.
Conzelmann, K.-K., “Nonsegmented Negative-Strand RNA Viruses: Genetics and Manipulation of Viral Genomes”, Annu. Rev. Genet., 32, (1998), 123-162.
Conzelmann, K.-K., “Rescue of Synthetic Genomic RNA Analogs of Rabies Virus by Plasmid-Encoded Proteins”, Journal of Virology, 68(2), (1994), 713-719.
Craven, R. C., et al., “Late Domain Function Identified in the Vesicular Stomatitis Virus M Protein by Use of Rhabdovirus-Retrovirus Chimeras”, Journal of Virology, 73(4), (1999), 3359-3365.
Crescenzo-Chaigne, B., et al., “Comparative Analysis of the Ability of the Polymerase Complexes of Influenza Viruses Type A, B and C to Assemble into Functional RNPs that Allow Expression and Replication of Heterotypic Model RNA Templates In Vivo”, Virology, 265(2), (1999), 342-353.

(56) References Cited

OTHER PUBLICATIONS

Cunningham, Brian C, et al., "High-Resolution Epitope Mapping of hGH-Receptor Interactions by Alanine-Scanning Mutagenesis", Science 244:4908, (1989), 6 pgs.
Da Silva, Diogo V, et al., "Assembly of Subtype 1 Influenza Neuraminidase Is Driven by Both the Transmembrane and Head Domains", Journal of Biological Chemistry, 288(1), (Jan. 1, 2013), 644-653.
Daddario-Dicaprio, K. M, et al., "Cross-protection against Marburg virus strains by using a live, attenuated recombinant vaccine", J Virol., 80(19), (Oct. 2006), 9659-66.
De, B. P., et al., "Requirements and Functions of Vesicular Stomatitis Virus L and NS Proteins in the Transcription Process in Vitro", Biochemical and Biophysical Research Communications, 126(1), (1985), 40-49.
De, B. P., et al., "Rescue of synthetic analogs of genome RNA of human parainfluenza virus type 3", Virology, 196(1), (Sep. 1993), 344-348.
De, B. P., et al., "Reverse Genetics of Negative Strand RNA Viruses", Indian Journal of Biochemistry & Biophysics, 31, (1994), 367-375.
De Filette, Marina, et al., "An influenza A vaccine based on tetrameric ectodomain of matrix protein 2", J Biol Chem. 2008 ; 283 (17):, (Feb. 5, 2008), 11382-7.
De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.
De La Luna, S., et al., "Influenza Virus NS1 Protein Enhances the Rate of Translation Initiation of Viral mRNAs", Journal of Virology, 69(4), (1995), 2427-2435.
Del Guidice, G., et al., "What are the limits of adjuvanticity?", (Abstract), Vaccine, 20(Suppl 1), S38-S41, (2001), 1 pg.
Desheva, J. A, et al., "Characterization of an influenza A H5N2 reassortant as a candidate for live-attenuated and inactivated vaccines against highly pathogenic H5N1 viruses with pandemic potential", Vaccine, 24, (2006), 6859-6866.
Desselberger, Ulrich, et al., "The 3' and 5'-terminal sequences of influenza A, B and C virus RNA segments are highly conserved and show partial inverted complementarity", Gene, 8 (3), (Feb. 1980), 315-328.
Dimmock, Nigel J, et al., "In vivo antiviral activity: defective interfering virus protects better against virulent Influenza A virus than avirulent virus", Journal of General Virology 87, (Jan. 8, 2006), 1259-1265.
Dimock, K., et al., "Rescue of Synthetic Analogs of Genomic RNA and Replicative-Intermediate RNA of Human Parainfluenza Virus Type 3", Journal of Virology, 67(5), (1993), 2772-2778.
Dollenmaier, G., et al., "Membrane-Associated Respiratory Syncytial Virus F Protein Expressed From A Human Rhinovirus Type 14 Vector Is Immunogenic", Virology, 281(2), (Mar. 15, 2001), 216-230.
Dos Santos Afonso, Emmanuel, et al., "The generation of recombinant influenza A viruses expressing a PB2 fusion protein requires the conservation of a packaging signal overlapping the coding and noncoding regions at the 5V end of the PB2 segment", Virology, 341, (2005), 34-46.
Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.
Du, Q., "Ribozyme Enzymology", http://academic.brooklyn.cuny.edu/chem/zhuang/QD/toppage1.htm, (Observed Feb. 25, 2003), 8 pgs.
Duff, K. C., et al., "The secondary structure of influenza A M2 transmembrane domain", FEBS Letters, 311 (3), (Oct. 1992), pp. 256-258.
Duff, K. C., et al., "The Transmembrane Domain of Influenza A M2 Protein Forms Amantadine-Sensitive Proton Channels in Planar Lipid Bilayers", Vilology, 190(1), (Sep. 1992), pp. 485-489.
Duhaut, S., et al., "Approximately 150 Nucleotides from the 5' End of an Influenza a segment 1 Defective Virion RNA Are needed for Genome Stability during passage of Defective Virus in Infected Cells", Virology, 275(2) 278-285 Academic Press, Orlando, US, (Sep. 30, 2000), 8 pgs.
Duhaut, S. D, et al., "Defective segment 1 RNAs that interfere with production of infectious influenza A virus require at least 150 nucleotides of 5' sequence: evidence from a plasmid-driven system", Journal of General Virology 83, (2002), 403-411.
Duhaut, S. D, et al., "Heterologous Protection of Misce from a lethal human HINI Influenza A Virus Infection by H3NB Equine Defective Interfering Virus: Comparison of Defective RNA Sequences Isolated from the DI Inoculum and Mouse Lung", Virology, 248(2), Academic Press, Orlando, US, (Sep. 1, 1998), 241-253.
Duhaut, Susan, et al., "Approximately 150 Nucleotides from the 5' End of an Influenza A Segment 1 defective virion RNA are Needed for Genome Stability During Passage of Defective Virus in Infected Cells.", Virology, 275(2), (2000), 278-285.
Dumoulin, Mireille, et al., "Single-domain antibody fragments with high conformational stability", Protein Science, 11, (2002), 500-515.
Dunham, Eleca J., et al., "Different Evolutionary Trajectories of European Avian-Like and Classical Swine H1N1 Influenza A Viruses", Journal of Virology, 83(11), (Jun. 2009), 5485-5494.
Dunn, E. F., et al., "Transcription of a recombinant bunyavirus RNA template by transiently expressed bunyavirus proteins", Virology, 211(1), (1995), 133-143.
Durbin, A. P, et al., "Human Parainfluenza Virus Type 3 (PIV3) Expressing the Hemagglutinin Protein of Measles Virus Provides A Potential Method for Immunization Against Measles Virus and PIV3 in Early Infancy", Journal of Virology, 74(15), (Aug. 2000), 6821-6831.
Durbin, A. P., et al., "Recovery of infectious human parainfluenza virus type 3 from cDNA", Virology, 235(2), (Sep. 1, 1997), 323-332.
Dyall, J., et al., ""Identification of inhibitors of Ebola virus with a subgenomic replication system"", Antiviral Research, 70(1), 19th International Conference on Antiviral Research, San Juan, PR (May 7-11, 20006), (May 2006), p. A39.
Elhefnawi, M, et al., "Identification of novel conserved functional motifs across most Influenza A viral strains", Virology Journal, 8:44, (2011), 10 pages.
Elliott, R. M., "Emerging Viruses: the Bunyaviridae", Molecular Medicine, 3(9), (1997), 572-577.
Elliott, R. M., et al., "Rescue of Infectious Bunyavirus Entirely From Cloned cDNA", 10th International Conference on Negative Strand Virus, (Abstract No. 96), (1997), 1 pg.
Elliott, R. M., et al., "Some Highlights of Virus Research in 1990", Journal of General Virology, 72(Part 8), (1991), 1761-1779.
Emerson, S. U., et al., "Both NS and L Proteins Are Required for In Vitro RNA Synthesis by Vesicular Stomatitis Virus", Journal of Virology, 15(6), (1975), 1348-1356.
Enami, K., et al., "Influenza virus NS1 protein stimulates translation of the M1 protein", Journal of Virology, 68 1432-1437, (1994), 6 pgs.
Enami, M., "An Influenza Virus Containing Nine Different RNA Segments", Virology, 185(1), (1991), 291-298.
Enami, M., et al., "High-Efficiency Formation of Influenza Virus Transfectants", Journal of Virology, 65(5), (1991), 2711-2713.
Enami, M., et al., "Introduction of Site-Specific Mutations Into the Genome of Influenza Virus", Proc. Natl. Acad. Sci. USA, 87, (1990), 3802-3805.
Enterlein, S., et al., "Antiviral Strategies Against : Exploring Gene Silencing Mechanisms to Identify Potential Antiviral Targets", Antiviral Research, 70(1), (Abstract 33), 19th International Conference on Antiviral Research, San Juan, PR (May 7-11, 2006), (May 2006), p. A38.
Enterlein, S., et al., "Untersuchungen zur Replikation und Transkription von Marburgund Ebolavirus", [Online]. 2005, Philipps-Universitat Marburg , XP002563470, Retrieved from the Internet:

(56) References Cited

OTHER PUBLICATIONS

<URL:http://deposit.ddb.de/cgi-bin/dokserv?>idn=977005607&dok_var=d1&dok_ext=pdf&filename=977005607 .pdf> [retrieved on Jan. 15, 2010], (2005), p. 70-p. 84.
Essere, Boris, et al., "Critical role of segment-specific packaging signals in genetic reassortment of influenza A viruses", Proc. Natl. Acad. Sci. USA, 110(40), (2013), E3840-E3848.
Fahey, J. L., et al., "Status of Immune-Based Therapies in HIV Infection and Aids", Clinincal and Experimental Immunology, 88(1), (1992), 1-5.
Fan, J, et al., "Preclinical study of influenza virus A M2 peptide conjugate vaccines in mice, ferrets, and rhesus monkeys", Vaccine, 22, (2004), 2993-3003.
Feng, L., et al., "The mouse Pol I terminator is more efficient than the hepatitis delta virus ribozyme in generating influenza-virus-like RNAs with precise 3' ends in a plasmid-only-based virus rescue system", Arch Virol., 154(7), (2009), 1151-6.
Fields, S., et al., "Nucleotides Sequences of Influenza Virus Segments 1 and 3 Reveal Mosaic Structure of Small Viral RNA Segment", Cell, 28, (1982), 303-313.
Fischer, W. B, et al., "Viral ion channels: structure and function.", Biochim Biophys Acta., 1561(1), (Mar. 19, 2002), 27-45.
Flandorfer, A., et al., "Chimeric Influenza A Viruses with a Functional Influenza B Virus Neuraminidase or Hemagglutinin", Journal of Virology, 77(17), (2003), 9116-9123.
Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(10), (2006), 860-869.
Fodor, E., et al., "Rescue of Influenza A Virus from Recombinant DNA", Journal of Virology, 73(11), XP002151487; ISSN:0022-538X, (Nov. 1999), 9679-9682.
Forbes, Nicole E, et al., "Multifunctional Adaptive NS1 Mutations Are Selected upon Human Influenza Virus Evolution in the Mouse", Plos One, vol. 7, No. 2, (Feb. 21, 2012), 20 pgs.
Fortes, P., et al., "Influenza Virus NS1 Protein Inhibits Pre-mRNA Splicing and Blocks mRNA Nucleocytoplasmic Transport", The EMBO Journal, 13(3), (1994), 704-712.
Fouchier, R. A. M., et al., "Avian Influenze A Virus (H7N7) Associated With Human Conjunctivitis and a Fatal Case of Acute Respiratory Distress Syndrome", Proc. Natl. Acad. Sci. USA, 101(5) 1356-1361, (2004), 6 pgs.
Friers, et al., "Soluble recombinant influenza vaccines", Phil. Trans. R. Soc. Lond. B (2001). vol. 356 1961-1963, (2001), 4 pgs.
Fuji, Y., et al., "Selective incorporation of influenza virus RNA segments into virions", Proc. Natl. Acad. Sci. USA, 100(4) 2002-2007, (2003), 6 pgs.
Fujii, Ken, et al., "Importance of both the Coding and the Segment-Speci?c Noncoding Regions of the In?uenza A Virus NS Segment for Its Ef?cient", Journal of Virology, 79(6), (Mar. 2005), 3766-3774.
Fujii, Y, et al., "The packaging of influenza viral genome", Virus, 52 (1), Uirusu (Japanese Journal Name), (Jun. 2002), 203-206.
Gao, Qinshan, et al., "A Nine-Segment In?uenza A Virus Carrying Subtype H1 and H3 Hemagglutinins", Journal of Virology, 84(16), (Aug. 2010), 8062-8071.
Gao, Qinshan, et al., "A Seven-Segmented Influenza A Virus Expressing the Influenza C Virus Glycoprotein HEF", Journal of Virology, 82(13), (Jul. 2008), 6419-6426.
Gao, Qinshan, et al., "The In?uenza A Virus PB2, PA, NP, and M Segments Play a Pivotal Role during Genome Packaging", Journal of Virology, 86(13), Chou, (Jul. 2011), 043-7051.
Garay, R. P, et al., "Cancer relapse under chemotherapy: why TLR2/4 receptor agonists can help", Eur J Pharmacol., 563(1-3), (Jun. 1, 2007), 1-17.
Garcia-Sastre, A., et al., "Genetic Manipulation of Negative-Strand RNA Virus Genomes", Annu. Rev. Microbiol., 47, (1993), 765-790.
Garcia-Sastre, A., et al., "Introduction of Foreign Sequences into the Genome of Influenza A Virus", Dev. Biol. Stand. Vol. 82, (1994), 237-246.
Garcia-Sastre, A., et al., "Introduction of Foreign Sequences into the Genome of Influenza A Virus", In: Recombinant Vectors in Vaccine Development. Dev. Biol. Stand., 82, Fred Brown, Editor, (1994), 237-246.
Garcia-Sastre, A., et al., "Introduction of foreign sequences into the genome of influenza A virus.", Dev Biol Stand., 82, (1994), 237-246.
Garcia-Sastre, A., et al., "The cytoplasmic tail of the neuraminidase protein of influenza A virus does not play an important role in the packaging of this protein into viral envelopes", Virus Research, 37(1), (1995), 37-47.
Garcia-Sastre, A., et al., "Use of a mammalian internal ribosomal entry site element for expression of a foreign protein by a transfectant influenza virus.", Journal of Virology, 68(10), (1994), 6254-6261.
Garcia-Sastre, Adolfo, et al., "Use of a Mammalian Internal Ribosomal Entry Site Element for Expression of a Foreign Protein by a Transfectant Influenza Virus", Journal of Virology, 68(10) 6254-6261, (Jun. 30, 1994), 8 pgs.
Garcin, D., et al., "A Highly Recombinogenic System for the Recovery of Infectious Sendal Paramyxovirus From cDNA: Generation of a Novel Copy-Back Nondefective Interfering Virus", The EMBO Journal, 14(24), (1995), 6087-6094.
Garrett, L., "Deadly Ebola, Avian Influenza Re-Emerging", Newsday.com, (Feb. 20, 2003), 3 pgs.
Genbank, "", ABD36884.1, (2007), 2 pgs.
Gerdil, C., "The Annual Production Cycle for Influenza Vaccine", Vaccine, 21 1776-1779, (2003), 4 pgs.
Ghate, Anita A, et al., "Influenza Type B Neuraminidase Can Replace the Function of Type A Neuraminidase", Virology, 264 (2), (Nov. 1999), 265-277.
Giddings, A M, et al., "The matrix protein of HIV-1 is not sufficient for assembly and release of virus-like particles", Virology, 248(1), (1998), 108-16.
Giles, Brendan Michael, "Development of Broadly Reactive Vaccine for Highly Pathogenic H5N1 Influenza", Retrieved from the Internet: URL<http//search.proquest.com/docview/928138363>, (Jan. 1, 2011), 283 pgs.
Gilleland, H. E, et al., "Chimeric Influenza Virus Incorporating Epitopes of Outer Membrane Protein F as a Vaccine Against Pulmonary Infection with Pseudomonas Aeruginosa", Behring Inst. Mitt. 98, (Feb. 28, 1997), 291-301.
Gomez-Puertas, P., et al., "Influenza Virus Matrix Protein Is the Major Driving Force in Virus Budding", Journal of Virology, 74 11538-11547, (Dec. 1, 2000), 10 pgs.
Gorman, O T, et al., "Evolution of influenza A virus PB2 genes: implications for evolution of the ribonucleoprotein complex and origin of human influenza A virus", J. Virol., 64(10), (Oct. 1990), 4893-4902.
Gotea, V, et al., "The functional relevance of somatic synonymous mutations in melanoma and other cancers", Pigment Cell & Melanoma Research, 28 issue 6, (Nov. 1, 15), 673-686.
Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.
Goto, Hideo, et al., "The Genome-Packaging Signal of the Influenza A Virus Genome Comprises a Genome Incorporation Signal and a Genome-Bundling Signal", Journal of Virology; vol. 87 No. 21, (Nov. 2013), 11316-11322.
Govorkova, E A, et al., "Replication of Influenza A Viruses in a Green Monkey Kidney Continuous Cell Line (Vero)", J. Infect. Dis. 172(1), (1995), 250-253.
Grambas, S., et al., "Influence of amantadine resistance mutations on the pH regulatory function of the M2 protein of influenza A viruses", Virology, 191(2), (Dec. 1992), 541-549.
Green, R. F., et al., "Glycosylation Does Not Determine Segregation of Viral Envelope Proteins in the Plasma Membrane of Epithelial Cells", J. Cell Biol., 89(2), (1981), 230-239.
Groseth, A., "13. Generation of Recombinant Ebola Viruses Using Reverse Genetics", In: Hoenen T., et al. (eds), Ebolaviruses: Methods and Protocols, Methods in Molecular Biology, vol. 162, (2017), 177-187.
Groseth, A., et al., "RNA Polymerase I-Driven Minigenome System for Ebola Viruses", Journal of Virology, 79(7), (2005), 4425-4433.

(56) References Cited

OTHER PUBLICATIONS

Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.
Gubareva, "Molecular mechanisms of influenza virus resistance to neuraminidase inhibitors", Virus Research, vol. 103, (2004), pp. 199-203.
Gunther, S, et al., "Application of real-time PCR for testing antiviral compounds against Lassa virus, SARS coronavirus and Ebola virus in vitro", Antiviral Research, Elsevier BV, NL, vol. 63, No. 3, XP004580000 ISSN: 0166-3542, (Sep. 1, 2004), 209-215.
Hagen, M., et al., "Recombinant Influenza Virus Polymerase: Requirement of both 5' and 3' Viral Ends for Endonuclease Activity", Journal of Virology, 68(3), (1994), 1509-1515.
Hai, Rong, et al., "Influenza B Virus NS1-Truncated Mutants: Live-Attenuated Vaccine Approach", Journal of Virology, 82(21), (2008), 10580-10590.
Halfmann, P., et al., "Generation of biologically contained Ebola viruses" Proceedings of the National Academy of Sciences of the United States of America 1129-1133, vol. 105, No. 4, XP002563467 ISSN: 1091-6490 the whole document, (Jan. 29, 2008), 6 pgs.
Halfmann, P., et al., "Replication-Deficient Ebolavirus as a Vaccine Candidate", Journal of Virology, vol. 83, No. 8 3810-3815, XP002563468; ISSN: 1098-5514; the whole document, (Apr. 2009), 6 pgs.
Halfmann, Peter J., et al., "Potent neutralization of SARS-COV-2 including variants of concern by vaccines presenting the receptor-binding domain multivalently from nanoscaffolds", Bioengineering & Translational Medicine, 6(3): e10253, (2021), 8 pgs.
Halperin, S. A., et al., "Safety and Immunogenicity of a Trivalent, Inactivated, Mammalian Cell Culture-Derived Influenza Vaccine in Healthy Adults, Seniors, and Children", Vaccine, 20 1240-1247, (2002), 8 pgs.
Harding, Alfred T, et al., "Rationally Designed Influenza Virus Vaccines That Are Antigenically Stable during Growth in Egg", MBIO, vol. 8, No. 3, eO0669-17, (Jul. 5, 2017), 1-16.
Harmsen, M. M., et al., "Properties, production, and applications of camelid single-domain antibody fragments", Appl Microbiol Biotechnol,77, (2007), 13-22.
Harty, R. N, et al., "A PPxY Motif within the VP40 Protein of Ebola Virus Interacts Physically and Functionally with a Ubiquitin Ligase: Implications for Filovirus Budding", Proc. Natl. Acad. Sci, 97 (25), (Dec. 5, 2000), 13871-13876.
Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.
Harvey, K. F, et al., "All three WW domains of murine Nedd4 are involved in the regulation of epithelial sodium channels by intracellular Na+.", J Biol Chem., 274(18), (Apr. 30, 1999), 12525-30.
Hatada, E., et al., "Binding of Influenza A Virus NS1 Protein to dsRNA in vitro", Journal of General Virology, 73, (1992), 3325-3329.
Hatakeyama, S., et al., "Dissection and identification of regions required to form pseudoparticles by the interaction between the nucleocapsid (N) and membrane (M) proteins of SARS coronavirus", Virology, 380(1), (2008), 99-108.
Hatakeyama, S., et al., "Emergence of Influenza B Viruses With Reduced Sensitivity to Neuraminidase Inhibitors", Journal of the American Medical Association, 297(13) 1435-1442, (Apr. 4, 2007), 8 pgs.
Hatakeyama, S., et al., "Enhanced Expression of an a2,6-Linked Sialic Acid on MDCK Cells Improves Isolation of Human Influenza Viruses and Evaluation of Their Sensitivity to a Neuraminidase Inhibitor", J Clin Microbiol, 43(8), (2005), 4139-4146.
Hatakeyma, S., et al., "The molecular basis of resistance to anti-influenza drugs", Japanese Journal of Clinical Medicine—Nippon Rinsho, 64(10) 1845-1852, (Oct. 1, 2006), 8 pgs.
Hatta, M., et al., "The NB protein of influenza B virus is not necessary for virus replication in vitro", Journal of Virology, 77(10), (May 2003), 6050-6054.
Hay, A. J., et al., "The role of the M2 protein in influenza A virus infection", Proceedings of the International Conference on Options for the Control of Influenza, Courchevel, (1992), 281-288.
He, B., et al., "Recovery of infectious SV5 from cloned DNA and expression of a foreign gene", Virology, 237(2), (1997), 249-260.
He, X., et al., "Generation of SARS-CoV-2 reporter replicon for high-throughput antiviral screening and testing", Proc. Natl. Acad. Sci. USA, 118(15): e2025866118, (2021), 8 pgs.
Helenius, A., "Unpacking the Incoming Influenza Virus", Cell, 69, (May 1992), pp. 577-578.
Hevey, Michael, et al., "Marburg virus vaccines based upon alphavirus replicons protect guinea pigs and nonhuman primates", Virology, 251(1), (Nov. 10, 1998), 28-37.
Hickman, Danielle, et al., "An avian live attenuated master backbone for potential use in epidemic and pandemic influenza vaccines", Journal of General Virology, 89(Part 11), (2008), 2682-2690.
Hiromoto, Y., et al., "Phylogenetic Analysis of the Three Polymerase Genes (PB1, PB2 and PA) of Influenza B Virus", Journal of General Virology, 81, (Apr. 2000), 929-937.
Hiti, A. L., et al., "P03470 —Neuraminidase", Entrez Protein Database, http://www.ncbi.nlm.nih.gov/entrez/viewer.fcgi?db=protein&val=84028231, (1982), 730-734.
Hiti, A. L., et al., "P03470—Neuraminidase", Entrez Protein Database, [online]. [retrieved on Aug. 30, 2006]. Retrieved from the Internet: <URL: http://www.ncbi.nlm.nih.gov/entrez/viewer.fcgi?db=protein&val=84028231>, (1982), 730-734 (8 pgs.).
Ho, Y., et al., "Assembly of human severe acute respiratory syndrome coronavirus-like particles", Biochem Biophys Res Commun, 318(4), (2004), 833-838.
Hoenen, T., et al., "11. Reverse Genetics Systems for Filoviruses", In: Perez, Daniel (Ed.), Reverse Genetics of RNA Viruses: Methods and Protocols, Methods in Molecular Biology, vol. 1602, (2017), 159-170.
Hoenen, Thomas, et al., "Minigenomes, Transcription and Replication Competent Virus-Like Particles and Beyong: Reverse Genetics Systgems for Filoviruses and other Negative Stranded Hemorrhagic Fever Viruses", Antiviral Res., 91:195, (2011), 30.
Hoffman, E., et al., "Ambisense Approach for the Generation of Influenza A Virus: vRNA and mRNA Synthesis from One Template", Virology 267(2) 310-317, (Feb. 15, 2006), 8 pgs.
Hoffman, Lucas R, et al., "Structure-Based Identification of an Inducer of the Low-pH Conformational Change in the Influenza Virus Hemagglutinin: Irreversible Inhibition of Infectivity", Journal of Virology , vol. 71, No. 11, (Nov. 1997), 8808-8820.
Hoffman, M. A., et al., "An Infectious Clone of Human Parainfluenza Virus Type 3", Journal of Virology, 71(6), (1997), 4272-4277.
Hoffmann, E., et al., "A DNA transfection system for generation of influenza A virus from eight plasmids", Proc Natl Acad Sci U S A., 97(11), (May 23, 2000), 6108-13.
Hoffmann, E., et al., "Ambisense Approach for the Generation of Influenza A Virus: vRNA and mRNA Synthesis from One Template", Virology, 267, (2000), 310-317.
Hoffmann, E., et al., "Eight-plasmid System for Rapid Generation of Influenza Virus (Vaccines", Vaccine, Butterworth Scientific Guildford, 20(25-56), (Aug., 19, 2002), 3165-3170.
Hoffmann, E., et al., "Rescue of Influenza B Virus from Eight Plasmids", Proceedings of the National Academy of Sciences of USA, National Academy of Science, 99(17), (Aug. 20, 2002), 11411-11416.
Hoffmann, Erich, et al., "A DNA transfection system for generation of influenza A virus from eight plasmids", Proceedings of the National Academy of Sciences, vol. 97, No. 11, (2000), 6108- 6113.
Holmes, E. C, et al., "Whole-Genome Analysis of Human Influenza A Virus Reveals Multiple Persistent Lineages and Reassortment Among Recent H3N2 Viruses", PLoS Biology, 3(9) 1579-1589, (2005), 11 pgs.
Holsinger, L. J., et al., "Influenza A Virus M2 Ion Channel Protein: a Structure-Function Analysis", Journal of Virology, 68 (3), (1994), pp. 1551-1563.

(56) References Cited

OTHER PUBLICATIONS

Honda, A., et al., "RNA Polymerase of Influenza Virus: Role of NP in RNA Chain Elongation", The Journal of Biochemistry, 104(6), (1988), 1021-1026.
Honda, Ayae, et al., "Differential Roles of Viral RNA and cRNA in Functional Modulation of the Influenza Virus RNA Polymerase", The Journal of Biological Chemistry, 276(33), (2001), 31179-31185.
Horimoto, "Designing Vaccines for Pandemic Influenza", Current Topics Microbiol Immunol 333, (2009), 165-176.
Horimoto, T., et al., "Enhanced growth of seed viruses for H5N1 influenza vaccines", Virology, 366(1), (Sep. 15, 2007), 23-27.
Horimoto, T., et al., "Generation of Influenza A Viruses with Chimeric (Type A/B) Hemagglutinins", Journal of Virology, 77(14) 8031-8038, (2003), 11 pgs.
Horimoto, T., et al., "Reverse Genetics Provides Direct Evidence for a Correction of Hemagglutinin Cleavability and Virulence of an Avian Influenza A Virus", Journal of Virology, 68(5), (1994), 3120-3128.
Horimoto, T., et al., "The Development and Characterization of H5 Influenza Virus Vaccines Derived from a 2003 Human Isolate", Vaccine, 24(17) 3669-3676, (2006), 8 pgs.
Hossain, M. J., et al., "Establishment and Characterization of a Madin-Darby Canine Kidney Reporter Cell Line for Influenza A Virus Assays", J Clin Microbiol, 48(7), (2010), 2515-2523.
Hsieh, P.-K., et al., "Assembly of Severe Acute Respiratory Syndrome Coronavirus RNA Packaging Signal into Virus-Like Particles Is Nucleocapsid Dependent", J Virol., 79(22), (2005), 13848-13855.
Huang, T. S, et al., "Determinaton of Influenza Virus Proteins Required for Genome Replication", Jounal of Virology, vol. 64 5669-5673, (1990), 5 pgs.
Huang, T.-S., et al., "Determination of Influenza Virus Proteins Required for Genome Replication", Journal of Virology, 64(11), (1990), 5669-5673.
Huang, Y., et al., "Generation of Synthetic Severe Acute Respiratory Syndrome Coronavirus Pseudoparticles: Implications for Assembly and Vaccine Production", J. Virol,, 78(22), (Nov. 2004), 12557-12565.
Huddleston, J. A., et al., "The Sequence of the Nucleoprotein Gene of Human Influenza A Virus, Strain A/NT/60/68", Nucleic Acids Research, 10(3), (1982), 1029-1038.
Huggins, J., et al., "Antiviral drug therapy of filovirus infections: S-adenosylhomocysteine hydrolase inhibitors inhibit Ebola virus in vitro and in a lethal mouse model.", Journal of Infectious Diseases, vol. 179, NR .(Suppl 1), XP002574255 ISSN: 0022-1899 abstract, (Feb. 1999), 240-247.
Hughes, M. T., et al., "Adaptation of Influenza A Viruses to Cells Expressing Low Levels of Sialic Acid Leads to Loss of Neuraminidase Activity", Journal of Virology, 75(8), (2001), 3766-3770.
Hughes, M. T., et al., "Influenza A Viruses Lacking Sialidase Activity Can Undergo Multiple Cycles of Replication in Cell Culture, Eggs, or Mice", Journal of Virology, 74 (11), (2000), 5206-5212.
Hughes, M. T, et al., "Influenza A Viruses Lacking Sialidase Activity Can Undergo Multiple Cycles of Replication in Cell Culture, Eggs, or Mice", Journal of Virology, 74(11) 5206-212, (2000), 7 pgs.
Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.
Hurt, A. C, et al., "Identification of a human influenza type B strain with reduced sensitivity to neuraminidase inhibitor drugs", Virus Research, vol. (103), (2004), 205-211.
Hutchinson, Edward C., et al., "Genome packaging in influenza A virus", Journal of General Virology, 91 (Pt 2), (2010), 313-328.
Hwang, Jung-Shan, et al., "Expression of Functional Influenza Virus RNA Polymerase in the Methylotrophic Yeast Pichia pastoris", Journal of Virology, 74(9), (2000), 4074-4084.
Isakova-Sivak, Irina, et al., "Characterization of Reverse Genetics-Derived Cold-Adapted Master Donor Virus A/Leningrad/134/17/57 (H2N2) and Reassortants with H5N1 Surface Genes in a Mouse Model", Clinical and Vaccine Immunology, 21(5), (May 2014), 722-731.
Ito, T, et al., "Differences in Sialic Acid-Galactose Linkages in the Chicken Egg Amnion and Allantois Influence Human Influenza Virus Receptor Specificity and Variant Selection", Journal of Virology, 71 (4), (Apr. 1997), 3357-3362.
Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.
Iwatsuki-Horimoto, K., et al., "The cytoplasmic tail of the influenza A virus M2 protein plays a role in viral assembly.", J Virol., 80(11), (Jun. 2006), 5233-40.
Jackson, et al., "Characterization of recombinant influenza B viruses with key neuraminidase inhibitor resistance mutations,", Journal of Antimicrobial Chemotherapy, vol. (55), (2005), 162-169.
Jackson, D., et al., "A reverse genetics approach for recovery of recombinant influenza B viruses entirely from cDNA.", J Virol., 76(22), (Nov. 2002), 11744-7.
Jahrling, P. B., et al., "Ebola Hemorrhagic Fever: Evaluation of Passive Immunotherapy in Nonhuman Primates", J. Infect. Dis. 196, (2007), 4 pgs.
Jang, S.-W., et al., "Deoxygedunin, a Natural Product with Potent Neurotrophic Activity in Mice", PLoS ONE 5(7): e11528, (2010), 1-15.
Jasenosky, Luke D, et al., "Ebola Virus VP40-Induced Particle Formation and Association with the Lipid Bilayer", Journal of Virology, 75 (110, (Jun. 2001), 5205-5214.
Jennings, Philip A., et al., "Does the Higher Order Structure of the Influenza Virus Ribonucleoprotein Guide Sequence Rearrangements in Influenza Viral RNA?", Cell, 34, (Sep. 1983), 619-627.
Jiang, H, et al., "Influenza virus genome C4 promoter/origin attenuates its transcription and replication activity by the low polymerase recognition activity", Virology, 408(2), (2010), 190-196.
Jiang, Y., et al., "Genome wide analysis of protein protein interactions and involvement of viral proteins in SARS CoV 2 replication", Cell Biosci, 11:140, 2021, 16 pgs., (2021), 16 pgs.
Jin, H., et al., "Imparting temperature sensitivity and attenuation in ferrets to A/Puerto Rico/8/34 influenza virus by transferring the genetic signature for temperature sensitivity from cold-adapted A/Ann Arbor/6/60", Journal of Virology, 78(2), (2004), 995-998.
Jin, H., et al., "Influenza virus hemagglutinin and neuraminidase cytoplasmic tails control particle shape", The EMBO Journal, 16(6), (1997), 1236-1247.
Jin, H., et al., "The influenza virus hemagglutinin cytoplasmic tail is not essential for virus assembly or infectivity", The EMBOL Journal, 13(22), (1994), 5504-5515.
Johnson, David A, et al., "TLR4 Agonists as Vaccine Adjuvants", Vaccine Adjuvants and Delivery Systems, (2007), 131-156.
Johnson, R. F., et al., "Ebola Virus VP35-VP40 Interaction Is Sufficient for Packaging 3E-5E Minigenome RNA into Virus-Like Particles", Journal of Virology, 80(11), (Jun. 2006), 5135-5144.
Ju, X., et al., "A novel cell culture system modeling the SARS-COV-2 life cycle", PloS Pathogens, 17(3): e1009439, (2021), 23 pgs.
Justice, P. A., et al., "Membrane Vesiculation Function and Exocytosis of Wild-Type and Mutant Matrix Proteins of Vesicular Stomatitis Virus", Journal of Virology, 69(5), (1995), 3156-3160.
Kang, Byoung-Hoon, et al., "Ultrafast and Real-Time Nanoplasmonic on-Chip Polymerase Chain Reaction for Rapid and Quantitative Molecular Diagnostics", ACS Nano, 15(6), (2021), 10194-10202.
Kaplan, G., et al., "In vitro Synthesis of Infectious Poliovirus RNA", Proc. Natl. Acad. Sci. USA, 82, (1985), 8824-8428.
Katinger, D., et al., "Attenuated Influenza Viruses as a Vector for Mucosal Immunization Against HIV-1", Vaccines, 97, Cold Spring Harbor, (1997), 315-319.
Kato, A., et al., "Initiation of Sendai Virus Multiplication From Transfected cDNA or RNA With Negative or Positive Sense", Genes to Cells, 1, (1996), 569-579.

(56) References Cited

OTHER PUBLICATIONS

Kawaoka, Y, et al., "Sequence requirements for cleavage activation of influenza virus hemagglutinin expressed in mammalian cells", Proc Natl Acad Sci., 85(2), (1988), 324-328.
Kawaoka, Y., "Identification by siRNA of host proteins involved in Ebolavirus replication", Great Lakes Regional Center of Excellence for Biodefense and Emerging Infectious Diseases Research, [Online]; Retrieved from the Internet: URL:http://www.rcebiodefense.org/gircе/docs/2007/Kawaoka.pdf> [retrieved on Jan. 13, 2010] p. 10, under item C, -& Anonymous: "Index of GLRCE: documents from 2007" Great Lakes Regional Center of Excellence Index, [Online] 2007, XP002563469 Retrieved from the Internet: URL:http://www.rcebiodefense.org/girce/docs/2007/> [retrieved on Jan. 14, 2010]-& Kawaoka Y.:, (2007), pp. 1-19.
Kawaoka, Y., "Mutant Cells With Altered Sialic Acid", U.S. Appl. No. 11/644,179 filed Dec. 22, 2006, 51 pgs.
Kawaoka, Y., "Prevention and Control of Ebola Virus Infection (Ongoing Research)", Great Lakes Regional Center of Excellence (GLRCE) Annual Meeting Schedule, (Abstract), [online] [retrieved on Jan. 14, 2010]. Retrieved from the Internet: <URL:http://www.rcebiodefense.org/girce/annualmeeting/2007Agenda.pdf>, (Nov. 29, 2007), 4 pgs.
Keitel, W. A., et al., "Chapter 28—Live Cold-Adapted, Reassortant Influenza Vaccines (USA)", In: Textbook of Influenza, Nicoholson, K. G., et al., Editors, Blackwell Science Ltd., (1998), 373-390.
Kijima, H., et al., "Therapeutic Application of Ribozymes", Pharmac. Ther., 68(2), (1995), 247-267.
Kilbourne, E. D, et al., "Related studies of a recombinant influenza-virus vaccine. I. Derivation and characterization of virus and vaccine", J Infect Dis., 124(5), (Nov. 1971), 449-62.
Kim, H., et al., "Cold adaptation generates mutations associated with the growth of influenza B vaccine viruses", Vaccine, 33(43), (2015), 5786-5793.
Kim, Min-Chul, et al., "Supplementation of Influenza Split Vaccines with Conserved M2 Ectodomains Overcomes Strain Specificity and Provides Long-term Cross Protection", Molecular Therapy, 22(7), (2014), 1364-1374.
Kimura, N., et al., "An In Vivo Study of the Replication Origin in the Influenza Virus Complementary RNA", The Journal of Biochemistry, 113(1), (1993), 88-92.
Kimura, N., et al., "Transcription of a Recombinant Influenza Virus RNA in Cells That Can Express the Influenza Virus RNA Polymerase and Nucleoprotein Genes", Journal of General Virology, 73, (1992), 1321-1328.
Kiseleva, I., et al., "Role of individual genes of the A-Leningrad/134/17/57 (H2N2) cold-adapted donor strain in manifestation of the temperature-sensitive phenotype of reassortant influenza A viruses", International Congress Series, vol. 1263, (2004), 547-550.
Kiseleva, Irina V, et al., "PB2 and PA genes control the expression of the temperature-sensitive phenotype of cold-adapted B/USSR/60/69 influenza master donor virus", Journal of General Virology, 91(4), (2010), 931-937.
Kistner, O., et al., "A Novel Mammalian Cell (Vero) Derived Influenza Virus Vaccine: Development, Characterization and Industrial Scale Production", Wiener Klinische Wochenschrift, 111/5, (1999), 207-214.
Kistner, O., et al., "Development of a mammalian cell (Vero) derived candidate influenza virus vaccine", Vaccine, 16(9-10), (May-Jun. 1998), 960-8.
Kistner, O., et al., "Development of a Vero Cell-Derived Influenza Whole Virus Vaccine", Dev. Biol. Stand., 98, (1999), 101-110.
Kistner, Otfried, et al., "Cell culture (Vero) derived whole virus (H5N1) vaccine based on wild-type virus strain induces cross-protective immune responses", Vaccine, 25(32), (2007), 6028-6036.
Kittel, Christian, et al., "Generation of an Influenza A Virus Vector Expressing Biologically Active Human Interleukin-2 from the NS Gene Segment", Journal of Virology, 79(16), (Aug. 2005), 10672-10677.
Kobayashi, H., et al., "A replication-incompetent influenza virus bearing the HN glycoprotein of human parainfluenza virus as a bivalent vaccine", Vaccine, 31(52), (2013), 6239-6246.
Kobayashi, M., et al., "Reconstitution of Influenza Virus RNA Polymerase From Three Subunits Expressed Using Recombinant Baculovirus System", Virus Research, 22, (1992), 235-245.
Ikochendoerfer, G. G, et al., "Total Chemical Synthesis of the Integral Membrane Protein Influenza A Virus M2: Role of its C-Terminal Domain in Tetramer Assembly", Biochemistry 38, (1999), 11905-11913.
Kon, Theone C, et al., "Influenza Vaccine Manufacturing: Effect of Inactivation, Splitting and Site of Manufacturing. Comparison of Influenza Vaccine Production Processes", PLoS ONE, 11(3), e0150700, (Mar. 9, 2016), 19 pgs.
Konarska, M. M., et al., "Structure of RNAs Replicated by the DNA-Dependent T7 RNA Polymerase", Cell, 63(2), (1990), 609-618.
Konduru, K., et al., "Ebola virus glycoprotein Fc fusion protein confers protection against lethal challenge in vaccinated mice", Vaccine, 29(16), (Apr. 5, 2011), 2968-77.
Koopmans, M., et al., "Transmission of H7N7 Avian Influenza Virus to Human Beings During a Large Outbreak in Commercial Poultry Farms in the Netherlands", The Lancet, 363 587-593, (2004), 7 pgs.
Kopecky, S. A, et al., "Matrix protein and another viral component contribute to induction of apoptosis in cells infected with vesicular stomatitis virus", J Virol., 75(24), (Dec. 2001), Abstract Only.
Kovacova, A., et al., "Sequence similarities and evolutionary relationships of influenza virus A hemagglutinins.", Virus Genes, 24(1), (2002), 57-63.
Kovesdi, I., et al., "Adenoviral Vectors for Gene Transfer", Current Opinion in Biotechnology, 8(5), (Oct. 1997), 583-589.
Krystal, M., et al., "Expression of the Three Influenza Virus Polymerase Proteins in a Single Cell Allows Growth Complementation of Viral Mutants", Proc. Natl. Acad. Sci. USA, 83, (1986), 2709-2713.
Krystal, M., "Influenza B/Lee/40, hemagglutinin (seg 4), complete segment.", Database EM_VI E.B.I. Hinxton U.K., (Apr. 25, 1990), 9 pgs.
Kugelman, J. R., et al., "Emergence of Ebola Virus Escape Variants in Infected Nonhuman Primates Treated with the MB-003 Antibody Cocktail", Cell Reports 12, (Sep. 2015), 2111-2120.
Kumar, P. K. R., et al., "Artificial Evolution and Natural Ribozymes", The FASEB Journal, 9, (1995), 1183-1195.
Kunik, Vered, et al., "Paratome: an online tool for systematic identification of antigen-binding regions in antibodies based on sequence or structure", Nucleic Acids Research, vol. 40, Issue W1, (2012), W521-W524.
Kunkel, T. A., "Rapid and Efficient Site-Specific Mutagenesis Without Phenotypic Selection", Proc. Natl. Acad. Sci. USA, 82, (1985), 488-492.
Kuwahara, Tomoko, et al., "Characterization of cell-derived and egg-passaged influenza A/Saitama/103/2014 (H3N2) strain", The 65th Annual Meeting of the Japanese Society of Virology, (2017), 1 pg.
Kuwahara, Tomoko, et al., "Isolation of an Egg-Adapted Influenza A(H3N2) Virus without Amino Acid Substitutions at the Antigenic Sites of Its Hemagglutinin", Japanese Journal of Infectious Diseases, 71(3), (2018), 234-238.
Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.
Latham, T, et al., "Formation of Wild-Type and Chimeric Influenza Virus-Like Particles following Simultaneous Expression of Only Four Structural Proteins", Journal of Virology 75 (13), (2001), 6154-6165.
Lawson, N. D., "Recombinant Vesicular Stomatitis Viruses From DNA", Proc. Natl. Acad. Sci. USA, 92(10), (1995), 4477-4481.
Laxman, B., "Noninvasive Real-Time Imaging of Apoptosis", PNAS, 99(26), (2002), 16551-16555.
Lazarovits, Janette, et al., "Endocytosis of Chimeric Influenza Virus Hemaggulutinin Proteins That Lack a Cytoplasmic Recognition Feature for Coated Pits", The Journal of Cell Biology, vol. 134, No. 2, (1996), 339-348.

(56) References Cited

OTHER PUBLICATIONS

Le, T., "CaSpeR5, a family of *Drosophila* transgenesis and shuttle vectors with improved multiple cloning sites", Biotechniques, 42(2), (Feb. 2007), 164-166.
Leahy, M. B., et al., "An Endonuclease Switching Mechanism in the Virion RNA and cRNA Promoters of Thogoto Orthomyxovirus", Journal of Virology, 72(3), (1998), 2305-2309.
Leahy, M. B., et al., "In Vitro Polymerase Activity of Thogoto Virus: Evidence for a Unique Cap-Snatching Mechanism in a Tick-Borne Orthomyxovirus", Journal of Virology, 71(11), (1997), 8347-8351.
Leahy, M. B., et al., "Striking Conformational Similarities between the Transcription Promoters of Thogoto and Influenza A Viruses: Evidence for Intrastrand Base Pairing in the 5' Promoter Arm", Journal of Virology, 71(11), (1997), 8352-8356.
Leal, et al., "New challenges in therapeutic vaccines against HIV infection", Expert Review of Vaccines, vol. 16, No. 6, (2017), 587-600.
Lee, C. W, et al., "Generation of reassortant influenza vaccines by reverse genetics that allows utilization of a DIVA (Differentiating Infected from Vaccinated Animals) strategy for the control of avian influenza", Vaccine, vol. 22, (2004), 3175-3181.
Lee, D.-H., et al., "H9N2 avian influenza virus-like particle vaccine provides protective immunity and a strategy for the differentiation of infected from vaccinated animals", Vaccine, vol. 29, (2011), 4003-4007.
Lee, Dong-Hun, et al., "Progress and hurdles in development of influenza virus-like particle vaccines for veterinary use", Korean Vaccine Society, (2014), 133-139.
Lee, Jeffrey E., et al., "Complex of a Protective Antibody with Its Ebola Virus GP Peptide Epitope: Unusual Features of a V?x Light Chain", J. Mol. Biol., 375, (2007), 202-216.
Lee, Jong-Soo, et al., "The Highly Conserved HA2 Protein of the Influenza A Virus Induces a Cross Protective Immune Response", Journal of Virological Methods, 194(1-2), (2013), 280-288.
Lee, M. S, et al., "Genetic and pathogenic characterization of H6NI avian influenza viruses isolated in Taiwan between 1972 and 2005", Avian Diseases, 50(4), (Dec. 2006), 561-571.
Lefranc, Marie-Paule, et al., "IMGT unique numbering for immunoglobulin and T cell receptor variable domains and Ig superfamily V-like domains", Developmental & Comparative Immunology, 27, (2003), 55-77.
Lembo, A, et al., "Administration of a synthetic TLR4 agonist protects mice from pneumonic tularemia.", J Immunol., 180(11), 7574-81.
Levis, R., et al., "Deletion Mapping of Sindbis Virus DI RNAs Derived From cDNAs Defines the Sequences Essential for Replication and Packaging", Cell, 44, (1986), 137-145.
Li, et al., "Selection of antigenically advanced variants of seasonal influenza viruses", Nature Microbiology, 1 (6), (2016), 1-10.
Li, Feng, et al., "Generation of Replication-Competent Recombinant Influenza A Viruses Carrying a Reporter Gene Harbored in the Neuraminidase Segment", Journal of Virology, 84(22), (Nov. 2010), 12075-12081.
Li, Junwei, et al., "Engineering Influenza Viral Vectors", Bioengineered, vol. 4, No. 1, (Jan. 1, 2013), 9-14.
Li, K. S., et al., "Genesis of a highly pathogenic and potentially pandemic H5N1 influenza virus in eastern Asia", Nature, vol. 430, (2004), 209-213 pgs.
Li, K. S, et al., "Genesis of a highly pathogenic and potentially pandemic H5NI influenza virus in eastern Asia", Nature, 430(6996), (Jul. 8, 2004), 209-213.
Li, Qi, et al., "Screening of the high yield influenza B virus on MDCK cell and cloning of its whole genome", (English Abstract), Chinese Journal of Virology, 3, (Sep. 30, 2004), 1 pg.
Li, Qi, et al., "Screening of the high yield influenza B virus on MDCK cell and cloning of its whole genome", International Congress Series 1263, (2004), 610-614.
Li, S., et al., "Electroporation of Influenza Virus Ribonucleoprotein Complexes for Rescue of the Nucleoprotein and Matrix Genes", Virus Research, 37(2), (1995), 153-161.
Li, S., et al., "Influenza A Virus Transfectants with Chimeric Hemagglutinins Containing Epitopes from Different Subtypes", Journal of Virology, 66(1), (1992), 399-404.
Li, S., et al., "Recombinant Influenza A Virus Vaccines for the Pathogenic Human A/Hong Kong/97 (H5N1) Viruses", J Infect Dis., 179(5), (1999), 1132-1138.
Li, Shengqiang, et al., "Influenza A Virus Transfectants with Chimeric Hemagglutinins containing Epitopes from different subtypes", Journal of Virology 399-404, (1992), 6 pgs.
Li, Y, et al., "The I binding specificity of human VH4-34 (VH4-21) encoded antibodies is determined by both VH framework region 1 and complementarity determining region 3", J. Mol. Biol. 256 577-589, (1996), 13 pgs.
Li, Y, et al., "Viral liposomes released from insect cells infected with recombinant baculovirus expressing the matrix protein of vesicular stomatitis virus", Journal of Virology, 67 (7), (1993), 4415-4420.
Lin, Y P, et al., "Adaptation of egg-grown and transfectant influenza viruses for growth in mammalian cells: selection of hemagglutinin mutants with elevated pH of membrane fusion", Virology, 233(2), (1997), 402-410.
Lin, Yi Pu, et al., "Adaptation of Egg-Grown and Transfectant Influenza Viruses for Growth in Mammalian Cells: Selection of Hemagglutinin Mutants with Elevated pH of Membrane Fusion", Virology, vol. 233, Issue 2, (1997), 402-410.
Liu, Bo, et al., "Comparison of three methods in construction fusion gene of influenza A virus Nucleoprotein", (English Abstract), Zhonghua Shi Yan He Lin Chuang Bing Du Xue Za Zhi, 26(1), 70-74, (Feb. 2012), 1 pg.
Liu, C., et al., "Influenza type A virus neuraminidase does not play a role in viral entry, replication, assembly, or budding.", Journal of Virology, 69(2), (1995), 1099-1106.
Liu, C., et al., "Selection and Characterization of a Neuraminidase-Minus Mutant of Influenza Virus and its Rescue by Cloned Neuraminidase Genes", Virology, 194(1), (1993), 403-407.
Liu, Y., et al., "A live-attenuated SARS-CoV-2 vaccine candidate with accessory protein deletions", bioRxiv [online]. [retrieved Jun. 10, 2022]. Retrieved from the Internet: <URL: https://www.biorxiv.org/content/10.1101/2022.02.14.480460v1.full.pdf>, (2022), 44 pgs.
Liu, Z, et al., "Fine mapping of the antigen-antibody interaction of scFv215 A recombinant antibody inhibiting RNA polymerase II from *Drosophila melanogaster*", J. Mol. Recog. 12:103-111. (1999). 9 pgs.
Lobo, Ingrid A., "Predicting Vaccine Effectiveness Using Systems Biology", Nature Education, 8(3):9, [online]. Retrieved from the Internet: <URL: https://www.nature.com/scitable/nated/topicpage/predicting-vaccine-effectiveness-using-systems-biology-132628443>, (2015), 4 pgs.
Longnecker, R., et al., "WWW- and SH3-domain interactions with Epstein-Barr virus LMP2A", Exp Cell Res., 257(2), (Jun. 15, 2000), Abstract Only.
Lott, W. B., et al., "A Two-Metal Ion Mechanism Operates in the Hammerhead Ribozyme-Mediated Cleavage of an RNA Substrate", Proc. Natl. Acad. Sci. USA, 95, (1998), 542-547.
Lu, Xiuhua, et al., "Cross-protective immunity in mice induced by live-attenuated or inactivated vaccines against highly pathogenic influenza A (H5N1) viruses", Vaccine, 24(44-46), (2006), 6588-6593.
Lugovtsev, V. Y., et al., "Genetic Composition and Mutational Pattern of Influenza B Viruses Adapted to Replication in Embryonated Eggs", GenBank: AAT69446.1, (2005), 1 pg.
Luo, M., "Inhibitors of Influenza Virus Neuraminidase", Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.
Luytjes, W., "Amplification, Expression, and Packaging of a Foreign Gene by Influenza Virus", Cell, 59(6), (1989), 1107-1113.
Ma, Y.-J., et al., "Cellular micro RNA let-7c inhibits M1 protein expression of the H1N1 influenza A virus in infected human lung epithelial cells", J. Cell. Mol. Med., 16(10), (2012), 2539-2546.
Manicassamy, Balaji, et al., "Analysis of in vivo dynamics of influenza virus infection in mice using a GFP reporter virus", Proc Natl Acad Sci. USA, 107(25), (2010), 11531-11536.

(56) References Cited

OTHER PUBLICATIONS

Mansky, L. M, "Retrovirus mutation rates and their role in genetic variation", J Gen Virol., 79 (Pt 6), (Jun. 1998), 1337-45.
Manz, Benjamin, et al., "Disruption of the Viral Polymerase Complex Assembly as a Novel Approach to Attenuate Influenza A Virus", The Journal of Biological Chemistry, 286(10), (2011), 8414-8424.
Mark, A, et al., "Effect of Mutations and Deletions in a Bicistronic mRNA on the Synthesis of Influenza B Virus NB and NA Glycoproteins", Journal of Virology, vol. 77, No. 10, (May 2003), 6050-6054.
Marsh, Glenn A., et al., "Specific Residues of the Influenza A Virus Hemagglutinin Viral RNA Are Important for Efficient Packaging into Budding Virions", Journal of Virology, 81(18), (Sep. 2007), 9727-9736.
Martin, J., et al., "Studies of the Binding Properties of Influenza Hemagglutinin Receptor-Site Mutants", Virology, 241(1), (Feb. 1, 1998), 101-111.
Martinez-Sobrido, L., et al., "Hemagglutinin-Pseudotyped Green Fluorescent Protein-Expressing Influenza Viruses for the Detection of Influenza Virus Neutralizing Antibodies", J Virol., 84(4), (2010), 2157-2163.
Martorelli Di, Genova B., et al., "Intestinal delta-6-desaturase activity determines host range for Toxoplasma sexual reproduction", PLOS Biology, vol. 17, No. 8, E3000364, (Aug. 20, 2019), XP055619380, (Aug. 20, 2019), 1-19.
Marzi, et al., "An Ebola whole-virus vaccine is protective in nonhuman primates", Science 348(6233) 439-442, (Apr. 2015), 4 pgs.
Masuda, H., et al., "Substitution of Amino Acid Residue in Influenza A Virus Hemagglutinin Affects Recognition of Sialyl-Oligosaccharides Containing N-Glycolylneuraminic Acid", FEBS Letters, 464, (1999), 71-74.
Matrosovich, M, et al., "Overexpression of the [alpha]-2,6-sialyltransferase in MDCK cells increases influenza virus sensitivity to neuraminidase inhibitors", Journal of Virology, the American Society for Microbiology, US, vol. 77, No. 15, (Aug. 1, 2003), 8418-8425.
Matsuoka, et al., "Neuraminidase Stalk Length and Additional Glycosylation of the Hemagglutinin Influence the Virulence of Influenza H5N1 Viruses for Mice", Journal of Virology, vol. 83, No. 9,, (2009), pp. 4704-4708.
Matsuzaki, Y., et al., "Epitope Mapping of the Hemagglutinin Molecule of A/(H1N1)pdm09 Influenza Virus by Using Monoclonal Antibody Escape Mutants", Journal of Virology, 88(21) 12364-12373, (2014), 10 pgs.
Matta, M, et al., "Cell-surface sialoglycoconjugate structures in wild-type and mutant Crithidia fasciculata", Parasitol. Res., 85(4), (1999), 293-299.
McCown, M F, et al., "The influenza A virus M2 cytoplasmic tail is required for infectious virus production and efficient genome packaging.", J Virol., 79(6), (Mar. 2005), 3595-605.
McCown, M. F, et al., "Distinct domains of the influenza a virus M2 protein cytoplasmic tail medlate binding to the M1 protein and facilitate infectious virus production.", J Virol., 80(16), (Aug. 2006), 8178-89.
McCullers, et al., "Multiple Genotypes of Influenza B Virus Circulated between 1979 and 2003,", Journal of Virology, vol. (78), No. (23) 12817-12828, (2004), 13 pgs.
McCullers, Jonathan A., et al., "A single amino acid change in the C-terminal domain of the matrix protein M1 of influenza B virus confers mouse adaption and virulence", Virology, 336(2) 318-326, (Jun. 5, 2005), 9 pgs.
McKee, Dwight L, et al., "Candidate drugs against SARS-CoV-2 and COVID-19", Pharmacological Research, Academic Press, London, GB, vol. 157, (Apr. 29, 2020), 9 pgs.
McKimm, J. L., et al., "Mutations in a Conserved Residue in the Influenza Virus Neuraminidase Active Site Decreases Sensitivity to Neu5Ac2en-Derived Inhibitors", Journal of Virology, 72(3), (1998), 2456-2462.
McSharry, J. J, et al., "Phenotypic Drug Susceptibility Assay for Influenza Virus Neuraminidase Inhibitors", Cinical and Diagnostic Laboratory Immunology vol. (11), No.(2)., (2004), 10 pgs.
Mebatsion, Teshome, et al., "Budding of Rabies Virus Particles in the Absence of the Spike Glycoprotein", Cell, 84(6), (1996), 941-951.
Mebatsion, Teshome, et al., "Matrix Protein of Rabies Virus Is Responsible for the Assembly and Budding of Bullet-Shaped Particles and Interacts with the Transmembrane Spike Glycoprotein G", Journal of Virology, 73 (1), (Jan. 1999), 242/250.
Mena, L., "Rescue of a Synthetic Choramphenicol Acetyltransferase RNA into influenza Virus-Like Particles obtained from recombinant plasmids", Journal of Virology, 70(8), (1996), 5016-5024.
Mena, I., et al., "Synthesis of biologically active influenza virus core proteins using a vaccinia virus- T7 RNA polymerase expression system", Journal of General Virology, 75 2109-2114, (1994), 6 pgs.
Mena, I., et al., "Synthesis of Biologically Active Influenza Virus Core Proteins Using a Vaccinia Virus-T7 RNA Polymerase Expression System", Journal of General Virology, 75, (1994), 2109-2114.
Mishin, V. P, et al., "Protection afforded by intranasal immunization with the neuraminidase-lacking mutant of influenza A virus in a ferret model", Vaccine, 23(22), (Apr. 22, 2005), 2922-7.
Mitnaul, et al., "The Cytoplasmic Tail of Influenza a Virus Neuraminidase (NA) Affects NA Incorporation into Virons, Viron Morphology, and Virulence in Mice but is not essential for Virus Replication", Journal of Virology, 70 (2), (1996), 873-879.
Mitnaul, L. J., et al., "Balanced Hemagglutinin and Neuraminidase Activities are Critical for Efficient Replication of Influenza A Virus", Journal of Virology, 74 (13), (2000), 6015-6020.
Mittler, E., et al., "Role of the transmembrane domain of marburg virus surface protein GP in assembly of the viral envelope.", J Virol., 81(8), (Apr. 2007), 3942-8.
Miyoshi, H., et al., "Development of Self-Inactivating Lentivirus Vector", Journal of Virology, 72(10), (1998), 8150-8157.
Monto, A. S, et al., "Detection of influenza viruses resistant to neuraminidase inhibitors in global surveillance during the first 3 years of their use", Antimicrobal Agents and Chemotherapy, 50(7) 2395-2402, (2006), 8 pgs.
Monto, Arnold S, et al., "Comparative efficacy of inactivated and live attenuated influenza vaccines.", N Engl J Med., 361(13) 1260-7, (Sep. 24, 2009), 8 pgs.
Morita, S., et al., "Plat-E: an efficient and stable system for transient packaging of retroviruses", Gene Therapy, 7(12), (2000), 1063-1066.
Moss, B., et al., "New Mammalian Expression Vectors", Nature, 348, (1990), 91-92.
Moyer, S. A., et al., "Assembly and Transcription of Synthetic Vesicular Stomatitis Virus Nucleocapsids", Journal of Virology, 65(5), (1991), 2170-2178.
Muhlberger, E., et al., "Comparision orf the Transcription and Replication Strategies of Marburg Virus and Ebola Virus by Using Artificial Replication Systems", Journal of Virology, 73(3) 2333-2342, (1999), 10 pgs.
Muhlberger, E., et al., "Three of the four nucleocapsid proteins of Marburg virus,NP VP35, and L, are sufficient to mediate replication and transcription of Marburg virus-specific monocistronic minigenomes", Joumal of Virology, 72(11) 8756-8764, (1998), 11 pgs.
Muhlberger, Elke, "Filovirus replication and transcription", Future Virol., 2:205, (2007), 16 pgs.
Murakami, Shin, et al., "Enhanced Growth of Influenza Vaccine Seed Viruses in Vero Cells Mediated by Broadening the Optimal pH Range for Virus Membrane Fusion", J Virol 86(3), (2012), 1405-1410.
Murakami, Shin, et al., "Growth Determinants for H5N1 Influenza Vaccine Seed Viruses in MDOK Cells", Journal of Virology, vol. 82, No. 21, (Nov. 2008), 10502-10509.
Muramoto, Y., et al., "Hierarchy among Viral RNA (vRNA) Segments in Their Role in vRNA Incorporation into Influenza A Virions", J. Virol., 80(5), (2006), 2318-2325.
Muramoto, Yukiko, "Hierarchy among Viral RNA (vRNA) Segments in Their Role in vRNA Incorporation into Influenza A Virions", Journal of Virology, 80(5), (2006), 2318-2325.

(56) References Cited

OTHER PUBLICATIONS

Murphy, B. R, et al., "An influenza A live attenuated reassortant virus possessing three temperature-sensitive mutations in the PB2 polymerase gene rapidly loses temperature sensitivity following replication in hamsters", Vaccine, 15(12-13) 1372-8, (1997), 7 pgs.
Murphy, Brian R, et al., "Virulence of Avian Influenza A Viruses for Squirrel Monkeys", Infection and Immunity 37 (3), (Sep. 1982), 1119-1126.
Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.
Muyldermans, S, "Nanobodies: Natural single-domain antibodies", Ann. Rev. Biochem. 82, (2013), 1 pg.
Naim, H. Y., et al., "Basis for Selective Incorporation of Glycoproteins into the Influenza Virus Envelope", Journal of Virology, 67(8), (1993), 4831-4841.
Naito, S., et al., "Function and Structure of RNA Polymerase From Vesicular Stomatitis Virus", The Journal of Biological Chemistry, 251(14), (1976), 4307-4314.
Nara, et al., "How Can Vaccines Against Influenza and Other Viral Diseases Be Made More Effective?", PLoS Biology, 8 (12), (2010), e1000571.
Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.
Neirynck, S., "A universal influenza A vaccine based on the extracellular domain of the M2 protein", Nature Medicine, 5 (10), (Oct. 1999), pp. 1157-1163.
Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.
Neumann, G., et al., "A Decade After the Generation of a Negative-Sense RNA Virus From Cloned cDNA-What Have We Learned?", Journal of General Virology, 83(11), (Nov. 2002), 2635-2662.
Neumann, G., et al., "An Improved Reverse Genetics System for Influenza A Virus Generation and Its Implications for Vaccine Production", Proc. Natl. Acad. Sci. USA, 102(46) 16825-16829, (2005), 5 pgs.
Neumann, G., et al., "An improved reverse genetics system for influenza A virus generation and its implications for vaccine production", Proc. Natl. Acad. Sci. USA. 102(46), (2005), 16825-16829.
Neumann, G., et al., "Emergence and pandemic potential of swine-origin HIN1 influenza virus", Nature (London), 459(7249), (Jun. 2009), 931-939.
Neumann, G., et al., "Generation of influenza A virus from cloned cDNAs—historical perspective and outlook for the new millenium.", Rev Med Virol., 12(1), XP002314285, (Jan.-Feb. 2002), 13-30.
Neumann, G., et al., "Generation of influenza A viruses entirely from cloned cDNAs", Proc. Natl. Acad. Scl. USA., 96(16), (1999), 9345-9350.
Neumann, G., et al., "Genetic Engineering of Influenza and Other Negative-Strand RNA Viruses Containing Segmented Genomes", Advances in Virus Research, 53, (1999), 265-300.
Neumann, G., et al., "Influenza A virus NS2 protein mediates vRNP nuclear export through NES-independent interaction with hCRM1", The EMBO Journal, 19 (24), (2000), 6751-6758.
Neumann, G., et al., "Mutational analysis of influenza virus promoter elements in vivo", Journal of General Virology, 76 1709-1717, (1995), 9 pgs.
Neumann, G., et al., "Nuclear Import and Export of Influenza Virus Nucleoprotein", Journal of Virology, 71(12), (1997), 9690-9700.
Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.
Neumann, G., et al., "Reverse genetics of influenza virus.", Virology, 287(2), (Sep. 1, 2001), 243-50.
Neumann, G., et al., "Reverse Genetics of Influenza Viruses—Applications in Research and Vaccine Design", Monographs in Virology, 27, (2008), 118-133.
Neumann, G., et al., "RNA Polymerase I-Mediated Expression of Influenza Viral RNA Molecules", Virology, 202(1), (1994), 477-479.
Neumann, G., et al., "Synthesis of Influenza Virus: New impetus from an old enzyme, RNA polymerase I", Virus Research 82(1-2), (Jan. 30, 2002), 153-158.
Neumann, Gabriele, "Minireview Reverse Genetics of Influenza Virus", Virology, vol. 287. (2001), 243-250.
Neumann, Gabriele, et al., "Reverse Genetics Demonstrates that Proteolytic Processing of the Ebola Virus Glycoprotein Is Not Essential for Replication in Cell Culture", Journal of Virology, 76 (1), (Jan. 2002), 406-410.
Nicolson, C., et al., "Generation of Influenza Vaccine Viruses on Vero Cells by Reverse Genetics: an H5N1 Candidate Vaccine Strain Produced Under a Quality System", Vaccine, 23 2943-2952, (2005), 10 pgs.
Niwa, H., et al., "Efficient Selection for High-Expression Transfectants With a Novel Eukaryotic Factor", Gene, 108(2), (1991), 193-199.
Noda, Takeshi, et al., "Three-dimensional analysis of ribonucleoprotein complexes in influenza A virus", Nature Communications, 3, (2012), 1-6.
Odagiri, T., et al., "Nucleotide Sequence of the PA Gene of Influenza A/WSN/33 (H1N1)", Nucleic Acids Research, 18 (3), Department of Virology, (Jan. 9, 1990), 1 pg.
Odagiri, Takato, et al., "Segment-Specific Noncoding Sequences of the In?uenza Virus Genome RNA Are Involved in the Speci?c Competition between Defective Interfering RNA and Its Progenitor RNA Segment at the Virion Assembly Step", Journal of Virology, 71(3), (1997), 2138-2145.
Olivo, P. D, et al., "Detection and quantitation of human respiratory syncytial virus (RSV) using minigenome cDNA and a Sindbis virus replicon: a prototype assay for negative-strand RNA viruses.", Virology, 251(1), (Nov. 10, 1998), 198-205.
Onishi, M., et al., "Applications of retrovirus-mediated expression cloning", Experimental Hematology, 24(2), (1996), 324-329.
Orkin, S. H, et al., "Report and Recommendations of the Panel to Assess the NIH Investment in Research on Gene Therapy", http://www.nih.gov/news/panelrep.html, (Dec. 7, 1995), 37 pgs.
Ozaki, "Generation of High-Yielding Influenza A Viruses in African Green Monkey Kidney (Vero) Cells by Reverse Genetics", J Virol 78(4), (2004), 1851-1857.
Ozaki, H., et al., "Generation of High-Yielding Influenza A Viruses in African Green Money Kidney (Vero) Cells by Reverse Genetiics", Journal of Virology, 78(4) 1851-1857, (2004), 6 pgs.
Ozawa, M., et al., "An adenovirus vector-mediated reverse genetics system for Influenza A virus generation", Journal of Virology, The American society for Microbiology, US vol. 81 (17), XP002471230, ISSN: 0022-538X, (Jun. 27, 2007), 9556-9559.
Ozawa, M., et al., "Replication-incompetent influenza A viruses that stably express a foreign gene", Journal of General Virology, 92(Part 12)., (2011), 2879-2888.
Palache, A. M., et al., "Safety, Reactogenicity and Immunogenicity of Madin Darby Canine Kidney Cell-Derived Inactivated Influenza Subunit Vaccine. A Meta-Analysis of Clinical Studies", Dev. Biol. Stand., 98 133-134 abstract, (1999), 1 pg.
Palese, P., et al., "47. Orthomyxoviridae: The Viruses and Their Replication", In: Fields Virology (5th Edition), (2007), 90 pgs.
Palese, P., "Negative-Strand RNA Viruses: Genetic Engineering and Applications", Proc. Natl. Acad. Sci. USA, 93(21), (1996), 11354-11358.
Park, Eun K., et al., "The M2 Ectodomain is important for its incorporation into influenza A virions", J. of Virology, vol. 72, No. 3, XP002196797, (Mar. 1998), 2449-2455.
Park, K. H., et al., "Rescue of a Foreign Gene by Sendai Virus", Proc. Natl. Acad. Sci. USA, 88, (1991), 5537-5541.
Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.

(56) References Cited

OTHER PUBLICATIONS

Pattnaik, A. K., et al., "The Termini of VSV DI Particle RNAs are Sufficient to Signal RNA Encapsidation, Replication, and Budding to Generate Infectious Particles", Virology, 206, (1995), 760-764.
Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.
Peiris, J. S. M., et al., "Re-Emergence of Fatal Human Influenza A Subtype H5N1 Disease", The Lancet, 363 617-619, (2004), 3 pgs.
Pekosz, A., "Commentary—Reverse Genetics of Negative-Strand RNA Viruses: Closing the Circle", Proc. Natl. Acad. Sci. USA, 96, (1999), 8804-8806.
Pekosz, A., et al., "Influenza C virus CM2 integral membrane glycoprotein is produced from a polypeptide precursor by cleavage of an internal signal sequence", PNAS, vol. 95, XP002196653, (Oct. 1998), 13233-13238.
Pelet, T., et al., "High throughput screening assay for negative single stranded RNA virus polymerase inhibitors", Journal of Virological Methods, 128 29-36, (2005), 8 pgs.
Percy, N., et al., "Expression of a Foreign Protein by Influenza A Virus", Journal of Virology, 68(7), (1994), 4486-4492.
Perdue, M., et al., "Virulence and the Avian Influenza Virus Hemagglutinin Gene", United States Department of Agriculture—Agriculture Research Service, http://www.nps.ars.usda.gov/publications/publications.htm?SEQ_NO_155=106036, (Observed Feb. 22, 2003), 1 pg.
Perez, D. R., et al., "The Matrix 1 Protein of Influenza A Virus Inhibits the Transcriptase Activity of a Model Influenza Reporter Genome in Vivo", Virology, 249(1), (1998), 52-61.
Perez, Jasmine T., et al., "Unit 15G.4 - Insertion of a GFP Reporter Gene in Influenza Virus", Curr Protoc Microbiol., (2013), 20 pgs.
Peterson, B. C., et al., "Homologous sequences other than insertion elements can serve as recombination sites in plasmid drug resistance gene amplification", Journal of Bacteriology, Oct. 1983. 156(1) 177-185, (1983), 5 pgs.
Piatti, G., "Identification of immunodominant epitopes in the filamentous Hemagglutinin of Bordetella pertusis", FEMS Immunology and Medical Microbiology, 23(3), (1999), 235-241.
Piller, S C., et al., "Vpr protein of human immunodeficiency virus type 1 forms cation-selective channels in planar lipid bilayers", PNAS, 93, (1996), 111-1115.
Ping, J., et al., "Development of high-yield influenza B virus vaccine viruses", Proc. Natl. Acad. Sci. USA, 113(51), (Dec. 5, 2016), E8296-E8305.
Ping, Jihui, et al., "Development of high-yield influenza A virus vaccine viruses", Nature Communications, [online]. Retrieved from the Internet: <http://www.nature.com/article-assets/npg/ncomms/2015/150902/ncomms9148/extref/ncomms9148-sl.pdf>, (Sep. 2, 2015), 50 pgs.
Pinto, L. H., et al., "Influenza Virus M2 Protein Has Ion Channel Activity", Cell, 69, (May 1992), pp. 517-528.
Pittman, Kelly J., et al., "Z-DNA Binding Protein Mediates Host Control of Toxoplasma gondii Infection", Infection and Immunity, 84(10), (Oct. 2016), 3063-3070.
Plant, E P, et al., "Mutations to A/PuertoRico/8/34 PB1 gene improves seasonal reassortant influenza A virus growth kinetics", Vaccine, 31(1), (Dec. 1, 2012), 207-212.
Pleschka, S., et al., "A Plasmid-Based Reverse Genetics System for Influenza A Virus", Journal of Virology, 70(6), (1996), 4188-4192.
Pley, H. W., et al., "Three-Dimensional Structure of a Hammerhead Ribozyme", Nature, 372, (1994), 68-74.
Popova, Lyubov, et al., "Immunodominance of Antigenic Site B over Site of Hemagglutinin of Recent H3N2 Influenza Viruses", PLOS ONE, vol. 7 No. 7, (Jul. 25, 2012), e41895.
Portela, A., et al., "Replication of orthomyxoviruses", Advances in Virus Research, 54, (1999), 319-348.
Potter, C. W., "Chapter 1—Chronicle of Influenza Pandemics", In: Textbook of Influenza, Nicoholson, K. G., et al., Editors, (Blackwell Scientific Publication), (1998), 3-18.
Powell, Robin H., et al., "WRN conditioned media is sufficient for in vitro propagation of intestinal organoids from large farm and small companion animals", Biology Open, vol. 6, No. 5, (Mar. 27, 2017), XP055620505, (Mar. 27, 2017), 698-705.
Preston, Andrew, "Choosing a Cloning Vector", Methods in Molecular Biology, vol. 235, *E. coli* Plasmid Vectors 19-27, Edited by: N. Casali and A. Preston, (2003), 9 pgs.
Pushko, P., et al., "Replicon-Helper Systems from Attenuated Venezuelan Equine Encephalitis Virus: Expression of Heterologous Genes in Vitro and Immunization against Heterologous Pathogens in Vivo", Virology, 239(2), (Abstract Only), (1997), 1 page.
Puzelli, S., et al., "Changes in the Hemagglutinins and Neuraminidase of Human Influenza B Viruses Isolated in Italy During the Feb. 2001, Mar. 2002, and Apr. 2003 Seasons", Journal of Medical Virology, 74(4) 629-640, (2004), 12 pgs.
Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.
Qiu, Y., et al., "The Influenza Virus NS1 Protein Is a Poly(A)-Binding Protein That Inhibits Nuclear Export of mRNAs Containing Poly(A)", Journal of Virology, 68(4), (1994), 2425-2432.
Racaniello, V. R., et al., "Cloned Poliovirus Complimentary DNA Is Infectious in Mammalian Cells", Science, 214, (1981), 4 pgs.
Radecke, F., et al., "Rescue of Measles Viruses From Cloned DNA", The EMBO Journal, 14(23), (1995), 5773-5784.
Radecke, F., et al., "Reverse Genetics Meets the Nonsegmented Negative-Strand RNA Viruses", Reviews in Medical Virology, 7, (1997), 49-63.
Ramanunninair, Manojkumar, et al., "Molecular Signature of High Yield (Growth) Influenza A Virus Reassortants Prepared as Candidate Vaccine Seeds", PLoS ONE, 8(6): e65955, (2013), 1-16.
Ray, M. K., et al., "A Novel Glycosylation Phenotype Expressed by Lec23, a Chinese Hamster Ovary Mutant Deficient in alpha-Glucosidase I", Journal of Biological Chemistry, 266(34), (1991), 22818-22825.
Rayner, J., et al., "Alphavirus vectors and vaccination", Reviews in Medical Virology, 12, (2002), 279-296.
Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.
Restifo, N. P., et al., "Transfectant Influenza A Viruses are Effective Recombinant Immunogens in the Treatment of Experimental Cancer", Virology, 249(1), (1998), 89-97.
Ricardo-Lax, I., et al., "Replication and single-cycle delivery of SARS-CoV-2 replicons". Science, 374(6571), (2021), 1099-1106 (9 pgs).
Rimmelzwaan, G. F., et al., "Use of GFP-expressing influenza viruses for the detection of influenza virus A/H5N1 neutralizing antibodies", Vaccine, 29(18), (2011), 3424-3430.
Roberts, A., et al., "Minireview—Recovery of Negative-Strand RNA Viruses From Plasmid DNAs: a Positive Approach Revitalizes a Negative Field", Virology, 247(1), (1998), 1-6.
Robison, C. S, et al., "The Membrane-Proximal Stem Region of Vesicular Stomatitis Virus G Protein Confers Efficient Virus Assembly", Journal of Virology, 74 (5), (Mar. 2000), 2239-2246.
Rodrigues, M., et al., "Influenza and Vaccinia Viruses Expressing Malaria CD8+ T and B Cell Epitopes. Comparison of Their Immunogenicity and Capacity to Induce Protective Immunity", J. Immunol., 153(10), (1994), 4636-4648.
Romanova, J., et al., "Live cold-adapted influenza A vaccine produced in Vero cell line", Virus Research, 103, (2004), 187-193.
Rose, J. K., "Positive Strands to the Rescue Again: a Segmented Negative-Strand RNA Virus Derived From Cloned cDNAs", Proc. Natl. Acad. Sci. USA, 94, (1996), 14998-15000.
Ruigrok, R W, et al., "Characterization of three highly purified influenza virus strains by electron microscopy", J Gen Virol 65 (Pt 4) 799-802, (Apr. 1984), 4 pgs.
Ruigrok, R W, et al., "Structural Characterization and Membrane Binding Properties of the Matrix Protein VP40 of Ebola Virus", Journal of Molecular Biology, 300(1), (2000), 103-112.
Ruiz-Arguello, M. B, et al., "Phosphatidylinositol-Dependent Membrane Fusion Induced by a Putative Fusogenic Sequence of Ebola Virus", Journal of Virology, 72(3), (Mar. 1998), 1775-1781.

(56) References Cited

OTHER PUBLICATIONS

Sansom, M. S., et al., "Influenza virus M2 Protein: a molecular modelling study of the ion channel", Protein Engineering, 6 (1), (1993), pp. 65-74.
Saphire, E. O., et al., "Feverish Quest for Ebola Immunotherapy: Straight or Cocktail", Trends Microbial, 24(9), (Sep. 2016), 684-686.
Satterlee, B., "Production of H5N1 avian influenza virus vaccine by plasmid-based reverse genetics technology", Basic Biotechnology eJournal, vol. 4, pp. 93-98, (2008). 93-98 Pgs.
Saunders, Kevin O., et al., "Neutralizing antibody vaccine for pandemic and pre-emergent coronaviruses", Nature, 594, (2021), 553-559 (27 pgs.).
Schares, G., et al., "Oocysts of Neospora caninum, Hammondia heydorni, Toxoplasma gondii and Hammondia hammondi in faeces collected from dogs in Germany", International Journal of Parasitology, vol. 35, No. 14, (Dec. 1, 2005), XP027737007, (Dec. 1, 2005), 1525-1537.
Schickli, J. H, et al., "Plasmid-only Rescue of Influenza A Virus Vaccine Candidates", Philosophical Transactions of the Royal Society of London. Series B, Biological Sciences, 356(1416), (Dec. 29, 2001), 1965-1973.
Schlesinger, S., "RNA Viruses as Vectors for the Expression of Heterologous Proteins", Molecular Biotechnology, 3(2), (1995), 155-165.
Schmidt, Kristina Maria, et al., "Marburg Virus Reverse Genetics Systems", Viruses 2016, 8, 178; doi: 10.3390 / v8060178, www.mdpi.com/journal/viruses, (2016), 17 pgs.
Schnell, M. J., "Infectious Rabies Viruses From Cloned cDNA", The EMBO Journal, 13(18), (1994), 4195-4203.
Schnell, Matthias J, et al., "Requirement for a non-specific glycoprotein cytoplasmic domain sequence to drive efficient budding of vesicular stomatitis virus", EMBO Journal, 17 (5), (1998), 1289-1296.
Schotsaert, M, et al., "Universal M2 ectodomain-based influenza A vaccines: preclinical and clinical developments", Expert Rev Vaccines. Apr. 2009;8(4):, 499-508.
Schultz-Cherry, S., et al., "Influenza Virus NS1 Protein Induces Apoptosis in Cultured Cells", Journal of Virology, 75(17), (2001), 7875-7881.
Seong, B. L., et al., "A New Method for Reconstituting Influenza Polymerase and RNA in Vitro: a Study of the Promoter Elements for cRNA and vRNA Synthesis in Vitro and Viral Rescue in Vivo", Virology, 186(1), (1992), 247-260.
Sheridan, Cormac, et al., "Innovators target vaccines for variants and shortages in global South", Nature Biotechnology, 39(4), (Apr. 2021), 393-396.
Shi, Pei-Yong, "Infectious cDNA Clone of the Epidemic West Nile Virus from New York City", Journal of Virology 5847-5856, (Jun. 2002), 10 pgs.
Shimojima, M., et al., "Tyro3 family-mediated cell entry of Ebola and Marburg viruses", J Virol., 80(20), (Oct. 2006), 10109-16.
Shinya, Kyoko, et al., "Characterization of a Neuraminidase-Deficient Influenza A Virus as a Potential Gene Delivery Vector and a Live Vaccine", Journal of Virology, 78(6), (2004), 3083-3088.
Shortridge, K. F., et al., "Characterization of Avian H5N1 Influenza Viruses From Poultry in Hong Kong", Virology, 252 331-342, (1998), 12 pgs.
Sidhu, M. S., et al., "Rescue of Synthetic Measles Virus Minireplicons: Measles Genomic Termini Direct Efficient Expression and Propagation of a Reporter Gene", Virology, 208, (1995), 800-807.
Silvas, J. A., et al., "Contribution of SARS-CoV-2 Accessory Proteins to Viral Pathogenicity in K18 Human ACE2 Transgenic Mice", J Virol, 95(17): e00402-21, (Sep. 2021), 1-14.
Siu, Y. L., et al., "The M, E, and N Structural Proteins of the Severe Acute Respiratory Syndrome Coronavirus Are Required for Efficient Assembly, Trafficking, and Release of Virus-Like Particles", J Virol., 82(22), (2008), 11318-11330.
Skehel, J. J., et al., "On the Mechanism of Inhibition of Influenza Virus Replication by Amantadine Hydrochloride", The Journal of General Virology, 38 (1), (1977), pp. 97-110.
Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.
Stray, S. J., et al., "Influenza virus infection of desialylated cells", Glycobiology, 10(7), (2000), 649-658.
Strobel, I., et al., "Efficient Expression of the Tumor-Associated Antigen MAGE-3 in Human Dendritic Cells, Using an Avian Influenza Virus Vector", Human Gene Therapy, 11(16), (2000), 2207-2218.
Stroud, Chad K., et al., "Disruption of FADS2 gene in mice impairs male reproduction and causes dermal and intestinal ulceration", Journal of Lipid Research, vol. 50, (2009), 1870-1880.
Subbarao, E. K., et al., "Rescue of an InfluenzaA Virus Wild-Type PB2 Gene and a Mutant Derivative Bearing a Site-Specific Temperature-Sensitive and Attenuating Mutation", Journal of Virology, 67(12), (1993), 7223-7228.
Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.
Subbarao, K., et al., "Characterization of an Avian Influenza A (H5N1) Virus Isolated From a Child With a Fatal Respiratory Illness", Science, 279, (1998), 393-396.
Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5, 2003), 192-200.
Sugawara, K., et al., "Development of Vero Cell-Derived Inactivated Japanese Encephalities Vaccine", Biologicals, 30 303-314, (2002), 12 pgs.
Sugrue, R. J., et al., "Specific structural alteration of the influenza haemagglutinin by amantadine", The EMBO Journal, 9 (11), (1990), pp. 3469-3476.
Sugrue, R. J., et al., "Structural Characteristics of the M2 Protein of Influenza A Viruses: Evidence That It Forms a Tetrameric Channel", Virology, 180, (1991), pp. 617-624.
Suguitan, A. L, et al., "Live, Attenuated Influenza A H5N1 Candidate Vaccines Provide Broad Cross-Protection in Mice and Ferrets", PLoS Med., 3(9), (2006), 1541-1555.
Sun, Weina, et al., "Development of Influenza B Universal Vaccine Candidates Usingthe "Mosaic" Hemagglutinin Approach", American Society for Microbiology, Journal of Virology, Vaccines and Antiviral Agents, vol. 93, Issue 12, (Jun. 2019), 17 pgs.
Sunstrom, N. A., et al., "Ion Channels formed by NB, an influenza B virus Protein", J. of Membrane Biology, vol. 150, XP002196654, (Dec. 1996), 127-132.
Sweet, T. M., et al., "Creation of amantadine resistant clones of influenza type A virus using a new transfection procedure.", J Virol Methods., 69(1-2), (Dec. 1997), 103-11.
Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.
Taira, K., et al., "Construction of a novel RNA-transcript-trimming plasmid which can be used both in vitro in place of run-off and (G)-free transcriptions and in vivo as multi-sequences transcription vectors", Nucleic Acids Research, 19(19), (1991), 5125-5130.
Takada, A., et al., "Downregulation of beta1 integrins by Ebola virus glycoprotein: implication for virus entry", Virology, 278(1), (Dec. 2000), Abstract Only.
Takada, Ayato, et al., "A system for functional analysis of Ebola? virus?glycoprotein", Proc. Natl. Acad. Sci. USA, 94(26), (1997), 14764-14769.
Takada, Ayato, et al., "Identification of Protective Epitopes on Ebola Virus Glycoprotein at the Single Amino Acid Level by Using Recombinant Vesicular Stomatitis Viruses", Journal of Virology, 77(2), (2003), 1069-1074.
Takada, Ayato, et al., "Protective efficacy of neutralizing antibodies against Ebola virus infection", Vaccine, 25(6), (2007), 993-999.
Takada, Ayato, et al., "The pathogenesis of Ebola hemorrhagic fever", Trends in Microbiology, 9(10), (2001), 506-511.

(56) References Cited

OTHER PUBLICATIONS

Takada, Kosuke, et al., "A Humanized MDCK Cell Line for the Efficient Isolation and Propagation of Human Influenza Viruses", Nature Microbiology, Nature Publishing Group UK, London, vol. 4, No. 8, (Apr. 29, 2019), 1268-1273.
Takeda, M., et al., "Influenza a virus M2 ion channel activity is essential for efficient replication in tissue culture.", J Virol., 76(3), (Feb. 2002), 1391-9.
Takeda, T., et al., "Expression of Podocalyxin Inhibits Cell-Cell Adhesion and Modifies Junctional Properties in Madin-Darby Canine Kidney Cells", Molecular Biology of the Cell, 11, (2000), 3219-3232.
Takeuchi, K., et al., "Influenza Virus M2 Protein Ion Channel Activity Stabilizes the Native Form of Fowl Plague Virus Hemagglutinin during Intracellular Transport", Journal of Virology, 68 (2), (Feb. 1994), pp. 911-919.
Tan, Tiong Kit, et al., "A COVID-19 vaccine candidate using SpyCatcher multimerization of the SARS-CoV-2 spike protein receptor-binding domain induces potent neutralising antibody responses", Nature Communications, 12: 542, (2021), 1-16.
Tang, et al., "Recombinant adenovirus encoding the HA gene from swine H3N2 influenza virus partially protects mice from challenge with heterologous virus: AIHK/1/68 (H3N2)", Archives of Virology, vol. 147 2125-2141, (2002), 17 pgs.
Tannock, G. A, et al., "Relative immunogenicity of the cold-adapted influenza virus A/Ann Arbor/6/60 (A/AA/6/60-ca), recombinants of A/AA/6/60-ca, and parental strains with similar surface antigens.", Infect Immun., 43(2), (Feb. 1984), 457-62.
Taylor, J., et al., "Newcastle Disease Virus Fusion Protein Expressed in a Fowlpox Virus Recombinant Confers Protection in Chickens", Journal of Virology, 64(4), (1990), 1441-1450.
Terry, G., et al., "The Contruction of Defective Interfering Rubella Virus Particles", Archives of Virology, 145(3), (2000), 625-633.
Tetsutani, K., et al., "Adjuvants in Influenza Vaccines", Vaccine 2012, vol. 30, (2012), 4 pgs.
Thao, Tran Thi Nhu, et al., "Rapid reconstruction of SARS-CoV-2 using a synthetic genomics platform", Nature, vol. 582 561-565, (2020), 24 pgs.
Theriault, S., "The role of reverse genetics systems in determining filovirus pathogenicity", Archives of Virology, Supplementum. 157-177, (2005), 22 pgs.
Thompson, Christine M, et al., "Critical assessment of influenza VLP production in Sf9 and HEK293 expression systems", BMC Biotechnology, 15(1), (May 16, 2015), 12 pgs.
Thompson, W. W., et al., "Mortality Associated With Influenza and Respiratory Syncytial Virus in the United States", JAMA, 289(2) 179-186, (2003), 8 pgs.
Tobler, K, et al., "Effect of cytoplasmic tail truncations on the activity of the M(2) ion channel of influenza A virus", J Virol., 73(12), (Dec. 1999), 9695-9701.
Towner, J S, et al., "Generation of eGFP express ing recombinant Zaire ebolavirus for analysis of early pathogenesis events and high-throughput antiviral drug screening"; Virology, Academic Press , Orlando, US, vol. 332, No. 1 20-27, XP004715289 ISSN: 0042-6822 the whole document, (Feb. 5, 2005), 8 pgs.
Treanor, J. J, et al., "The B allele of the NS gene of avian influenza viruses, but not the A allele, attenuates a human influenza a virus for squirrel monkeys", Virology, 171(1), (1989), 1-9.
Uraki, R., et al., "A Bivalent Vacine Based on a PB2-Knockout Influenza Virus Protects Mice From Secondary Pneumoccal Pneumonia", The Journal of Infectious Diseases, 212(12), (2015), 1939-1948.
Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.
Vaishnava, Shipra, et al., "The Antibacterial Lectin RegIIIy Promotes the Spatial Segregation of Microbiota and Host in the Intestine", Science, 334 255-258, (2011), 4 pgs.
Vanessa, Monteil, et al., "Inhibition of SARS-CoV-2 Infections in Engineered Human Tissues Using Clinical-Grade Soluble Human ACE2", Cell, vol. 181 905-913, Retrieved from the Internet: <URL:https://www.ncbi.nlm.nih.gov/pmc/articles/PMC7181998/pdf/main.pdf>, (Apr. 24, 2020), 17 pgs.
Varner, Chad, "Developing Synthetic Multivalent Cellular Effectors", Thesis, School of Chemical and Biomolecular Engineering, Georgia Institute of Technology, (Aug. 2017), 88 pgs.
Verma, I. M, et al., "Gene Therapy—Promises, Problems and Prospects", Nature, 389, (1997), 239-242.
Via, L. E, et al., "Isolation of restriction fragments from large plasmids recovered from bacteria with multiple plasmids", Biotechniques, 11(4), (Oct. 1991), Abstract Only.
Victor, Sylvia, et al., "A Replication-Incompetent PB2-Knockout Influenza A Virus Vaccine Vector", Journal of Virology, vol. 86, No. 8, (Apr. 2012), 4123-4128.
Victor, Sylvia T., et al., "A Replication-Incompetent PB2-Knockout Influenza A Virus Vaccine Vector", Journal of Virology, 2012, 86(8):4123; DOL: 10.1128/JVI.06232-11. Journals.ASM.org;, Downloaded from http://jvi.asm.org/ on Aug. 20, 2012 by Univ. of Wisonsin—Mad, (Feb. 1, 2012), 7.
Vincke, C, et al., "Introduction to heavy chain antibodies and derived nanobodies", Meth. Mol. Biol. 911, (2012), 13 pgs.
Voeten, J. T, et al., "Characterization of high-growth reassortant influenza A viruses generated in MDCK cells cultured in serum-free medium", Vaccine, vol. 17, (1999), 1942-1950.
Volchkov, Viktor E, et al., "Recovery of Infectious Ebola Virus from Complementary DNA: RNA Editing of the GP Gene and Viral Cytotoxicity", Science Magazine, 291, (Mar. 2001). 1965-1969.
Von Wielink, R., et al., "Mutations in the M-Gene Segment can Substantially Increase Replication Efficiency of NS1 Deletion Influenza A Virus in MCK Cells", Journal of Virology. vol. 86, (2012), 12341-12350.
Waap, Helga, et al., "In vitro isolation and seroprevalence ofin stray cats and pigeons in Lisbon, Portugal", Veterinary Parasitology, vol. 187, No. 3 XP028492469 542-547, (Jan. 17, 2012), 6 pgs.
Wagner, R., et al., "Interdependence of hemagglutinin glycosylation and neuraminidase as regulators of influenza virus growth: a study by reverse genetics", Journal of Virology, 74 (14), (Jul. 2000), 6316-6323.
Walker, W. S, et al., "HEL-Flu: an influenza virus containing the hen egg lysozyme epitope recognized by CD4+ T cells from mice transgenic for an alphabeta TCR", J. Immunol., 159(6), (Sep. 1997), 2563-2566.
Wang, et al., "Glycoengineering of CHO Cells to Improve Product Quality", Methods in Molecular Biology book series (MIMB, vol. 1603) 25-44, (May 11, 2017), 256 pgs.
Wang, B., et al., "Construction of Non-infectious SARS-CoV-2 Replicons and Their Application in Drug Evaluation", Virologica Sinica, 36, (2021), 890-900.
Wang, C., et al., "Ion Channel Activity of Influenza A Virus M2 Protein: Characterization of the Amantadine Block", Journal of Virology, 67 (9), (Sep. 1993), pp. 5585-5594.
Wang, Weijia, et al., "Identification of Critical Residues in the Hemagglutinin and Neuraminidase of Influenza Virus H1N1pdm for Vaccine Virus Replication in Embryonated Chicken Eggs", Journal of Virology, 87(8), (2013), 4642-4649.
Wang, Wenlig, et al., "Robust Immunity and Heterologous Protection against Influenza in Mice Elicited by a Novel Recombinant NP-M2e Fusion Protein Expressed in *E. coli*", PLoS ONE 7(12): e52488, (Dec. 2012), 1-13.
Ward, C. D., et al., "Direct Measurement of the Poliovirus RNA Polymerase Error Frequency In Vitro", Journal of Virology, 62(2), (1988), 558-562.
Wareing, M. D, et al., "Immunogenic and isotype-specific responses to Russian and US cold-adapted influenza a vaccine donor strains A/Leningrad/134/17/57, A/Leningrad/134/47/57, and A/Ann Arbor/6/60 (H2N2) in mice.", J Med Virol., 65(1), (Sep. 2001), 171-7.
Warfield, et al., "", PNAS, vol. 100(26), (2003), pp. 5889-15894.
Watanabe, S., et al., "Ebola virus (EBOV) VP24 inhibits transcription and replication of the EBOV genome", J Infect Dis., 196(Suppl 2), (Nov. 15, 2007), S284-90.

(56) References Cited

OTHER PUBLICATIONS

Watanabe, S., et al., “Influenza A Virus Lacking M2 Protein as a Live Attenuated Vaccine” Journal of Virology, 83(11), (2009), 5947-5950.
Watanabe, S., et al., “Production of Novel Ebola Virus-Like Particles from cDNAs: an Alternative to Ebola Virus Generation by Reverse Genetics”, Journal of Virology, 78(2), (Jan. 2004), 999-1005.
Watanabe, T., et al., “Influenza A virus can undergo multiple cycles of replication without M2 ion channel activity”, J Virol., 75(12), (Jun. 2001), 5656-62.
Watanabe, T., et al., “Influenza A Virus with Defective M2 Ion Channel Activity as a Live Vaccine”, Virology, 299(2), (Aug. 1, 2002), 266-270.
Watanabe, T., et al., “Novel Approach to the Development of Effective H5N1 In?uenza A Virus Vaccines: Use of M2 Cytoplasmic Tail Mutants”, Journal of Virology, 82(5), (2008), 2486-2492.
Watanabe, Tokiko, et al., “Exploitation of Nucleic Acid Packaging Signals to Generate a Novel In?uenza Virus-Based Vector Stably Expressing Two Foreign Genes”, Journal of Virology, 77(19), (Oct. 2003), 10575-10583.
Watanabe, Tokiko, et al., “Exploitation of Nucleic Acid Packaging Signals to Generate a Novel Influenza Virus-Based Vector Stably Expressing Two Foreign Genes”, Journal of Virology, 77(19), (Oct. 2003), 10575-10583.
Watanabe, Tokiko, et al., “Influenza A Virus Can Undergo Multiple Cycles of Replication without M2 Ion Channel Activity”, Journal of Virology 75(12), (2001), 5656-5662.
Weber, F., et al., “Conserved vRNA end sequences of Thogoto-orthomyxovirus suggest a new panhandle structure”, Archives of Virology, 142(5), (1997), 1029-1033.
Weber, F., et al., “Nucleoprotein Viral RNA and mRNA of Thogoto Virus: a Novel “Cap-Stealing” Mechanism in Tick-Borne Othomyxoviruses?”, Journal of Virology, 70(12), (1996), 8361-8367.
Webster, R G, et al., “Evolution and molecular epidemiology of H9N2 influenza A viruses from quail in southern China”, XP002744257, retrieved from EBI accession No. UNIPROT:A3R6C9 Database accession No. A3R6C9 the whole document, (Apr. 3, 2007), 1 pg.
Wei, Hung-Ju, et al., “Fabrication of influenza virus-like particles using M2 fusion proteins for imaging single viruses and designing vaccines”, Vaccine, 29, (2011), 7163-7172.
Wei, Kai, et al., “Influenza A Virus Acquires Enhanced Pathogenicity and Transmissibility after Serial Passages in Swine”, Journal of Virology, 88(20), (Oct. 2014), 11981-11994.
Wentworth, D E, et al., “The NIAID Influenza Genome Sequencing Project”, XP002744258, retrieved from EBI accession No. UNIPROT:U3S198 Database accession No. U3S198 the whole document, (Dec. 11, 2013), 1 pg.
Whelan, S. P. J., et al., “Efficient Recovery of Infectious Vesicular Stomatitis Virus Entirely from cDNA Clones”, Proc. Natl. Acad. Sci. USA, 92, (1995), 8388-8392.
Wiedmer, T., et al., “Identification of three new members of the phospholipid scramblase gene family”, Biochim Biophys Acta, 1467(1), (Jul. 31, 2000), Abstract Only.
Williams, Mark A., et al., “Effect of Mutations and Deletions in a Bicistronic mRNA on the Synthesis of Influenza B Virus NB and NA Glycoproteins”, Journal of Virology, 63(1), (1989), 28-35.
Wills, J. W., et al., “An Assembly Domain of the Rous Sarcoma Virus Gag Protein Required Late in Budding”, Journal of Virology, 68(10), (1994), 6605-6618.
Wilson, et al., “Vaccine Potential of Ebola Virus VP24, VP30, VP35 and VP40 Proteins”, Virology 286, (2001), 384-90.
Wilson, Julie A, et al., “Epitopes Involved in Antibody-Mediated Protection from Ebola Virus”, Science, 287(5458), (Mar. 2000), 1664-1666.
Winkler, K, et al., “Changing the antigen binding specificity by single point mutations of an anti-p24 (HIV-1) antibody”, J. Immunol. 165 4505-4514, (2000), 11 pgs.
Winter, G., et al., “The use of synthetic oligodeoxynucleotide primers in cloning and sequencing segment 8 of influenza virus (A/PR/8/34)”, Nucleic Acids Res., 9(2), (1981), 237-245.
Wolff, et al., “Downstream porcessing of cell culture-derived virus particles”, Expert Rev. Vaccines 10(10) 1451-1475, (2011), 25 pgs.
Wood, J. M., et al., “From Lethal Virus to Life-Saving Vaccine: Developing Inactivated Vaccines for Pandemic Influenza”, Nature Reviews Microbiology, 2(10), (2004), 842-847.
Wu, Rui, et al., “A live bivalent influenza vaccine based on a H9N2 virus strain”, Vaccine, 28, (2010), 673-680.
Wu, Tai Te, et al., “An Analysis of the Sequences of the Variable Regions of Bence Jones Proteins and Myeloma Light Chains and Their Implications for Anti-body complementarity”, J. Exp. Med., 132(2), (1970), 211-250.
Xiang, J, et al., “Modification in framework region I results in a decreased affinity of chimeric anti-Tag72 antibody”, Mol. Immunol. 28(1/2), (1991), 141-148.
Xu, Jiayu, et al., “The Cold-Adapted, Temperature-Sensitive SARS-Co V-2 Strain TS11 Is Attenuated in Syrian Hamsters and a Candidate Attenuated Vaccine”, Viruses 2023, 15, 95. https://doi.org/10.3390/v15010095, (2023), 23.
Xu, Ruodan, et al., “Construction of SARS-CoV-2 Virus-Like Particles by Mammalian Expression System”, Frontiers in Bioengineering and Technology, 8:862, (2020), 1-6.
Xu, X., et al., “Reassortment and evolution of current human influenza A and B viruses”, Virus Research, 103, (2004), 55-60.
Yagi, Y., et al., “In silico panning for a non-competitive peptide inhibitor”, BMC Bioinformatics, 8(11), (2007), 11 pgs.
Yamamoto, K., et al., “Orientation Dependence in Homologous Recombination”, Genetics May 1996; 143(1): 27-36, (1996), 27-36.
Yamanaka, K., et al., “In vivo Analysis of the Promoter Structure of the Influenza Virus RNA Genome Using a Transfection System With an Engineered RNA”, Proc. Natl. Acad. Sci. USA, 88, (1991), 5369-5373.
Yang, P., et al., “Hemagglutinin Specificity and Neuraminidase Coding Capacity of Meuraminidase-Deficient Influenza Viruses”, Virology, 229(1), (1997), 155-165.
Yang, Z. Y, et al., “Identification of the Ebola virus glycoprotein as the main viral determinant of vascular cell cytotoxicity and injury”, Nat Med., 6(8), (Aug. 2000), Abstract Only.
Yannarell, Dean A., et al., “Factors affecting the yield of cold-adapted influenza virus vaccine”, Journal of Virological Methods, vol. 64, 161-169, (1997), 1 pg.
Yasuda, J., “Growth Control of Influenza A Virus by M1 Protein: Analysis of Transfectant Viruses Carrying the Chimeric M Gene”, Journal of Virology, 68(12), (1994), 8141-8146.
Yen, H L, et al., “Neuraminidase Inhibitor-Resistant Recombinant A/Vietnam/1203/04 (K5N1) Influenza Viruses Retain Their Replication Efficiency and Pathogenicity In Vitro and In Vivo”, Journal of Virology., vol. 81, No. 22, (Nov. 15, 2007), 12418-12426.
Yi, Pu Lin, et al., “Adaptation of Egg-Grown and Transfectant Influenza Viruses for Growth in Mammalian Cells: Selection of Hemagglutinin Mutants with Elevated pH of Membrane Fusion”, Virology, 233(2), (Jul. 7, 1997), 402-410.
Yonezawa, A., et al., “Studies of Eboa Virus Glycoprotein-Mediated Entry and Fusion by Using Pseudotyped Human Immunodeficiency Virus Type 1 Virions: Involvement of Cytoskeletal Proteins and Enhancement by Tumor Necrosis Factor Alpha”, Journal of Virology, 79(2), (2005), 918-926.
Yu, Q., et al., “Functional cDNA Clones of the Human Respiratory Syncytial (RS) Virus N, P, and L Proteins Support Replication of RS Virus Genomic RNA Analogs and Define Minimal trans-Acting Requirements for RNA Replication”, Journal of Virology, 69(4), (1995), 2412-2419.
Yusoff, K., et al., “Nucleotide Sequence Analysis of the L Gene of Newcastle Disease Virus: Homologies With Sendai and Vesicular Stomatitis Viruses”, Nucleic Acids Research, 15(10), (1987), 3961-3976.
Zaghouani, H, et al., “Induction of Antibodies to the Envelope Protein of the Human Immunodeficiency Virus by Immunization With Monoclonal Anti-Idiotypes”, Proc. Natl. Acad. Sci. USA, 88, (1991), 5645-5649.

(56) References Cited

OTHER PUBLICATIONS

Zaghouani, H., et al., "Cells Expressing an H Chain 1g Gene Carrying a Viral T Cell Epitope are Lysed by Specific Cytolytic T Cells", The Journal of Immunology, 148(11), (1992), 3604-3609.
Zanin, M., et al., "An Amino Acid in the Stalk Domain of N1 Neuraminidase Is Critical for Enzymatic Activity", Journal of Virology, 2017, Vo. 91, No. 2, (Jan. 2017), 12 pgs.
Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.
Zeitlin, L., et al., "Antibody Therapeutics for Ebola Virus Disease", Curr. Opin. Viral. 17:, (2016), 11 pgs.
Zhang, Baoshan, et al., "A platform incorporating trimeric antigens into self-assembling nanoparticles reveals SARS-CoV-2-spike nanoparticles to elicit substantially higher neutralizing responses than spike alone", Scientific Reports 10, Article No. 18149, (2020), 13 pgs.
Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.
Zhang, Q.-Y., et al., "SARS-CoV-2 replicon for high-throughput antiviral screening", J Gen Virol,, 102(5), (2021), 1-4.
Zhang, V. Q, et al., "Easy two-step method for randomizing and cloning gene fragments", Methods Mol Biol., 634, (2010), Abstract Only.
Zhang, Xuming, et al., "Expression of Interferon-y by a Coronavirus Defective-Interfering RNA Vector and its Effect on Viral Replication, Spread, and Pathogenicity", Medical Institute, University of Southern California School of Medicine, (May 1997), 327-338.
Zhang, Y., et al., "A bacterial artificial chromosome (BAC)-vectored noninfectious replicon of SARS-CoV-2", Antiviral Research, vol. 185, 104974, (Jan. 2021), 1-9.
Zhao, Lili, et al., "New Insights into the Nonconserved Noncoding Region of the Subtype-Determinant Hemagglutinin and Neuraminidase Segments of Influenza A Viruses", Journal of Virology, 88(19) 11493-11503, (Oct. 2014), 11 pgs.
Zhou, Yan, "Membrane-Anchored Incorporation of a Foreign Protein in Recombinant Influenza Virions", Virology 246(1), (1998), 83-94.
Zobel, A., et al., "RNA Polymerase I Catalysed Transcription of Insert Viral cDNA", Nucleic Acids Research, 21(16), (1993), 3607-3614.
U.S. Appl. No. 09/834,095 U.S. Pat. No. 6,872,395, filed Apr. 12, 2001, Viruses Comprising Mutant Ion Channel Protein.
U.S. Appl. No. 11/043,768 U.S. Pat. No. 8,057,806, filed Jan. 26, 2005, Viruses Comprising Mutant Ion Channel Protein.
U.S. Appl. No. 10/081,170 U.S. Pat. No. 7,176,021, filed Feb. 22, 2002, Methods to Identify Mutant Cells Wilth Altered Sialic Acid.
U.S. Appl. No. 11/644,179 U.S. Pat. No. 8,679,819, filed Dec. 22, 2006, Mutant Cells With Altered Sialic Acid.
U.S. Appl. No. 11/654,863, filed Jan. 18, 2007, Filovirus Vectors and Particles Produced Therefrom.
U.S. Appl. No. 10/353,856 U.S. Pat. No. 7,211,378, filed Jan. 29, 2003, Filovirus Vectors and Noninfectious Filovirus-Based Particles.
U.S. Appl. No. 12/245,296 U.S. Pat. No. 8,900,595, filed Oct. 3, 2008, Filovirus Vectors and Noninfectious Filovirus-Based Particles.
U.S. Appl. No. 15/915,486, filed Mar. 8, 2018, Filovirus Vectors and Particles Produced Therefrom.
U.S. Appl. No. 60/438,679, filed Jan. 7, 2003, Signal for Packaging of Influenza Virus Vectors.
U.S. Appl. No. 10/366,630 U.S. Pat. No. 7,226,774, filed Feb. 12, 2003, Signal for Packaging of Influenza Virus Vectors.
U.S. Appl. No. 11/509,249 U.S. Pat. No. 7,585,657, filed Aug. 24, 2006, Signal for Packaging of Influenza Virus Vectors.
U.S. Appl. No. 12/470,287 U.S. Pat. No. 8,298,805, filed May 21, 2009, Signal for Packaging of Influenza Virus Vectors.
U.S. Appl. No. 10/827,995 U.S. Pat. No. 7,588,769, filed Apr. 20, 2004, Viruses Encoding Mutant Membrane Protein.
U.S. Appl. No. 12/467,492, filed May 18, 2009, Viruses Encoding Mutant Membrane Protein.
U.S. Appl. No. 10/855,975 U.S. Pat. No. 7,723,094, filed May 27, 2004, Recombinant Influenza Vectors With a Polii Promoter and Ribozymes for Vaccines and Gene Therapy.
U.S. Appl. No. 10/855,875 U.S. Pat. No. 8,475,806, filed May 27, 2004, High Titer Recombinant Influenza Viruses for Vaccines and Gene Therapy.
U.S. Appl. No. 11/283,498 U.S. Pat. No. 7,968,101, filed Nov. 18, 2005, Recombinant Influenza Vectors With Tandem Transcription Units.
U.S. Appl. No. 13/113,244 U.S. Pat. No. 8,877,209, filed May 23, 2011, Recombinant Influenza Vectors With Tandem Transcription Units.
U.S. Appl. No. 14/528,997 U.S. Pat. No. 10,358,630, filed Oct. 30, 2014, Recombinant Influenza Vectors With Tandem Transcription Units.
"U.S. Appl. No. 17/229,001, Response filed Feb. 14, 2024 to Non Final Office Action mailed Oct. 19, 2023", 12 pgs.
"U.S. Appl. No. 17/266,049, Response filed Feb. 15, 2024 to Final Office Action mailed Aug. 15, 2023", 11 pgs.
"U.S. Appl. No. 17/813,200, Response filed Feb. 23, 2024 to Non Final Office Action mailed Oct. 23, 2023", 12 pgs.
"Japanese Application Serial No. 2022-544779, Response filed Jan. 10, 2024 to Notification of Reasons for Refusal mailed Aug. 22, 2023", w English claims, 12 pgs.
"Japanese Application Serial No. 2023-204069, Voluntary Amendment filed Dec. 28, 2023", w English claim, 8 pgs.
"U. S. Appl. No. 17/835,830, Response filed Feb. 29, 2024 to Restriction Requirement mailed Dec. 26, 2023", 6 pgs.
"U.S. Appl. No. 17/546,967, Non Final Office Action mailed Mar. 8, 2024", 9 pgs.
"U.S. Appl. No. 17/352,845, Supplemental Notice of Allowability mailed Sep. 28, 2023", 2 pgs.
"Japanese Application Serial No. 2022-161803, Notification of Reasons for Refusal mailed Sep. 12, 2023", w English Translation, 4 pgs.
"Japanese Application Serial No. 2022-544779, Notification of Reasons for Refusal mailed Aug. 22, 2023", w English Translation, 10 pgs.
"U.S. Appl. No. 17/229,001, Non Final Office Action mailed Oct. 19, 2023", 15 pgs.
"U.S. Appl. No. 17/813,200, Non Final Office Action mailed Oct. 23, 2023", 11 pgs.
"International Application Serial No. PCT US2023 027622, International Search Report mailed Nov. 7, 2023", 5 pgs.
"International Application Serial No. PCT US2023 027622, Written Opinion mailed Nov. 7, 2023", 6 pgs.
"U.S. Appl. No. 16/785,449, Corrected Notice of Allowability mailed Nov. 8, 2023", 10 pgs.
"U.S. Appl. No. 16/785,449, Corrected Notice of Allowability mailed Nov. 17, 2023", 10 pgs.
"Japanese Application Serial No. 2019-171818, Notification of Reasons for Rejection mailed Sep. 26, 2023", w English Translation, 12 pgs.
Liu, Shufeng, "Stable Cell Clones Harboring Self-Replicating SARS-CoV-2 RNAs for Drug Screen", Journal of Virology, vol. 96, No. 6, [Online] Retrieved from the internet:https: www.ncbi.nlm.nih.gov pmc articles PMC8941906 pdf jvi.02216-21.pdf, (Mar. 23, 2022), 13 pgs.
Netland, Jason, "Immunization with an attenuated severe acute respiratory syndrome coronavirus deleted in E protein protects against lethal respiratory disease", Virolog, vol. 399, No. 1, (Jan. 27, 2010), 9 pgs.
Zhang, Xianwen, "A trans-complementation system for SARS-CoV-2 recapitulates authentic viral replication without virulence", Cell, Elsevier, Amsterdam NL, vol. 184, No. 8, (Feb. 23, 2021), 24 pgs.
"U.S. Appl. No. 17/546,967, Response filed Nov. 22, 2023 to Restriction Requirement mailed May 23, 2023", 9 pgs.

(56) References Cited

OTHER PUBLICATIONS

"U.S. Appl. No. 17/813,178, Non Final Office Action mailed Dec. 6, 2023", 13 pgs.
"Japanese Application Serial No. 2022-513269, Response filed Dec. 6, 2023 to Notification of Reasons for Refusal mailed Jun. 6, 2023", w english claims, 34 pgs.
"U.S. Appl. No. 17/835,830, Restriction Requirement mailed Dec. 26, 2023", 8 pgs.
"Japanese Application Serial No. 2021-542525, Response filed Dec. 1, 2023 to Examiners Decision of Final Refusal mailed Aug. 1, 2023", w english claim, 7 pgs.
"Japanese Application Serial No. 2022-016436, Notification of Reasons for Refusal mailed Dec. 5, 2023", w English Translation, 10 pgs.
"Japanese Application Serial No. 2022-016436, Response filed Oct. 11, 2023 to Notification of Reasons for Refusal mailed Apr. 11, 2023", w English claims, 15 pgs.
"European Application Serial No. 16778485.9, Response filed Dec. 15, 2023 to Communication Pursuant to Article 94(3) EPC mailed Jun. 9, 2023", 54 pgs.
Burke, "A Recommended numbering Scheme for Influenza A HA Subtypes", PLoS One. 9, (2014), 6 pgs.
Li, "Selection of antigenically advanced variants of seasonal influenza viruses", Nature Microbiology 1 (6): Supplementary Infiormation, (2016), 10 pgs.
"Japanese Application Serial No. 2022-513269, Notification of Reasons for Refusal mailed Feb. 20, 2024", w English translation, 5 pgs.
"U.S. Appl. No. 17/546,835, Restriction Requirement mailed Mar. 20, 2024", 9 pgs.
"European Application Serial No. 17709236.8, Communication Pursuant to Article 94(3) EPC mailed Mar. 14, 2024", 6 pgs.
"Japanese Application Serial No. 2021-536228, Response filed Feb. 22, 2024 to Notification of Reasons for Rejection mailed Aug. 22, 2023", w English claims, 30 pgs.
"Japanese Application Serial No. 2022-144599, Response filed Feb. 22, 2024 to Notification of Reasons for Refusal mailed Aug. 22, 2023", w English claims, 8 pgs.
"Japanese Application Serial No. 2021-546853, Response filed Feb. 29, 2024 to Notification of Reasons for Refusal mailed Aug. 29, 2023", w English claims, 15 pgs.
"Japanese Application Serial No. 2020-182549, Notification of Reasons for Refusal mailed Feb. 20, 2024", w English Translation, 8 pgs.
"U.S. Appl. No. 17/266,049, Non Final Office Action mailed Apr. 12, 2024", 12 pgs.
"U.S. Appl. No. 17/229,001, Notice of Allowance mailed Apr. 24, 2024", 6 pgs.
"Japanese Application Serial No. 2019-171818, Response Filed Mar. 26, 2024 to Notification of Reasons for Rejection mailed Sep. 26, 2023", w English Claims, 21 pgs.
"Japanese Application Serial No. 2022-161803, Response Filed Mar. 12, 2024 to Notification of Reasons for Refusal mailed Sep. 12, 2023", 15 pgs.
"European Application Serial No. 18800815.5, Communication Pursuant to Article 94(3) EPC mailed May 9, 2023", 6 pgs.
"U.S. Appl. No. 16/785,449, Response filed May 22, 2023 to Final Office Action mailed Mar. 22, 2023", 9 pgs.
"U.S. Appl. No. 17/546,967, Restriction Requirement mailed May 23, 2023", 10 pgs.
"Japanese Application Serial No. 2022-016436, Notification of Reasons for Refusal mailed Apr. 11, 2023", w English translation, 13 pgs.
"Japanese Application Serial No. 2021-542525, Response filed May 18, 2023 Notification of Reasons for Refusal mailed Dec. 13, 2022", w English Claims, 58 pgs.
"U.S. Appl. No. 17/229,001, Non Final Office Action mailed Jun. 6, 2023", 15 pgs.
"U.S. Appl. No. 17/352,845, Notice of Allowance mailed Jun. 7, 2023", 5 pgs.
"U.S. Appl. No. 16/785,449, Advisory Action mailed Jun. 7, 2023", 17 pgs.
"U.S. Appl. No. 17/266,049, Response filed Jun. 14, 2023 to Non Final Office Action mailed Mar. 14, 2023", 10 pgs.
"European Application Serial No. 16778485.9, Communication Pursuant to Article 94(3) EPC mailed Jun. 9, 2023", 4 pgs.
"U.S. Appl. No. 18/173,535, Preliminary Amendment filed Jun. 26, 2023", 16 pgs.
"Japanese Application Serial No. 2022-513269, Notification of Reasons for Refusal mailed Jun. 6, 2023", w English Translation, 15 pgs.
"U.S. Appl. No. 16/785,449, Response filed Jul. 13, 2023 to Advisory Action mailed Jun. 7, 2023", 12 pgs.
"Japanese Application Serial No. 2021-546853, Response Filed Jul. 13, 2023 to Notification of Reasons for Refusal mailed Apr. 18, 2023", W English Claims, 12 pgs.
"U.S. Appl. No. 17/004,583, Notice of Allowability mailed Aug. 1, 2023", 2 pgs.
"U.S. Appl. No. 18/365,082, Preliminary Amendment filed Aug. 3, 2023", 4 pgs.
"U.S. Appl. No. 16/785,449, Notice of Allowance mailed Aug. 7, 2023", 14 pgs.
"U.S. Appl. No. 17/266,049, Final Office Action mailed Aug. 15, 2023", 12 pgs.
"U.S. Appl. No. 17/229,001, Response filed Aug. 28, 2023 to Non Final Office Action mailed Jun. 6, 2023", 13 pgs.
"Japanese Application Serial No. 2021-542525, Examiners Decision of Final Refusal mailed Aug. 1, 2023", w English Translation, 7 pgs.
"International Application Serial No. PCT US2023 063136, International Search Report mailed Sep. 8, 2023", 6 pgs.
"International Application Serial No. PCT US2023 063136, Written Opinion mailed Sep. 8, 2023", 7 pgs.
"U.S. Appl. No. 16/785,449, Corrected Notice of Allowability mailed Sep. 11, 2023", 10 pgs.
"Japanese Application Serial No. 2022-144599, Notification of Reasons for Refusal mailed Aug. 22, 2023", w English translation, 19 pgs.
"Japanese Application Serial No. 2021-546853, Office Action Mailed Aug. 29, 2023", w English Translation, 10 pgs.
"Japanese Application Serial No. 2021-546853, Notification of Reasons for Refusal mailed Aug. 29, 2023", w English Translation, 6 pgs.
"Japanese Application Serial No. 2021-536228, Notification of Reasons for Rejection mailed Aug. 22, 2023", W English Translation, 13 pgs.
Abdoli, Mohsen, "Intranasal administration of cold-adapted live-attenuated SARS-CoV-2 candidate vaccine confers protection against SARS-CoV-2", Virus Research 319 198857, (2022), 10 pgs.
Faizuloev, Evgeny, "Cold-adapted SARS-CoV-2 variants with different sensitivity exhibit an attenuated phenotype and confer protective immunity", Science Direct Vaccine 41 892-902, (2023), 12 pgs.
Lu, Shan, "The SARS-CoV-2 nucleocapsid phosphoprotein forms mutually exclusive condensates with RNA and the membrane-associated M protein", nature communications 12:502, (2021), 15 pgs.
Matrosovich, "Early Alteration of the Receptor-Binding Properties of H1, H2, and H3 Avian Influenza Virus Hemagglutinins after Their Introduction to Mammals", J. Virology, 74(18) 8502-8512, (Sep. 2000), 11 pgs.
Matrosovich, Mikhail, "Overexpression of the a-2,6-Sialyltransferase in MDCK Cells Increases Influenza Virus Sensitivity to Neuraminidase Inhibitors", Journal of Virology, Aug. 2003, p. 8418-8425, (2003), 9 pgs.
Plescia, Caroline B, "SARS-CoV-2 viral budding and entry can be modeled using BSL-2 level virus-like particles" JBC Research Article, (Nov. 19, 2020), 10 pgs.
Seo, Sang Heui, "Cold-Adapted Live Attenuated SARS-CoV-2 Vaccine Completely Protects Human ACE2 Transgenic Mice from SARS-Cov-2 Infection", Vaccines 2020 8, 584, (Oct. 3, 2020), 17 pgs.

(56) References Cited

OTHER PUBLICATIONS

Swann, Heather, "Minimal system for assembly of SARS CoV 2 virus like particles", Scientific Reports 10:21877 nature portfolio, (2020), 1-5.
Zhang, Zhikuan, "Structure of SARS-CoV-2 membrane protein essential for virus assembly", nature communications 13:4399, (Aug. 5, 2022), 12 pgs.
"U.S. Appl. No. 17/229,001, Corrected Notice of Allowability mailed Jul. 22, 2024", 2 pgs.
"U.S. Appl. No. 17/266,049, Examiner Interview Summary mailed Oct. 16, 2024", 2 pgs.
"U.S. Appl. No. 17/266,049, Final Office Action mailed Oct. 31, 2024", 14 pgs.
"U.S. Appl. No. 17/266,049, Response filed Oct. 14, 2024 to Non Final Office Action mailed Apr. 12, 2024", 12 pgs.
"U.S. Appl. No. 17/266,049, Response filed Dec. 4, 2024 to Final Office Action mailed Oct. 31, 2024", 12 pgs.
"U.S. Appl. No. 17/546,835, Non Final Office Action mailed Sep. 27, 2024", 9 pgs.
"U.S. Appl. No. 17/546,835, Response filed Jun. 6, 2024 to Restriction Requirement mailed Mar. 20, 2024", 9 pgs.
"U.S. Appl. No. 17/546,967, Notice of Allowance mailed Oct. 15, 2024", 8 pgs.
"U.S. Appl. No. 17/546,967, Response filed Jun. 24, 2024 to Non Final Office Action mailed Mar. 8, 2024", 9 pgs.
"U.S. Appl. No. 17/813,178, Corrected Notice of Allowability mailed Jul. 31, 2024", 2 pgs.
"U.S. Appl. No. 17/813,178, Notice of Allowance mailed Jul. 10, 2024", 5 pgs.
"U.S. Appl. No. 17/813,178, Response filed Jun. 10, 2024 to Non Final Office Action mailed Dec. 13, 2023", 14 pgs.
"U.S. Appl. No. 17/813,200, Corrected Notice of Allowability mailed Jul. 31, 2024", 2 pgs.
"U.S. Appl. No. 17/813,200, Corrected Notice of Allowability mailed Aug. 23, 2024", 2 pgs.
"U.S. Appl. No. 17/813,200, Corrected Notice of Allowability mailed Sep. 17, 2024", 2 pgs.
"U.S. Appl. No. 17/813,200, Notice of Allowance mailed Jun. 6, 2024", 6 pgs.
"U.S. Appl. No. 17/835,830, Non Final Office Action mailed Jun. 6, 2024", 6 pgs.
"U.S. Appl. No. 17/835,830, Non Final Office Action mailed Dec. 4, 2024", 7 pgs.
"U.S. Appl. No. 17/835,830, Response filed Aug. 12, 2024 to Non Final Office Action mailed Jun. 6, 2024", 5 pgs.
"U.S. Appl. No. 18/365,082, Restriction Requirement mailed Oct. 24, 2024", 12 pgs.
"U.S. Appl. No. 18/461,321, Non Final Office Action mailed Nov. 14, 2024", 6 pgs.
"U.S. Appl. No. 18/525,460, Notice of Allowance mailed Oct. 23, 2024", 11 pgs.
"U.S. Appl. No. 18/525,460, Preliminary Amendment filed Jun. 7, 2024", 6 pgs.
"Chinese Application Serial No. 202080025289.6, Office Action mailed May 15, 2024", w/ English Translation, 18 pgs.
"Chinese Application Serial No. 202080025289.6, Office Action mailed Oct. 9, 2024", W/English Translation, 14 pgs.
"Chinese Application Serial No. 202080025289.6, Response filed Sep. 14, 2024 to Office Action mailed May 15, 2024", w/ current English claims, 16 pgs.
"European Application Serial No. 17709236.8, Response filed Sep. 16, 2024 to Communication Pursuant to Article 94(3) EPC mailed Mar. 14, 2024", 16 pgs.
"European Application Serial No. 19778696.5, Communication Pursuant to Article 94(3) EPC mailed Jun. 3, 2024", 6 pgs.
"European Application Serial No. 20714015.3, Communication Pursuant to Article 94(3) EPC mailed Aug. 5, 2024", 4 pgs.
"Extending the Stalk Enhances Immunogenicity of the Influenza Virus Neuraminidase", J Virol, vol. 93, No. 18, Article No. e00840-19, (Aug. 29, 2019), 1-12.
"International Application Serial No. PCT/US2023/063136, International Preliminary Report on Patentability mailed Sep. 6, 2024", 9 pgs.
"International Application Serial No. PCT/US2024/020952, International Search Report mailed Jul. 30, 2024", 3 pgs.
"International Application Serial No. PCT/US2024/020952, Written Opinion mailed Jul. 3, 2024", 5 pgs.
"Japanese Application Serial No. 2019-171818, Notification of Reasons for Rejection mailed May 14, 2024", w/ English Translation, 7 pgs.
"Japanese Application Serial No. 2020-182549, Response filed Aug. 20, 2024 to Notification of Reasons for Refusal mailed Feb. 20, 2024", w/ English claims, 12 pgs.
"Japanese Application Serial No. 2021-509824, Notification of Reasons for Rejection mailed Jun. 4, 2024", W/English Translation, 18 pgs.
"Japanese Application Serial No. 2021-546853, Examiners Decision of Final Refusal mailed May 7, 2024", w/ English translation, 5 pgs.
"Japanese Application Serial No. 2021-546853, Response filed Sep. 6, 2024 to Examiners Decision of Final Refusal mailed May 7, 2024", w/ English claims, 12 pgs.
"Japanese Application Serial No. 2022-016436, Examiners Decision of Final Refusal mailed Aug. 13, 2024", w/ English translation, 7 pgs.
"Japanese Application Serial No. 2022-016436, Response filed Jun. 4, 2024 to Notification of Reasons for Refusal mailed Dec. 5, 2023", w/ English claims, 12 pgs.
"Japanese Application Serial No. 2022-144599, Notification of Reasons for Rejection mailed May 14, 2024", W/English Translation, 8 pgs.
"Japanese Application Serial No. 2022-144599, Response filed Aug. 14, 2024 to Notification of Reasons for Rejection mailed May 14, 2024", w/ English claims, 9 pgs.
"Japanese Application Serial No. 2022-161803, Notification of Reasons for Refusal mailed Jun. 4, 2024", w/ English Translation, 13 pgs.
"Japanese Application Serial No. 2022-513269, Response filed Aug. 19, 2024 to Notification of Reasons for Refusal mailed Feb. 20, 2024", w/ English claims, 23 pgs.
"Japanese Application Serial No. 2022-544779, Examiners Decision of Final Refusal mailed Apr. 23, 2024", w/ English translation, 5 pgs.
"Japanese Application Serial No. 2022-544779, Response filed Aug. 22, 2024 to Examiners Decision of Final Refusal mailed Apr. 23, 2024", w/ English claims, 20 pgs.
"Japanese Application Serial No. 2023-204069, Voluntary Amendment filed Jun. 11, 2024", w/ English Claims, 9 pgs.
"Japanese Application Serial No. 2024-050083, Voluntary Amendment Filed Apr. 25, 2024", w/ English Claims, 22 pgs.
Aria, Yasuha, et al., "PB2 mutations arising during H9N2 influenza evolution in the Middle East confer enhanced replication and growth in mammals", PLOS Pathogens 15(7): e1007919. https://doi.org/10.1371/journal.ppat.1007919, (Jul. 2, 2019), 25 pages.
Chang, Chi-Chieh, et al., "Subunit vaccines with a saponin-based adjuvant boost humoral and cellular immunity to MERS coronavirus", Vaccine 41 (2023) 3337-3346, journal homepage: www.elsevier.com/locate/vaccine, (2023), 11.
Chen, Xiaorui, et al., "Comparison of four adjuvants revealed the strongest protection against lethal pneumococcal challenge following immunization with PsaA-PspA fusion protein and AS02 as adjuvant", https://pubmed.ncbi.nlm.nih.gov/30707297/ (abstract), (2019), 1 pg.
Da Silva, V. Diogo, et al., "Assembly of Subtype 1 Influenza Neuraminidase is Driven by Both the Transmembrane and Head Domains", J Biol Chem, vol. 288, No. 1 pp. 644-653, (Jan. 4, 2023), 10 p.
Fan, Haitian, et al., "Structures of influenza A virus RNA polymerase offer insight into viral genome replication", Nature 573, 287-290 (2019). https://doi.org/10.1038/s41586-019-1530-7, (Sep. 4, 2019), 35 pages.
Giles, Brendan Michael, "Development of a broadly reactive vaccine for highly pathogenic H5N1 influenza", [Online]. Retrieved

(56) References Cited

OTHER PUBLICATIONS from the Internet: <URL: http://search.proquest.com/docview/928138363>, (Jan. 11, 2011), 24 pgs.
Ho, Nataschja I, et al., "Saponin-based adjuvants enhance antigen cross-presentation in human CD11c+ CD1c+ CD5- CD163+ conventional type 2 dendritic cells", J Immunother Cancer 2023, (2023), 17.
Kamiki, Haruhiko, et al., "Novel Biological System with Terminal Sialic Acid Knockout Cells", J Virol 96:e00416-22. https://doi.org/10.1128/jvi.00416-22, (Jul. 18, 2022), 15 pages.
Klimov, A.I., et al., "Correlation of amino acid residues in the M1 and M2 proteins of influenza virus with high yielding properties", Virus Research, vol. 19, Issue 1, 1991, pp. 105-114, ISSN 0168-1702, https://doi.org/10.1016/0168-1702(91)90098-G. (https://www.sciencedirect.com/science/article/pii/016817029190098G), (Mar. 1991), 10 pages.
Ma, Wenjun, et al., "The NS Segment of an H5N1 Highly Pathogenic Avian Influenza Virus (HPAIV) Is Sufficient to Alter Replication Efficiency, Cell Tropism, and Host Range of an H7N1 HPAIV", J Virol. Feb. 2010;84(4):2122-33. doi: 10.1128/JVI.01668-09. Epub Dec. 9, 2009. PMID: 20007264; PMCID: PMC2812369., (Feb. 2010), 12 pages.
Mahesutihan, Madina, et al., "CypA Regulates AIP4-Mediated M1 Ubiquitination of Influenza A Virus", Virologica Sinica 33 (2018): 440-448., (Oct. 16, 2018), 9 pages.
Zhao, Tingmei, et al., "Vaccine adjuvants: mechanisms and platforms", Signal Transduction and Targeted Therapy, www.nature.com/sigtrans, (Jul. 19, 2023), 24.
"U.S. Appl. No. 17/266,049 Corrected Notice of Allowability mailed Jan. 31, 2025", 3 pgs.
"U.S. Appl. No. 17/266,049, Notice of Allowance mailed Jan. 23, 2025", 11 pgs.
"U.S. Appl. No. 17/546,835, Response filed Jan. 22, 2025 to Non Final Office Action nailed Sep. 27, 2024", 9 pgs.
"U.S. Appl. No. 17/546,967, Corrected Notice of Allowability mailed Jan. 29, 2025", 2 pgs.
"U.S. Appl. No. 18/461,321, Response filed Jan. 7, 2025 to Non Final Office Action mailed Nov. 14, 2024", 6 pgs.
"Chinese Application Serial No. 202080025289.6, Decision of Rejection mailed Jan. 14, 2025", W/English Translation, 15 pgs.
"Chinese Application Serial No. 202080025289.6, Response filed Dec. 9, 2024 to Office Action mailed Oct. 9, 2024", w/ English claims, 13 pgs.
"Chinese Application Serial No. 202080048487.4, Office Action mailed Dec. 30, 2024", w/ English translation, 18 pgs.
"European Application Serial No. 17709236.8,Supplementary Response filed Jan. 7, 2025 to Communication Pursuant to Article 94(3) EPC mailed Mar. 14, 2024", 8 pgs.
"European Application Serial No. 19778696.5, Response filed Dec. 3, 2024 to Communication Pursuant to Article 94(3) EPC mailed Jun. 3, 2024", 26 pgs.
"International Application Serial No. PCT/US2023/027622, International Preliminary Report on Patentability mailed Jan. 23, 2025", 8 pgs.
"Japanese Application Serial No. 2020-182549, Response filed Dec. 4, 2024 to Notification of Reasons for Refusal mailed Oct. 15, 2024", w/ English claims, 10 pgs.
"Japanese Application Serial No. 2021-509824, Response filed Nov. 29, 2024 to Notification of Reasons for Rejection mailed Jun. 4, 2024", w/ English claims, 41 pgs.
"Japanese Application Serial No. 2022-016436, Appeal filed Dec. 13, 2024 to Examiners Decision of Final Refusal mailed Aug. 13, 2024", w/ English claims, 15 pgs.
"Japanese Application Serial No. 2022-161803, Response filed Dec. 4, 2024 to Notification of Reasons for Refusal mailed Jun. 4, 2024", w/ English claims, 13 pgs.
"Japanese Application Serial No. 2024-176620, Voluntary Amendment filed Dec. 11, 2024", w/ English claims, 13 pgs.
Ping, J., et al., "Development of high-yield influenza A virus vaccine viruses", Nature CommunicaTions, vol. 6, (Dec. 31, 2015), 1-15.
Zhu, Guangrui, et al., "Progress on Pathogenic Mechanism of Influenza A (H1N1) Virus", Progress in Veterinary Medicine, 08, (Aug. 20, 2011), 70-74.
"European Application Serial No. 20714015.3, Response filed Nov. 25, 2024 to Communication Pursuant to Article 94(3) EPC mailed Aug. 5, 2024", 9 pgs.
"Japanese Application Serial No. 2019-171818, Response filed Nov. 14, 2024 to Notification of Reasons for Rejection mailed May 14, 2024", w English claims, 12 pgs.

* cited by examiner

PR8(CAMBRIDGE)

PB2

AGCGAAAGCAGGTCAATTATATTCAATATGGAAAGAATAAAAGAACTAAGAAATCTAATGTCGCAGTCTCGCACCCGCGAGATA
CTCACAAAAACCACCGTGGACCATATGGCCATAATCAAGAAGTACACATCAGGAAGACAGGAGAAGAACCCAGCACTTAGGATG
AAATGGATGATGGCAATGAAATATCCAATTACAGCAGACAAGAGGATAACGGAAATGATTCCTGAGAGAAATGAGCAAGGACAA
ACTTTATGGAGTAAAATGAATGATGCCGGATCAGACCGAGTGATGGTATCACCTCTGGCTGTGACATGGTGGAATAGGAATGGA
CCAATGACAAATACAGTTCATTATCCAAAAATCTACAAAACTTATTTTGAAAGAGTCGAAAGGCTAAAGCATGGAACCTTTGGC
CCTGTCCATTTTAGAAACCAAGTCAAAATACGTCGGAGAGTTGACATAAATCCTGGTCATGCAGATCTCAGTGCCAAGGAGGCA
CAGGATGTAATCATGGAAGTTGTTTTCCCTAACGAAGTGGGAGCCAGGATACTAACATCGGAATCGCAACTAACGATAACCAAA
GAGAAGAAAGAAGAACTCCAGGATTGCAAAATTTCTCCTTTGATGGTTGCATACATGTTGGAGAGAGAACTGGTCCGCAAAACG
AGATTCCTCCCAGTGGCTGGTGGAACAAGCAGTGTGTACATTGAAGTGTTGCATTTGACTCAAGGAACATGCTGGGAACAGATG
TATACTCCAGGAGGGGAAGTGAAGAATGATGATGTTGATCAAAGCTTGATTATTGCTGCTAGGAACATAGTGAGAAGAGCTGCA
GTATCAGCAGACCCACTAGCATCTTTATTGGAGATGTGCCACAGCACACAGATTGGTGGAATTAGGATGGTAGACATCCTTAAG
CAGAACCCAACAGAAGAGCAAGCCGTGGATATATGCAAGGCTGCAATGGGACTGAGAATTAGCTCATCCTTCAGTTTTGGTGGA
TTCACATTTAAGAGAACAAGCGGATCATCAGTCAAGAGAGAGGAAGAGGTGCTTACGGGCAATCTTCAAACATTGAAGATAAGA
GTGCATGAGGGATCTGAAGAGTTCACAATGGTTGGGAGAAGAGCAACAGCCATACTCAGAAAAGCAACCAGGAGATTGATTCAG
CTGATAGTGAGTGGGAGAGACGAACAGTCGATTGCCGAAGCAATAATTGTGGCCATGGTATTTTCACAAGAGGATTGTATGATA
AAAGCAGTTAGAGGTGATCTGAATTTCGTCAATAGGGCGAATCAGCGACTGAATCCTATGCATCAACTTTTAAGACATTTTCAG
AAGGATGCGAAAGTGCTTTTTCAAAATTGGGGAGTTGAACCTATCGACAATGTGATGGGAATGATTGGGATATTGCCCGACATG
ACTCCAAGCATCGAGATGTCAATGAGAGGAGTGAGAATCAGCAAAATGGGTGTAGATGAGTACTCCAGCACGGAGAGGGTAGTG
GTGAGCATTGACCGGTTCTTGAGAGTCAGGGACCAACGAGGAAATGTACTACTGTCTCCCGAGGAGGTCAGTGAAACACAGGGA
ACAGAGAAACTGACAATAACTTACTCATCGTCAATGATGTGGGAGATTAATGGTCCTGAATCAGTGTTGGTCAATACCTATCAA
TGGATCATCAGAAACTGGGAAACTGTTAAAATTCAGTGGTCCCAGAACCCTACAATGCTATACAATAAAATGGAATTTGAACCA
TTTCAGTCTTTAGTACCTAAGGCCATTAGAGGCCAATACAGTGGGTTTGTAAGAACTCTGTTCCAACAAATGAGGGATGTGCTT
GGGACATTTGATACCGCACAGATAATAAAACTTCTTCCCTTCGCAGCCGCTCCACCAAAGCAAAGTAGAATGCAGTTCTCCTCA
TTTACTGTGAATGTGAGGGGATCAGGAATGAGAATACTTGTAAGGGGCAATTCTCCTGTATTCAACTACAACAAGGCCACGAAG
AGACTCACAGTTCTCGGAAAGGATGCTGGCACTTTAACCGAAGACCCAGATGAAGGCACAGCTGGAGTGGAGTCCGCTGTTCTG
AGGGGATTCCTCATTCTGGGCAAAGAAGACAGGAGATATGGGCCAGCATTAAGCATCAATGAACTGAGCAACCTTGCGAAAGGA
GAGAAGGCTAATGTGCTAATTGGGCAAGGAGACGTGGTGTTGGTAATGAAACGAAAACGGACTCTAGCATACTTACTGACAGC
CAGACAGCGACCAAAAGAATTCGGATGGCCATCAATTAGTGTCGAATAGTTTAAAAACGACCTTGTTTCTACT (SEQ ID NO:11)

PR8(CAMBRIDGE)

AGCGAAAGCAGGCAAACCATTTGAATGGATGTCAATCCGACCTTACTTTTCTTAAAAGTGCCAGCACAAAATGCTATAAGCACA
ACTTTCCCTTATACCGGAGACCCTCCTTACAGCCATGGGACAGGAACAGGATACACCATGGATACTGTCAACAGGACACATCAG
TACTCAGAAAAGGGAAGATGGACAACAAACACCGAAACTGGAGCACCGCAACTCAACCCGATTGATGGGCCACTGCCAGAAGAC
AATGAACCAAGTGGTTATGCCCAAACAGATTGTGTATTGGAAGCAATGGCTTTCCTTGAGGAATCCCATCCTGGTATTTTTGAA
AACTCGTGTATTGAAACGATGGAGGTTGTTCAGCAAACACGAGTAGACAAGCTGACACAAGGCCGACAGACCTATGACTGGACT
TTAAATAGAAACCAGCCTGCTGCAACAGCATTGGCCAACACAATAGAAGTGTTCAGATCAAATGGCCTCACGGCCAATGAGTCA
GGAAGGCTCATAGACTTCCTTAAGGATGTAATGGAGTCAATGAAAAAAGAAGAAATGGGGATCACAACTCATTTTCAGAGAAAG
AGACGGGTGAGAGACAATATGACTAAGAAAATGATAACACAGAGAACAATAGGTAAAAGGAAACAGAGATTGAACAAAAGGGGT
TATCTAATTAGAGCATTGACCCTGAACACAATGACCAAAGATGCTGAGAGAGGGAAGCTAAAACGGAGAGCAATTGCAACCCCA
GGGATGCAAATAAGGGGGTTTGTATACTTTGTTGAGACACTGGCAAGGAGTATATGTGAGAAACTTGAACAATCAGGGTTGCCA
GTTGGAGGCAATGAGAAGAAAGCAAAGTTGGCAAATGTTGTAAGGAAGATGATGACCAATTCTCAGGACACCGAACTTTCTTTC
ACCATCACTGGAGATAACACCAAATGGAACGAAAATCAGAATCCTCGGATGTTTTTGGCCATGATCACATATATGACCAGAAAT
CAGCCCGAATGGTTCAGAAATGTTCTAAGTATTGCTCCAATAATGTTCTCAAACAAAATGGCGAGACTGGGAAAAGGGTATATG
TTTGAGAGCAAGAGTATGAAACTTAGAACTCAAATACCTGCAGAAATGCTAGCAAGCATTGATTTGAAATATTTCAATGATTCA
ACAAGAAAGAAGATTGAAAAAATCCGACCGCTCTTAATAGAGGGGACTGCATCATTGAGCCCTGGAATGATGATGGCATGTTC
AATATGTTAAGCACTGTATTAGGCGTCTCCATCCTGAATCTTGGACAAAAGAGATACACCAAGACTACTTACTGGTGGGATGGT
CTTCAATCCTCTGACGATTTTGCTCTGATTGTGAATGCACCCAATCATGAAGGGATTCAAGCCGGAGTCGACAGGTTTTATCGA
ACCTGTAAGCTACTTGGAATCAATATGAGCAAGAAAAAGTCTTACATAAACAGAACAGGTACATTTGAATTCACAAGTTTTTTC
TATCGTTATGGGTTTGTTGCCAATTTCAGCATGGAGCTTCCCAGTTTTGGGGTGTCTGGGATCAACGAGTCAGCGGACATGAGT
ATTGGAGTTACTGTCATCAAAAACAATATGATAAACAATGATCTTGGTCCAGCAACAGCTCAAATGGCCCTTCAGTTGTTCATC
AAAGATTACAGGTACACGTACCGATGCCATAGAGGTGACACACAAATACAAACCCGAAGATCATTTGAAATAAAGAAACTGTGG
GAGCAAACCCGTTCCAAAGCTGGACTGCTGGTCTCCGACGGAGGCCCAAATTTATACAACATTAGAAATCTCCACATTCCTGAA
GTCTGCCTAAAATGGGAATTGATGGATGAGGATTACCAGGGGCGTTTATGCAACCCACTGAACCCATTTGTCAGCCATAAAGAA
ATTGAATCAATGAACAATGCAGTGATGATGCCAGCACATGGTCCAGCCAAAAACATGGAGTATGATGCTGTTGCAACAACACAC
TCCTGGATCCCCAAAAGAAATCGATCCATCTTGAATACAAGTCAAAGAGGAGTACTTGAAGATGAACAAATGTACCAAAGGTGC
TGCAATTTATTTGAAAAATTCTTCCCCAGCAGTTCATACAGAAGACCAGTCGGGATATCCAGTATGGTGGAGGCTATGGTTTCC
AGAGCCCGAATTGATGCACGGATTGATTTCGAATCTGGAAGGATAAAGAAAGAAGAGTTCACTGAGATCATGAAGATCTGTTCC
ACCATTGAAGAGCTCAGACGGCAAAAATAGTGAATTTAGCTTGTCCTTCATGAAAAAATGCCTTGTTTCTACT (SEQ ID NO:10)

Fig. 1B

PR8(CAMBRIDGE)

PA

AGCGAAAGCAGGTACTGATTCAAAATGGAAGATTTTGTGCGACAATGCTTCAATCCGATGATTGTCGAGCTTGCGGAAAAAACA
ATGAAAGAGTATGGGGAGGACCTGAAAATCGAAACAAACAAATTTGCAGCAATATGCACTCACTTGGAAGTATGCTTCATGTAT
TCAGATTTCCACTTCATCAATGAGCAAGGCGAGTCAATAATCGTAGAACTTGGTGATCCTAATGCACTTTTGAAGCACAGATTT
GAAATAATCGAGGGAAGAGATCGCACAATGGCCTGGACAGTAGTAAACAGTATTTGCAACACTACAGGGGCTGAGAAACCAAAG
TTTCTACCAGATTTGTATGATTACAAGGAAAATAGATTCATCGAAATTGGAGTAACAAGGAGAGAAGTTCACATATACTATCTG
GAAAAGGCCAATAAAATTAAATCTGAGAAAACACACATCCACATTTTCTCGTTCACTGGGGAAGAAATGGCCACAAGGGCCGAC
TACACTCTCGATGAAGAAAGCAGGGCTAGGATCAAAACCAGGCTATTCACCATAAGACAAGAAATGGCCAGCAGAGGCCTCTGG
GATTCCTTTCGTCAGTCCGAGAGAGGAGAAGAGACAATTGAAGAAAGGTTTGAAATCACAGGAACAATGCGCAAGCTTGCCGAC
CAAAGTCTCCCGCCGAACTTCTCCAGCCTTGAAAATTTTAGAGCCTATGTGGATGGATTCGAACCGAACGGCTACATTGAGGGC
AAGCTGTCTCAAATGTCCAAAGAAGTAAATGCTAGAATTGAACCTTTTTTGAAAACAACACCACGACCACTTAGACTTCCGAAT
GGGCCTCCCTGTTCTCAGCGGTCCAAATTCCTGCTGATGGATGCCTTAAAATTAAGCATTGAGGACCCAAGTCATGAAGGAGAG
GGAATACCGCTATATGATGCAATCAAATGCATGAGAACATTCTTTGGATGGAAGGAACCCAATGTTGTTAAACCACACGAAAAG
GGAATAAATCCAAATTATCTTCTGTCATGGAAGCAAGTACTGGCAGAACTGCAGGACATTGAGAATGAGGAGAAAATTCCAAAG
ACTAAAAATATGAAAAAAACAAGTCAGCTAAAGTGGGCACTTGGTGAGAACATGGCACCAGAAAAGGTAGACTTTGACGACTGT
AAAGATGTAGGTGATTTGAAGCAATATGATAGTGATGAACCAGAATTGAGGTCGCTTGCAAGTTGGATTCAGAATGAGTTCAAC
AAGGCATGCGAACTGACAGATTCAAGCTGGATAGAGCTTGATGAGATTGGAGAAGATGTGGCTCCAATTGAACACATTGCAAGC
ATGAGAAGGAATTATTTCACATCAGAGGTGTCTCACTGCAGAGCCACAGAATACATAATGAAGGGGGTGTACATCAATACTGCC
TTACTTAATGCATCTTGTGCAGCAATGGATGATTTCCAATTAATTCCAATGATAAGCAAGTGTAGAACTAAGGAGGGAAGGCGA
AAGACCAACTTGTATGGTTTCATCATAAAAGGAAGATCCCACTTAAGGAATGACACCGACGTGGTAAACTTTGTGAGCATGGAG
TTTTCTCTCACTGACCCAAGACTTGAACCACACAAATGGGAGAAGTACTGTGTTCTTGAGATAGGAGATATGCTTCTAAGAAGT
GCCATAGGCCAGGTTTCAAGGCCCATGTTCTTGTATGTGAGGACAAATGGAACCTCAAAAATTAAAATGAAATGGGGAATGGAG
ATGAGGCGTTGTCTCCTCCAGTCACTTCAACAAATTGAGAGTATGATTGAAGCTGAGTCCTCTGTCAAAGAGAAAGACATGACC
AAAGAGTTCTTTGAGAACAAATCAGAAACATGGCCCATTGGAGAGTCTCCCAAAGGAGTGGAGGAAAGTTCCATTGGGAAGGTC
TGCAGGACTTTATTAGCAAAGTCGGTATTTAACAGCTTGTATGCATCTCCACAACTAGAAGGATTTTCAGCTGAATCAAGAAAA
CTGCTTCTTATCGTTCAGGCTCTTAGGGACAATCTGGAACCTGGGACCTTTGATCTTGGGGGGCTATATGAAGCAATTGAGGAG
TGCCTAATTAATGATCCCTGGGTTTTGCTTAATGCTTCTTGGTTCAACTCCTTCCTTACACATGCATTGAGTTAGTTGTGGCAG
TGCTACTATTTGCTATCCATACTGTCCAAAAAAGTACCTTGTTTCTACT (SEQ ID NO:12)

*Fig. 1C*

PR8(CAMBRIDGE)

NP

AGCAAAAGCAGGGTAGATAATCACTCACTGAGTGACATCAAAATCATGGCGTCCCAAGGCACCAAACGGTCTTACGAACAGATG
GAGACTGATGGAGAACGCCAGAATGCCACTGAAATCAGAGCATCCGTCGGAAAAATGATTGGTGGAATTGGACGATTCTACATC
CAAATGTGCACAGAACTTAAACTCAGTGATTATGAGGGACGGTTGATCCAAAACAGCTTAACAATAGAGAGAATGGTGCTCTCT
GCTTTTGACGAAAGGAGAAATAAATACCTGGAAGAACATCCCAGTGCGGGGAAAGATCCTAAGAAAACTGGAGGACCTATATAC
AGAAGAGTAAACGGAAAGTGGATGAGAGAACTCATCCTTTATGACAAAGAAGAAATAAGGCGAATCTGGCGCCAAGCTAATAAT
GGTGACGATGCAACGGCTGGTCTGACTCACATGATGATCTGGCATTCCAATTTGAATGATGCAACTTATCAGAGGACAAGGGCT
CTTGTTCGCACCGGAATGGATCCCAGGATGTGCTCTCTGATGCAAGGTTCAACTCTCCCTAGGAGGTCTGGAGCCGCAGGTGCT
GCAGTCAAAGGAGTTGGAACAATGGTGATGGAATTGGTCAGGATGATCAAACGTGGGATCAATGATCGGAACTTCTGGAGGGGT
GAGAATGGACGAAAAACAAGAATTGCTTATGAAAGAATGTGCAACATTCTCAAAGGGAAATTTCAAACTGCTGCACAAAAAGCA
ATGATGGATCAAGTGAGAGAGAGCCGGAACCCAGGGAATGCTGAGTTCGAAGATCTCACTTTTCTAGCACGGTCTGCACTCATA
TTGAGAGGGTCGGTTGCTCACAAGTCCTGCCTGCCTGCCTGTGTGTATGGACCTGCCGTAGCCAGTGGGTACGACTTTGAAAGA
GAGGGATACTCTCTAGTCGGAATAGACCCTTTCAGACTGCTTCAAAACAGCCAAGTGTACAGCCTAATCAGACCAAATGAGAAT
CCAGCACACAAGAGTCAACTGGTGTGGATGGCATGCCATTCTGCCGCATTTGAAGATCTAAGAGTATTGAGCTTCATCAAAGGG
ACGAAGGTGGTCCCAAGAGGGAAGCTTTCCACTAGAGGAGTTCAAATTGCTTCCAATGAAAATATGGAGACTATGGAATCAAGT
ACACTTGAACTGAGAAGCAGGTACTGGGCCATAAGGACCAGAAGTGGAGGAAACACCAATCAACAGAGGGCATCTGCGGGCCAA
ATCAGCATACAACCTACGTTCTCAGTACAGAGAAATCTCCCTTTTGACAGAACAACCGTTATGGCAGCATTCACTGGGAATACA
GAGGGGAGAACATCTGACATGAGGACCGAAATCATAAGGATGATGGAAAGTGCAAGACCAGAAGATGTGTCTTTCCAGGGGCGG
GGAGTCTTCGAGCTCTCGGACGAAAAGGCAGCGAGCCCGATCGTGCCTTCCTTTGACATGAGTAATGAAGGATCTTATTTCTTC
GGAGACAATGCAGAGGAGTACGACAATTAAAGAAAAATACCCTTGTTTCTACT (SEQ ID NO:13)

*Fig. 1D*

PR8(CAMBRIDGE)

M

AGCAAAAGCAGGTAGATATTGAAAGATGAGTCTTCTAACCGAGGTCGAAACGTACGTTCTCTCTATCATCCCGTCAGGCCCCCT
CAAAGCCGAGATCGCACAGAGACTTGAAGATGTCTTTGCAGGGAAGAACACCGATCTTGAGGTTCTCATGGAATGGCTAAAGAC
AAGACCAATCCTGTCACCTCTGACTAAGGGGATTTTAGGATTTGTGTTCACGCTCACCGTGCCCAGTGAGCGAGGACTGCAGCG
TAGACGCTTTGTCCAAAATGCCCTTAATGGGAACGGGGATCCAAATAACATGGACAAAGCAGTTAAACTGTATAGGAAGCTCAA
GAGGGAGATAACATTCCATGGGGCCAAAGAAATCTCACTCAGTTATTCTGCTGGTGCACTTGCCAGTTGTATGGGCCTCATATA
CAACAGGATGGGGGCTGTGACCACTGAAGTGGCATTTGGCCTGGTATGTGCAACCTGTGAACAGATTGCTGACTCCCAGCATCG
GTCTCATAGGCAAATGGTGACAACAACCAACCCACTAATCAGACATGAGAACAGAATGGTTTTAGCCAGCACTACAGCTAAGGC
TATGGAGCAAATGGCTGGATCGAGTGAGCAAGCAGCAGAGGCCATGGAGGTTGCTAGTCAGGCTAGGCAAATGGTGCAAGCGAT
GAGAACCATTGGGACTCATCCTAGCTCCAGTGCTGGTCTGAAAAATGATCTTCTTGAAAATTTGCAGGCCTATCAGAAACGAAT
GGGGGTGCAGATGCAACGGTTCAAGTGATCCTCTCGCTATTGCCGCAAATATCATTGGGATCTTGCACTTGATATTGTGGATTC
TTGATCGTCTTTTTTTCAAATGCATTTACCGTCGCTTTAAATACGGACTGAAAGGAGGGCCTTCTACGGAAGGAGTGCCAAAGT
CTATGAGGGAAGAATATCGAAAGGAACAGCAGAGTGCTGTGGATGCTGACGATGGTCATTTTGTCAGCATAGAGCTGGAGTAAA
AAACTACCTTGTTTCTACT (SEQ ID NO:14)

NS

AGCAAAAGCAGGGTGACAAAGACATAATGGATCCAAACACTGTGTCAAGCTTTCAGGTAGATTGCTTTCTTTGGCATGTCCGCA
AACGAGTTGCAGACCAAGAACTAGGTGATGCCCCATTCCTTGATCGGCTTCGCCGAGATCAGAAATCCCTAAGAGGAAGGGGCA
GCACTCTTGGTCTGGACATCGAGACAGCCACACGTGCTGGAAAGCAGATAGTGGAGCGGATTCTGAAAGAAGAATCCGATGAGG
CACTTAAAATGACCATGGCCTCTGTACCTGCGTCGCGTTACCTAACCGACATGACTCTTGAGGAAATGTCAAGGGAATGGTCCA
TGCTCATACCCAAGCAGAAAGTGGCAGGCCCTCTTTGTATCAGAATGGACCAGGCGATCATGGATAAAAACATCATACTGAAAG
CGAACTTCAGTGTGATTTTTGACCGGCTGGAGACTCTAATATTGCTAAGGGCTTTCACCGAAGAGGGAGCAATTGTTGGCGAAA
TTTCACCATTGCCTTCTCTTCCAGGACATACTGCTGAGGATGTCAAAAATGCAGTTGGAGTCCTCATCGGAGGACTTGAATGGA
ATGATAACACAGTTCGAGTCTCTGAAACTCTACAGAGATTCGCTTGGAGAAGCAGTAATGAGAATGGGAGACCTCCACTCACTC
CAAAACAGAAACGAGAAATGGCGGGAACAATTAGGTCAGAAGTTTGAAGAAATAAGATGGTTGATTGAAGAAGTGAGACACAAA
CTGAAGGTAACAGAGAATAGTTTTGAGCAAATAACATTTATGCAAGCCTTACATCTATTGCTTGAAGTGGAGCAAGAGATAAGA
ACTTTCTCATTTCAGCTTATTTAATAATAAAAAACACCCTTGTTTCTACT (SEQ ID NO:15)

Fig. 1E

Figure 3 Summary of HA assay of 1434 individual clones

| Groups | Numbers of clone | Fold change | % |
|---|---|---|---|
| WT HA titer = $2^7$ | - | - | - |
| HA titer =$2^{>9-9.5}$ | 8 | >4 | 0.6% |
| HA titer =$2^{>8.5-9}$ | 23 | >2.8 - 4 | 1.6% |
| HA titer =$2^{7-8.5}$ | 748 | 1 - 2.8 | 52.2% |
| HA titer < $2^7$ | 655 | <1 | 45.6% |
| Total | 1434 | - | 100% |

Figure 4 Recombinant viruses generated from dominant mutations

| Viruses | Gene backbone | | | | | | | | Virus stock titer | |
|---|---|---|---|---|---|---|---|---|---|---|
| | HA | NA | PB2 | PB1 | PA | NP | M | NS | $2^n$ | Pfu/ml |
| WT | Indo/NC/09 delHA | Indo/NC/09 NA | PR8-wt | PR8-wt | PR8-wt | PR8-wt | PR8-wt | PR8-wt | 7 | 3.0E+07 |
| 1 | | | M202L F323L | M507V V644A | | I116L | | K55E | 9~9.5 | 2.0E+08 |
| 2 | | | M202L F323L | Q247H | R401K | | | T49A | 9 | 1.0E+08 |
| 3 | | | I504V | M507V V644A | I550L | R74K N417D | | K55E | 8~8.5 | 5.7E+07 |
| 4 | | | I505V | E112G | I550L | R74K | | S161T | 9 | 1.6E+08 |
| 5 | | | M202L F323L | E112G | | | | S161T | 8.5 | 1.3E+08 |
| 6 | | | M66R | M40I G180W | | R74K | | S161T | 8~8.5 | 2.3E+07 |

Figure 5A Growth curve – PB2 mutants
(MOI=0.001)
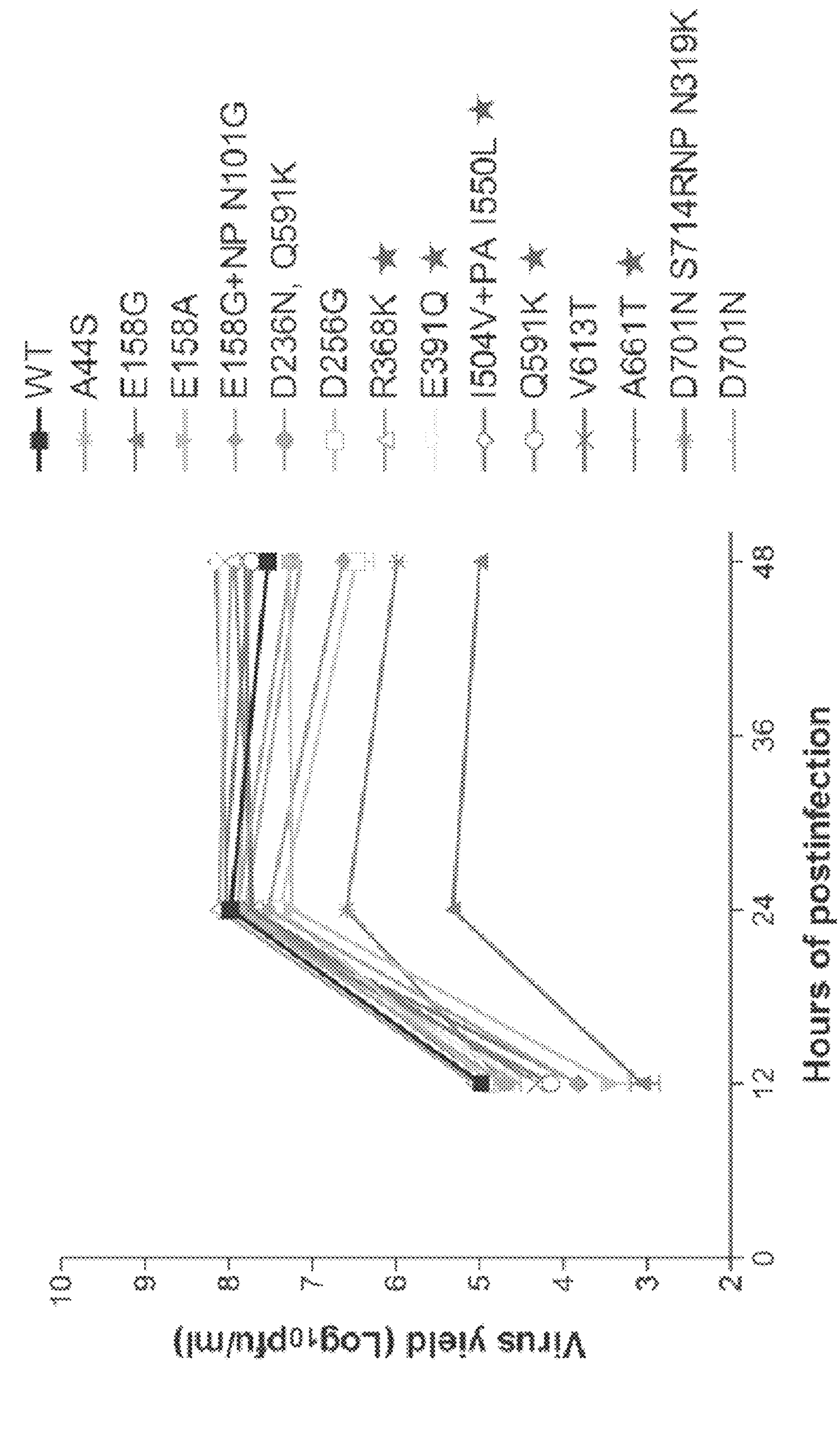

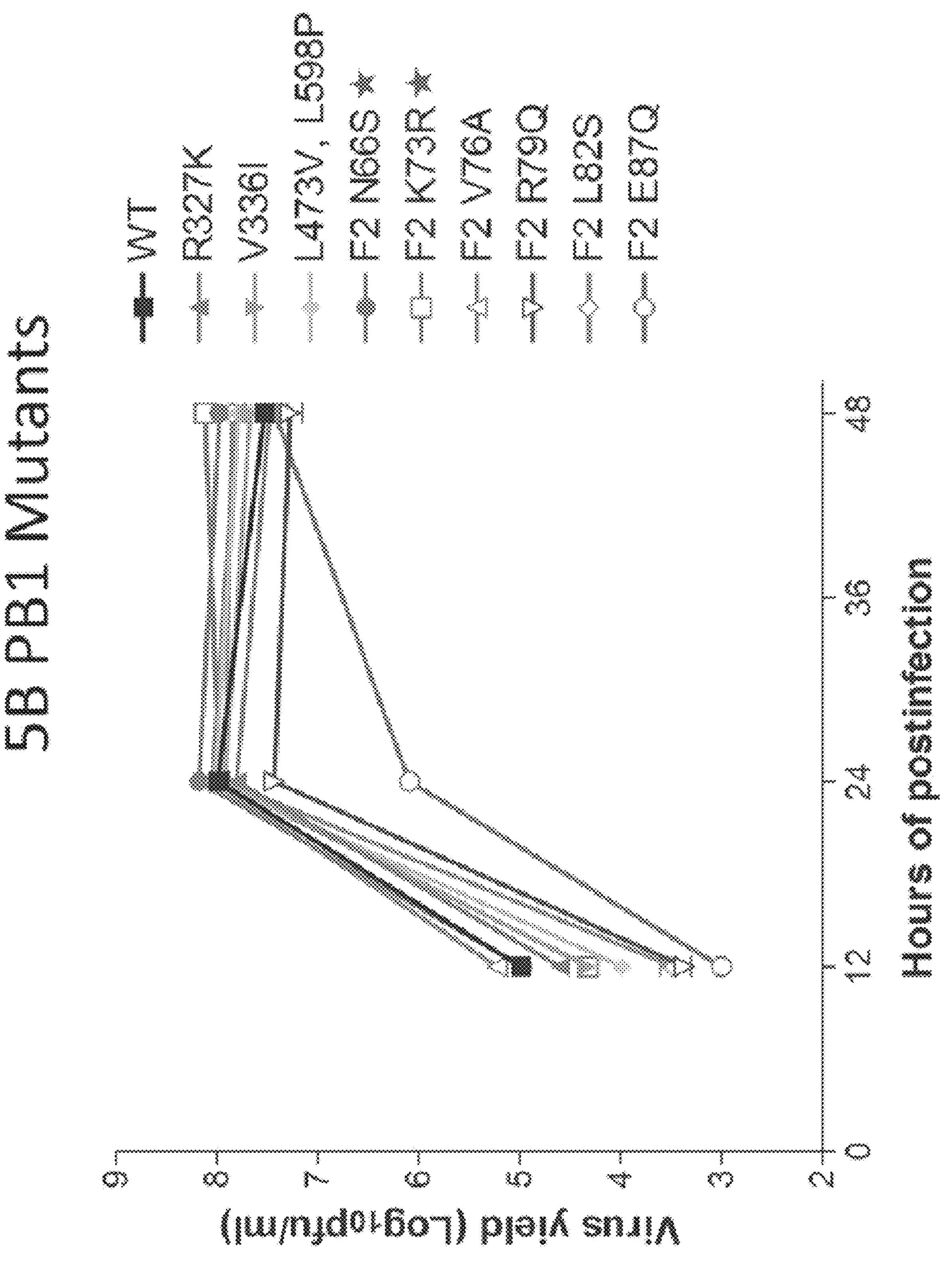
5B PB1 Mutants
WT
R327K
V336I
L473V, L598P
F2 N66S ★
F2 K73R ★
F2 V76A
F2 R79Q
F2 L82S
F2 E87Q
Virus yield ($Log_{10}$pfu/ml)
9
8
7
6
5
4
3
2
0
12
24
36
48
Hours of postinfection Figure 5C PA Mutants
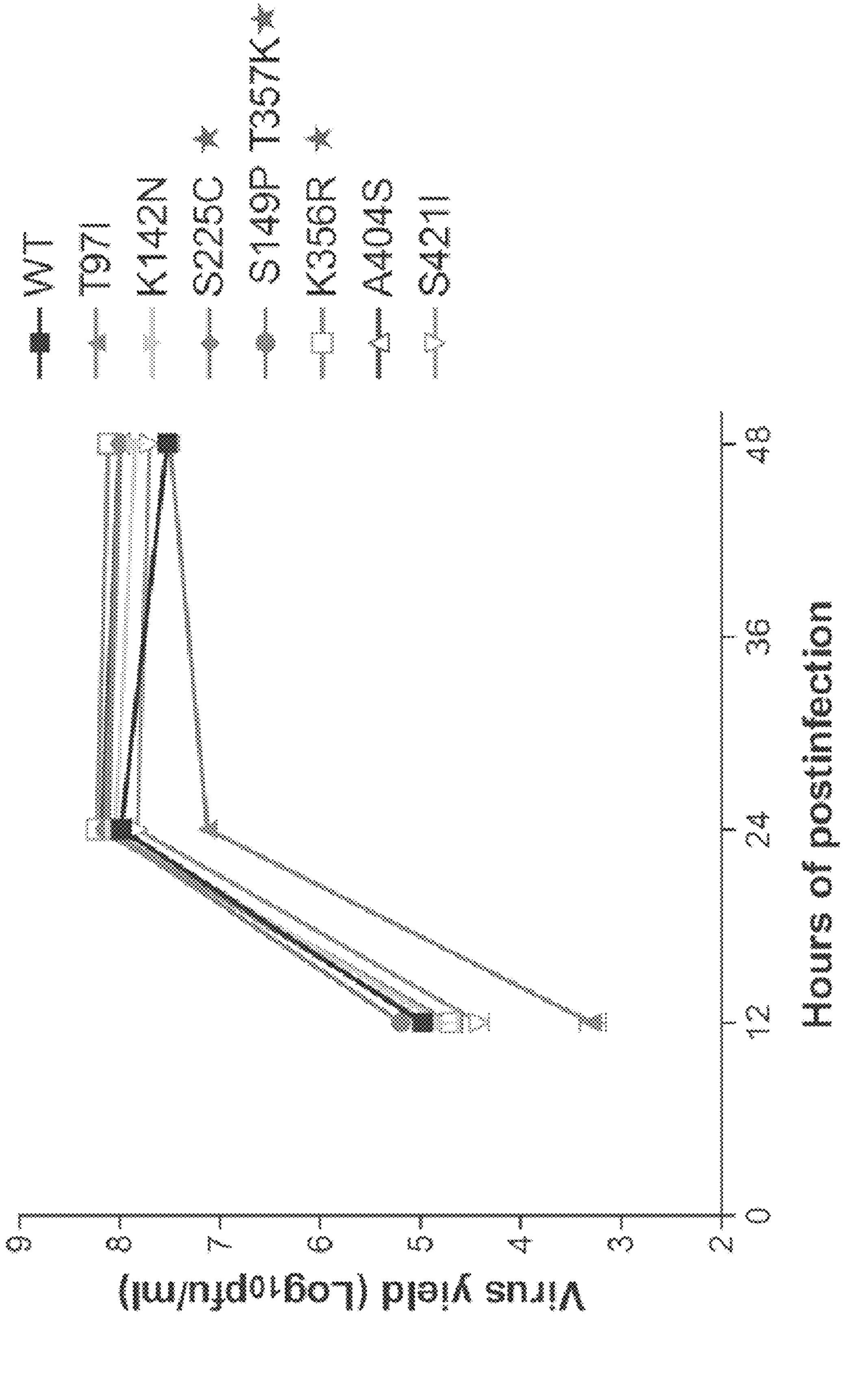

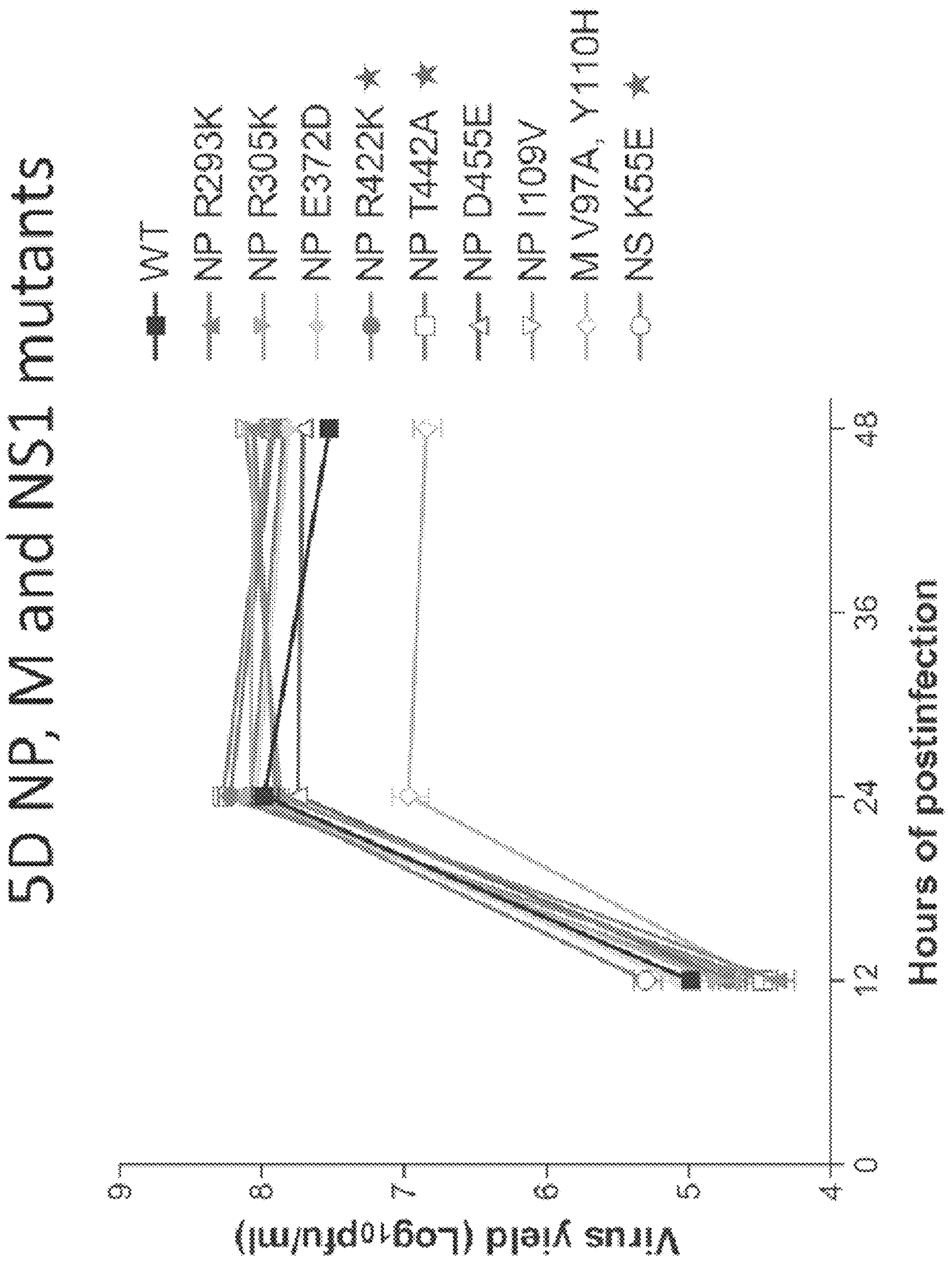
5D NP, M and NS1 mutants
WT
NP R293K
NP R305K
NP E372D
NP R422K ★
NP T442A ★
NP D455E
NP I109V
M V97A, Y110H
NS K55E ★
Virus yield (Log10pfu/ml)
4
5
6
7
8
9
0
12
24
36
48
Hours of postinfection

Figure 6 Confirmed high replicative mutations

| Gene | Screened from viruses libraries | Described in literature |
|---|---|---|
| PB2 | M202L F323L, I504V, M66R | A44S, E158G, E158A, D236N, D256G, R368K, E391Q, I504V, Q591K, V613T, A661T, D701N, D701N S714R |
| PB1 | M507V V644A, V644A, R54I, Q247H, E112G, M40I G180W, I667T M714T | R327K, V336I, L473V L598P |
| PB1 F2 | - | N66S, K73R, V76A, R79Q, L82S, E87Q |
| PA | F105C, R401K | T97I, K142N, S225C, S149PP T357K, K356R, A404S, S421I |
| NP | R293M, I116L, N224I, R74K, R74K N417D, | R293K, R305K, E372D, R422K, T442A, D455E, I109V, N101G, N319K |
| M | P90S | V97A, Y100H, V97A Y100H |
| NS | A30P, T49A, R140Q, S161T, A223E | K55E |

Figure 7A Recombinant viruses generated by RGS

| Virus # | Gene backbone | | | | | | | | Virus stock titer | |
|---|---|---|---|---|---|---|---|---|---|---|
| | HA | NA | PB2 | PB1 | PA | NP | M | NS | $2^n$ | Pfu/ml |
| wt | Inda/NC/09 delHA | Indo/NC/09 NA | wt | wt | wt | wt | wt | wt | 7 | 3.0E+07 |
| 1 | | | M202L F323L | M507V V644A | | I116L | | K55E | 9~9.5 | 2.0E+08 |
| 4 | | | M202L F323L | M507V V644A | K356R | T442A | V97A Y100H | K55E | 10~10.5 | 1.6E+08 |
| 36 | | | I504V | E112G | I550L | I112L | Y100H | R140Q | 9.5 | 1.3E+08 |
| 38 | | | M202L F323L | M507V V644A | | I116L | Y100H | K55E | 10~10.5 | 2.3E+08 |
| HY-#17 | | | I504V | E112G | S225C | R74K N417D | V97A Y100H | K55E | 9.5~10 | 5.8E+08 |
| HY-#61 | | | M202L F323L | Q247H | K142N | R74K | V97A Y100H | K55E | 10~10.5 | 2.0E+08 |
| HY-#26 | | | M202L F323L | M40L G180W | S225C | R422K | V97A Y100H | K55E | 10 | 3.0E+08 |

Figure 7B Growth characteristics (MOI=0.001)
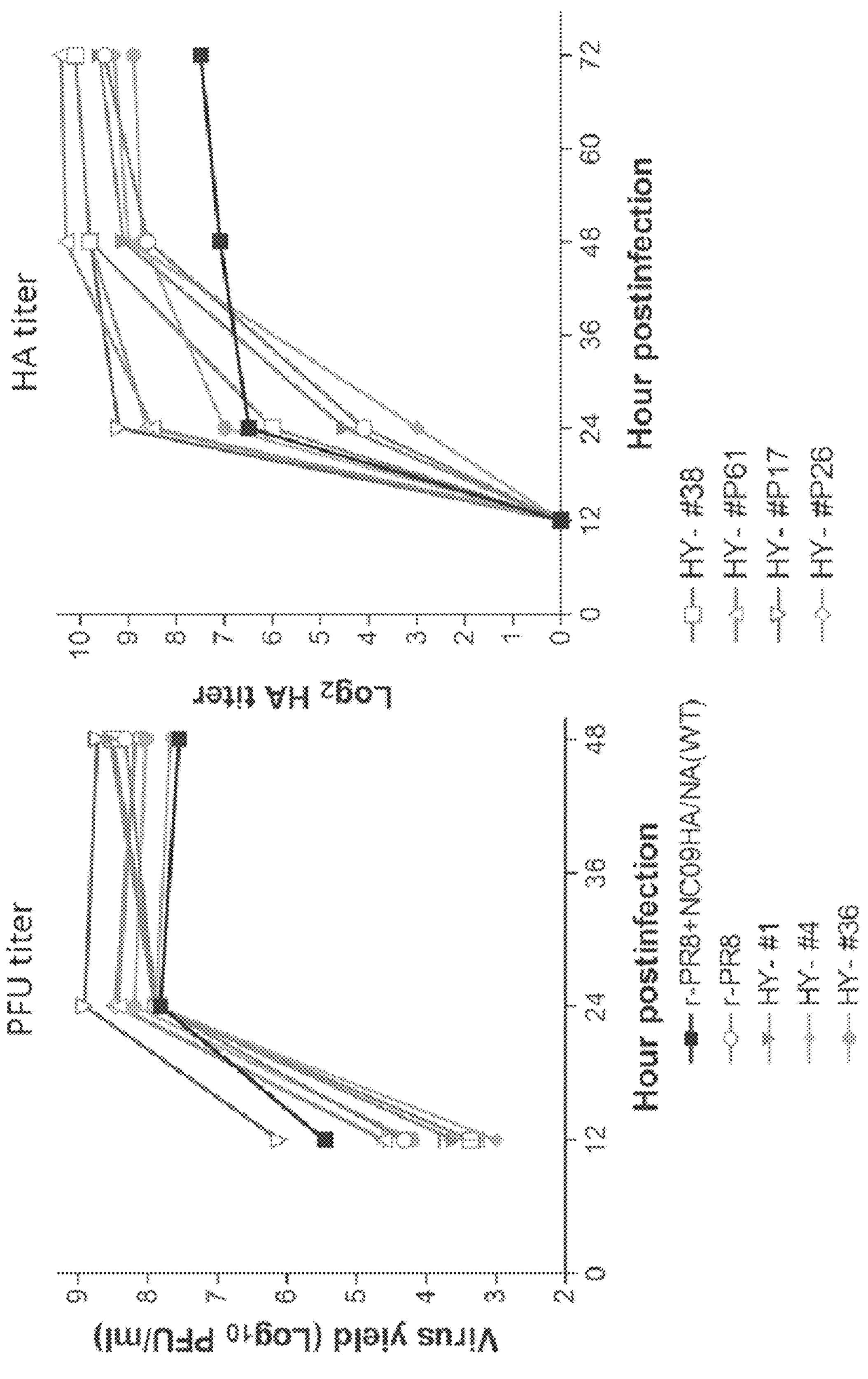

Total viral protein yield: 4.2 fold

Figure 8C SDS-PAGE analysis
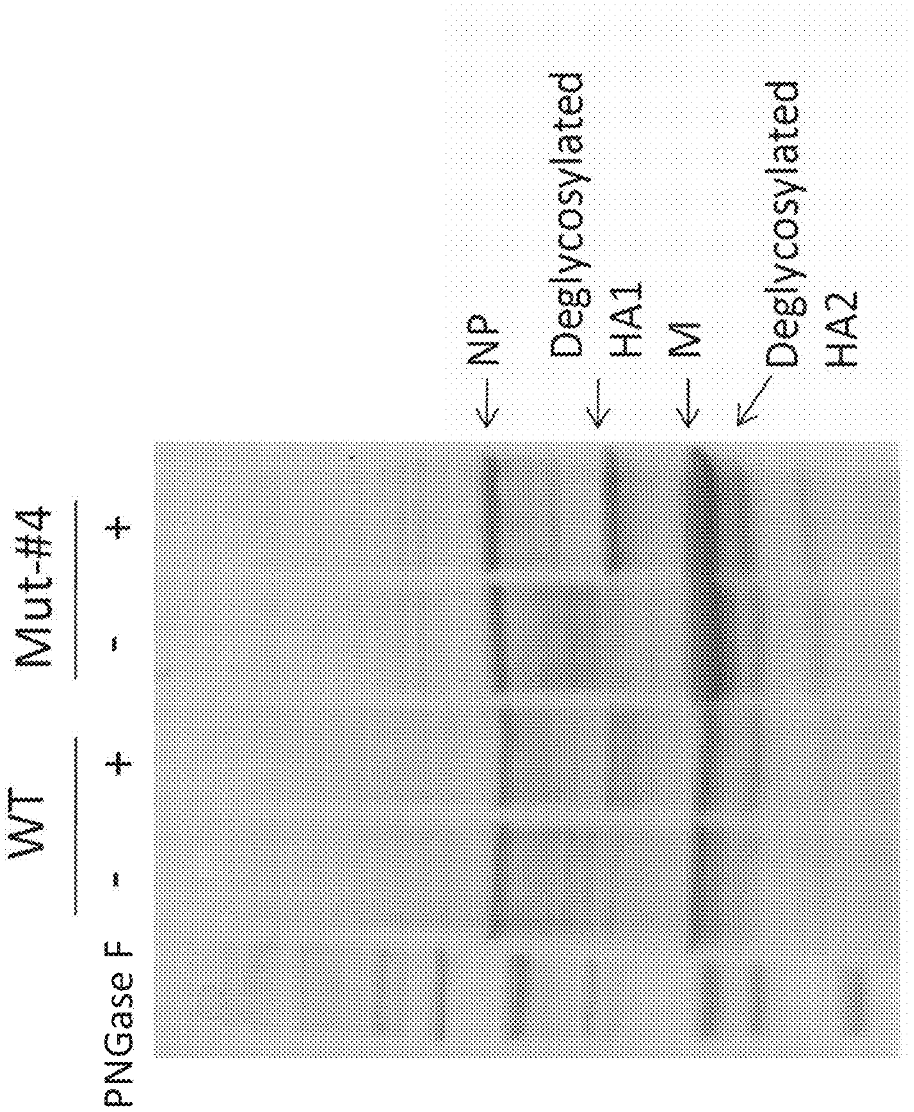
Mutant virus generates much more M1 and HA1 proteins than wild type.

Figure 9A Wild type VS. mutant

| # | Gene backbone | | | | | | | | Virus stock titer | |
|---|---|---|---|---|---|---|---|---|---|---|
| | HA | NA | PB2 | PB1 | PA | NP | M | NS | HA titer ($2^n$) | Pfu/ml |
| WT | Indo/NC/09 delHA | Indo/NC/09 NA | PR8-wt | PR8-wt | PR8-wt | PR8-wt | PR8-wt | PR8-wt | 7 | 3.0E+07 |
| 4 | | | M202L F323L | M507V V644A | K356R | T442A | V97A Y100H | K55E | 10~10.5 | 1.6E+08 |

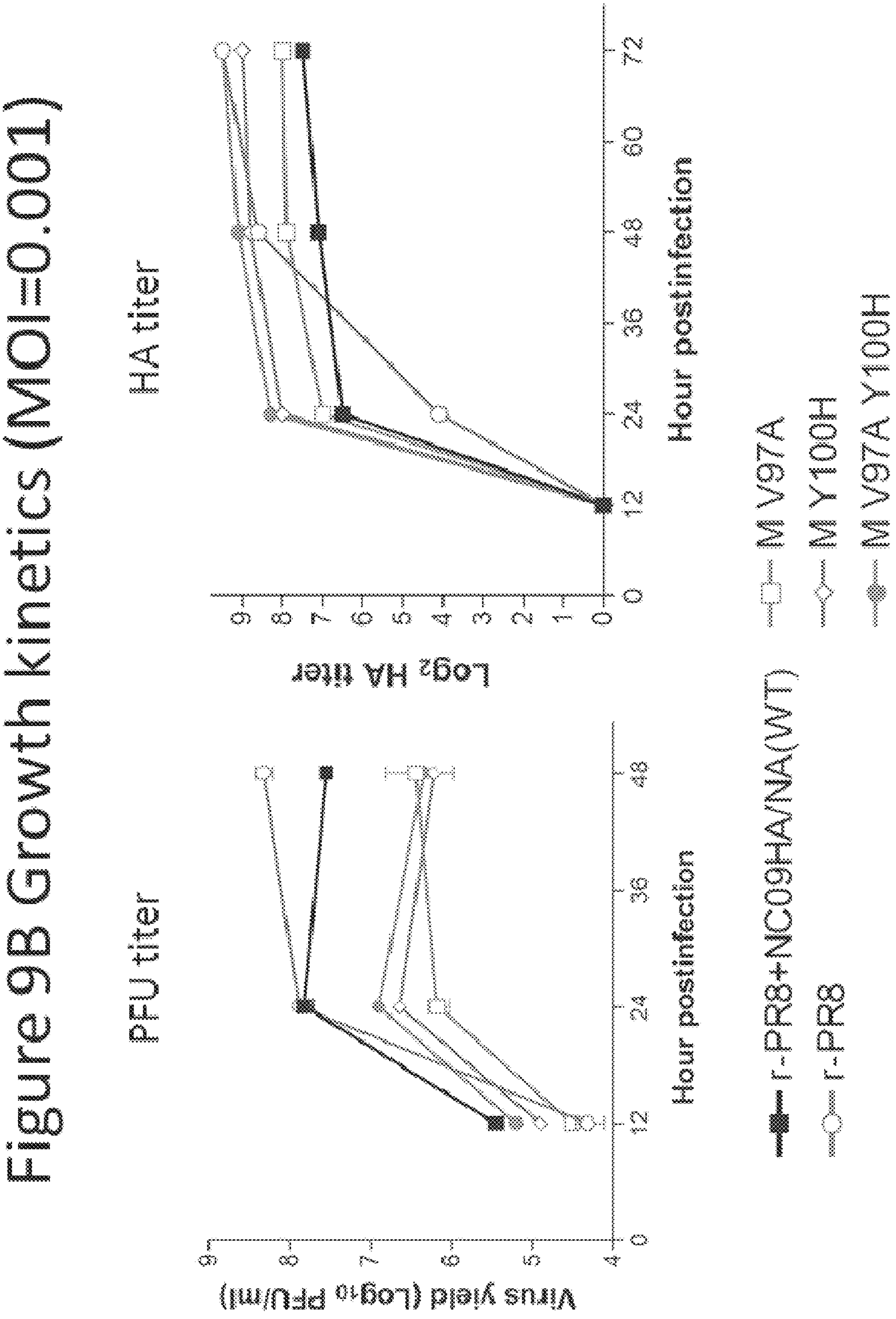
Figure 9B Growth kinetics (MOI=0.001)
PFU titer
Virus yield (Log10 PFU/ml)
Hour postinfection
HA titer
Log2 HA titer
Hour postinfection
r-PR8+NC09HA/NA(WT)
r-PR8
M V97A
M Y100H
M V97A Y100H CANIS FAMILIARIS [gbmam]: 1194 CDS's(559501 CODONS)

FIELDS: [TRIPLET] [AMINO ACID] [FRACTION] [FREQUENCY: PER THOUSAND] ([NUMBER])

| | | | |
|---|---|---|---|
| UUU F 0.41 17.1 ( 9540) | UCU S 0.18 13.8 ( 7723) | UAU Y 0.40 11.5 ( 6456) | UGU C 0.42 10.1 ( 5665) |
| UUC F 0.59 24.4 (13671) | UCC S 0.24 18.4 (10299) | UAC Y 0.60 17.5 ( 9786) | UGC C 0.58 13.8 ( 7723) |
| UUA L 0.06 5.8 ( 3270) | UCA S 0.13 9.8 ( 5487) | UAA * 0.27 0.6 ( 325) | UGA * 0.53 1.1 ( 642) |
| UUG L 0.12 11.8 ( 6627) | UCG S 0.06 4.6 ( 2584) | UAG * 0.21 0.5 ( 254) | UGG W 1.00 13.8 ( 7704) |
| CUU L 0.12 11.7 ( 6523) | CCU P 0.27 15.6 ( 8713) | CAU H 0.39 9.0 ( 5039) | CGU R 0.07 3.9 ( 2163) |
| CUC L 0.22 21.8 (12224) | CCC P 0.35 20.4 (11422) | CAC H 0.61 14.1 ( 7888) | CGC R 0.20 10.6 ( 5943) |
| CUA L 0.06 6.5 ( 3644) | CCA P 0.25 14.6 ( 8157) | CAA Q 0.25 11.0 ( 6149) | CGA R 0.11 5.6 ( 3155) |
| CUG L 0.43 42.8 (23966) | CCG P 0.12 7.0 ( 3892) | CAG Q 0.75 32.6 (18244) | CGG R 0.21 11.0 ( 6132) |
| AUU I 0.32 15.5 ( 8662) | ACU T 0.22 12.3 ( 6886) | AAU N 0.43 16.5 ( 9253) | AGU S 0.14 10.8 ( 6029) |
| AUC I 0.53 25.7 (14391) | ACC T 0.39 21.4 (11979) | AAC N 0.57 21.6 (12104) | AGC S 0.25 18.9 (10595) |
| AUA I 0.15 7.2 ( 4017) | ACA T 0.26 14.2 ( 7972) | AAA K 0.40 22.2 (12410) | AGA R 0.20 10.5 ( 5847) |
| AUG M 1.00 22.7 (12717) | ACG T 0.13 7.2 ( 4005) | AAG K 0.60 33.9 (18967) | AGG R 0.21 11.1 ( 6228) |
| GUU V 0.14 9.3 ( 5189) | GCU A 0.25 17.2 ( 9609) | GAU D 0.43 19.7 (11012) | GGU G 0.16 11.3 ( 6298) |
| GUC V 0.27 17.2 ( 9607) | GCC A 0.44 30.3 (16927) | GAC D 0.57 26.2 (14655) | GGC G 0.35 24.2 (13513) |
| GUA V 0.10 6.5 ( 3660) | GCA A 0.20 13.7 ( 7651) | GAA E 0.40 26.4 (14776) | GGA G 0.24 16.9 ( 9465) |
| GUG V 0.48 31.0 (17366) | GCG A 0.11 7.9 ( 4431) | GAG E 0.60 40.3 (22552) | GGG G 0.25 17.4 ( 9718) |

CODING GC 53.16% 1ST LETTER GC 55.35% 2ND LETTER GC 41.92% 3RD LETTER GC 62.22%

GENETIC CODE 1: STANDARD

*Fig. 10A*

Figure 10D Growth kinetics in MDCK cells
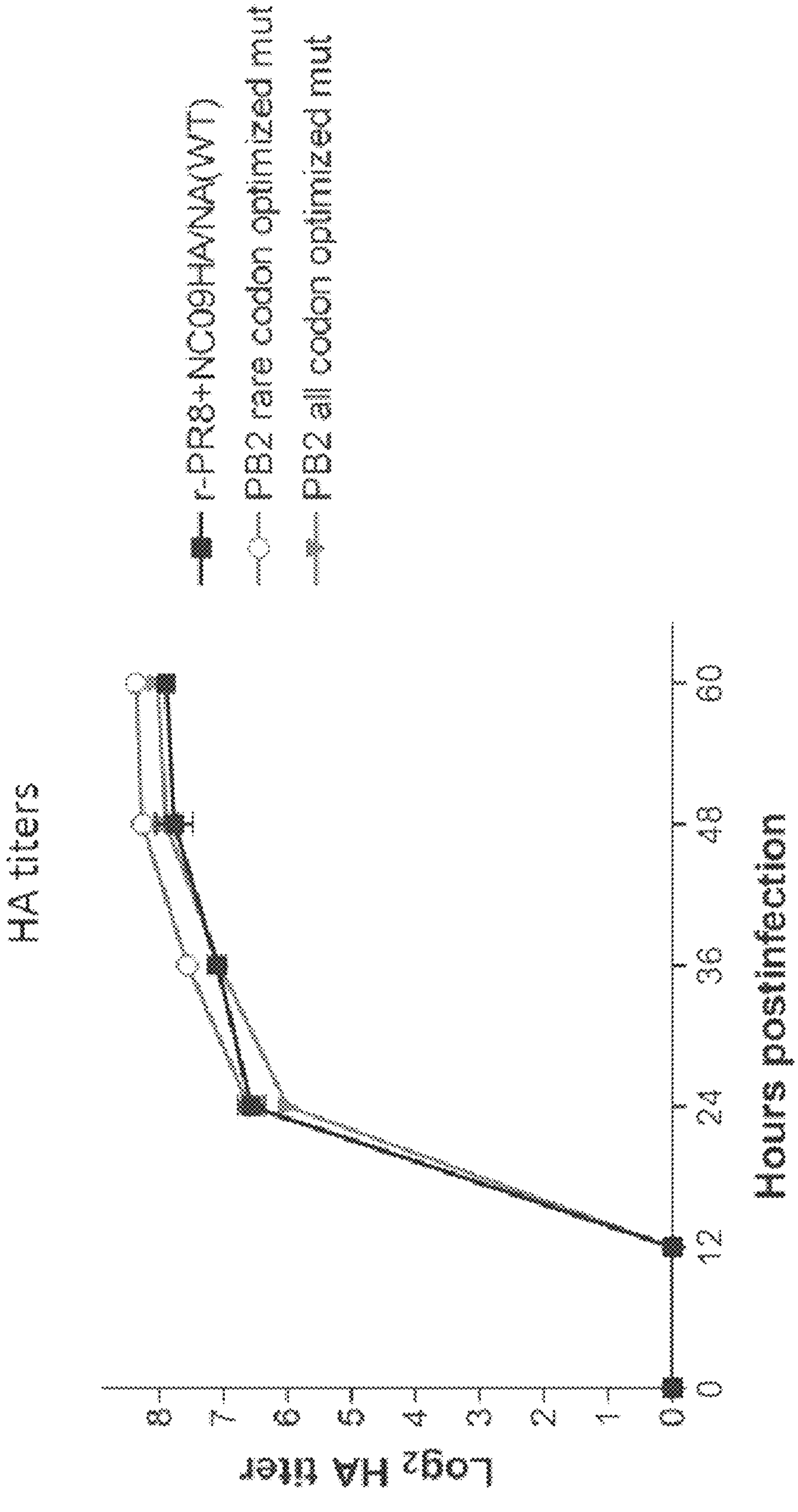

PR8-UW PB2:

AGCGAAAGCAGGTCAATTATATTCAATATGGAAAGAATAAAAGAACTACGAAATCTAATGTCGCAGTCTCGCACCCGCGA
GATACTCACAAAAACCACCGTGGACCATATGGCCATAATCAAGAAGTACACATCAGGAAGACAGGAGAAGAACCCAGCAC
TTAGGATGAAATGGATGATGGCAATGAAATATCCAATTACAGCAGACAAGAGGATAACGGAAATGATTCCTGAGAGAAAT
GAGCAAGGACAAACTTTATGGAGTAAAATGAATGATGCCGGATCAGACCGAGTGATGGTATCACCTCTGGCTGTGACATG
GTGGAATAGGAATGGACCAATAACAAATACAGTTCATTATCCAAAAATCTACAAAACTTATTTTGAAAGAGTCGAAAGGC
TAAAGCATGGAACCTTTGGCCCTGTCCATTTTAGAAACCAAGTCAAAATACGTCGGAGAGTTGACATAAATCCTGGTCAT
GCAGATCTCAGTGCCAAGGAGGCACAGGATGTAATCATGGAAGTTGTTTTCCCTAACGAAGTGGGAGCCAGGATACTAAC
ATCGGAATCGCAACTAACGATAACCAAAGAGAAGAAAGAAGAACTCCAGGATTGCAAAATTTCTCCTTTGATGGTTGCAT
ACATGTTGGAGAGAGAACTGGTCCGCAAAACGAGATTCCTCCCAGTGGCTGGTGGAACAAGCAGTGTGTACATTGAAGTG
TTGCATTTGACTCAAGGAACATGCTGGGAACAGATGTATACTCCAGGAGGGGAAGTGAGGAATGATGATGTTGATCAAAG
CTTGATTATTGCTGCTAGGAACATAGTGAGAAGAGCTGCAGTATCAGCAGATCCACTAGCATCTTTATTGGAGATGTGCC
ACAGCACACAGATTGGTGGAATTAGGATGGTAGACATCCTTAGGCAGAACCCAACAGAAGAGCAAGCCGTGGATATATGC
AAGGCTGCAATGGGACTGAGAATTAGCTCATCCTTCAGTTTTGGTGGATTCACATTTAAGAGAACAAGCGGATCATCAGT
CAAGAGAGAGGAAGAGGTGCTTACGGGCAATCTTCAAACATTGAAGATAAGAGTGCATGAGGGATATGAAGAGTTCACAA
TGGTTGGGAGAAGAGCAACAGCCATACTCAGAAAAGCAACCAGGAGATTGATTCAGCTGATAGTGAGTGGGAGAGACGAA
CAGTCGATTGCCGAAGCAATAATTGTGGCCATGGTATTTTCACAAGAGGATTGTATGATAAAAGCAGTCAGAGGTGATCT
GAATTTCGTCAATAGGGCGAATCAACGATTGAATCCTATGCATCAACTTTTAAGACATTTTCAGAAGGATGCGAAAGTGC
TTTTTCAAAATTGGGGAGTTGAACCTATCGACAATGTGATGGGAATGATTGGGATATTGCCCGACATGACTCCAAGCATC
GAGATGTCAATGAGAGGAGTGAGAATCAGCAAAATGGGTGTAGATGAGTACTCCAGCACGGAGAGGGTAGTGGTGAGCAT
TGACCGTTTTTTGAGAATCCGGGACCAACGAGGAAATGTACTACTGTCTCCCGAGGAGGTCAGTGAAACACAGGGAACAG
AGAAACTGACAATAACTTACTCATCGTCAATGATGTGGGAGATTAATGGTCCTGAATCAGTGTTGGTCAATACCTATCAA
TGGATCATCAGAAACTGGGAAACTGTTAAAATTCAGTGGTCCCAGAACCCTACAATGCTATACAATAAAATGGAATTTGA
ACCATTTCAGTCTTTAGTACCTAAGGCCATTAGAGGCCAATACAGTGGGTTTGTAAGAACTCTGTTCCAACAAATGAGGG
ATGTGCTTGGGACATTTGATACCGCACAGATAATAAAACTTCTTCCCTTCGCAGCCGCTCCACCAAAGCAAAGTAGAATG
CAGTTCTCCTCATTTACTGTGAATGTGAGGGGATCAGGAATGAGAATACTTGTAAGGGGCAATTCTCCTGTATTCAACTA
TAACAAGGCCACGAAGAGACTCACAGTTCTCGGAAAGGATGCTGGCACTTTAACTGAAGACCCAGATGAAGGCACAGCTG
GAGTGGAGTCCGCTGTTCTGAGGGGATTCCTCATTCTGGGCAAAGAAGACAAGAGATATGGGCCAGCACTAAGCATCAAT
GAACTGAGCAACCTTGCGAAAGGAGAGAAGGCTAATGTGCTAATTGGGCAAGGAGACGTGGTGTTGGTAATGAAACGGAA
ACGGGACTCTAGCATACTTACTGACAGCCAGACAGCGACCAAAAGAATTCGGATGGCCATCAATTAGTGTCGAATAGTTT
AAAAACGACCTTGTTTCTACT (SEQ ID NO:3)

FIG. 10F

Canine codon optimized PR8-PB2:

AGCGAAAGCAGGTCAATTATATTCAATATGGAAAGAATAAAAGAACTACGAAATCTAATGTCGCAGTCTCGCACCCGCGA
GATACTCACAAAAACCACCGTGGACCATATGGCCATAATCAAGAAGTACACATCAGGAAGACAGGAGAAGAACCCAGCAC
TGAGGATGAAATGGATGATGGCAATGAAATATCCAATTACAGCAGACAAGAGGATCACCGAAATGATTCCTGAGAGAAAT
GAGCAGGGACAGACTCTGTGGAGTAAAATGAATGATGCCGGATCAGACCGAGTGATGGTGTCACCTCTGGCTGTGACATG
GTGGAATAGGAATGGACCAATCACAAATACAGTGCATTATCCAAAAATCTACAAAACTTATTTTGAAAGAGTCGAAAGGC
TGAAGCATGGAACCTTTGGCCCTGTCCATTTTAGAAACCAGGTCAAAATCCGGCGGAGAGTGGACATCAATCCTGGTCAT
GCAGATCTCAGTGCCAAGGAGGCACAGGATGTGATCATGGAAGTGGTGTTCCCTAACGAAGTGGGAGCCAGGATTCTGAC
ATCCGAATCCCAGCTGACCATTACCAAAGAGAAGAAAGAAGAACTCCAGGATTGCAAAATTTCTCCTCTGATGGTGGCAT
ACATGCTGGAGAGAGAACTGGTCCGCAAAACAAGATTCCTCCCAGTGGCTGGTGGAACAAGCAGTGTGTACATTGAAGTG
CTGCATCTGACTCAGGGAACATGCTGGGAACAGATGTATACTCCAGGAGGGGAAGTGAGGAATGATGATGTGGATCAGAG
CCTGATTATTGCTGCTAGGAACATTGTGAGAAGAGCTGCAGTGTCAGCAGATCCACTGGCATCTCTGCTGGAGATGTGCC
ACAGCACACAGATTGGTGGAATTAGGATGGTGGACATCCTGAGGCAGAACCCAACAGAAGAGCAGGCCGTGGATATTTGC
AAGGCTGCAATGGGACTGAGAATTAGCTCATCCTTCAGTTTTGGTGGATTCACATTTAAGAGAACAAGCGGATCATCAGT
CAAGAGAGAGGAAGAGGTGCTGACCGGCAATCTGCAGACACTGAAGATCAGAGTGCATGAGGGATATGAAGAGTTCACAA
TGGTGGGGAGAAGAGCAACAGCCATCCTCAGAAAAGCAACCAGGAGACTGATTCAGCTGATCGTGAGTGGGAGAGACGAA
CAGTCCATTGCCGAAGCAATTATTGTGGCCATGGTGTTTTCACAGGAGGATTGTATGATTAAAGCAGTCAGAGGTGATCT
GAATTTCGTCAATAGGGCCAATCAGCGACTGAATCCTATGCATCAGCTGCTGAGACATTTTCAGAAGGATGCCAAAGTGC
TGTTTCAGAATTGGGGAGTGGAACCTATCGACAATGTGATGGGAATGATTGGGATCCTGCCCGACATGACTCCAAGCATC
GAGATGTCAATGAGAGGAGTGAGAATCAGCAAAATGGGTGTGGATGAGTACTCCAGCACCGAGAGGGTCGTGGTGAGCAT
TGACAGATTTCTGAGAATCCGGGACCAGCGAGGAAATGTGCTCCTGTCTCCCGAGGAGGTCAGTGAAACACAGGGAACAG
AGAAACTGACAATTACTTACTCATCCTCAATGATGTGGGAGATTAATGGTCCTGAATCAGTGCTGGTCAATACCTATCAG
TGGATCATCAGAAACTGGGAAACTGTGAAAATTCAGTGGTCCCAGAACCCTACAATGCTGTACAATAAAATGGAATTTGA
ACCATTTCAGTCTCTGGTGCCTAAGGCCATTAGAGGCCAGTACAGTGGGTTTGTGAGAACTCTGTTCCAGCAGATGAGGG
ATGTGCTGGGGACATTTGATACCGCACAGATTATTAAACTGCTGCCCTTCGCAGCCGCTCCACCAAAGCAGAGTAGAATG
CAGTTCTCCTCATTTACTGTGAATGTGAGGGGATCAGGAATGAGAATCCTGGTGAGGGGCAATTCTCCTGTGTTCAACTA
TAACAAGGCCACCAAGAGACTCACAGTGCTCGGAAAGGATGCTGGCACTCTGACTGAAGACCCAGATGAAGGCACAGCTG
GAGTGGAGTCCGCTGTGCTGAGGGGATTCCTCATTCTGGGCAAAGAAGACAAGAGATATGGGCCAGCACTGAGCATCAAT
GAACTGAGCAACCTGGCCAAAGGAGAGAAGGCTAATGTGCTAATTGGGCAAGGAGACGTGGTGTTGGTAATGAAACGGAA
ACGGGACTCTAGCATACTTACTGACAGCCAGACAGCGACCAAAAGAATTCGGATGGCCATCAATTAGTGTCGAATAGTTT
AAAAACGACCTTGTTTCTACT (SEQ ID NO:16)

AGCGAAAGCAGGCAAACCATTTGAATGGATGTCAATCCGACCTTACTTTTCTTAAAAGTGCCAGCACAAAATGCTATAAG

CACAACTTTCCCTTATACTGGAGACCCTCCTTACAGCCATGGGACAGGAACAGGATACACCATGGATACTGTCAACAGGA

CACATCAGTACTCAGAAAAGGGAAGATGGACAACAAACACCGAAACTGGAGCACCGCAACTCAACCCGATTGATGGGCCA

CTGCCAGAAGACAATGAACCAAGTGGTTATGCCCAAACAGATTGTGTATTGGAGGCGATGGCTTTCCTTGAGGAATCCCA

TCCTGGTATTTTTGAAAACTCGTGTATTGAAACGATGGAGGTTGTTCAGCAAACACGAGTAGACAAGCTGACACAAGGCC

GACAGACCTATGACTGGACTCTAAATAGAAACCAACCTGCTGCAACAGCATTGGCCAACACAATAGAAGTGTTCAGATCA

AATGGCCTCACGGCCAATGAGTCTGGAAGGCTCATAGACTTCCTTAAGGATGTAATGGAGTCAATGAACAAAGAAGAAAT

GGGGATCACAACTCATTTTCAGAGAAAGAGACGGGTGAGAGACAATATGACTAAGAAAATGATAACACAGAGAACAATGG

GTAAAAAGAAGCAGAGATTGAACAAAAGGAGTTATCTAATTAGAGCATTGACCCTGAACACAATGACCAAAGATGCTGAG

AGAGGGAAGCTAAAACGGAGAGCAATTGCAACCCCAGGGATGCAAATAAGGGGGTTTGTATACTTTGTTGAGACACTGGC

AAGGAGTATATGTGAGAAACTTGAACAATCAGGGTTGCCAGTTGGAGGCAATGAGAAGAAAGCAAAGTTGGCAAATGTTG

TAAGGAAGATGATGACCAATTCTCAGGACACCGAACTTTCTTTCACCATCACTGGAGATAACACCAAATGGAACGAAAAT

CAGAATCCTCGGATGTTTTTGGCCATGATCACATATATGACCAGAAATCAGCCCGAATGGTTCAGAAATGTTCTAAGTAT

TGCTCCAATAATGTTCTCAAACAAAATGGCGAGACTGGGAAAAGGGTATATGTTTGAGAGCAAGAGTATGAAACTTAGAA

CTCAAATACCTGCAGAAATGCTAGCAAGCATCGATTTGAAATATTTCAATGATTCAACAAGAAAGAAGATTGAAAAAATC

CGACCGCTCTTAATAGAGGGGACTGCATCATTGAGCCCTGGAATGATGATGGGCATGTTCAATATGTTAAGCACTGTATT

AGGCGTCTCCATCCTGAATCTTGGACAAAAGAGATACACCAAGACTACTTACTGGTGGGATGGTCTTCAATCCTCTGACG

ATTTTGCTCTGATTGTGAATGCACCCAATCATGAAGGGATTCAAGCCGGAGTCGACAGGTTTTATCGAACCTGTAAGCTA

CTTGGAATCAATATGAGCAAGAAAAAGTCTTACATAAACAGAACAGGTACATTTGAATTCACAAGTTTTTTCTATCGTTA

TGGGTTTGTTGCCAATTTCAGCATGGAGCTTCCCAGTTTTGGGGTGTCTGGGATCAACGAGTCAGCGGACATGAGTATTG

GAGTTACTGTCATCAAAAACAATATGATAAACAATGATCTTGGTCCAGCAACAGCTCAAATGGCCCTTCAGTTGTTCATC

AAAGATTACAGGTACACGTACCGATGCCATATAGGTGACACACAAATACAAACCCGAAGATCATTTGAAATAAAGAAACT

GTGGGAGCAAACCCGTTCCAAAGCTGGACTGCTGGTCTCCGACGGAGGCCCAAATTTATACAACATTAGAAATCTCCACA

TTCCTGAAGTCTGCCTAAAATGGGAATTGATGGATGAGGATTACCAGGGGCGTTTATGCAACCCACTGAACCCATTTGTC

AGCCATAAAGAAATTGAATCAATGAACAATGCAGTGATGATGCCAGCACATGGTCCAGCCAAAAACATGGAGTATGATGC

TGTTGCAACAACACACTCCTGGATCCCCAAAAGAAATCGATCCATCTTGAATACAAGTCAAAGAGGAGTACTTGAGGATG

AACAAATGTACCAAAGGTGCTGCAATTTATTTGAAAAATTCTTCCCCAGCAGTTCATACAGAAGACCAGTCGGGATATCC

AGTATGGTGGAGGCTATGGTTTCCAGAGCCCGAATTGATGCACGGATTGATTTCGAATCTGGAAGGATAAAGAAAGAAGA

GTTCACTGAGATCATGAAGATCTGTTCCACCATTGAAGAGCTCAGACGGCAAAAATAGTGAATTTAGCTTGTCCTTCATG

AAAAAATGCCTTGTTTCTACT (SEQ ID NO:2)

FIG. 10H

Canine codon optimized PR8 PB1:

AGCGAAAGCAGGCAAACCATTTGAATGGATGTCAATCCGACCTTACTTTTCTTAAAAGTGCCAGCACAAAATGCTATAAG
CACAACTTTCCCTTATACTGGAGACCCTCCTTACAGCCATGGGACAGGAACAGGATACACCATGGATACTGTCAACAGGA
CACATCAGTACTCAGAAAAGGGAAGATGGACAACAAACACCGAAACTGGAGCACCGCAACTCAACCCGATTGATGGGCCA
CTGCCAGAAGACAATGAACCAAGTGGTTATGCCCAAACAGATTGTGTATTGGAGGCGATGGCTTTCCTTGAGGAATCCCA
TCCTGGTATTTTTGAAAACTCGTGTATTGAAACGATGGAGGTTGTTCAGCAAACACGAGTGGACAAGCTGACACAGGGCC
GACAGACCTATGACTGGACTCTGAATAGAAACCAGCCTGCTGCAACAGCACTGGCCAACACAATCGAAGTGTTCAGATCA
AATGGCCTCACCGCCAATGAGTCTGGAAGGCTCATCGACTTCCTGAAGGATGTGATGGAGTCAATGAACAAAGAAGAAAT
GGGGATCACAACTCATTTTCAGAGAAAGAGACGGGTGAGAGACAATATGACTAAGAAAATGATTACACAGAGAACAATGG
GTAAAAAGAAGCAGAGACTGAACAAAAGGAGTTATCTGATTAGAGCACTGACCCTGAACACAATGACCAAAGATGCTGAG
AGAGGGAAGCTGAAACGGAGAGCAATTGCAACCCCAGGGATGCAGATTAGGGGGTTTGTGTACTTTGTGGAGACACTGGC
AAGGAGTATTTGTGAGAAACTGGAACAGTCAGGGCTGCCAGTGGGAGGCAATGAGAAGAAAGCAAAGCTGGCAAATGTGG
TGAGGAAGATGATGACCAATTCTCAGGACACCGAACTGTCTTTCACCATCACTGGAGATAACACCAAATGGAACGAAAAT
CAGAATCCTCGGATGTTTCTGGCCATGATCACATATATGACCAGAAATCAGCCCGAATGGTTCAGAAATGTGCTGAGTAT
TGCTCCAATTATGTTCTCAAACAAAATGGCCAGACTGGGAAAAGGGTATATGTTTGAGAGCAAGAGTATGAAACTGAGAA
CTCAGATTCCTGCAGAAATGCTGGCAAGCATCGATCTGAAATATTTCAATGATTCAACAAGAAAGAAGATTGAAAAAATC
CGACCCCTCCTGATTGAGGGGACTGCATCACTGAGCCCTGGAATGATGATGGGCATGTTCAATATGCTGAGCACTGTGCT
GGGCGTCTCCATCCTGAATCTGGGACAGAAGAGATACACCAAGACTACTTACTGGTGGGATGGTCTGCAGTCCTCTGACG
ATTTTGCTCTGATTGTGAATGCACCCAATCATGAAGGGATTCAGGCCGGAGTCGACAGGTTTTATCGAACCTGTAAGCTG
CTGGGAATCAATATGAGCAAGAAAAAGTCTTACATCAACAGAACAGGTACATTTGAATTCACAAGTTTTTTCTATCGCTA
TGGGTTTGTGGCCAATTTCAGCATGGAGCTGCCCAGTTTTGGGGTGTCTGGGATCAACGAGTCAGCCGACATGAGTATTG
GAGTGACTGTCATCAAAAACAATATGATCAACAATGATCTGGGTCCAGCAACAGCTCAGATGGCCCTGCAGCTGTTCATC
AAAGATTACAGGTACACCTACCGATGCCATATCGGTGACACACAGATTCAGACCCGAAGATCATTTGAAATCAAGAAACT
GTGGGAGCAGACCCGCTCCAAAGCTGGACTGCTGGTCTCCGACGGAGGCCCAAATCTGTACAACATTAGAAATCTCCACA
TTCCTGAAGTCTGCCTGAAATGGGAACTGATGGATGAGGATTACCAGGGGCGCCTGTGCAACCCACTGAACCCATTTGTC
AGCCATAAAGAAATTGAATCAATGAACAATGCAGTGATGATGCCAGCACATGGTCCAGCCAAAAACATGGAGTATGATGC
TGTGGCAACAACACACTCCTGGATCCCCAAAAGAAATCGATCCATCCTGAATACAAGTCAGAGAGGAGTGCTGGAGGATG
AACAGATGTACCAGAGGTGCTGCAATCTGTTTGAAAAATTCTTCCCCAGCAGTTCATACAGAAGACCAGTCGGGATCTCC
AGTATGGTGGAGGCTATGGTGTCCAGAGCCCGAATTGATGCACGGATTGATTTCGAATCTGGAAGGATCAAGAAAGAAGA
GTTCACTGAGATCATGAAGATCTGTTCCACCATTGAAGAGCTCAGACGGCAAAAATAGTGAATTTAGCTTGTCCTTCATG
AAAAAATGCCTTGTTTCTACT (SEQ ID NO:17)

AGCGAAAGCAGGTACTGATCCAAAATGGAAGATTTTGTGCGACAATGCTTCAATCCGATGATTGTCGAGCTTGCGGAAAA
AACAATGAAAGAGTATGGGGAGGACCTGAAAATCGAAACAAACAAATTTGCAGCAATATGCACTCACTTGGAAGTATGCT
TCATGTATTCAGATTTTCACTTCATCAATGAGCAAGGCGAGTCAATAATCGTAGAACTTGGTGATCCAAATGCACTTTTG
AAGCACAGATTTGAAATAATCGAGGGAAGAGATCGCACAATGGCCTGGACAGTAGTAAACAGTATTTGCAACACTACAGG
GGCTGAGAAACCAAAGTTTCTACCAGATTTGTATGATTACAAGGAGAATAGATTCATCGAAATTGGAGTAACAAGGAGAG
AAGTTCACATATACTATCTGGAAAAGGCCAATAAAATTAAATCTGAGAAAACACACATCCACATTTTCTCGTTCACTGGG
GAAGAAATGGCCACAAAGGCAGACTACACTCTCGATGAAGAAAGCAGGGCTAGGATCAAAACCAGACTATTCACCATAAG
ACAAGAAATGGCCAGCAGAGGCCTCTGGGATTCCTTTCGTCAGTCCGAGAGAGGAGAAGAGACAATTGAAGAAAGGTTTG
AAATCACAGGAACAATGCGCAAGCTTGCCGACCAAAGTCTCCCGCCGAACTTCTCCAGCCTTGAAAATTTTAGAGCCTAT
GTGGATGGATTCGAACCGAACGGCTACATTGAGGGCAAGCTGTCTCAAATGTCCAAAGAAGTAAATGCTAGAATTGAACC
TTTTTTGAAAACAACACCACGACCACTTAGACTTCCGAATGGGCCTCCCTGTTCTCAGCGGTCCAAATTCCTGCTGATGG
ATGCCTTAAAATTAAGCATTGAGGACCCAAGTCATGAAGGAGAGGGAATACCGCTATATGATGCAATCAAATGCATGAGA
ACATTCTTTGGATGGAAGGAACCCAATGTTGTTAAACCACACGAAAAGGGAATAAATCCAAATTATCTTCTGTCATGGAA
GCAAGTACTGGCAGAACTGCAGGACATTGAGAATGAGGAGAAAATTCCAAAGACTAAAAATATGAAGAAAACAAGTCAGC
TAAAGTGGGCACTTGGTGAGAACATGGCACCAGAAAAGGTAGACTTTGACGACTGTAAAGATGTAGGTGATTTGAAGCAA
TATGATAGTGATGAACCAGAATTGAGGTCGCTTGCAAGTTGGATTCAGAATGAGTTTAACAAGGCATGCGAACTGACAGA
TTCAAGCTGGATAGAGCTCGATGAGATTGGAGAAGATGTGGCTCCAATTGAACACATTGCAAGCATGAGAAGGAATTATT
TCACATCAGAGGTGTCTCACTGCAGAGCCACAGAATACATAATGAAGGGAGTGTACATCAATACTGCCTTGCTTAATGCA
TCTTGTGCAGCAATGGATGATTTCCAATTAATTCCAATGATAAGCAAGTGTAGAACTAAGGAGGGAAGGCGAAAGACCAA
CTTGTATGGTTTCATCATAAAAGGAAGATCCCACTTAAGGAATGACACCGACGTGGTAAACTTTGTGAGCATGGAGTTTT
CTCTCACTGACCCAAGACTTGAACCACATAAATGGGAGAAGTACTGTGTTCTTGAGATAGGAGATATGCTTATAAGAAGT
GCCATAGGCCAGGTTTCAAGGCCCATGTTCTTGTATGTGAGAACAAATGGAACCTCAAAAATTAAAATGAAATGGGGAAT
GGAGATGAGGCGTTGCCTCCTCCAGTCACTTCAACAAATTGAGAGTATGATTGAAGCTGAGTCCTCTGTCAAAGAGAAAG
ACATGACCAAAGAGTTCTTTGAGAACAAATCAGAAACATGGCCCATTGGAGAGTCCCCCAAAGGAGTGGAGGAAAGTTCC
ATTGGGAAGGTCTGCAGGACTTTATTAGCAAAGTCGGTATTCAACAGCTTGTATGCATCTCCACAACTAGAAGGATTTTC
AGCTGAATCAAGAAAACTGCTTCTTATCGTTCAGGCTCTTAGGGACAACCTGGAACCTGGGACCTTTGATCTTGGGGGGC
TATATGAAGCAATTGAGGAGTGCCTGATTAATGATCCCTGGGTTTTGCTTAATGCTTCTTGGTTCAACTCCTTCCTTACA
CATGCATTGAGTTAGTTGTGGCAGTGCTACTATTTGCTATCCATACTGTCCAAAAAAGTACCTTGTTTCTACT (SEQ ID NO:1)

FIG. 10J

Canine codon optimized PR8 PA:

AGCGAAAGCAGGTACTGATCCAAAATGGAAGATTTTGTGCGACAATGCTTCAATCCGATGATTGTCGAGCTTGCGGAAAA

AACAATGAAAGAGTATGGGGAGGACCTGAAAATCGAAACAAACAAATTTGCAGCAATATGCACTCACTTGGAAGTATGCT

TCATGTATTCAGATTTTCACTTCATCAATGAGCAAGGCGAGTCAATAATCGTAGAACTTGGTGATCCAAATGCACTTTTG

AAGCACAGATTTGAAATAATCGAGGGAAGAGATCGCACAATGGCCTGGACAGTAGTAAACAGTATTTGCAACACTACAGG

GGCTGAGAAACCAAAGTTTCTACCAGATTTGTATGATTACAAGGAGAATAGATTCATCGAAATTGGAGTAACAAGGAGAG

AAGTTCACATATACTATCTGGAAAAGGCCAATAAAATTAAATCTGAGAAAACACACATCCACATTTTCTCGTTCACTGGG

GAAGAAATGGCCACAAAGGCAGACTACACTCTCGATGAAGAAAGCAGGGCTAGGATCAAAACCAGACTATTCACCATAAG

ACAAGAAATGGCCAGCAGAGGCCTCTGGGATTCCTTTCGTCAGTCCGAGAGAGGAGAAGAGACAATTGAAGAAAGGTTTG

AAATCACAGGAACAATGCGCAAGCTTGCCGACCAAAGTCTCCCGCCGAACTTCTCCAGCCTTGAAAATTTTAGAGCCTAT

GTGGATGGATTCGAACCGAACGGCTACATTGAGGGCAAGCTGTCTCAAATGTCCAAAGAAGTAAATGCTAGAATTGAACC

TTTTCTGAAAACAACACCACGACCACTGAGACTGCCCAATGGGCCTCCCTGTTCTCAGCGGTCCAAATTCCTGCTGATGG

ATGCCCTGAAACTGAGCATTGAGGACCCAAGTCATGAAGGAGAGGGAATTCCCCTGTATGATGCAATCAAATGCATGAGA

ACATTCTTTGGATGGAAGGAACCCAATGTGGTGAAACCACACGAAAAGGGAATCAATCCAAATTATCTGCTGTCATGGAA

GCAGGTGCTGGCAGAACTGCAGGACATTGAGAATGAGGAGAAAATTCCAAAGACTAAAAATATGAAGAAAACAAGTCAGC

TGAAGTGGGCACTGGGTGAGAACATGGCACCAGAAAAGGTGGACTTTGACGACTGTAAAGATGTGGGTGATCTGAAGCAG

TATGATAGTGATGAACCAGAACTGAGGTCCCTGGCAAGTTGGATTCAGAATGAGTTTAACAAGGCATGCGAACTGACAGA

TTCAAGCTGGATTGAGCTCGATGAGATTGGAGAAGATGTGGCTCCAATTGAACACATTGCAAGCATGAGAAGGAATTATT

TCACATCAGAGGTGTCTCACTGCAGAGCCACAGAATACATCATGAAGGGAGTGTACATCAATACTGCCCTGCTGAATGCA

TCTTGTGCAGCAATGGATGATTTCCAGCTGATTCCAATGATCAGCAAGTGTAGAACTAAGGAGGGAAGGCGAAAGACCAA

CCTGTATGGTTTCATCATCAAAGGAAGATCCCACCTGAGGAATGACACCGACGTGGTGAACTTTGTGAGCATGGAGTTTT

CTCTCACTGACCCAAGACTGGAACCACATAAATGGGAGAAGTACTGTGTGCTGGAGATTGGAGATATGCTGATCAGAAGT

GCCATTGGCCAGGTGTCAAGGCCCATGTTCCTGTATGTGAGAACAAATGGAACCTCAAAAATTAAAATGAAATGGGGAAT

GGAGATGAGGCGCTGCCTCCTCCAGTCACTGCAGCAGATTGAGAGTATGATTGAAGCTGAGTCCTCTGTCAAAGAGAAAG

ACATGACCAAAGAGTTCTTTGAGAACAAATCAGAAACATGGCCCATTGGAGAGTCCCCCAAAGGAGTGGAGGAAAGTTCC

ATTGGGAAGGTCTGCAGGACTCTGCTGGCAAAGTCCGTGTTCAACAGCCTGTATGCATCTCCACAGCTGGAAGGATTTTC

AGCTGAATCAAGAAAACTGCTGCTGATCGTGCAGGCTCTGAGGGACAACCTGGAACCTGGGACCTTTGATCTGGGGGGGC

TGTATGAAGCAATTGAGGAGTGCCTGATTAATGATCCCTGGGTGCTGCTGAATGCTTCTTGGTTCAACTCCTTCCTTACA

CATGCATTGAGTTAGTTGTGGCAGTGCTACTATTTGCTATCCATACTGTCCAAAAAAGTACCTTGTTTCTACT (SEQ ID NO:18)

AGCAAAAGCAGGGTAGATAATCACTCACTGAGTGACATCAAAATCATGGCGTCTCAAGGCACCAAACGATCTTACGAACA

GATGGAGACTGATGGAGAACGCCAGAATGCCACTGAAATCAGAGCATCCGTCGGAAAAATGATTGGTGGAATTGGACGAT

TCTACATCCAAATGTGCACCGAACTCAAACTCAGTGATTATGAGGGACGGTTGATCCAAAACAGCTTAACAATAGAGAGA

ATGGTGCTCTCTGCTTTTGACGAAAGGAGAAATAAATACCTTGAAGAACATCCCAGTGCGGGGAAAGATCCTAAGAAAAC

TGGAGGACCTATATACAGGAGAGTAAACGGAAAGTGGATGAGAGAACTCATCCTTTATGACAAAGAAGAAATAAGGCGAA

TCTGGCGCCAAGCTAATAATGGTGACGATGCAACGGCTGGTCTGACTCACATGATGATCTGGCATTCCAATTTGAATGAT

GCAACTTATCAGAGGACAAGAGCTCTTGTTCGCACCGGAATGGATCCCAGGATGTGCTCTCTGATGCAAGGTTCAACTCT

CCCTAGGAGGTCTGGAGCCGCAGGTGCTGCAGTCAAAGGAGTTGGAACAATGGTGATGGAATTGGTCAGAATGATCAAAC

GTGGGATCAATGATCGGAACTTCTGGAGGGGTGAGAATGGACGAAAAACAAGAATTGCTTATGAAAGAATGTGCAACATT

CTCAAAGGGAAATTTCAAACTGCTGCACAAAAAGCAATGATGGATCAAGTGAGAGAGAGCCGGAACCCAGGGAATGCTGA

GTTCGAAGATCTCACTTTTCTAGCACGGTCTGCACTCATATTGAGAGGGTCGGTTGCTCACAAGTCCTGCCTGCCTGCCT

GTGTGTATGGACCTGCCGTAGCCAGTGGGTACGACTTTGAAAGGGAGGGATACTCTCTAGTCGGAATAGACCCTTTCAGA

CTGCTTCAAAACAGCCAAGTGTACAGCCTAATCAGACCAAATGAGAATCCAGCACACAAGAGTCAACTGGTGTGGATGGC

ATGCCATTCTGCCGCATTTGAAGATCTAAGAGTATTAAGCTTCATCAAAGGGACGAAGGTGCTCCCAAGAGGGAAGCTTT

CCACTAGAGGAGTTCAAATTGCTTCCAATGAAAATATGGAGACTATGGAATCAAGTACACTTGAACTGAGAAGCAGGTAC

TGGGCCATAAGGACCAGAAGTGGAGGAAACACCAATCAACAGAGGGCATCTGCGGGCCAAATCAGCATACAACCTACGTT

CTCAGTACAGAGAAATCTCCCTTTTGACAGAACAACCATTATGGCAGCATTCAATGGGAATACAGAGGGGAGAACATCTG

ACATGAGGACCGAAATCATAAGGATGATGGAAAGTGCAAGACCAGAAGATGTGTCTTTCCAGGGGCGGGGAGTCTTCGAG

CTCTCGGACGAAAAGGCAGCGAGCCCGATCGTGCCTTCCTTTGACATGAGTAATGAAGGATCTTATTTCTTCGGAGACAA

TGCAGAGGAGTACGACAATTAAAGAAAAATACCCTTGTTTCTACT (SEQ ID NO:4)

FIG. 10L

Canine codon optimized NP:

AGCAAAAGCAGGGTAGATAATCACTCACTGAGTGACATCAAAATCATGGCGTCTCAAGGCACCAAACGATCTTACGAACA
GATGGAGACTGATGGAGAACGCCAGAATGCCACTGAAATCAGAGCATCCGTCGGAAAAATGATTGGTGGAATTGGACGAT
TCTACATCCAGATGTGCACCGAACTCAAACTCAGTGATTATGAGGGACGGCTGATCCAGAACAGCCTGACAATCGAGAGA
ATGGTGCTCTCTGCTTTTGACGAAAGGAGAAATAAATACCTGGAAGAACATCCCAGTGCCGGGAAAGATCCTAAGAAAAC
TGGAGGACCTATCTACAGGAGAGTGAACGGAAAGTGGATGAGAGAACTCATCCTGTATGACAAAGAAGAAATCAGGCGAA
TCTGGCGCCAGGCTAATAATGGTGACGATGCAACCGCTGGTCTGACTCACATGATGATCTGGCATTCCAATCTGAATGAT
GCAACTTATCAGAGGACAAGAGCTCTGGTGCGCACCGGAATGGATCCCAGGATGTGCTCTCTGATGCAGGGTTCAACTCT
CCCTAGGAGGTCTGGAGCCGCAGGTGCTGCAGTCAAAGGAGTGGGAACAATGGTGATGGAACTGGTCAGAATGATCAAAA
GAGGGATCAATGATCGGAACTTCTGGAGGGGTGAGAATGGACGAAAAACAAGAATTGCTTATGAAAGAATGTGCAACATT
CTCAAAGGGAAATTTCAGACTGCTGCACAGAAAGCAATGATGGATCAGGTGAGAGAGAGCCGGAACCCAGGGAATGCTGA
GTTCGAAGATCTCACTTTTCTGGCACGGTCTGCACTCATCCTGAGAGGGTCCGTGGCTCACAAGTCCTGCCTGCCTGCCT
GTGTGTATGGACCTGCCGTGGCCAGTGGGTACGACTTTGAAAGGGAGGGATACTCTCTGGTCGGAATTGACCCTTTCAGA
CTGCTGCAGAACAGCCAGGTGTACAGCCTGATCAGACCAAATGAGAATCCAGCACACAAGAGTCAGCTGGTGTGGATGGC
ATGCCATTCTGCCGCATTTGAAGATCTGAGAGTGCTGAGCTTCATCAAAGGGACCAAGGTGCTCCCAAGAGGGAAGCTGT
CCACTAGAGGAGTGCAGATTGCTTCCAATGAAAATATGGAGACTATGGAATCAAGTACACTGGAACTGAGAAGCAGGTAC
TGGGCCATCAGGACCAGAAGTGGAGGAAACACCAATCAGCAGAGGGCATCTGCCGGCCAGATCAGCATTCAGCCTACCTT
CTCAGTGCAGAGAAATCTCCCTTTTGACAGAACAACCATTATGGCAGCATTCAATGGGAATACAGAGGGGAGAACATCTG
ACATGAGGACCGAAATCATCAGGATGATGGAAAGTGCAAGACCAGAAGATGTGTCTTTCCAGGGGCGGGGAGTCTTCGAG
CTCTCGGACGAAAAGGCAGCGAGCCCGATCGTGCCTTCCTTTGACATGAGTAATGAAGGATCTTATTTCTTCGGAGACAA
TGCAGAGGAGTACGACAATTAAAGAAAAATACCCTTGTTTCTACT (SEQ ID NO:19)

FIG. 10M

Figure 11 A Nucleotide mutation in position 4 of ea ch gene of PR8 and Indo/NC/09.

| Genes | Position 4 of vRNA | |
|---|---|---|
| PR8 PB2 | C | |
| PR8 PB1 | C | |
| PR8 PA | C | |
| PR8 NP | | U |
| PR8 M | | U |
| PR8 NS | | U |
| Inda/NC/09 HA | | U |
| Inda/NC/09 NA | | U |

Figure 11B All 3’C4U mutant

| Genes | Position 4 of vRNA | |
|---|---|---|
| PR8 PB2 | | U |
| PR8 PB1 | | U |
| PR8 PA | | U |
| PR8 NP | | U |
| PR8 M | | U |
| PR8 NS | | U |
| Inda/NC/09 HA | | U |
| Inda/NC/09 NA | | U |

Figure 11C Growth kinetics of 3' C4U mutant
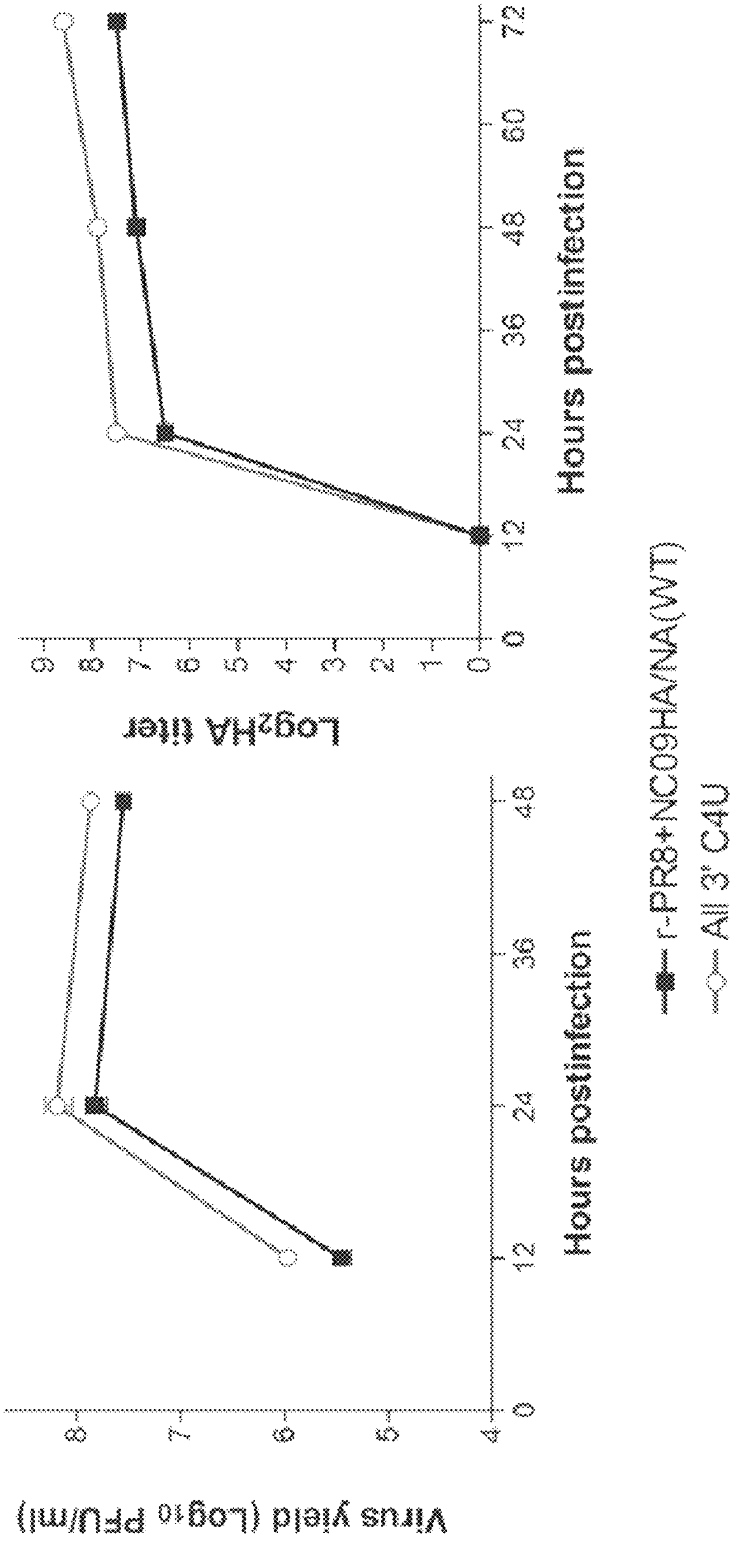

HA atgaacactcaaatcctggtattcgctctgattgcgatcattccaacaaatgcagacaaaatctgcctcggacatcatgccgtgtcaaacggaaccaaagtaaa
cacattaactgaaagaggagtggaagtcgtcaatgcaactgaaacagtggaacgaacaaacatccccaggatctgctcaaaagggaaaaggacagttgacc
tcggtcaatgtggactcctggggacaatcactggaccacctcaatgtgaccaattcctagaattttcagccgatttaattattgagaggcgagaaggaagtgatg
tctgttatcctgggaaattcgtgaatgaagaagctctgaggcaaattctcagagaatcaggcggaattgacaaggaagcaatgggattcacatacagtggaat
aagaactaatggagcaaccagtgcatgtaggagatcaggatcttcattctatgcagaaatgaaatggctcctgtcaaacacagataatgctgcattcccgcaga
tgactaagtcatataaaaatacaagaaaaagcccagctctaatagtatggggatccatcattccgtatcaactgcagagcaaaccaagctatatgggagtgg
aaacaaactggtgacagttgggagttctaattatcaacaatcttttgtaccgagtccaggagcgagaccacaagttaatggtctatctggaagaattgactttcat
tggctaatgctaaatcccaatgatacagtcactttcagtttcaatggggctttcatagctccagaccgtgcaagcttcctgagaggaaaatctatgggaatccag
agtggagtacaggttgatgccaattgtgaaggggactgctatcatagtggaggacaataataagtaacttgccatttcagaacatagatagcagggcagttg
gaaaatgtccgagatatgttaagcaaaggagtctgctgctagcaacagggatgaagaatgttcctgagattccaaagggaagaggcctatttggtgctatagc
gggtttcattgaaaatggatgggaaggcctaattgatggttggtatggtttcagacaccagaatgcacagggagagggaactgctgcagattacaaaagcact
caatcggcaattgatcaaataacaggaaaattaaaccggcttatagaaaaaaccaaccaacaatttgagttgatagacaatgaattcaatgaggtagagaag
caaatcggtaatgtgataaattggaccagagattctataacagaagtgtggtcatacaatgctgaactcttggtagcaatggagaaccagcatacaattgatct
ggctgattcagaaatggacaaactgtacgaacgagtgaaaagacagctgagagagaatgctgaagaagatggcactggttgctttgaaatatttcacaagtgt
gatgatgactgtatggccagtattagaaataacacctatgatcacagcaaatacagggaagaggcaatgcaaaatagaatacagattgacccagtcaaacta
agcagcggctacaaagatgtgatactttggtttagcttcggggcatcatgtttcatacttctagccattgtaatgggccttgtcttcatatgtgtaaagaatggaaa
catgcggtgcactatttgtatataa (SEQ ID NO:20)

MNTQILVFAL IAIIPTNADK ICLGHHAVSN GTKVNTLTER GVEVVNATET VERTNIPRIC
SKGKRTVDLG QCGLLGTITG PPQCDQFLEF SADLIIERRE GSDVCYPGKF VNEEALRQIL
RESGGIDKEA MGFTYSGIRT NGATSACRRS GSSFYAEMKW LLSNTDNAAF PQMTKSYKNT
RKSPALIVWG IHHSVSTAEQ TKLYGSGNKL VTVGSSNYQQ SFVPSPGARP QVNGLSGRID
FHWLMLNPND TVTFSFNGAF IAPDRASFLR GKSMGIQSGV QVDANCEGDC YHSGGTIISN
LPFQNIDSRA VGKCPRYVKQ RSLLLATGMK NVPEIPKGRG LFGAIAGFIE NGWEGLIDGW
YGFRHQNAQG EGTAADYKST QSAIDQITGK LNRLIEKTNQ QFELIDNEFN EVEKQIGNVI
NWTRDSITEV WSYNAELLVA MENQHTIDLA DSEMDKLYER VKRQLRENAE EDGTGCFEIF
HKCDDDCMAS IRNNTYDHSK YREEAMQNRI QIDPVKLSSG YKDVILWFSF GASCFILLAI
VMGLVFICVK NGNMRCTICI (SEQ ID NO:21)

NA atgaatccaaatcagaagattctatgcacttcagccactgctatcataataggcgcaatcgcagtactcattggaatagcaaacctaggattgaacataggact
gcatctaaaaccgggctgcaattgctcacactcacaacctgaaacaaccaacacaagccaaacaataataaacaactattataatgaaacaaacatcaccaa
catccaaatggaagagagaacaagcaggaatttcaataacttaactaaagggctctgtactataaattcatggcacatatatgggaaagacaatgcagtaaga
attggagagagctcggatgttttagtcacaagagaaccctatgtttcatgcgacccagatgaatgcaggttctatgctctcagccaaggaacaacaatcagagg
gaaacactcaaacggaacaatacacgataggtcccagtatcgcgccctgataagctggccactatcatcaccgcccacagtgtacaacagcagggtggaatg
cattgggtggtcaagtactagttgccatgatggcaaatccaggatgtcaatatgtatatcaggaccaaacaacaatgcatctgcagtagtatggtacaacagaa
ggcctgttgcagaaattaacacatgggcccgaaacatactaagaacacaggaatctgaatgtgtatgccacaacggcgtatgcccagtagtgttcaccgatgg
gtctgccactggacctgcagacacaagaatatactattttaaagagggaaaatattgaaatgggagtctctgactggaactgctaagcatattgaagaatgct
catgttacggggaacgaacaggaattacctgcacatgcagggacaattggcagggctcaaatagaccagtgattcagatagacccagtagcaatgacacaca
ctagtcaatatatatgcagtcctgttcttacagacaatccccgaccgaatgacccaaatataggtaagtgtaatgacccttatccaggtaataataacaatggag
tcaagggattctcatacctggatggggctaacacttggctagggaggacaataagcacagcctcgaggtctggatacgagatgttaaaagtgccaaatgcatt
gacagatgatagatcaaagcccattcaaggtcagacaattgtattaaacgctgactggagtggttacagtggatctttcatggactattgggctgaaggggact
gctatcgagcgtgtttttatgtggagttgatacgtggaagacccaaggaagataaagtgtggtggaccagcaatagtatagtatcgatgtgttccagtacagaat
tcctgggacaatggaactggcctgatggggctaaaatagagtacttcctctaa (SEQ ID NO:22)

MNPNQKILCTSATAIIIGAIAVLIGIANLGLNIGLHLKPGCNCSHSQPETTNTSQTIINNYYNETNITNIQMEERTSRNFNNLTKGL
CTINSWHIYGKDNAVRIGESSDVLVTREPYVSCDPDECRFYALSQGTTIRGKHSNGTIHDRSQYRALISWPLSSPPTVYNSRVECI
GWSSTSCHDGKSRMSICISGPNNNASAVVWYNRRPVAEINTWARNILRTQESECVCHNGVCPVVFTDGSATGPADTRIYYFK

FIG. 12A

EGKILKWESLTGTAKHIEECSCYGERTGITCTCRDNWQGSNRPVIQIDPVAMTHTSQYICSPVLTDNPRPNDPNIGKCNDPYPG NNNNGVKGFSYLDGANTWLGRTISTASRSGYEMLKVPNALTDDRSKPIQGQTIVLNADWSGYSGSFMDYWAEGDCYRACF Y VELIRGRPKEDKVWWTSNSIVSMCSSTEFLGQWNWPDGAKIEYFL (SEQ ID NO:23)

HA atgaacactcaaatcctggtattcgctctgattgcgatcattccaacaaatgcagacaaaatctgcctcggacatcatgctgtgtcaaacggaaccaaagtaaa cacattaactgaaagaggagtggaagtcgtcaatgcaactgaaacagtggaacgaacaaacatccccaggatctgctcaaaagggaaaaggacagttgacc tcggtcaatgtggactcctggggacaatcactggaccacctcaatgtgaccaattcctagaattttcagccgatttaattattgagaggcgagaaggaagtgatg tctgttatcctgggaaattcgtgaatgaagaagctctgaggcaaattctcagagaatcaggcggaattgacaaggaagcaatgggattcacatacagtggaat aagaactaatggagcaaccagttcatgtaggagatcaggatcttcattctatgcagaaatgaaatggctcctgtcaaacacagataatgctgcattcccgcaga tgactaagtcatataaaaatacaagaaaaaacccagctctaatagtatggggggatccatcattccggatcaactgcagagcaaaccaagctatatgggagtgg aaacaaactggtgacagttgggagttctaattatcaacaatcttttgtaccgagtccgggagcgagaacacaagttaatggtcaatctggaagaattgactttca ttggctaatgctaaatcccaatgatacagtcactttcagtttcaatggggctttcatagctccagaccgtgcaagcttcctgagaggaaaatctatgggaatccag agtggagtacaggttgatgccgattgtgaaggggactgctattatagtggagggacaataataagtaacttgccatttcagaacatagatagcagggcagttgg aaaatgtccgagatatgttaagcaaaggagtctgctgctagcaacagggatgaagaatgttcctgagattccaaagggaagaggcctatttggtgctatagcg ggtttcattgaaaatggatgggaaggcctaattgatggttggtatggtttcagacaccagaatgcacagggagagggaactgctgcagattacaaaagcactc aatcggcaattgatcaaataacaggaaaattaaaccggcttatagaaaaaaccaaccaacaatttgagttgatagacaatgaattcactgaggtagagaagc aaatcggtaatgtgataaattggaccagagattctataacagaagtgtggtcatacaatgctgaactcttggtagcaatggagaaccagcatacaattgatctg gctgattcagaaatggacaaactgtacgaacgagtgaaaagacagctgagagagaatgctgaagaagatggcactggttgctttgaaatatttcacaagtgtg atgatgactgtatggccagcattagaaataacacctatgatcacagcaaatacagggaagaggcaatgcaaaatagaatacagattgacccagtcaaactaa gcagcggctacaaagatgtgatactttggtttagcttcggggcatcatgtttcatacttctagccattgcaatgggccttgtcttcatatgtgtaaagaatggaaa c atgcggtgcactatttgtatataa (SEQ ID NO:24)

MNTQILVFALIAIIPTNADKICLGHHAVSNGTKVNTLTERGVEVVNATETVERTNIPRICSKGKRTVDLGQCGLLGTITGPPQCDQ FLEFSADLIIERREGSDVCYPGKFVNEEALRQILRESGGIDKEAMGFTYSGIRTNGATSSCRRSGSSFYAEMKWLLSNTDNAAFP QMTKSYKNTRKNPALIVWGIHHSGSTAEQTKLYGSGNKLVTVGSSNYQQSFVPSPGARTQVNGQSGRIDFHWLMLNPNDTV TFSFNGAFIAPDRASFLRGKSMGIQSGVQVDADCEGDCYYSGGTIISNLPFQNIDSRAVGKCPRYVKQRSLLLATGMKNVPEIP KGRGLFGAIAGFIENGWEGLIDGWYGFRHQNAQGEGTAADYKSTQSAIDQITGKLNRLIEKTNQQFELIDNEFTEVEKQIGNVI NWTRDSITEVWSYNAELLVAMENQHTIDLADSEMDKLYERVKRQLRENAEEDGTGCFEIFHKCDDDCMASIRNNTYDHSKY R EEAMQNRIQIDPVKLSSGYKDVILWFSFGASCFILLAIAMGLVFICVKNGNMRCTICI (SEQ ID NO:25)

NA atgaatccaaatcagaagattctatgcacttcagccactgctatcataataggcgcaatcgcagtactcattggaatagcaaacctaggattgaacataggact gcatctaaaaccgagctgcaattgctcacactcacaacctgaaacaaccaacacaagccaaacaataataaacaactattataatgaaacaaacatcaccaa catccaaatggaagagagaacaagcaggaatttcaataacttaactaaagggctctgtactataaattcatggcacatatatgggaaagacaatgcggtaaga attggagagagctcggatgttttagtcacaagagaaccctatgtttcatgcgacccagatgaatgcaggttctatgctctcagccaaggaacaacaatcagagg aaaacactcaaacggaacaatacacgataggtcccagtatcgcgccctgataagctggccactatcatcaccgcccacagtgtacaacagcagggtggaatg cattgggtggtcaagtactagttgccatgatggcaaatccaggatgtcaatatgtatatcaggaccaaacaacaatgcatctgcagtagtatggtacaacagaa ggcctgttgcagaaattaacacatgggcccgaaacatactaagaacacaggaatctgaatgtgtatgccacaacggcgtatgcccagtagtgttcaccgatgg gtctgccactggacctgcagacacaagaatatactattttaaagagggggaaatattgaaatgggagtctctgactggaactgctaagcatattgaagaatgct catgttacggggaacgaacaggaattacctgcacatgcaaggacaattggcagggctcaaatagaccagtgattcagatagatccagtagcaatgacacaca ctagtcagtatatatgcagtcctgttcttacagacaatccccgaccgaatgacccaaatataggtaagtgtaatgacccttatccaggtaataataacaatggag tcaagggattctcatacctggatggggctaacacttggctagggaggacaataagcacagcctcgaggtctggatacgagatgttaaaagtgccaaatgcatt gacagatgatagatcaaagcccattcaaggtcagacaattgtattaaacgctgactggagtggttacagtggatctttcatggactattgggctgaggggggact gctatcgagcgtgttttatgtggaattgatacgtggaagacccaaggaggataaagtgtggtggaccagcaatagtatagtatcgatgtgttccagtacagaat tcctgggacaatggaactggcctgatggggctaaaatagagtacttcctctaa (SEQ ID NO:26)

MNPNQKILCTSATAIIIGAIAVLIGIANLGLNIGLHLKPSCNCSHSQPETTNTSQTIINNYYNETNITNIQMEERTSRNFNNLTKGL CTINSWHIYGKDNAVRIGESSDVLVTREPYVSCDPDECRFYALSQGTTIRGKHSNGTIHDRSQYRALISWPLSSPPTVYNSRVECI GWSSTSCHDGKSRMSICISGPNNNASAVVWYNRRPVAEINTWARNILRTQESECVCHNGVCPVVFTDGSATGPADTRIYYFK

FIG. 12B

EGKILKWESLTGTAKHIEECSCYGERTGITCTCKDNWQGSNRPVIQIDPVAMTHTSQYICSPVLTDNPRPNDPNIGKCNDPYPG
NNNNGVKGFSYLDGANTWLGRTISTASRSGYEMLKVPNALTDDRSKPIQGQTIVLNADWSGYSGSFMDYWAEGDCYRACF
Y VELIRGRPKEDKVWWTSNSIVSMCSSTEFLGQWNWPDGAKIEYFL (SEQ ID NO:27)

FIG. 12C

Figure 13A Construct chimeric HA &NA to increase virus replication
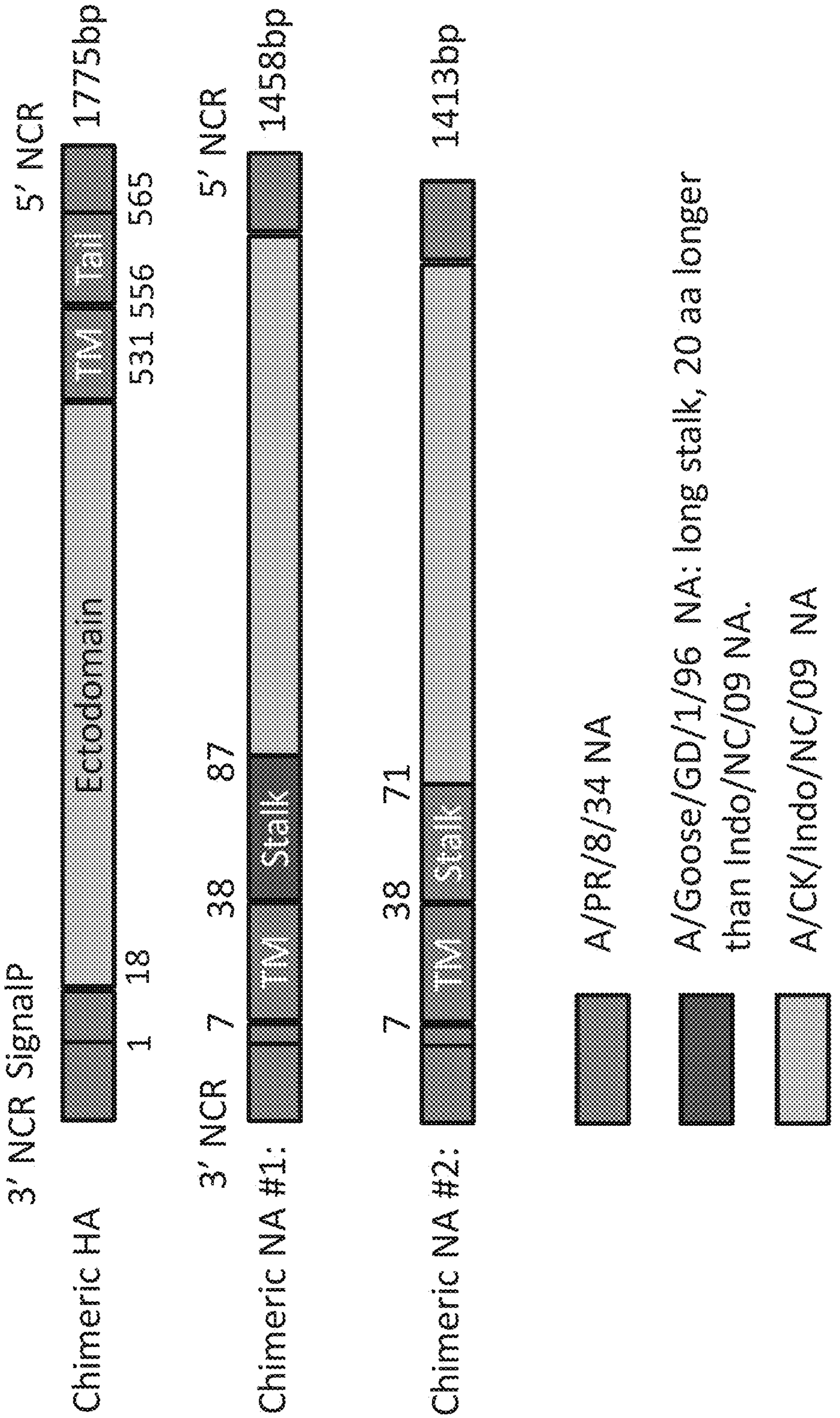

Figure 13B Growth kinetics in MDCK cells
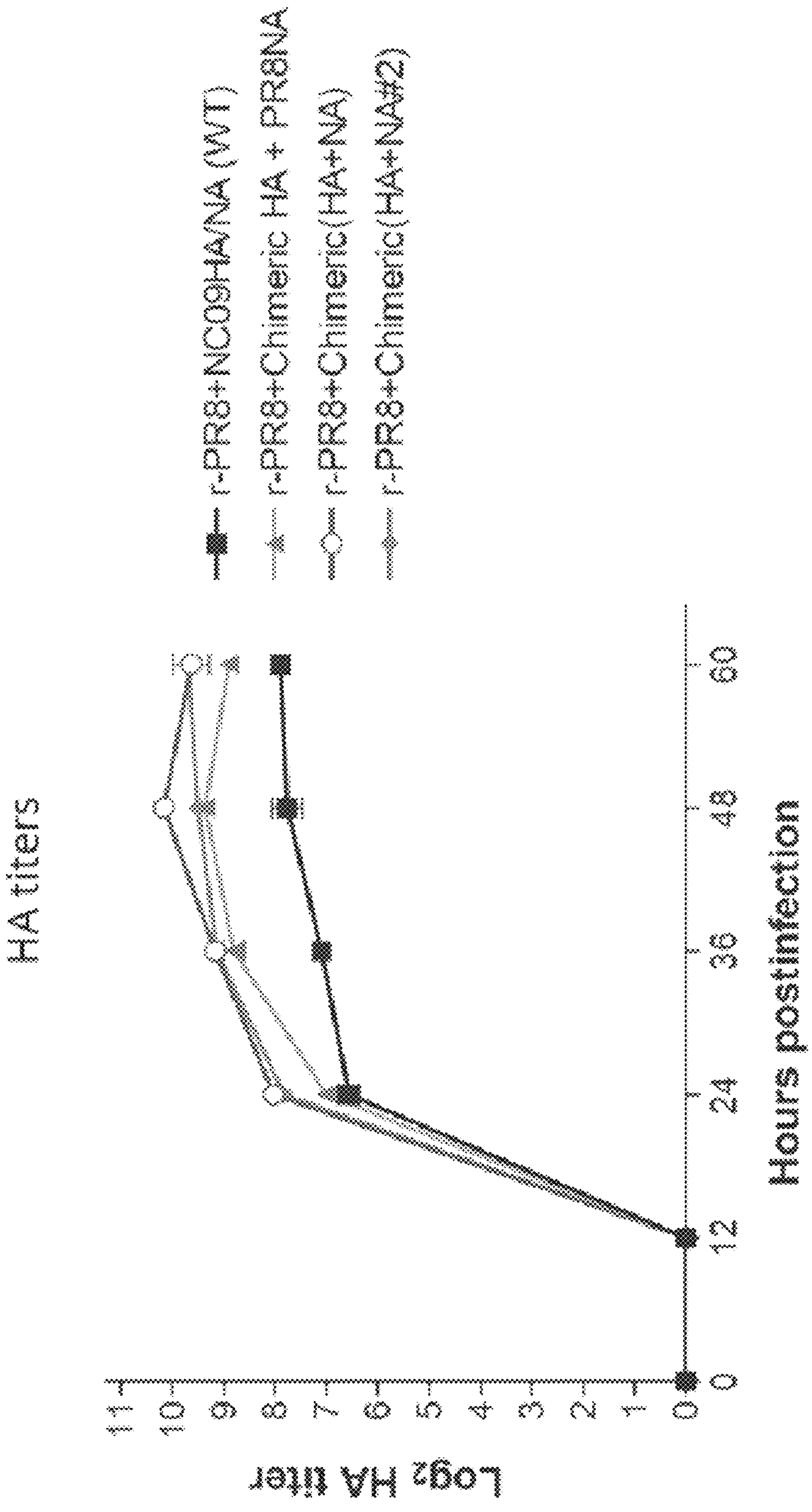

Figure 14A Growth kinetics in MDCK cells
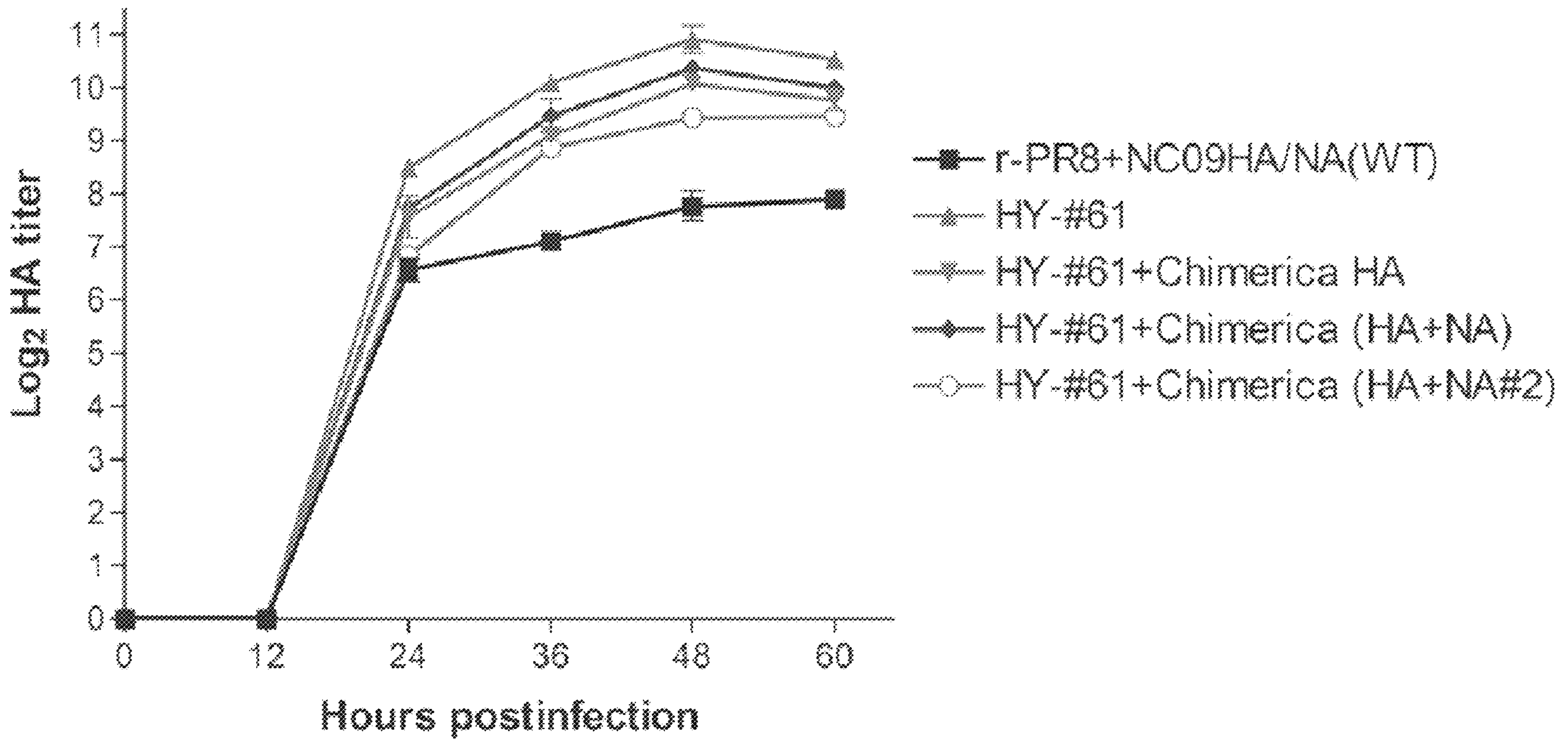
HY-#61 includes PB2: M202L F323L, PB1 Q247H, PA K142N, NP R74K, M V97A Y100H and NS K55E mutations.

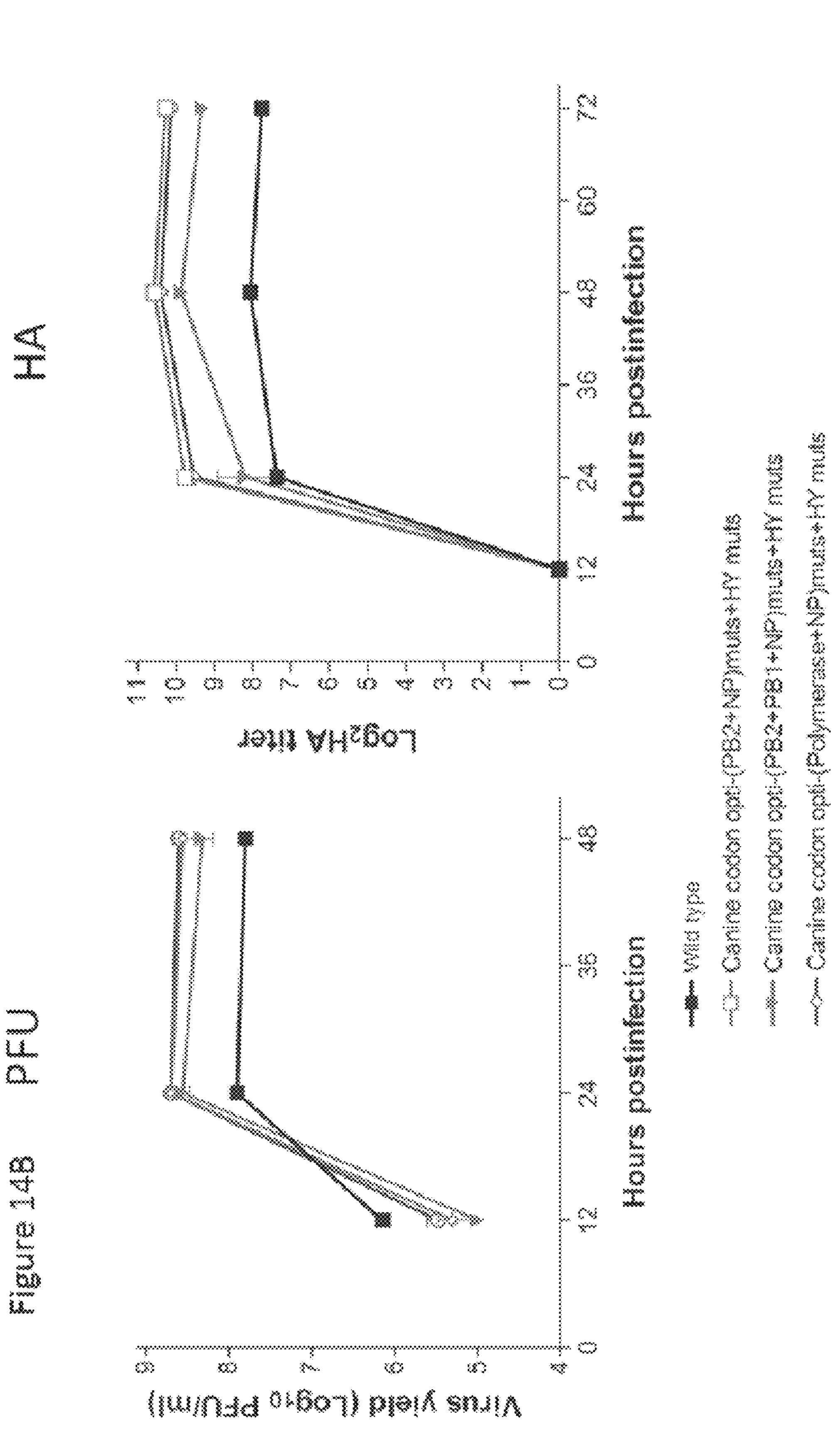
HY mutations include PB2: M202L F323L, PB1 Q247H, PA K142N, NP R74K, M V97A Y100H and NS K55E mutations.

Schematic diagram of screening high growth mutations in eggs.

Figure 16 Summary of HA assay of individual clones purified from Vero cells

| Groups | Numbers of clone | Fold change | % |
|---|---|---|---|
| WT HA titer = $2^{6.5}$ | 5 | - | 2.3% |
| HA titer =$2^{>9-9.5}$ | 16 | >5.6 | 7.4% |
| HA titer =$2^{>8-9}$ | 91 | >2.8 -5.6 | 42.2% |
| HA titer =$2^{6.5-8}$ | 80 | 1 - 2.8 | 37.0% |
| HA titer < $2^{6.5}$ | 24 | <1 | 11.1% |
| Total | 216 | - | 100% |

Figure 17Recombinant viruses generated with different PR8 backbone mutants.

| # | Del-HA & NA genes | PB2 | PB1 | PA | NP | M | NS |
|---|---|---|---|---|---|---|---|
| WT | CK/Indo/NC/09 | WT | WT | WT | WT | WT | WT |
| HY-1 | | I504V | M40L G180W | R401K | I116L | WT | A30P R118K |
| HY-2 | | E391Q | | I30T E31K K142N | R74K S377N | WT | S161T |
| HY-3 | | I504V | | K142N | I116L | V97A Y100H | V136M S161T |
| HY-4 | | M202L F323L | | K356R | I116L | V97A Y100H | K55E |
| HY-5 | | | | K356R | R422L | WT | K55E |

| Virus number | Surface genes | | UW-PR8 internal gene | | | | | | Growth substrate | Viral titer or HA titer | Fold change |
|---|---|---|---|---|---|---|---|---|---|---|---|
| | HA (H3 numbering) | NA | PB2 | PB1 | PA | NP | M1 | NS1 | | | |
| 1 | M476I | | M202L F323L | | | R293M | | | MDCK | HA titer | 2.8 |
| 2 | F252I | L55S | M202L F323L | | | I116L | | | MDCK | HA titer | 2.8 |
| 3 | | | M202L F323L | | | | | A223E | MDCK | HA titer | 2.8 |
| 4 | L182V | | M202L F323L | | | | | | MDCK | HA titer | 2.8~4 |
| 5 | | | | E112G (PB1-F2 R81G)[5] | | | | | MDCK | HA titer | 2.8 |
| 6 | E136D/ Q179L/ A194V | | | R54I | | | | | MDCK | HA titer | 2.8~4 |
| 7 | K162E | | | I667T/M714T | | | | | MDCK | HA titer | 4 |
| 8 | L182V | | | | | I116L | | R140Q | MDCK | HA titer | 2.8~4 |
| 9 | L182V | | | | | | | | MDCK | HA titer | 2.8~4 |
| 10 | L182V | | M202L F323L | | | | | | MDCK | HA titer | 4 |
| 11 | L182V | | M66R | | | | | | MDCK | HA titer | 2.8~4 |
| 12 | L182V | | M202L F323L | | | | | | MDCK | HA titer | 4 |
| 13 | | | M202L F323L | M507V/V644 A | | | | | MDCK | HA titer | 4 |
| 14 | L182V | | I504V | | | R74K/ N417D | | A30P | MDCK | HA titer | 2.8 |
| 15 | K162E | | | E112G (PB1-F2-R81G) | | | | S161T | MDCK | HA titer | 2.8 |
| 16 | | | | I667T | | | | | MDCK | HA titer | 2.8 |
| 17 | K449E | | | M40L/G180W | | | | | MDCK | HA titer | 2.8 |
| 18 | K162E | | | E112G (PB1-F2-R81G)/ L624V | | | | S161T | MDCK | HA titer | 2.8~4 |

FIG. 19A

| Virus number | Surface genes | | UW-PR8 internal gene | | | | | | Growth substrate | Viral titer or HA titer | Fold change |
|---|---|---|---|---|---|---|---|---|---|---|---|
| | HA (H3 numbering) | NA | PB2 | PB1 | PA | NP | M1 | NS1 | | | |
| 19 | | | | E112G (PB1-F2-R81G) | | | | | MDCK | HA titer | 2.8 |
| 20 | | | | M40L G180W | | | | S161T | MDCK | HA titer | 2.8~4 |
| 21 | | | M202L F323L M243I | R54I | | | | | MDCK | HA titer | 4~5.7 |
| 22 | V184I | | M202L F323L | | F105C | | P90S | | MDCK | HA titer | 2.8~4 |
| 23 | | | M202L F323L | Q247H | | | | | MDCK | HA titer | 2.8~4 |
| 24 | | | M202L F323L | | | N224I | | | MDCK | HA titer | 2.8~4 |
| 25 | M476I | | I504V | | | R74K/ N417D | | | MDCK | HA titer | 2.8~4 |
| 26 | M476I | | M202L F323L | V644A | R401K | | | T49A | MDCK | HA titer | 4~5.7 |
| 27 | F252I | | I504V | V644A | | M371V | | | MDCK | HA titer | 2.8 |
| 28 | M476I | A265V | I504V | T59I G62A A63P V644A N694K L695T | | R74K/ N417D | | | MDCK | HA titer | 2.8 |
| 29 | M476I | | I504V | | | | | | MDCK | HA titer | 2.8~4 |
| 30 | F252I | | I504V | E75V D76G E78P P79V S80G V644A E697P F699L F700L P701H S702R Y705T | | R74K | | | MDCK | HA titer | 2.8~4 |
| 31 | L182V | | I504V | | | R74K | | | MDCK | HA titer | 2.8~4 |
| 32 | F252I | | M202L F323L | V644A | | | | | MDCK | HA titer | 4 |

FIG. 19B

| Virus number | Surface genes | | UW-PR8 internal gene | | | | | | Growth substrate | Viral titer or HA titer | Fold change |
|---|---|---|---|---|---|---|---|---|---|---|---|
| | HA (H3 numbering) | NA | PB2 | PB1 | PA | NP | M1 | NS1 | | | |
| 33 | | | I57V<br>T58G<br>A59V<br>K61Q<br>E677D<br>D678E<br>P679M | E112G (PB1-F2-R81G)<br>S713C | | | | | MDCK | HA titer | 2.8 |
| 34 | | | | M40I<br>G180W | | | | S161T | MDCK | HA titer | 2.8 |
| 35 | | | R368K | | | | | | MDCK | Viral titer | 2.8 |
| 36 | | | E391K | | | | | | MDCK | Viral titer | 3.8 |
| 37 | | | I504V | | I550L | | | | MDCK | Viral titer | 4.3 |
| 38 | | | | PB1 F2 N66S | | | | | MDCK | Viral titer | 2.78 |
| 39 | | | | PB1 F2 K73R | | | | | MDCK | Viral titer | 3.9 |
| 40 | | | | | K142N | | | | MDCK | Viral titer | 2.1 |
| 41 | | | | | K356R | | | | MDCK | Viral titer | 3.9 |
| 42 | | | | | | R293K | | | MDCK | Viral titer | 3.36 |
| 43 | | | | | | R442K | | | MDCK | Viral titer | 2.4 |
| 44 | | | | | | T442A | | | MDCK | Viral titer | 2.6 |
| 46 | | | | | | | V97A | | MDCK | HA titer | 8 |
| 47 | | | | | | | Y100H | | MDCK | HA titer | 9 |
| 48 | | | | | | | V97A<br>Y100H | | MDCK | HA titer | 9.5 |
| 49 | | | | | | | | K55E | MDCK | Viral titer | 2.1 |
| 50 | | | M202L<br>F323L | M507V<br>V644A | | I116L | | K55E | MDCK | Viral titer | 9.9 |
| | | | | | | | | | | HA titer | 4.3 |
| 51 | | | M202L<br>F323L | M507V<br>V644A | K356R | T442A | V97A<br>Y100H | K55E | MDCK | Viral titer | 1.3 |
| | | | | | | | | | | HA titer | 3.7 |
| 52 | | | I504V | E112G (PB1-F2-R81G) | I550L | I112L | Y100H | R140Q | MDCK | Viral titer | 3 |
| | | | | | | | | | | HA titer | 3 |

FIG. 19C

| Virus number | Surface genes | | UW-PR8 internal gene | | | | | | Growth substrate | Viral titer or HA titer | Fold change |
|---|---|---|---|---|---|---|---|---|---|---|---|
| | HA (H3 numbering) | NA | PB2 | PB1 | PA | NP | M1 | NS1 | | | |
| 53 | | | M202L F323L | M507V V644A | | I116L | Y100H | K55E | MDCK | Viral titer | 9 |
| | | | | | | | | | | HA titer | 6.5 |
| 54 | | | M202L F323L | Q247H | K142N | R74K | V97A Y100H | K55E | MDCK | Viral titer | 4.3 |
| | | | | | | | | | | HA titer | 9.2 |
| 55 | | | I504V | E112G (PB1-F2-R81G) | S225C | R74K N417D | V97A Y100H | K55E | MDCK | Viral titer | 14.9 |
| | | | | | | | | | | HA titer | 6.5 |
| 56 | | | M202L F323L | M40L G180W | S225C | R422K | V97A Y100H | K55E | MDCK | Viral titer | 4.2 |
| | | | | | | | | | | HA titer | 6.5 |
| 57 | | | *C4U* | *C4U* | *C4U* | | | | MDCK | Viral titer | 3.3 |
| | | | | | | | | | | HA titer | 2.1 |
| 58 | X-181 HA &NA (Derived from A/California/ 07/2009 pdmH1N1) | | | G180E S261G S361R Q621R N654S | | | | | MDCK | Viral titer | 3.5 |
| | | | | | | | | | | HA titer | 2.1 |
| 59 | A/Chicken/Indonesia/NC/2009, A/Vietnam/1203/2004, A/Hubei/1/2010, A/Egypt/N03072/2010, A/Indonesia/5/2005, A/Anhui/1/2013, X-181, X-223A | | *C4U* I504V | *C4U* M40L G180W | *C4U* R401K | I116L | | A30P R118K | Vero | Viral titer | 5.1~269 |
| | | | | | | | | | | HA titer | 2.2~134 |
| | | | | | | | | | MDCK | Viral titer | 1.8~29 |
| | | | | | | | | | | HA titer | 1.3~5.5 |
| | | | | | | | | | Eggs | Viral titer | 4.6~172 |
| | | | | | | | | | | HA titer | 1.3~17.7 |
| 60 | A/Chicken/Indonesia/NC/2009 | | C4U I504V | C4U M40L G180W | C4U R401K | I116L | *G1012C, A1013U, U1014A* | A30P R118K | Vero | Viral titer | 2.8 |
| | | | | | | | | | | HA titer | 1.2 |
| | | | | | | | | | Egg | Viral titer | 1.5 |
| | | | | | | | | | | HA titer | 1.6 |

Note: 1. The HA and NA genes of #1-58 come from A/Chicken/Indonesia/NC/2009 (H5N1) or mutant HA and NA of A/Chicken/Indonesia/NC/2009.
2:All the H5N1 HAs used in this study were mutated to remove multibasic cleavage sites to create lowly pathogenicity mutants.

QIA98554

1 mfvflvllpl vssqcvnltt rtqlppaytn sftrgvyypd kvfrssvlhs tqdlflpffs
61 nvtwfhaihv sgtngtkrfd npvlpfndgv yfasteksni irgwifgttl dsktqslliv
121 nnatnvvikv cefqfcndpf lgvyyhknnk swmesefrvy ssannctfey vsqpflmdle
181 gkqgnfknlr efvfknidgy fkiyskhtpi nlvrdlpqgf saleplvdlp iginitrfqt
241 llalhrsylt pgdsssgwta gaaayyvgyl qprtfllkyn engtitdavd caldplsetk
301 ctlksftvek giyqtsnfrv qptesivrfp nitnlcpfge vfnatrfasv yawnrkrisn
361 cvadysvlyn sasfstfkcy gvsptklndl cftnvyadsf virgdevrqi apgqtgkiad
421 ynyklpddft gcviawnsnn ldskvggnyn ylyrlfrksn lkpferdist eiyqagstpc
481 ngvegfncyf plqsygfqpt ngvgyqpyrv vvlsfellha patvcgpkks tnlvknkcvn
541 fnfngltgtg vltesnkkfl pfqqfgrdia dttdavrdpq tleilditpc sfggvsvitp
601 gtntsnqvav lyqdvnctev pvaihadqlt ptwrvystgs nvfqtragcl igaehvnnsy
661 ecdipigagi casyqtqtns prrarsvasq siiaytmslg aensvaysnn siaiptnfti
721 svtteilpvs mtktsvdctm yicgdstecs nlllqygsfc tqlnraltgi aveqdkntqe
781 vfaqvkqiyk tppikdfggf nfsqilpdps kpskrsfied llfnkvtlad agfikqygdc
841 lgdiaardli caqkfngltv lppllddemi aqytsallag titsgwtfga gaalqipfam
901 qmayrfngig vtqnvlyenq klianqfnsa igkiqdslss tasalgklqd vvnqnaqaln
961 tlvkqlssnf gaissvlndi lsrldkveae vqidrlitgr lqslqtyvtq qliraaeira
1021 sanlaatkms ecvlgqskrv dfcgkgyhlm sfpqsaphgv vflhvtyvpa qeknfttapa
1081 ichdgkahfp regvfvsngt hwfvtqrnfy epqiittdnt fvsgncdvvi givnntvydp
1141 lqpeldsfke eldkyfknht spdvdlgdis ginasvvniq keidrlneva knlneslidl
1201 qelgkyeqyi kwpwyiwlgf iagliaivmv timlccmtsc csclkgccsc gscckfdedd
1261 sepvlkgvkl hyt (SEQ ID NO:28)

BCA87361

1 mfvflvllpl vssqcvnltt rtqlppaytn sftrgvyypd kvfrssvlhs tqdlflpffs
61 nvtwfhaihv sgtngtkrfd npvlpfndgv yfasteksni irgwifgttl dsktqsllív
121 nnatnvvikv cefqfcndpf lgvyyhknnk swmesefrvy ssannctfey vsqpflmdle
181 gkqgnfknlr efvfknidgy fkiyskhtpi nlvrdlpqgf saleplvdlp iginitrfqt
241 llalhrsylt pgdsssgwta gaaayyvgyl qprtfllkyn engtitdavd caldplsetk
301 ctlksftvek giyqtsnfrv qptesivrfp nitnlcpfge vfnatrfasv yawnrkrisn
361 cvadysvlyn sasfstfkcy gvsptklndl cftnvyadsf virgdevrqi apgqtgkiad
421 ynyklpddft gcviawnsnn ldskvggnyn ylyrlfrksn lkpferdist eiyqagstpc
481 ngvegfncyf plqsygfqpt ngvgyqpyrv vvlsfellha patvcgpkks tnlvknkcvn
541 fnfngltgtg vltesnkkfl pfqqfgrdia dttdavrdpq tleilditpc sfggvsvitp
601 gtntsnqvav lyqdvnctev pvaihadqlt ptwrvystgs nvfqtragcl igaehvnnsy
661 ecdipigagi casyqtqtns prrarsvasq siiaytmslg aensvaysnn siaiptnfti
721 svtteilpvs mtktsvdctm yicgdstecs nlllqygsfc tqlnraltgi aveqdkntqe
781 vfaqvkqiyk tppikdfggf nfsqilpdps kpskrsfied llfnkvtlad agfikqygdc
841 lgdiaardli caqkfngltv lppllddemi aqytsallag titsgwtfga gaalqipfam
901 qmayrfngig vtqnvlyenq klianqfnsa igkiqdslss tasalgklqd vvnqnaqaln
961 tlvkqlssnf gaissvlndi lsrldkveae vqidrlitgr lqslqtyvtq qliraaeira
1021 sanlaatkms ecvlgqskrv dfcgkgyhlm sfpqsaphgv vflhvtyvpa qeknfttapa
1081 ichdgkahfp regvfvsngt hwfvtqrnfy epqiittdnt fvsgncdvvi givnntvydp
1141 lqpeldsfke eldkyfknht spdvdlgdis ginasvvniq keidrlneva knlneslidl
1201 qelgkyeqyi kwpwyiwlgf iagliaivmv timlccmtsc csclkgccsc gscckfdedd
1261 sepvlkgvkl hyt (SEQ ID NO:27)

QIK50427

1 mfvflvllpl vssqcvnltt rtqlppaytn sftrgvyypd kvfrssvlhs tqdlflpffs
61 nvtwfhaihv sgtngtkrfd npvlpfndgv yfasteksni irgwifgttl dsktqsllív

Figure 23 (Cont.)

```
 121 nnatnvvikv cefqfcndpf lgvyyhknnk swmesefrvy ssannctfey vsqpflmdle
 181 gkqgnfknlr efvfknidgy fkiyskhtpi nlvrdlpqgf saleplvdlp iginitrfqt
 241 llalhrsylt pgdsssgwta gaaayyvgyl qprtfllkyn engtitdavd caldplsetk
 301 ctlksftvek giyqtsnfrv qptesivrfp nitnlcpfge vfnatrfasv yawnrkrisn
 361 cvadysvlyn sasfstfkcy gvsptklndl cftnvyadsf virgdevrqi apgqtgkiad
 421 ynyklpddft gcviawnsnn ldskvggnyn ylyrlfrksn lkpferdist eiyqagstpc
 481 ngvegfncyf plqsygfqpt ngvgyqpyrv vvlsfellha patvcgpkks tnlvknkcvn
 541 fnfngltgtg vltesnkkfl pfqqfgrdia dttdavrdpq tleilditpc sfggvsvitp
 601 gtntsnqvav lyqgvnctev pvaihadqlt ptwrvystgs nvfqtragcl igaehvnnsy
 661 ecdipigagi casyqtqtns prrarsvasq siiaytmslg aensvaysnn siaiptnfti
 721 svtteilpvs mtktsvdctm yicgdstecs nlllqygsfc tqlnraltgi aveqdkntqe
 781 vfaqvkqiyk tppikdfggf nfsqilpdps kpskrsfied llfnkvtlad agfikqygdc
 841 lgdiaardli caqkfngltv lppll tdemi aqytsallag titsgwtfga gaalqipfam
 901 qmayrfngig vtqnvlyenq klianqfnsa igkiqdslss tasalgklqd vvnqnaqaln
 961 tlvkqlssnf gaissvlndi lsrldkveae vqidrlitgr lqslqtyvtq qliraaeira
1021 sanlaatkms ecvlgqskrv dfcgkgyhlm sfpqsaphgv vflhvtyvpa qeknfttapa
1081 ichdgkahfp regvfvsngt hwfvtqrnfy epqiittdnt fvsgncdvvi givnntvydp
1141 lqpeldsfke eldkyfknht spdvdlgdis ginasvvniq keidrlneva knlneslidl
1201 qelgkyeqyi kwpwyiwlgf iagliaivmv timlccmtsc csclkgccsc gscckfdedd
1261 sepvlkgvkl hyt (SEQ ID NO:26)
```

QHU79173

```
1 mfvflvllpl vssqcvnltt rtqlppaytn sftrgvyypd kvfrssvlys tqdlflpffs
  61 nvtwfhaihv sgtngtkrfd npvlpfndgv yfasteksni irgwifgttl dsktqsllivvv
 121 nnatnvvikv cefqfcndpf lgvyyhknnk swmesefrvy ssannctfey vsqpflmdle
 181 gkqgnfknlr efvfknidgy fkiyskhtpi nlvrdlpqgf saleplvdlp iginitrfqt
 241 llalhrsylt pgdsssgwta gaaayyvgyl qprtfllkyn engtitdavd caldplsetk
 301 ctlksftvek giyqtsnfrv qptesivrfp nitnlcpfge vfnatrfasv yawnrkrisn
 361 cvadysvlyn sasfstfkcy gvsptklndl cftnvyadsf virgdevrqi apgqtgkiad
 421 ynyklpddft gcviawnsnn ldskvggnyn ylyrlfrksn lkpferdist eiyqagstpc
 481 ngvegfncyf plqsygfqpt ngvgyqpyrv vvlsfellha patvcgpkks tnlvknkcvn
 541 fnfngltgtg vltesnkkfl pfqqfgrdia dttdavrdpq tleilditpc sfggvsvitp
 601 gtntsnqvav lyqdvnctev pvaihadqlt ptwrvystgs nvfqtragcl igaehvnnsy
 661 ecdipigagi casyqtqtns prrarsvasq siiaytmslg aensvaysnn siaiptnfti
 721 svtteilpvs mtktsvdctm yicgdstecs nlllqygsfc tqlnraltgi aveqdkntqe
 781 vfaqvkqiyk tppikdfggf nfsqilpdps kpskrsfied llfnkvtlad agfikqygdc
 841 lgdiaardli caqkfngltv lpplltdemi aqytsallag titsgwtfga gaalqipfam
 901 qmayrfngig vtqnvlyenq klianqfnsa igkiqdslss tasalgklqd vvnqnaqaln
 961 tlvkqlssnf gaissvlndi lsrldkveae vqidrlitgr lqslqtyvtq qliraaeira
1021 sanlaatkms ecvlgqskrv dfcgkgyhlm sfpqsaphgv vflhvtyvpa qeknfttapa
1081 ichdgkahfp regvfvsngt hwfvtqrnfy epqiittdnt fvsgncdvvi givnntvydp
1141 lqpeldsfke eldkyfknht spdvdlgdis ginasvvniq keidrlneva knlneslidl
1201 qelgkyeqyi kwpwyiwlgf iagliaivmv timlccmtsc csclkgccsc gscckfdedd
1261 sepvlkgvkl hyt (SEQ ID NO:25)
```

YP_009724390

```
1 mfvflvllpl vssqcvnltt rtqlppaytn sftrgvyypd kvfrssvlhs tqdlflpffs
  61 nvtwfhaihv sgtngtkrfd npvlpfndgv yfasteksni irgwifgttl dsktqslliv
 121 nnatnvvikv cefqfcndpf lgvyyhknnk swmesefrvy ssannctfey vsqpflmdle
 181 gkqgnfknlr efvfknidgy fkiyskhtpi nlvrdlpqgf saleplvdlp iginitrfqt
 241 llalhrsylt pgdsssgwta gaaayyvgyl qprtfllkyn engtitdavd caldplsetk
 301 ctlksftvek giyqtsnfrv qptesivrfp nitnlcpfge vfnatrfasv yawnrkrisn
 361 cvadysvlyn sasfstfkcy gvsptklndl cftnvyadsf virgdevrqi apgqtgkiad
 421 ynyklpddft gcviawnsnn ldskvggnyn ylyrlfrksn lkpferdist eiyqagstpc
 481 ngvegfncyf plqsygfqpt ngvgyqpyrv vvlsfellha patvcgpkks tnlvknkcvn
```

Figure 23 (Cont.)

```
 541 fnfngltgtg vltesnkkfl pfqqfgrdia dttdavrdpq tleilditpc sfggvsvitp
 601 gtntsnqvav lyqdvnctev pvaihadqlt ptwrvystgs nvfqtragcl igaehvnnsy
 661 ecdipigagi casyqtqtns prrarsvasq siiaytmslg aensvaysnn siaiptnfti
 721 svtteilpvs mtktsvdctm yicgdstecs nlllqygsfc tqlnraltgi aveqdkntqe
 781 vfaqvkqiyk tppikdfggf nfsqilpdps kpskrsfied llfnkvtlad agfikqygdc
 841 lgdiaardli caqkfngltv lpplltdemi aqytsallag titsgwtfga gaalqipfam
 901 qmayrfngig vtqnvlyenq klianqfnsa igkiqdslss tasalgklqd vvnqnaqaln
 961 tlvkqlssnf gaissvlndi lsrldkveae vqidrlitgr lqslqtyvtq qliraaeira
1021 sanlaatkms ecvlgqskrv dfcgkgyhlm sfpqsaphgv vflhvtyvpa qeknfttapa
1081 ichdgkahfp regvfvsngt hwfvtqrnfy epqiittdnt fvsgncdvvi givnntvydp
1141 lqpeldsfke eldkyfknht spdvdlgdis ginasvvniq keidrlneva knlneslidl
1201 qelgkyeqyi kwpwyiwlgf iagliaivmv timlccmtsc csclkgccsc gscckfdedd
1261 sepvlkgvkl hyt (SEQ ID NO:50)
```

QII57161

```
   1 mfvflvllpl vssqcvnltt rtqlppaytn sftrgvyypd kvfrssvlhs tqdlflpffs
  61 nvtwfhaihv sgtngtkrfd npvlpfndgv yfasteksni irgwifgttl dsktqsiliv
 121 nnatnvvikv cefqfcndpf lgvyyhknnk swmesefrvy ssannctfey vsqpflmdle
 181 gkqgnfknlr efvfknidgy fkiyskhtpi nlvrdlpqgf saleplvdlp iginitrfqt
 241 llalhrsylt pgdsssgwta gaaayyvgyl qprtfllkyn engtitdavd caldplsetk
 301 ctlksftvek giyqtsnfrv qptesivrfp nitnlcpfge vfnatrfasv yawnrkrisn
 361 cvadysvlyn sasfstfkcy gvsptklndl cftnvyadsf virgdevrqi apgqtgkiad
 421 ynyklpddft gcviawnsnn ldskvggnyn ylyrlfrksn lkpferdist eiyqagstpc
 481 ngvegfncyf plqsygfqpt ngvgyqpyrv vvlsfellha patvcgpkks tnlvknkcvn
 541 fnfngltgtg vltesnkkfl pfqqfgrdia dttdavrdpq tleilditpc sfggvsvitp
 601 gtntsnqvav lyqdvnctev pvaihadqlt ptwrvystgs nvfqtragcl igaehvnnsy
 661 ecdipigagi casyqtqtns prrarsvasq siiaytmslg aensvaysnn siaiptnfti
 721 svtteilpvs mtktsvdctm yicgdstecs nlllqygsfc tqlnraltgi aveqdkntqe
 781 vfaqvkqiyk tppikdfggf nfsqilpdps kpskrsfied llfnkvtlad agfikqygdc
 841 lgdiaardli caqkfngltv lpplltdemi aqytsallag titsgwtfga gaalqipfam
 901 qmayrfngig vtqnvlyenq klianqfnsa igkiqdslss tasalgklqd vvnqnaqaln
 961 tlvkqlssnf gaissvlndi lsrldkveae vqidrlitgr lqslqtyvtq qliraaeira
1021 sanlaatkms ecvlgqskrv dfcgkgyhlm sfpqsaphgv vflhvtyvpa qeknfttapa
1081 ichdgkahfp regvfvsngt hwfvtqrnfy epqiittdnt fvsgncdvvi givnntvydp
1141 lqpeldsfke eldkyfknht spdvdlgdis ginasvvniq keidrlneva knlneslidl
1201 qelgkyeqyi kwpwyiwlgf iagliaivmv timlccmtsc csclkgccsc gscckfdedd
1261 sepvlkgvkl hyt (SEQ ID NO:51)
```

QIJ96493

```
   1 mfvflvllpl vssqcvnltt rtqlppaytn sftrgvyypd kvfrssvlhs tqdlflpffs
  61 nvtwfhaihv sgtngtkrfd npvlpfndgv yfasteksni irgwifgttl dsktqsiliv
 121 nnatnvvikv cefqfcndpf lgvyyhknnk swmesefrvy ssannctfey vsqpflmdle
 181 vkqgnfknlr efvfknidgy fkiyskhtpi nlvrdlpqgf saleplvdlp iginitrfqt
 241 llalhrsylt pgdsssgwta gaaayyvgyl qprtfllkyn engtitdavd caldplsetk
 301 ctlksftvek giyqtsnfrv qptesivrfp nitnlcpfge vfnatrfasv yawnrkrisn
 361 cvadysvlyn sasfstfkcy gvsptklndl cftnvyadsf virgdevrqi apgqtgkiad
 421 ynyklpddft gcviawnsnn ldskvggnyn ylyrlfrksn lkpferdist eiyqagstpc
 481 ngvegfncyf plqsygfqpt ngvgyqpyrv vvlsfellha patvcgpkks tnlvknkcvn
 541 fnfngltgtg vltesnkkfl pfqqfgrdia dttdavrdpq tleilditpc sfggvsvitp
 601 gtntsnqvav lyqdvnctev pvaihadqlt ptwrvystgs nvfqtragcl igaehvnnsy
 661 ecdipigagi casyqtqtns prrarsvasq siiaytmslg aensvaysnn siaiptnfti
 721 svtteilpvs mtktsvdctm yicgdstecs nlllqygsfc tqlnraltgi aveqdkntqe
```

Figure 23 (Cont.)

```
 781 vfaqvkqiyk tppikdfggf nfsqilpdps kpskrsfied llfnkvtlad agfikqygdc
 841 lgdiaardli caqkfngltv lppll tdemi aqytsallag titsgwtfga gaalqipfam
 901 qmayrfngig vtqnvlyenq klianqfnsa igkiqdslss tasalgklqd vvnqnaqaln
 961 tlvkqlssnf gaissvlndi lsrldkveae vqidrlitgr lqslqtyvtq qliraaeira
1021 sanlaatkms ecvlgqskrv dfcgkgyhlm sfpqsaphgv vflhvtyvpa qeknfttapa
1081 ichdgkahfp regvfvsngt hwfvtqrnfy epqiittdnt fvsgncdvvi givnntvydp
1141 lqpeldsfke eldkyfknht spdvdlgdis ginasvvniq keidrlneva knlneslidl
1201 qelgkyeqyi kwpwyiwlgf iagliaivmv timlccmtsc csclkgccsc gscckfdedd
1261 sepvlkgvkl hyt (SEQ ID NO:52)
```

RECOMBINANT MULTIVALENT INFLUENZA VIRUSES

CROSS-REFERENCE TO RELATED APPLICATIONS

This application claims the benefit of the filing date of U.S. application No. 62/994,738, filed on Mar. 25, 2020, the disclosure of which is incorporated by reference herein.

SUMMARY

In one embodiment, this disclosure provides a coronavirus/influenza virus vaccine. In one embodiment, the vaccine employs a single-replication (SR; a 'single cycle' that results in transcription of vRNAs but no progeny virus production in vivo; that is, a single cycle virus is replication incompetent as a result of not being capable of producing progeny) platform in which the genome of an influenza virus virion lacks at least a portion of a coding region for at least one influenza virus protein, which influenza virus protein is supplied in trans in vitro in cell lines but is restricted to a single round of replication in wild-type cells. In one embodiment, the vaccine employs a M2 Single-Replication (M2SR) platform in which an influenza virus lacking the M2 ion channel protein replicates to high titers in cell lines expressing M2 but is restricted to a single round of replication in wild-type cells. In one embodiment the open reading frame for M2 in M2SR has one or more stop codons, or one or more stop codons and a deletion in M2, rendering the protein non-functional, e.g., the transmembrane domain and/or cytoplasmic domain, or both are not expressed. As described herein, this platform was modified to generate a bivalent coronavirus/influenza virus vaccine (called CoroFlu M2SR) that expresses a secreted version of the spike (S) protein of coronavirus, e.g., SARS-CoV-2.

In one embodiment, a vaccine provides a humoral, mucosal, innate, and/or cell-mediated immune response. In one embodiment, this disclosure provides a replication competent coronavirus/influenza virus vaccine. In one embodiment, the vaccine is inactivated, including chemically inactivated, e.g., with formalin or β-propiolactone.

In one embodiment, a coronavirus/influenza virus expresses a full-length spike protein, e.g., but does not express HA and/or NA. In one embodiment, a bivalent coronavirus/influenza virus expresses a truncated version of the spike protein, e.g., including the S1 or receptor-binding (RBD) domain of S, in addition to at least one other antigenic molecule such as influenza HA and/or NA. In vaccinated individuals, the full-length protein or a portion thereof, e.g., a secreted S protein, elicits protective antibodies against SARS-CoV-2 after administration to a vertebrate, e.g., a mammal such as a human. In one embodiment, the vaccine is a bivalent vaccine where the virus also expresses influenza virus HA and/or NA proteins or other microbial proteins. In one embodiment, a bivalent coronavirus/influenza virus expresses a full-length spike protein. In one embodiment, a bivalent coronavirus/influenza virus expresses a truncated version of the spike protein, e.g., including the S1 or RBD domain of S, and influenza HA and NA. In vaccinated individuals, the full-length protein or a portion thereof, e.g., a secreted S protein, elicits protective antibodies against SARS-CoV-2, while the influenza viral HA protein will elicit protective antibodies against influenza virus, after administration to a vertebrate, e.g., a mammal such as a human. In contrast to the majority of influenza and experimental coronavirus vaccines, this vaccine mimics the natural infection process and stimulates mucosal, innate, humoral, and/or cell-mediated immune responses.

In one embodiment, an isolated, single cycle recombinant influenza virus having at least seven viral segments selected from PA, PB1, PB2, NP, NS, M, HA or NA (or HEF) viral segments, one of which segments comprises sequences for a heterologous antigen is provided. In one embodiment, the heterologous antigen comprises coronavirus protein sequences. In one embodiment, the coronavirus protein sequences comprise spike protein sequences or a soluble portion thereof. In one embodiment, the portion comprises S1. In one embodiment, the portion comprises the receptor binding domain. In one embodiment, the spike protein sequences or a portion thereof have at least 80% amino acid sequence identity to one of SEQ ID Nos. 25-28 and 50-52 and 50-52. In one embodiment, the spike protein has 1 to 7 proline residues (see Hsieh et al., which is incorporated by reference herein), which in turn stabilize the protein prefusion, e.g., proline at position 817, 892, 895, 899, 912, 942, or 946. In one embodiment, the virus comprises eight viral segments. In one embodiment, the virus comprises nine viral segments, where the ninth segment comprises the coronavirus sequences, e.g., on a PB2 or NS segment that does not express PB2 or NS1 or NS2, respectively. In one embodiment, the virus comprises nine viral segments, where the ninth segment comprises the coronavirus sequences, e.g., on a PA, PB1, NA, or M segment that does not express PA, PB1, NA, or M1 or M2, respectively. In one embodiment, the virus is an influenza A virus. In one embodiment, the virus is an influenza B virus. In one embodiment, the virus is an influenza C virus. In one embodiment, the virus is an influenza D virus. In one embodiment, the sequences for a heterologous antigen are inserted into or replace at least some of the coding sequences for one of PA, P81, PB2, NP, NS1, NS2, M1. M2, HA or NA (or HEF), e.g., at least a portion of the coding sequences for the influenza virus protein are deleted. In one embodiment, sequences for a heterologous antigen are inserted into or replace at least some of the coding sequences for one of PB1, PB2, NA, or M2. In one embodiment, sequences for a heterologous antigen are inserted into or replace at least some of the coding sequences for one of NS1, NS2, HA, or PA. Cell lines employed to prepare such viruses provide one or more influenza proteins in trans so as to complement any non-functional proteins resulting from the deletion. In one embodiment, the sequences for a heterologous antigen are inserted into coding sequences in the viral segment of one of PA, PB1, PB2, NP, NS, M, HA or NA (or HEF) viral segments. In one embodiment, sequences for a heterologous antigen are inserted, e.g., up to 3 to 4 kb into, e.g., expressed as a fusion polypeptide, coding sequences for one of PB1, PB2, NS1, NS2, or M2. Cell lines employed to prepare such viruses may provide one or more influenza proteins in trans so as to complement any non-functional proteins resulting from the insertion. In one embodiment, the virus is a single cycle bivalent virus. In one embodiment, the virus is a single cycle trivalent virus. Multivalent viruses within the scope of this disclosure may express at least two of the following: homologous influenza HA and/or NA, heterologous influenza HA and/or NA, heterologous viral gene products such as coronavirus gene products, or other viral gene products useful to elicit a protective immune response, rhabdovirus GP protein, e.g., VSV-G, a filovirus protein, e.g., Ebolavirus GP, an alphavirus protein, a lentivirus protein, a retrovirus protein, a paramyxovirus protein, a rhinovirus protein, a bunyavirus protein an arenavirus protein a flavivirus protein, or a rhabdovirus protein, fungal gene products, or bacterial gene products. For example, a HA viral segment employed in the virus may replace the HA coding region with VSV-G coding sequences, or other host cell binding sequences, a NA viral segment employed in the virus may replace NA coding sequences with sequences from those from a paramyxovirus, e.g., type 3; heterologous antigenic coding sequences may be added to a viral coding region, e.g., added to the open reading frame for PB2 or NA, or may replace PB2 coding sequences. In one embodiment, the M viral segment is mutated so that upon viral replication the mutant M gene expresses a functional M1 protein and a mutant M2 protein with a deletion of the cytoplasmic tail and either lacking a transmembrane domain or having a mutated transmembrane domain, wherein the replication of the recombinant virus in vivo is limited to a single cycle (e.g., no progeny viruses are produced) relative to a corresponding influenza virus with a wild-type M viral segment. In one embodiment, the M2 coding region is modified to include one or more stop codons, e.g., at or near the splice site(s), and may also include a deletion of, e.g., downstream, coding sequences so as to result in a truncated M2 protein. In one embodiment, the mutant M2 protein comprises the M2 extracellular domain. In one embodiment, the M2 extracellular domain comprises less than 24 residues. In one embodiment, the M2 extracellular domain comprises at least 9 residues. In one embodiment, the mutation in the transmembrane domain comprises at least one amino acid substitution. In one embodiment, the mutation in the transmembrane domain comprises a deletion in the transmembrane domain. In one embodiment, the deletion in the transmembrane domain includes residues 29 to 31. In one embodiment, the deletion in the transmembrane domain comprises at least 10 residues. In one embodiment, the deletion in the M2 protein deletes the cytoplasmic tail which protein in turn when present in a virus, results in an attenuated virus. In one embodiment, one or more of the PA, PB1, PB2, NP, NS, and M viral segments have selected amino acid residues at positions 30, 31, 105, 142, 149, 225, 356, 357, 401, and/or 550 in PA: positions 40, 54, 59, 62, 63, 75, 76, 78, 79, 80, 112, 180, 247, 327, 507, 624, 644, 667, 694, 695, 697.699, 700, 701, 702, 705, 713, and/or 714 in PB1; positions 57, 58, 59, 61, 66, 202, 323, 368, 391, 504, 591, 677, 678, and/or 679, in PB2; positions 74, 112, 116, 224, 293, 371, 377, 417, 422 or 442 in NP; positions 90, 97 and/or 100 in M1; or positions 30, 49, 55, 118, 140, 161 and/or 223 in NS1. In one embodiment, the virus is bivalent. In one embodiment, the PB1 viral segment encodes a polypeptide having a residue other than glycine, serine, serine, glutamine or asparagine at position 62, 261, 361, 621, and/or 654 in PB1 or a residue other than arginine at position 81 in F2. In one embodiment, the virus is in a vaccine formulation. In one embodiment, the vaccine comprises influenza A HA, e.g., H1, H3, H5 or H7 HA. In one embodiment, the HA in the recombinant virus is modified at the HA cleavage site. In one embodiment, the vaccine further comprises a different influenza virus. In one embodiment, the vaccine further comprises two different influenza viruses.

For example, in one embodiment, to prepare recombinant virus, vectors for vRNA or cRNA are introduced to host cells expressing M2 in trans. One of vectors has sequences for the M segment and that segment is modified so that functional M2 is not expressed from that segment. In one embodiment, one or two stop codons are introduced, and optionally some M2 coding sequences are deleted. One of the vectors for vRNA or cRNA has the heterologous antigen sequences. For example, the heterologous antigen sequences may be inserted at the end of the coding region for NS1.

In another embodiment, to prepare recombinant virus, vectors for vRNA or cRNA are introduced to host cells expressing PB2 in trans. One of the vectors for vRNA or cRNA has the heterologous antigenic sequences. For example, the heterologous antigen sequences may be inserted at the end of the coding region for NS1 or into the coding sequences for PB2. One of vectors has sequences for the PB2 segment and that segment is modified so that functional PB2 is not expressed from that segment. In one embodiment, at least some PB2 coding sequences are deleted. In one embodiment, the modified PB2 viral gene segment includes 5' and/or 3' PB2 viral non-coding and coding incorporation sequences, optionally flanking a heterologous nucleotide sequence, and does not include contiguous sequences corresponding to sequences encoding a functional PB2. In one embodiment, the heterologous nucleotide sequence is about 30 to about 5,000, e.g., about 100 to about 4,500 or about 500 to about 4,000, nucleotides in length. In one embodiment, the deletion of PB2 coding sequences includes 1 or more contiguous or noncontiguous nucleotides of PB2 and may include a deletion of the entire coding region, e.g., a region encoding 759 amino acids. In one embodiment, the deletion includes at least 10%, 30%, 40%, 50%, 70%, 80%, 85%, 90%, 93%, 95% and up to 99%, or a percent numerical value that is any integer between 10 and 99, but not all, of the PB2 coding region. In one embodiment, the deletion of PB2 coding sequences does not include the deletion of 5' or 3' coding sequences that enhance incorporation of the resulting viral gene segment into virions, e.g., sequences that are contiguous to 3' or 5' non-coding PB2 sequences, relative to a recombinant viral gene segment with only non-coding PB2 incorporation sequences. For instance, if present in the PB2 segment, the heterologous nucleotide sequence may encode coronavirus sequences, and may be flanked by about 3 to about 400 nucleotides of the 5' and/or 3' PB2 coding region adjacent to non-coding sequence. In one embodiment, the 3' PB2 incorporation sequences correspond to nucleotides 3 to 400, nucleotides 3 to 300, nucleotides 3 to 100, nucleotides 3 to 50, or any integer between 3 and 400, of the N-terminal and/or C-terminal PB2 coding region. In one embodiment, the heterologous nucleotide sequence is flanked by about 3 to about 400 nucleotides of the 5' and/or 3' PB2 coding region adjacent to non-coding sequence. In one embodiment, the heterologous nucleotide sequence is flanked by about 100 to about 300, or 120 to about 150 nucleotides of the 5' and/or 3' PB2 terminal sequences which include coding and non-coding sequences. In one embodiment, heterologous sequences, e.g., antigenic sequences for a virus other than influenza virus or for an influenza virus protein from an isolate other than the strain employed to provide the internal viral segments or for the HA and NA viral segments, may be inserted at the end of the coding region for NS1.

In one embodiment, a method to immunize a vertebrate is provided. The method includes administering to the vertebrate the vaccine. In one embodiment, the vertebrate is an avian. In one embodiment, the vertebrate is a mammal. In one embodiment, the vertebrate is a human. In one embodiment, the vaccine is intranasally administered. In one embodiment, the vaccine is intramuscularly administered.

In one embodiment, the internal viral segments (PA, PB1, PB2, NS, M, and NP viral segments) are from a vaccine strain, e.g., the PR8/UW, PR8HY or PR8/Cambridge strain. In one embodiment, the internal viral segments may be modified to enhance replication in host cell used to generate the vaccine. In one embodiment, in addition to the presence of certain amino acid residues in the coding regions of six internal viral segments, e.g., relative to PR8HY or the PR8/Cambridge strain, mutations in non-coding regions were observed to increase viral liters, including promoter mutations, for instance, C-to-U mutations at position 4 from the 3' end of the PB2, PB1, and/or PA vRNA segments. The resulting sequences may be also codon-usage optimized, e.g., optimized for expression in mammalian cells such as canine cells or primate cells, or avian cells, e.g., chicken embryos. The mutations can be used in various combinations, with results influenced by the cell line (or egg) in use and the desired level of improvement in the replication of the virus.

In one embodiment, the virus is administered intramuscularly while in another embodiment, the virus is administered intranasally. In some dosing protocols, all doses may be administered intramuscularly or intranasally, while in others a combination of intramuscular and intranasal administration is employed. The vaccine may further contain other isolates of influenza virus including recombinant influenza virus, other pathogen(s), additional biological agents or microbial components, e.g., to form a multivalent vaccine. In one embodiment, intranasal vaccination, for instance containing with inactivated influenza virus, and a mucosal adjuvant may induce virus-specific IgA and neutralizing antibody in the nasopharynx as well as serum IgG.

The invention provides isolated recombinant, e.g., reassortant, influenza viruses with, e.g., 7, 8 or 9 viral segments, one of which includes sequences for a microbial pathogen. e.g., sequences for a coronavirus spike protein, or a portion thereof. In one embodiment, the coronavirus sequences replace influenza virus sequences. e.g., replace coding sequences in one of PA, PB1, PB2, NP, M (encoding M1 and M2 proteins), NS (encoding NS1 and NS2 proteins), HA or NA (or HEF) viral segments. In one embodiment, the coronavirus sequences replace influenza virus sequences, e.g., replace coding sequences in one of PA, PB1, PB2, NP, M (encoding M1 and M2 proteins), or NS (encoding NS1 and NS2 proteins). In one embodiment, the coronavirus sequences are inserted into influenza virus sequences, e.g., into coding sequences in one of PA, PB1, PB2, NP, M (encoding M1 and M2 proteins), NS (encoding NS1 and NS2 proteins), HA or NA (or HEF) viral segments in influenza A viral segments. In one embodiment, the coronavirus sequences are inserted into, e.g., fused to, influenza virus coding sequences, e.g., into coding sequences for one of PA. PB1, PB2, NP, M (encoding M1 and M2 proteins), or NS (encoding NS1 and NS2 proteins). In one embodiment, the coronavirus sequences are expressed as a fusion with influenza virus protein sequences, e.g., a fusion with PA, PB1, PB2, NP, M1, M2, NS1, or NS2 proteins. In one embodiment, the coronavirus sequences are inserted into influenza virus coding sequences and the resulting fusion polypeptide is cleaved to release the coronavirus S protein sequences. For example, coronavirus coding sequences flanked by protease recognition sequences, e.g., self-cleaving sites such as those from foot and mouth disease or 2A sequences, for example, T2A (EGRGSLLTCGDVEENPGP; SEQ ID NO:53), P2A (ATNFSLLKQAGDVEENPGP; SEQ ID NO:54), E2A (QCTNYALLKLAGDVESNPGP; SEQ ID NO:55) or F2A (VKQTLNFDLLKAGDVESNPGP; SEQ ID NO:56) sequences, are inserted into the NS viral segment, e.g., between NS1 and NS2 coding sequences. In one embodiment, coronavirus sequences are introduced to a viral segment that, in the recombinant virus, is a ninth viral segment, where the other eight segments are the PA, PB1, PB2, NP, M, NS, HA and NA viral segments. In one embodiment, the M viral segment encodes a truncated M2 protein. In one embodiment, the coronavirus sequences replace coding sequences, e.g., PB1 or PB2 coding sequences. In one embodiment, the coronavirus sequences encode a protein having at least 80%, 82%, 84%, 85%, 87%, 90%, 92%, 94%, 95%, 97%, 98%, 99% or more amino acid sequence identity with one of SEQ ID Nos. 25-28 and 50-52. In one embodiment, the coronavirus sequences encode a S1 protein having at least 80%, 82%, 84%, 85%, 87%, 90%, 92%, 94%, 95%, 97%, 98%, 99% or more amino acid sequence identity with S1 in one of SEQ ID Nos. 25-28 and 50-52. In one embodiment, the coronavirus sequences encode a RBD having at least 80%, 82%, 84%, 85%, 87%, 90%, 92%, 94%, 95%, 97%, 98%, 99% or more amino acid sequence identity with the RBD in one of SEQ ID Nos. 25-28 and 50-52. In one embodiment, the coronavirus sequences encode a protein having at least 80%, 82%, 84%, 85%, 87%, 90%, 92%, 94%, 95%, 97%, 98%, 99% or more amino acid sequence identity with S1 in one of SEQ ID NOS. 25-28 and 50-52. In one embodiment, the coronavirus sequences encode a protein having at least 80%, 82%, 84%, 85%, 87%, 90%, 92%, 94%, 95%, 97%, 98%, 99% or more amino acid sequence identity with the RBD in one of SEQ ID Nos. 25-28 and 50-52.

In one embodiment, the influenza virus is a recombinant influenza virus having a particular amino acid residue at specified positions in one or more of PA, PB1, PB2, NP, M1 and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, such as a polypeptide with a residue that is a conservative substitution relative to M202 in PB2, R74 in NP, and/or V97 in M1.

In one embodiment, the influenza virus is a recombinant influenza virus having a particular amino acid residue at specified positions in PA, PB1, PB2, NP, M1 and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-8 or 10-15, e.g., a polypeptide with a residue that is a non-conservative substitution relative to K142 in PA, Q247 in PB1, M202, F323 or I504 in PB2, R74 I112, I116, J442 or N417 in NP, V97 and/or Y100 in M1, and/or K55 or R140 in NS1.

In one embodiment, the influenza virus is a recombinant influenza virus having a particular amino acid residue at specified positions in PA, PB1, PB2, NP, M1 and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-8 or 10-15, e.g., a PB2 viral segment with a residue other than isoleucine and that is a conservative substitution for isoleucine at residue 504; a PB1 viral segment with a non-conservative substitution for E112; a PA viral segment with a substitution for S225; a NP viral segment with a conservative substitution for R74 and N417; a M viral segment with a conservative substitution for V97 and a non-conservative substitution for Y100; and a NS viral segment with a non-conservative substitution for K55.

In one embodiment, the influenza virus is a recombinant influenza virus having a particular amino acid residue at specified positions in PA, PB1, PB2, NP, M1 and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, e.g., a PB2 viral segment with a non-conservative substitution for M202 and F323; a PB1 viral segment with a non-conservative substitution for Q247; a PA viral segment with a non-conservative substitution for K142; a NP viral segment with a conservative substitution for R74; a M viral segment with a conservative substitution for V97 and a non-conservative substitution for Y100; and a NS viral segment with a conservative substitution for K55E.

In one embodiment, the influenza virus is a recombinant influenza virus having a particular amino acid residue at specified positions in PA, PB1, PB2, NP, M1 and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, e.g., a PB2 segment with a conservative substitution for 1504; a PB1 segment with a conservative substitution for M40L and a non-conservative substitution for G180; a PA segment with a conservative substitution for R401; a NP segment with a conservative substitution for I116; a NS viral segment with a conservative substitution for A30 or R118.

In one embodiment, the influenza virus is a recombinant influenza virus having a particular amino acid residue at specified positions in one or more of PA, PB1, PB2, NP, M1 and/or NS1 and an amino acid sequence with at least 80%, e.g., 90%, 92%, 95%, 97% or 99%, including any integer between 80 and 99, contiguous amino acid sequence identity to a corresponding polypeptide encoded by one of SEQ ID Nos. 1-6 or 10-15, such as a polypeptide with a residue that is a non-conservative substitution relative to K142 in PA, Q247 in PB1, F323 in PB2, Y100 in M1, and/or K55 in NS1. In one embodiment, the amino acid residue that is replaced has an aliphatic side chain, amide-containing side chain, basic side chain, or sulfur containing side chain and the replacement of an aromatic side chain or acidic side chain (a nonconservative substitution). In one embodiment, the recombinant influenza virus has a residue that is a neutral or positively charged residue that is replaced with a polar or negatively charged residue.

Viral segments for PA, PB1, PB2, NP, M and/or NS may be combined with a viral segment for HA, e.g., H1. H2, H3, H4, H5, H6, H7, H8, H9, H10, H11, H12, H13, H14, H15, H16, H17, or H18 and a viral segment for NA. e.g., N1, N2, N3, N4, N5, N6, N7, N8, N9, N10, or N11, and any combination of HA and NA, to provide the reassortant vaccine viruses. In one embodiment, the HA is H1, H5 or H7. In one embodiment the NA is N1 or N9. In one embodiment, the HA viral segment in the recombinant or reassortant virus is heterologous to the viral segments for PA, PB1, PB2, NP, M and NS. In one embodiment, the NA viral segment in the recombinant or reassortant virus is heterologous to the viral segments for PA, PB1, PB2, NP, M and NS. In one embodiment, the HA viral segment in the recombinant or reassortant virus has viral segments for PA, PB1, PB2, NP, M and NS from one influenza virus isolate or strain ("parent"), or a variant thereof, e.g., one with viral segments encoding influenza virus proteins with at least 95%, 96%, 97%, 98%, 99%, or 99.5% amino acid sequence identity, or having 1, 2, 5, 10, or 20 substitutions relative, to sequences in a parent influenza virus isolate or strain. In one embodiment, the parent strain has viral segments with sequences corresponding to SEQ ID Nos. 1-6 or 10-15. In one embodiment, the HA viral segment in the recombinant or reassortant virus is a chimeric HA viral segment, e.g., a chimera of heterologous HA ectodomain sequences linked to HA signal peptide sequences and/or HA transmembrane domain sequences from the HA viral segment of the parent isolate or strain, or variant thereof. In one embodiment, the NA viral segment in the isolated recombinant virus is a chimeric NA viral segment e.g., a chimera of heterologous NA ectodomain sequences linked to NA transmembrane domain sequences from the NA viral segment of the parent isolate or strain, or variant thereof, and/or stalk sequences from the parent isolate or strain, or variant thereof. In one embodiment, the NA viral segment in the isolated recombinant virus is a chimeric NA viral segment e.g., a chimera of heterologous NA ectodomain sequences linked to NA transmembrane domain sequences from the NA viral segment of the parent isolate or strain, or variant thereof, and/or stalk sequences from a second isolate or strain, or variant thereof. In one embodiment, the isolated recombinant virus has a heterologous HA viral segment, a heterologous NA viral segment, a chimeric HA viral segment, a chimeric NA viral segment, or any combination thereof. The nucleic acid sequences employed to prepare vRNA or cRNA may be ones that introduce the residues at the specified positions via recombinant methodology or may be selected as having the residues at the specified positions. Other reassortants with internal genes from other PR8 isolates or other vaccine viruses may be employed in recombinant reassortant viruses.

Vaccine viruses may be grown or passaged in cells in culture, e.g., MDCK or Vero cells or eggs. In one embodiment, the cells are canine or primate, e.g., human or monkey, cells.

The invention provides a plurality of influenza virus vectors, e.g., those useful to prepare reassortant viruses including 6:1:1 reassortants, 6:2 reassortants and 7:1 reassortants. A 6:1:1 reassortant is an influenza virus with 6 internal viral segments from a vaccine virus, a NA viral segment from a different (second) viral isolate, and a HA viral segment from a third isolate; a 6:2 reassortant within the scope of the present invention is an influenza virus with 6 internal viral segments from a vaccine virus, and a NA viral segment and a HA viral segment from a different (second) viral isolate; and a 7:1 reassortant within the scope of the present invention is an influenza virus with 6 internal viral segments and a NA viral segment from a vaccine virus, and a HA viral segment from a different viral source than the vaccine virus, or an influenza virus with 6 internal viral segments and a HA viral segment from the vaccine virus, and a NA viral segment is from a different viral source than the vaccine virus.

In one embodiment, the plurality of vectors includes vectors for vRNA or cRNA production selected from a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising a promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a operably linked to an influenza virus NS DNA linked to a transcription termination sequence. In one embodiment, the DNAs for vRNA or cRNA production of PB1, PB2, PA, NP, M, and NS, have sequences from an influenza virus that replicates to high titers in cultured mammalian cells such as MDCK cells, e.g., humanized MDCK cells, Vero cells or PER.C6® cells and also optionally embryonated eggs, and/or from a vaccine virus, e.g., one that does not cause significant disease in humans. The DNA for vRNA or cRNA production of NA may be from any NA, e.g., any of N1-N11, and the DNA for vRNA or cRNA production of HA may be from any HA, e.g., H1-H18. In one embodiment, the DNAs for vRNA or cRNA production may be for an influenza B, C or D virus. The DNAs for vRNA or cRNA production of NA and HA may be from different strains or isolates (6:1:1 reassortants) or from the same strain or isolate (6:2 reassortants), or the NA may be from the same strain or isolate as that for the internal genes (7:1 reassortant). The plurality also includes vectors for mRNA production selected from a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. The vectors encoding viral proteins may further include a transcription termination sequence.

Viruses within the scope of the invention include viruses that have high titers in, for example, MDCK cells, e.g., titers of at least about $10^5$ PFU/mL, e.g., at least $10^8$ PFU/mL, $10^7$ PFU/mL or $10^8$ PFU/mL; high titers in embryonated eggs, e.g., titers of at least about $10^7$ $EID_{50}$/mL, e.g., at least $10^8$ $EID_{50}$/mL, $10^9$ $EID_{50}$/mL or $10^{10}$ $EID_{50}$/mL; high titers in cells such as MDCK cells. e.g., titers of at least about 107 PFU/mL, e.g., at least $10^8$ PFU/mL, or high titers in two of more of those host cells.

In one embodiment, the DNAs for the internal genes for PB1, PB2, PA, NP, M, and NS encode proteins with substantially the same activity as a corresponding polypeptide encoded by one of SEQ ID NOs:1-6 or 10-15. As used herein, "substantially the same activity" includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the nucleic acid a sequence encoding a polypeptide which is substantially the same as, e.g., having at least 80%, e.g., 90%, 92%, 95%, 97%, 98%, or 99%, including any integer between 80 and 99, contiguous amino acid sequence identity to, a polypeptide encoded by one of SEQ ID NOs:1-6 or 10-15. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of SEQ ID NOs:1-6 or 10-15 and, in one embodiment, also encodes a polypeptide having at least 80%, e.g., 90%, 92%, 95%, 97%, 98%, or 99%, including any integer between 80 and 99, contiguous amino acid sequence identity to a polypeptide encoded by one of SEQ ID NOs:1-6 or 10-15. In one embodiment, the influenza virus polypeptide has one or more, for instance, 2, 5, 10, 15, 20 or more, conservative amino acids substitutions, e.g., conservative substitutions of up to 10% or 20% of 2, 5, 10, 15, 20 or more, of a combination of conservative and non-conservative amino acids substitutions, e.g., conservative substitutions of up to 10% or 20% of the residues, or relative to a polypeptide encoded by one of SEQ IS NOs:1-6 or 10-15, and has a characteristic residue in two or more of PA, PB1, PB2, NP, M1, and/or NS1 the residues, relative to a polypeptide encoded by one of SEQ ID NOs:1-6 or 10-15, and has a characteristic residue in two or more of the viral segments for PA, PB1, PB2, NP, M1, and/or NS1, e.g., there is an asparagine or glutamine at position 142 in PA; a histidine, arginine or lysine at position 247 in PB1; a leucine, alanine, valine, isoleucine, glycine, or serine at position 202 and/or position 323 in PB2; a lysine or a histidine at position 74 in NP: a leucine, isoleucine, alanine, glycine, or serine at position 202 and/or a lysine, arginine, or histidine position 100 in M1; or an asparagine, aspartic acid, glutamic acid or glutamine at position 44 in NS1. In one embodiment, the influenza virus polypeptide has one or more, for instance, 2, 3, 4, 5, 6, 7 or 8 conservative and/or nonconservative amino acid substitutions, relative to a polypeptide encoded by one of SEQ ID NOs:1-6 or 10-15, e.g., those in virus isolates 1, 4, 36, 38, P17, P25 or P61 in Table 4.

The invention thus includes the use of isolated and purified vectors or plasmids, which express or encode influenza virus proteins, or express or encode influenza vRNA or cRNA, both native and recombinant vRNA or cRNA. The vectors comprise influenza cDNA, e.g., influenza A (e.g., any influenza A gene including any of the 18 HA or 11 NA subtypes), B, C or D DNA (see Fields *Virology* (Fields et al. (eds.), $7^{th}$ edition, Wolter, Kluwer (2020), which is specifically incorporated by reference herein). Any suitable promoter or transcription termination sequence may be employed to express a protein or peptide, e.g., a viral protein or peptide, a protein or peptide of a nonviral pathogen, or a therapeutic protein or peptide.

A composition or plurality of vectors comprises a heterologous gene or open reading frame of interest, e.g., a foreign gene encoding an immunogenic peptide or protein useful as a vaccine. When preparing virus, the vector or plasmid comprising the gene or cDNA of interest may substitute for a vector or plasmid for an influenza viral gene or may be in addition to vectors or plasmids for all influenza viral genes. Thus, another embodiment comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA or cRNA corresponding to the heterologous sequences of the vector.

The promoter in a vector for vRNA or cRNA production may be a RNA polymerase I promoter, a RNA polymerase II promoter, a RNA polymerase III promoter, a T7 promoter, or a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, the RNA polymerase I promoter is a human RNA polymerase I promoter.

The promoter or transcription termination sequence in a vRNA, cRNA or virus protein expression vector may be the same or different relative to the promoter or any other vector. In one embodiment, the vector or plasmid which expresses influenza vRNA or cRNA comprises a promoter suitable for expression in at least one particular host cell, e.g., avian or mammalian host cells such as canine, feline, equine, bovine, ovine, or primate cells including human cells, or for expression in more than one host.

In one embodiment, at least one vector for vRNA or cRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA or cRNA comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA or cRNA vector may be the same or different as the RNA polymerase II promoter in any other vRNA or cRNA vector. Similarly, each ribozyme sequence in each vRNA or cRNA vector may be the same or different as the ribozyme sequences in any other vRNA or cRNA vector. In one embodiment, the ribozyme sequences in a single vector are not the same.

In one embodiment, the invention provides a plurality of influenza virus vectors for a recombinant or reassortant virus comprising a vector for vRNA or cRNA production comprising a promoter operably linked to an influenza virus PA DNA linked to a transcription termination sequence, a vector for vRNA or cRNA production comprising a promoter operably linked to an influenza virus PB1 DNA linked to a transcription termination sequence, a vector for vRNA or cRNA production comprising a promoter operably linked to an influenza virus PB2 DNA linked to a transcription termination sequence, a vector for vRNA or cRNA production comprising a promoter operably linked to an influenza virus HA DNA linked to a transcription termination sequence, a vector for vRNA or cRNA production comprising a promoter operably linked to an influenza virus NP DNA linked to a transcription termination sequence, a vector for vRNA or cRNA production comprising a promoter operably linked to an influenza virus NA DNA linked to a transcription termination sequence, a vector for vRNA or cRNA production comprising a promoter operably linked to an influenza virus M DNA linked to a transcription termination sequence, and a vector for vRNA or cRNA production comprising a promoter operably linked to an influenza virus NS cDNA linked to a transcription termination sequence, wherein the DNAs for PB1, PB2, PA, NP, NS, and M are from one or more influenza vaccine seed viruses; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2. In one embodiment, at least one vector comprises sequences corresponding to those encoding PB1, PB2, PA, NP, M, or NS, or a portion thereof, having substantially the same activity as a corresponding polypeptide encoded by one of SEQ ID NOs:1-6 or 10-15, e.g., a sequence encoding a polypeptide with at least 80%, e.g., 85%, 90%, 92%, 95%, 98%, 99% or 100%, including any integer between 80 and 100, amino acid identity to a polypeptide encoded by one of SEQ ID NOs:1-6 or 10-15. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

A plurality of the vectors of the invention may be physically linked or each vector may be present on an individual plasmid or other, e.g., linear, nucleic acid delivery vehicle. In one embodiment, each vRNA or cRNA production vector is on a separate plasmid. In one embodiment, each mRNA production vector is on a separate plasmid.

The invention also provides a method to prepare influenza virus. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with the plurality of vectors or virus of the invention. In another embodiment, the invention includes contacting the cell with one or more vectors, either vRNA, cRNA or protein production vectors, prior to other vectors, either vRNA or protein production vectors. In one embodiment, the promoter for vRNA or cRNA vectors employed in the method is a RNA polymerase I promoter, a RNA polymerase II promoter, a RNA polymerase III promoter, a T3 promoter or a T7 promoter. In one embodiment, the RNA polymerase I promoter is a human RNA polymerase I promoter. In one embodiment, each vRNA or cRNA vector employed in the method is on a separate plasmid. In one embodiment, the vRNA or cRNA vectors employed in the method are on one plasmid or on two or three different plasmids. In one embodiment, each mRNA vector employed in the method is on a separate plasmid. In one embodiment, the mRNA vectors for PA. PB1, PB2 and NP employed in the method are on one plasmid or on two or three different plasmids.

The methods of producing virus described herein, which do not require helper virus infection, are useful in viral mutagenesis studies, and in the production of vaccines (e.g., for coronavirus, AIDS, influenza, hepatitis B, hepatitis C, rhinovirus, filoviruses, malaria, herpes, and foot and mouth disease).

The invention also provides isolated viral polypeptides, and methods of preparing and using a recombinant virus of the invention. The methods include administering to a host organism, e.g., a mammal, an effective amount of the influenza virus of the invention, e.g., an inactivated virus preparation, optionally in combination with an adjuvant and/or a carrier, e.g., in an amount effective to prevent or ameliorate infection of an animal such as a mammal by that virus or an antigenically closely related virus. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. The vaccine may further contain other isolates of influenza virus including recombinant influenza virus, other pathogen(s), additional biological agents or microbial components, e.g., to form a multivalent vaccine. In one embodiment, intranasal vaccination, for instance containing with live attenuated or single cycle influenza virus, and a mucosal adjuvant may induce virus-specific IgA and neutralizing antibody in the nasopharynx as well as serum IgG.

The influenza virus of the invention may employed with other anti-virals, e.g., protease inhibitors, for instance, remdesivir, anti-malarials, e.g., chloroquine, amantadine, rimantadine, and/or neuraminidase inhibitors, e.g., may be administered separately in conjunction with those anti-virals, for instance, administered before, during and/or after.

BRIEF DESCRIPTION OF THE FIGURES

FIGS. 1A-1E. Nucleotide sequence for PR8(Cambridge) genes (SEQ ID NOs:10-15).

FIG. 3. Number of clones with random mutations having specified HA titers.

FIG. 4. Titers of clones having selected mutations.

FIGS. 5A-5D. Growth curves of UW-PR8 viruses possessing previously identified mutations in PB2 (A), PB1 (B), PA (C), and NP, M or NS1 (D).

FIG. 6. Summary of mutations that confer high replicative property in MDCK cells.

FIGS. 7A-7B. A) Virus stocks were tested for HA titers (in $2^n$) and virus titers (in PFU/mL). B) Growth curves in MDCK cells.

FIGS. 8A-8C. A) HA titer of wild type (UW-PR8) and clone #4. B) Viral protein for wild type (UW-PR8) and #4. C) SDS-PAGE analysis of viral proteins of wild type and #4.

FIGS. 9A-9B. A) Comparison of titers of wild type virus (UW-PR8) and high replicative virus with mutations in M1. B) Growth kinetics of wild type virus (UW-PR8) and high replicative virus with mutations in M1.

FIGS. 10A-10M. A) Codon usage table for canines. B) Relative adaptiveness of wild type (UW-PR8) and "rare" codon optimized PB2 viruses. C) Relative adaptiveness of wild type (UW-PR8) and 'all' codon optimized PB2 viruses. D) Growth kinetics of PB2 codon optimized viruses. E) Growth kinetics of viruses with codon optimized PB2, PB1, PA, or NP viral segment or combinations of segments. F) Sequence of PB2, PB1, PA and NP viral segments of UW-PR8 and sequence of canine codon-usage optimized PB2, PB1, PA and NP viral segments of UW-PR8 (SEQ ID NOs: 3, 13, 2, 12, 1, 11, 4).

FIGS. 11A-11C. A) Nucleotide position 4 of each gene of PR8 and Indo/NC/09. B) All 3'C4U mutant. C) Growth kinetics of a recombinant UW-PR8 virus encoding 'C' at position 4 of the PB2, PB1, and PA genes (black), and a mutant encoding 'U' at position 4 of all eight segments (red).

FIG. 12A-12C. Nucleotide and amino acid sequences for H7 and N9 which are exemplary sequences for use with the internal viral segment sequences disclosed herein useful to provide high titer influenza viruses for vaccines (SEQ ID NOs: 20-24 and 29-31).

FIGS. 13A-13B. A) Schematic of chimeric HA and NA genes to increase virus titer. B) Growth kinetics of chimeric viruses.

FIGS. 14A-14B. A) Growth kinetics of viruses with combinations of mutations. B) PFU and HA titers of viruses with combinations of mutations.

FIG. 16. HA titers of 216 clones isolated from Vero cells.

FIG. 17. Recombinant viruses generated with different PR8 backbone mutations.

FIGS. 19A-19D. Exemplary high yield substitutions (relative to PR8 (UW)).

FIG. 23. Exemplary SARS-CoV-2 spike (S) protein sequences (SEQ ID Nos. 25-28 and 50-52). The S1 portion of S is generally from residues 1 to 681 and the receptor binding domain in S1 is within residues 330 to 521 (see, e.g., Wrapp et al., *Science,* 67:1260 (2020), the disclosure of which is incorporated by reference herein).

DETAILED DESCRIPTION

Definitions

Figure 2:
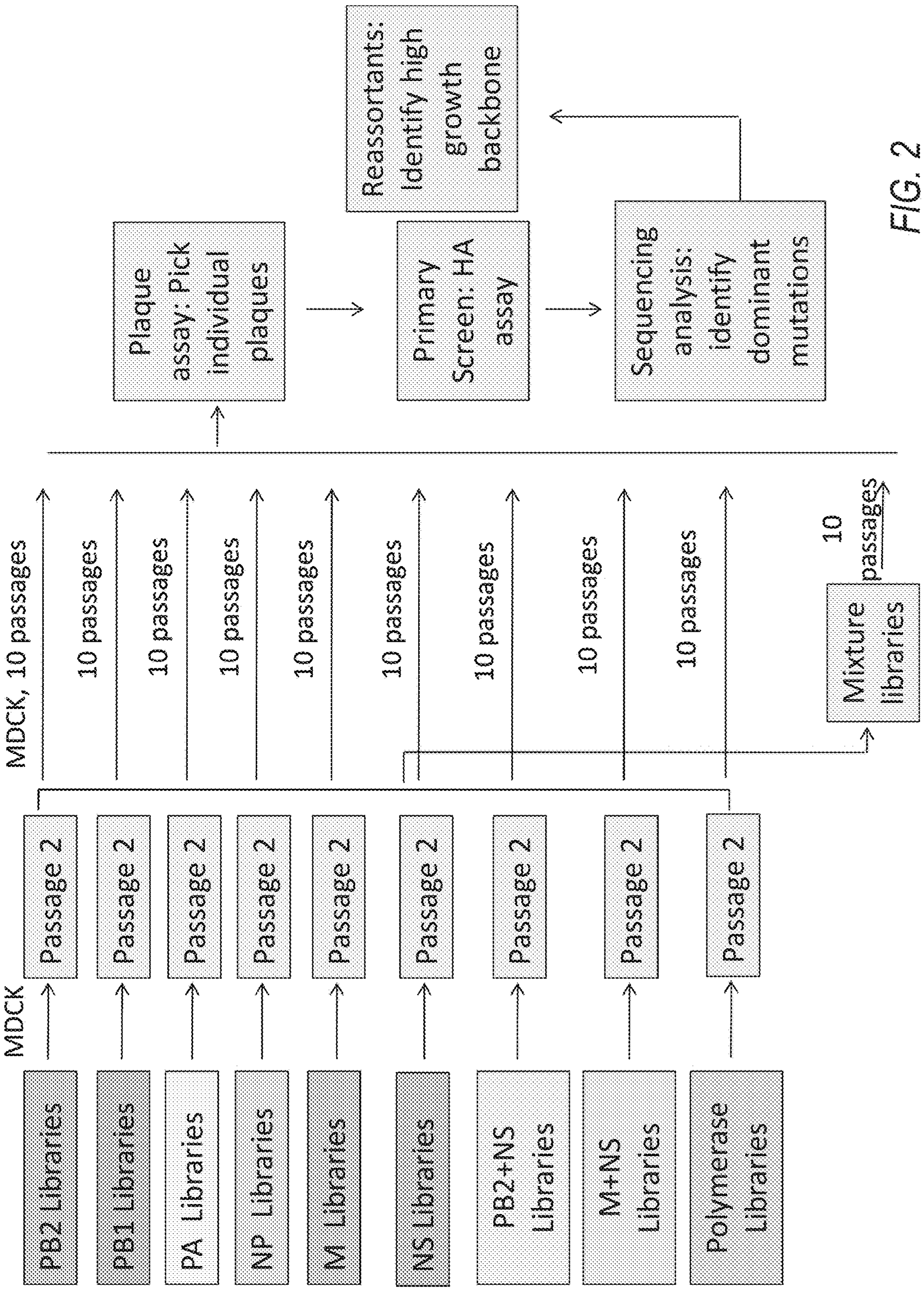
FIG. 2: Overview of library passages and the identification of high-yield candidates.

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater. e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, a "heterologous" influenza virus gene or viral segment is from an influenza virus source that is different than a majority of the other influenza viral genes or viral segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or"recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information (http://www.ncbi.nlm.nih.gov/). The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5, N=−4, and a comparison of both strands. For amino acid sequences, the BLASTP program may use as defaults a wordlength (W) of 3, an expectation (E) of 10, and the BLOSUM62 scoring matrix. See http://www.ncbi.nlm.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Influenza Virus Structure and Propagation

Influenza A viruses possess a genome of eight single-stranded negative-sense viral RNAs (vRNAs) that encode at least ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cRNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein with ion channel activity but has BM2 and has a viral segment with both NA and NB sequences. Influenza C virus and Influenza D virus have only seven viral segments.

Cell Lines that can be Used in the Present Invention

Any cell, e.g., any avian or mammalian cell, such as a human, e.g., 293T or PER.C6@ cells, or canine, e.g., MDCK, e.g., humanized MDCK cells (see U.S. application Ser. No. 16/785,449, filed on Feb. 7, 2020, which is incorporated herein by reference) or M2 expressing cell line (see Itwasuki et al., *J. Virol.,* 80:5233 (2006), the disclosure of which is incorporated by reference herein), bovine, equine, feline, swine, ovine, rodent, for instance mink, e.g., MvLu1 cells, or hamster, e.g., CHO cells, or non-human primate, e.g., Vero cells, including mutant cells, which supports efficient replication of influenza virus can be employed to isolate and/or propagate influenza viruses. Isolated viruses can be used to prepare a reassortant virus. In one embodiment, host cells for vaccine production are continuous mammalian or avian cell lines or cell strains. A complete characterization of the cells to be used, may be conducted so that appropriate tests for purity of the final product can be included. Data that can be used for the characterization of a cell includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. In one embodiment, the passage level, or population doubling, of the host cell used is as low as possible.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The virus may be purified by a process that has been shown to give consistent results, before vaccine production (see, e.g., World Health Organization, 1982).

Virus produced by the host cell may be highly purified prior to vaccine or gene therapy formulation. Generally, the purification procedures result in extensive removal of cellular DNA and other cellular components, and adventitious agents. Procedures that extensively degrade or denature DNA may also be used.

Influenza Vaccines

A vaccine of the invention includes an isolated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with a virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with a virus of the invention in a multivalent vaccine.

Inactivated Vaccines. Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines. Live, attenuated influenza virus vaccines, can be used for preventing or treating influenza virus infection. In one embodiment, attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes may be derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated, single cycle (live) or inactivated, formulated and administered, according to known methods, as a vaccine to induce an immune response in an animal, e.g., a mammal. Methods are well-known in the art for determining whether such attenuated, live single cycle or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and nucleic acid screening (such as probe hybridization or PCR) to confirm that donor genes encoding the antigenic determinants (e.g., HA or NA genes) are not present in attenuated viruses.

Pharmaceutical Compositions

Pharmaceutical compositions of the present invention, suitable for inoculation, e.g., nasal, parenteral or oral administration, comprise one or more influenza virus isolates, e.g., one or more attenuated, live single cycle or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 μg, e.g., 30 to 100 μg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscamet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound (s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition of the present invention may confer resistance to one or more pathogens, e.g., one or more influenza virus strains, by either passive immunization or active immunization. In active immunization, an attenuated or single cycle live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is single cycle, attenuated or inactivated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$~$10^{18}$, e.g., $10^3$-$10^{12}$, plaque forming units (PFU)/kg, or any range or value therein. The dose of inactivated vaccine may range from about 0.1 to 1000, e.g., 30 to 100 μg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 30 to 100 μg or any range or value therein, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 μg or any range or value therein, or the amount recommended by the U.S. Public Health Service (PHS), which is usually 15 μg per component for older children (greater than or equal to 3 years of age), and 7.5 μg per component for children less than 3 years of age. The quantity of NA can also be standardized, however, this glycoprotein can be labile during the processor purification and storage (Kendal et al., 1980; Kerr et al., 1975). Each 0.5-ml dose of vaccine may contains approximately 1-50 billion virus particles, and preferably 10 billion particles.

In one embodiment, the vaccine generally contains about 0.1 to 200 μg, e.g., 30 to 100 μg, 0.1 to 2 μg, 0.5 to 5 μg, 1 to 10 μg, 10 μg to 20 μg, 15 μg to 30 μg, or 10 to 30 μg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

In one embodiment, the dosage of a live, attenuated or killed virus vaccine for an animal such as a mammalian adult organism may be from about $10^{20}$-$10^{20}$, e.g., $10^3$-$10^{12}$, $10^2$-$10^{10}$, $10^5$-$10^{10}$, $10^5$-$10^{15}$, $10^2$-$10^{10}$, or $10^{15}$-$10^{20}$ plaque forming units (PFU)/kg, or any range or value therein. The dose of one viral isolate vaccine, e.g., in an inactivated vaccine, may range from about 0.1 to 1000, e.g., 0.1 to 10 μg, 1 to 20 μg, 30 to 100 μg, 10 to 50 μg, 50 to 200 μg, or 150 to 300 μg, of HA protein. However, the dosage should be a safe and effective amount as determined by conventional methods, using existing vaccines as a starting point.

In one embodiment, the dosage of immunoreactive HA in each dose of replicated virus vaccine may be standardized to contain a suitable amount, e.g., 0.1 μg to 1 μg, 0.5 μg to 5 μg, 1 μg to 10 μg, 10 μg to 20 μg, 15 μg to 30 μg, or 30 μg to 100 μg or any range or value therein, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 μg or any range or value therein, or the amount recommended by the U.S. Public Health Service (PHS), which is usually 15 μg, per component for older children >3 years of age, and 7.5 μg per component for children <3 years of age. The quantity of NA can also be standardized, however, this glycoprotein can be labile during the processor purification and storage (Kendal et al., 1980: Kerr et al., 1975). Each 0.5-ml dose of vaccine may contain approximately 0.1 to 0.5 billion viral particles, 0.5 to 2 billion viral particles, 1 to 50 billion virus particles, 1 to 10 billion viral particles, 20 to 40 billion viral particles, 1 to 5 billion viral particles, or 40 to 80 billion viral particles.

Exemplary Embodiments for High Growth PR8 or Cambridge Variants

In one embodiment, the invention provides an isolated recombinant influenza virus having PA, PB1, PB2, NP, NS, and M viral segments from a first influenza vaccine virus isolate, a heterologous influenza virus NA viral segment, and a heterologous HA viral segment, wherein two or more of the PA, PB1, PB2, NP, NS, and M viral segments have selected amino acid residues at positions 30, 31, 105, 142, 149, 225, 356, 357, 401, and/or 550 in PA; positions 40, 54, 59, 62, 63, 75, 76, 78, 79, 80, 112, 180, 247, 327, 507, 624, 644, 667, 694, 695, 697, 699, 700, 701, 702, 705, 713, and/or 714 in PB1; positions 57, 58, 59, 61, 66, 202, 323, 368, 391, 504, 591, 677, 678, and/or 679, in PB2; positions 74, 112, 116, 224, 293, 371, 377, 417, 422 or 442 in NP; positions 90, 97 and/or 100 in M1; or positions 30, 49, 55, 118, 140, 161 and/or 223 in NS1. In one embodiment, the isolated virus has 142N, 225C, 358R, or 550L in PA; has one or more of 112G, 247H, 507V, or 644A in PB1; has one or more of 202L, 323L or 504V in PB2; has one or more of 74K, 112L, 116L, 417D, or 442A in NP; 97A and/or 100H in M1; and/or 55E and/or 140Q in NS1, or combinations thereof, e.g., has at least one of 202L and/or 323L in PB2, 247H in PB1 or 74K in NP and optionally at least one of 142N in PA1, 55K in NS1 or 97A and/or 100H in M1 or has at least one of 202L and/or 323L in PB2, 247H in PB1 or 74K in NP and at least one of 142N in PA1, 55K in NS1 or 97A and/or 100H in M1. In one embodiment, the virus has at least one of 202L and/or 323L in PB2, 247H in PB1 or 74K in NP and optionally at least one of 142N in PA1, 55K in NS1 or 97A and/or 100H in M1. In one embodiment, the virus has at least one of 202L and/or 323L in PB2, 247H in PB1 or 74K in NP and at least one of 142N in PA1, 55K in NS1 or 97A and/or 100H in M1. In one embodiment, the isolated virus has 202L and/or 323L in PB2, and optionally has 247H in PB1 and optionally 74K in NP. In one embodiment, the isolated virus has 247H in PB1 and optionally 74K in NP. In one embodiment, the isolated virus has 401, 40L, 112G, 180W, 247H, 507V, or 644A in PB1 and optionally has 202L and/or 323L in PB2, and optionally has 74K, 112L, 116L, 377N, 417D, or 422L in NP, and optionally has 30P, 118K, 161T or 140Q in NS1, and optionally has 142N, 225C, 356R, 401K, or 550L in PA. In one embodiment, the isolated virus has 401, 40L, 112G, 180W, 247H, 507V, or 644A in PB1. In one embodiment, the isolated virus has 202L and/or 323L in PB2. In one embodiment, the isolated virus has 74K, 112L, 116L, 377N, 417D, or 422L in NP. In one embodiment, the isolated virus has 30P, 118K, 161T or 140Q in NS1. In one embodiment, the isolated virus has 142N, 225C, 356R, 401K, or 550L in PA. In one embodiment, the selected amino acid residues at specified positions in the PA is/are at position(s) 97, 105, 142, 149, 225, 356, 357, 401, 404, and/or 421. In one embodiment, the selected amino acid residues at specified positions in the PB1 is/are at position(s) 12, 40, 54, 59, 62, 63, 66, 75, 76, 78, 79, 80, 180, 247, 507, 624, 644, 694, 695, 697, 699, 700, 701, 705, 713, 714, and/or 762. In one embodiment, the selected amino acid residues at specified positions in the PB2 is/are at position(s) 57, 58, 59, 61, 68, 202, 243, 323, 504, 677, 678, and/or 679. In one embodiment, the selected amino acid residues at specified positions in the NP is/are at position(s) 74, 112, 116, 224, 293, 417, and/or 442. In one embodiment, the selected amino acid residues at specified positions in the M1 is/are at position(s) 90, 97, and/or 100. In one embodiment, the selected amino acid residues at specified positions in the NS1 is/are at position(s) 49, 30, 55, 161, and/or 223. In one embodiment, the selected amino acid residues at specified positions in the PA is/are at position(s) 97, 105, 142, 149, 225, 356, 357, 401, 404, and/or 421; and optionally the selected amino acid residues at specified positions in the PB1 is/are at position(s) 12, 40, 54, 59, 62, 63, 66, 75, 76, 78, 79, 80, 180, 247, 507, 624, 644, 694, 695, 697, 699, 700, 701, 705, 713, 714, and/or 762, in any combination with the selected residues for PA; and optionally the selected amino acid residues at specified positions in the PB2 is/are at position(s) 57, 58, 59, 61, 66, 202, 243, 323, 504, 677, 678, and/or 679 in any combination with the selected residues for PA and/or PB1; and optionally the selected amino acid residues at specified positions in the NP is/are at position(s) 74, 112, 116, 224, 293, 417, and/or 442 any combination with the selected residues for PA, PB1 and/or PB2; and optionally the selected amino acid residues at specified positions in the M1 is/are at position(s) 90, 97, and/or 100 any combination with the selected residues for PA, PB1, PB2, and/or NP; and optionally the selected amino acid residues at specified positions in the NS1 is/are at position(s) 49, 30, 55, 161, and/or 223, or in any combination with the selected residues for PA, PB1, PB2, NP, and/or M1.

For any of the exemplary viruses disclosed above, in one embodiment, the PA, PB1, PB2, NP, NS, and M viral segments comprise sequences for at least one of the following: a PB1 having the amino acid sequence encoded by SEQ ID NO:2 or PB1 with at least 95% amino acid sequence identity to the PB1 encoded by SEQ ID NO:2; a PB2 having the amino acid sequence encoded by SEQ ID NO:3 or PB2 with at least 95% amino acid sequence identity to the PB2 encoded by SEQ ID NO:3; a PA having the amino acid sequence encoded by SEQ ID NO:1 or PA with at least 95% amino acid sequence identity to the PA encoded by SEQ ID NO:1; a NP having the amino acid sequence encoded by SEQ ID NO:4 or NP with at least 95% amino acid sequence identity to the NP encoded by SEQ ID NO:4; a M having the amino acid sequence encoded by SEQ ID NO:5 or M with at least 95% amino acid sequence identity to the M encoded by SEQ ID NO:5; or a NS having the amino acid sequence encoded by SEQ ID NO:6 or NS with at least 95% amino acid sequence identity to the NS encoded by SEQ ID NO:6, or the PA, PB1, PB2, NP, NS, and M viral segments comprise sequences for at least one of the following: a PB1 having the amino acid sequence encoded by SEQ ID NO:10 or PB1 with at least 95% amino acid sequence identity to the PB1 encoded by SEQ ID NO:10; a PB2 having the amino acid sequence encoded by SEQ ID NO:11 or PB2 with at least 95% amino acid sequence identity to the PB2 encoded by SEQ ID NO:11; a PA having the amino acid sequence encoded by SEQ ID NO:12 or PA with at least 95% amino acid sequence identity to the PA encoded by SEQ ID NO:12; a NP having the amino acid sequence encoded by SEQ ID NO:13 or NP with at least 95% amino acid sequence identity to the NP encoded by SEQ ID NO:13; a M having the amino acid sequence encoded by SEQ ID NO:14 or M with at least 95% amino acid sequence identity to the M encoded by SEQ ID NO:14; or a NS having the amino acid sequence encoded by SEQ ID NO:15 or NS with at least 95% amino acid sequence identity to the NS encoded by SEQ ID NO:15.

For any of the exemplary viruses disclosed above, in one embodiment, at least one of the PA, PB1, PB2, NP, NS, and M viral segments has a C to U promoter mutation.

Any of the isolated viruses disclosed herein may be employed in a vaccine.

In one embodiment, the invention provides a plurality of influenza virus vectors for preparing a reassortant. In one embodiment, the plurality includes a vector for vRNA or cRNA production comprising a promoter operably linked to an influenza virus PA DNA linked to a transcription termination sequence, a vector for vRNA or cRNA production comprising a promoter operably linked to an influenza virus PB1 DNA linked to a transcription termination sequence, a vector for vRNA or cRNA production comprising a promoter operably linked to an influenza virus PB2 DNA linked to a transcription termination sequence, a vector for vRNA or cRNA production comprising a promoter operably linked to an influenza virus HA DNA linked to a transcription termination sequence, a vector for vRNA or cRNA production comprising a promoter operably linked to an influenza virus NP DNA linked to a transcription termination sequence, a vector for vRNA or cRNA production comprising a promoter operably linked to an influenza virus NA DNA linked to a transcription termination sequence, a vector for vRNA or cRNA production comprising a promoter operably linked to an influenza virus M DNA linked to a transcription termination sequence, and a vector for vRNA or cRNA production comprising a promoter operably linked to an influenza virus NS cDNA linked to a transcription termination sequence, wherein the PB1, PB2, PA, NP, NS, and M DNAs in the vectors for vRNA or cRNA production are from one or more influenza vaccine virus isolates, wherein the NA DNA in the vector for vRNA production of NA has sequences for a heterologous NA, and wherein the HA DNA in the vector for vRNA or cRNA production of HA has sequences for a heterologous HA, 30, 31, 105, 142, 149, 225, 356, 357, 401, and/or 550 in PA; 40, 54, 59, 62, 63, 75, 76, 78, 79, 80, 112, 180, 247, 327, 507, 624, 644, 667, 694, 695, 697, 699, 700, 701, 702, 705, 713, or 714 and/or 247 in PB1; 57, 58, 59, 61, 66, 202, 323, 368, 391, 504, 591, 677, 678, or 679, 202 and/or 323 in PB2; 74, 112, 116, 224, 293, 371, 377, 417, 422 and/or 442 in NP; 90, 97 and/or 100 in M1; or 30, 49, 55, 118, 140, 161 and/or 223 in NS; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2. In one embodiment, the PB1, PB2, PA, NP, NS, and M DNAs in the vectors for vRNA or cRNA production have a sequence corresponding to one that encodes a polypeptide having at least 95% amino acid sequence identity to a corresponding polypeptide encoded by SEQ ID NOs:1-6 or 10-15. In one embodiment, the promoter for vRNA or cRNA vectors is a RNA polymerase I promoter, a RNA polymerase II promoter, a RNA polymerase III promoter, a T3 promoter or a T7 promoter. In one embodiment, the NA is N9. In one embodiment, the HA is H7. In one embodiment, the PA, PB1, PB2, NP, NS, and/or M viral segments has/have a promoter C to a mutation.

In one embodiment, the invention provides a method to prepare influenza virus. The method includes contacting a cell with: a vector for vRNA or cRNA production comprising a promoter operably linked to an influenza virus PA DNA linked to a transcription termination sequence, a vector for vRNA or cRNA production comprising a promoter operably linked to an influenza virus PB1 DNA linked to a transcription termination sequence, a vector for vRNA or cRNA production comprising a promoter operably linked to an influenza virus PB2 DNA linked to a transcription termination sequence, a vector for vRNA or cRNA production comprising a promoter operably linked to an influenza virus HA DNA linked to a transcription termination sequence, a vector for vRNA or cRNA production comprising a promoter operably linked to an influenza virus NP DNA linked to a transcription termination sequence, a vector for vRNA or cRNA production comprising a promoter operably linked to an influenza virus NA DNA linked to a transcription termination sequence, a vector for vRNA or cRNA production comprising a promoter operably linked to an influenza virus M DNA linked to a transcription termination sequence, and a vector for vRNA or cRNA production comprising a promoter operably linked to an influenza virus NS DNA linked to a transcription termination sequence, wherein the PB1, PB2, PA, NP, NS, and M DNAs in the vectors for vRNA or cRNA production are from one or more influenza vaccine virus isolates, wherein the NA DNA in the vector for vRNA or cRNA production of NA has sequences for a heterologous NA, and wherein the HA DNA in the vector for vRNA or cRNA production of HA has sequences for a heterologous HA, 30, 31, 105, 142, 149, 225, 356, 357, 401, and/or 550 in PA; 40, 54, 59, 62, 63, 75, 76, 78, 79, 80, 112, 180, 247, 327, 507, 624, 644, 667, 694, 695, 697, 699, 700, 701, 702, 705, 713, and/or 714 and/or 247 in PB1; 57, 58, 59, 61, 66, 202, 323, 368, 391, 504, 591, 677, 678, and/or 679, 202 and/or 323 in PB2; 74, 112, 116, 224, 293, 371, 377, 417, 422 and/or 442 in NP; 90, 97 and/or 100 in M1; or 30, 49, 55, 118, 140, 161 or 223 in NS; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2; in an amount effective to yield infectious influenza virus. In one embodiment, the cell is an avian cell or a mammalian cell, e.g., a Vero cell, a human cell or a MDCK cell. In one embodiment, the PB1, PB2. PA, NP. NS, and M DNAs in the vectors for vRNA productions have a sequence that corresponds to one that encodes a polypeptide having at least 95% amino acid sequence identity to a corresponding polypeptide encoded by SEQ ID NOs:1-6 or 10-15. In one embodiment, the method includes isolating the virus. In one embodiment, at least one of PA, PB1, or PB2 viral segments has a C to U promoter mutation.

Further provided is a vector for vRNA, cRNA or mRNA expression of influenza virus PA having at least 95% amino acid sequence identity to a polypeptide encoded by SEQ ID NO:1 and having a threonine at position 30, a lysine at position 31, cysteine at position 105 or a lysine at position 401; a vector for vRNA, cRNA or mRNA expression of influenza virus PB1 having at least 95% amino acid sequence identity to a polypeptide encoded by SEQ ID NO:2 and having a leucine at position 40, an alanine or isoleucine at position 54, glycine at position 112, histidine at position 247, valine at position 507, alanine at position 644, or cysteine at position 713; a vector for vRNA, cRNA or mRNA expression of PB2 having at least 95% amino acid sequence identity to a polypeptide encoded by SEQ ID NO:3 and a leucine at position 202 and/or 323; a vector for vRNA, cRNA or mRNA expression of influenza virus NP having at least 95% amino acid sequence identity to a polypeptide encoded by SEQ ID NO:4 and having a lysine at position 74, leucine at position 116, isoleucine at position 224, lysine at position 293, asparagine at position 377, or aspartic acid at position 417; a vector for vRNA, cRNA or mRNA expression of influenza virus NS1 having at least 95% amino acid sequence identity to a NS1 polypeptide encoded by SEQ ID NO:6 and having a proline at position 30, alanine at position 49, lysine at position 118, glutamine at position 140, threonine at position 161, or glutamic acid at position 223; and a vector for vRNA, cRNA or mRNA expression of influenza virus M1 having at least 95% amino acid sequence identity to a M1 polypeptide encoded by SEQ ID NO:5 and having a serine at position 90.

Exemplary M Viral Segments

Wild-type influenza A virus M2 protein consists of three structural domains: a 24-amino-acid extracellular domain, a 19-amino-acid transmembrane domain, and a 54-amino-acid cytoplasmic tail domain. The M2 transmembrane domain has ion channel activity, which functions at an early stage of the viral life cycle between the steps of virus penetration and uncoating. The M2 cytoplasmic tail domain may also have an important role in viral assembly and morphogenesis. M1 protein and M2 protein share N-terminal sequences. The M2 protein is encoded by a spliced transcript and RNAs encoding the M1 protein and the M2 protein share 3' sequences, although the coding sequences for M1 and M2 in those 3' sequences are in different reading frames. The C-terminal residues of M1 and C-terminal portion of the extracellular domain of M2 are encoded by the overlapping 3' coding sequences.

A "functional" M1 protein provides for export of viral nucleic acid from the host cell nucleus, a viral coat, and/or virus assembly and budding. Thus, the M1 protein in the recombinant influenza viruses of the invention has substantially the same function (e.g., at least 10%, 20%, 50% or greater) as a wild-type M1 protein. Thus, any alteration in the M1 coding region in a mutant M viral segment in a recombinant influenza virus does not substantially alter the replication of that virus, e.g., in vitro, for instance, viral titers are not reduced more than about 1 to 2 logs in a host cell that supplies M2 in trans.

In one embodiment, an isolated recombinant influenza virus comprises a mutant M2 protein having a deletion of one or more residues of the cytoplasmic tail of M2, which virus replicates in vitro, e.g., producing titers that are substantially the same or at most 10, 100 or 1,000 fold less than a corresponding wild-type influenza virus, but wherein the replication of the recombinant virus in vivo is limited to a single cycle (e.g., no progeny viruses are produced). In one embodiment, the deletion includes 2 or more residues and up to 21 residues of the cytoplasmic tail of M2. In one embodiment, the M viral segment for the mutant M2 has one to two stop codons near the splice donor or splice acceptor site for the M2 transcript. In one embodiment, the coding region for the transmembrane and/or cytoplasmic domain of M2 is also deleted.

In one embodiment, the deletion of M2 includes 21 or more residues and up to 54 residues, i.e., the entire cytoplasmic tail, of the cytoplasmic tail of M2. In one embodiment, the mutant M2 protein may also comprise at least one amino acid substitution relative to a corresponding wild-type M2 protein. The substitution(s) in the M2 protein may be in the extracellular domain, the transmembrane (TM) domain, or the cytoplasmic domain, or any combination thereof. For example, substitutions in the TM domain may be at residues 25 to 43 of M2, e.g., positions 27, 30, 31, 34, 38, and/or 41 of the TM domain of M2. In another embodiment, the mutant M2 protein may also comprise a deletion in at least a portion of the extracellular domain and/or the TM domain, e.g., a deletion of residues 29 to 31, relative to a corresponding wild-type M2 protein. In yet another embodiment, the mutant M2 protein further comprises a heterologous protein, e.g., the cytoplasmic domain of a heterologous protein (a non-influenza viral protein), which may have a detectable phenotype, fused to the cytoplasmic tail or extracellular domain of M2, forming a chimeric protein. In one embodiment, a cytoplasmic domain of a heterologous protein is fused to the remaining residues of the cytoplasmic tail of the deleted M2 protein. In one embodiment, the presence of one or more substitutions, deletions, or insertions of heterologous sequences, or any combination thereof, does not substantially alter the properties of the recombinant influenza virus, e.g., the presence of one or more substitutions, deletions, or insertions of heterologous sequences does not result in virus titers in vitro that are more than about 1.5 to 2 logs lower, but allows for a single cycle of replication in vivo (e.g., no progeny viruses are produced) for a recombinant influenza virus comprising a mutant M2 protein having a deletion of one or more residues of the cytoplasmic tail of M2.

In one embodiment, the deletion in the cytoplasmic domain of M2 includes 2, 3, 4, 5 or more, e.g., 11, 12, 13, 14, or 15 residues, but less than 22 residues, of the C-terminus of the cytoplasmic tail of M2. In one embodiment, the deletion is 2 up to 10 residues, including any integer in between. In one embodiment, the deletion is from 1 up to less than 8 residues, including any integer in between. In one embodiment, the deletion is from 5 up to 21 residues, including any integer in between. In one embodiment, the deletion is from 5 up to less than 28 residues, including any integer in between. In one embodiment, the deletion is from 9 up to 15 residues, including any integer in between. In one embodiment, the deletion is from 9 up to 23 residues, including any integer in between.

In one embodiment, the deletion in the cytoplasmic domain of M2 includes 22, 23, 24, 25 or more. e.g., 41, 42, 43, 44, or 45 residues, but less than 54 residues, of the C-terminus of the cytoplasmic tail of M2.

In one embodiment, the deletion is from 22 up to 35 residues, including any integer in between. In one embodiment, the deletion is from 29 up to 35 residues, including any integer in between. In one embodiment, the deletion is from 35 up to 45 residues, including any integer in between.

In one embodiment, the deletion is from 9 to less than 28 residues, including any integer in between.

In one embodiment, an isolated recombinant influenza virus is provided comprising a mutant M viral segment that is mutated so that upon viral replication, the mutant M gene expresses a functional M1 protein and a mutant M2 protein with a deletion of the cytoplasmic tail and a deletion of at least a portion of the transmembrane domain, e.g., internal or C-terminal deletions, and/or includes one or more substitutions in the transmembrane domain. In one embodiment, the mutant M2 protein has a deletion that includes the entire cytoplasmic tail and transmembrane domain of M2, and has one or more residues of the extracellular domain, e.g., has the first 9 to 15 residues of the extracellular domain. The replication of the recombinant virus is, in one embodiment, a single cycle in vivo relative to a corresponding virus without a mutant M viral segment. The recombinant influenza virus replicates in vitro in the presence of M2 supplied in trans, e.g., producing titers that are substantially the same or at most 10, 100 or 1,000 fold less than a corresponding wild-type influenza virus.

In one embodiment, a live single cycle or attenuated influenza virus elicits both systemic and mucosal immunity at the primary portal of infection. In one embodiment, the live, single cycle or attenuated influenza virus has reduced replication in lung compared to wild-type influenza virus, e.g., the live, single cycle or attenuated influenza virus has titers in lung that are at least one to two logs less, and in one embodiment, replication in nasal turbinates is not detectable. The live, single cycle or attenuated virus may be employed in a vaccine or immunogenic composition, and so is useful to immunize a vertebrate, e.g., an avian or a mammal, or induce an immune response in a vertebrate, respectively.

In one embodiment, the mutations in the M2 gene result in a mutant M2 protein with a deletion of the entire cytoplasmic tail and deletion or substitution of one or more residues in the transmembrane (TM) domain of M2 and may also comprise at least one amino acid substitution in the extracellular domain, or a combination thereof, relative to a corresponding wild-type M2 protein encoded by a M viral segment. For example, substitutions in the TM domain may include those at residues 25 to 43 of M2, e.g., positions 27, 30, 31, 34, 38, and/or 41 of the TM domain of M2. Substitutions and/or deletions in the TM domain may result in a truncated M2 protein that is not embedded in the viral envelope. For example, a deletion of 10 residues at the C-terminus of the transmembrane domain may result in a truncated M2 protein that is not embedded in the viral envelope. In another embodiment, the mutant M2 protein may also comprise a deletion in at least a portion of the extracellular domain in addition to deletion of the cytoplasmic domain and a deletion in the TM domain. In one embodiment, the mutant M2 protein has a deletion of the entire cytoplasmic tail and the TM domain and at least one residue of the extracellular domain, e.g., 1 to 15 residues, or any integer in between, of the C-terminal portion of the extracellular domain. In yet another embodiment, the mutant M2 protein having at least a portion of the extracellular domain further comprises a heterologous protein, e.g., the cytoplasmic and/or TM domain of a heterologous protein (a non-influenza viral protein), which may have a detectable phenotype, that is fused to the C-terminus of at least the extracellular domain of M2, forming a chimeric protein. In one embodiment, the presence of one or more substitutions, deletions, or insertions of heterologous sequences, or any combination thereof, in the M2 gene does not substantially alter the properties of the recombinant influenza virus, e.g., the presence of one or more substitutions, deletions, or insertions of heterologous sequences does not result in virus titers in vitro that are more than about 1.5 to 2 logs lower, and/or but allows for a single cycle (e.g., no progeny viruses are produced) of replication in vivo for the recombinant influenza virus with a mutant M2 protein gene having a deletion of the cytoplasmic tail and TM domain of M2.

In one embodiment, the deletion in the TM domain of M2 includes 1, 2, 3, 4, 5 or more, e.g., 11, 12, 13, 14, or 15 residues, up to 19 residues. In one embodiment, the deletion is from 2 up to 9 residues, including any integer in between. In one embodiment, the deletion is from 15 up to 19 residues, including any integer in between. In one embodiment, the deletion is from 10 up to 19 residues, including any integer in between. In one embodiment, the deletion is the result of at least one substitution of a codon for an amino acid to a stop codon. In one embodiment, the deletion is the result of deletion of at least one codon for an amino acid. In one embodiment, the TM domain of M2 has one or more substitutions, e.g., includes 1, 2, 3, 4, 5 or more, e.g., 11, 12, 13, 14, or 15 substitutions, up to 19 residues of the TM domain. In one embodiment, the one or more amino acid deletions and/or substitutions in the TM domain in a mutant M2 protein that also lacks the cytoplasmic tail of M2, provides for a mutant M2 protein that lacks M2 activity and/or when expressed in a virus yields a live, single cycle virus.

In one embodiment, a deletion in the extracellular (ectodomain) domain of M2 may include 1, 2, 3, 4 or more, e.g., 5, 10, 15, or 20 residues, up to 24 residues of the extracellular domain. In one embodiment, the deletion in the extracellular domain is from 1 up to 15 residues, including any integer in between. In one embodiment, the deletion is the result of at least one substitution of a codon for an amino acid to a stop codon. In one embodiment, the deletion is the result of deletion of at least codon for an amino acid. In one embodiment, the extracellular domain of M2 may also include one or more substitutions. In one embodiment, the mutations in the M2 gene of a M viral segment that result in deletion(s) or substitution(s) in the extracellular domain of M2 do not substantially alter the function of the protein encoded by the M1 gene.

In one embodiment, fewer than 20%, e.g., 10% or 5%, of the residues in the TM domain or extracellular domain are substituted. In one embodiment, fewer than 60%, e.g., 50%, 40%, 30%, 20%, 10%, or 5% of the residues in the extracellular domain are deleted. In one embodiment, more than 20%, e.g., 30%, 40%, 50%, 80% or more, of the residues in the TM domain are deleted.

Exemplary PR8 Viral Segment Variants

Example A

Methods

Cells and Viruses 293T human embryonic kidney cells are maintained in Dulbecco's modified Eagle's minimal essential medium (DMEM) with 10% fetal calf serum and antibiotics. Madin-Darby canine kidney (MDCK) cells are grown in MEM with 5% newbom calf serum and antibiotics. African green monkey Vero WCB cells, which had been established after biosafety tests for use in human vaccine production (Sugawara et al., 2002), are maintained in serum-free VP-SFM medium (GIBCO-BRL) with antibiotics. Cells are maintained at 37° C. in 5% $CO_2$. A WHO-recommended vaccine seed virus is NIBRG-14.

Construction of Plasmids and Reverse Genetics

To generate reassortants of influenza A viruses, a plasmid-based reverse genetics (Neumann et al., 1999) is used. The full-length cDNAs were cloned into a plasmid under control of the human polymerase I promoter and the mouse RNA polymerase I terminator (PolI plasmids).

A previously produced series of PolI constructs, derived from A/WSN/33 (H5N1; WSN) or PR8 strains is used, for reverse genetics (Horimoto et al., 2006; Neumann et al., 1999). The World Health Organization (WHO) recommends A/Puerto Rico/8/34 (H1N1; PR8) as a donor virus, because of its safety in humans (Wood & Robertson, 2004; Webby & Webster, 2003).

Plasmids expressing WSN or PR8 NP, PA, PB1, or PB2 under control of the chicken actin, e.g., beta-actin, promoter are used for all reverse genetics experiments (Horimoto et al., 2006; Neumann et al., 1999). Briefly, PolI plasmids and protein expression plasmids are mixed with a transfection reagent, Trans-IT 293T (Panvera), incubated at room temperature for 15 minutes, and then added to 293T cells. Transfected cells are incubated in Opti-MEM I (GIBCO-BRL) for 48 hours. For reverse genetics in Vero WCB cells, an electroporator (Amaxa) is used to transfect the plasmid mixtures according to the manufacturer's instructions. Sixteen hours after transfection, freshly prepared Vero WCB cells were added onto the transfected cells and TPCK-trypsin (1 μg/mL) is added to the culture 6 hours later. Transfected cells are incubated in serum-free VP-SFM for a total of 4 days. Supernatants containing infectious viruses are harvested, and may be biologically cloned by limiting dilution.

A recombinant virus having the HA and NA genes from A/Hong Kong/213/2003 (H5N1) and the remainder of the type A influenza virus genes from PR8(UW) was prepared. The titer of the recombinant virus was $10^{10.87}$ $EID_{50}$/mL, and the HA titer was 1:1600

TABLE 1

| Virus possessing PR8 genes together with the following HA and NA | HA titer (HAU/mL) in each dilition | | | | | | |
|---|---|---|---|---|---|---|---|
| genes | 10-2 | 10-3 | 10-4 | 10-5 | 10-6 | 10-7 | 10-8 |
| WSN-HA NA | 160 | 40 | 40 | 320 | 40 | 640 | <1 |
| HK-HAavir NA | 400 | 800 | 400 | 400 | 400 | 800 | <1 |

The sequences of PR8 (UVV) genes are as follows: Exemplary viral sequences for a master vaccine strain (PR8UW)

HA (SEQ ID NO: 32)

AGCAAAAGCAGGGGAAAATAAAAACAACCAAAATGAAGGCAAACCTACT

GGTCCTGTTATGTGCACTTGCAGCTGCAGATGCAGACACAATATGTATA

GGCTACCATGCGAACAATTCAACCGACACTGTTGACACAGTACTCGAGA

AGAATGTGACAGTGACACACTCTGTTAACCTGCTCGAAGACAGCCACAA

CGGAAAACTATGTAGATTAAAAGGAATAGCCCCACTACAATTGGGGAAA

TGTAACATCGCCGGATGGCTCTTGGGAAACCCAGAATGCGACCCACTGC

-continued

TTCCAGTGAGATCATGGTCCTACATTGTAGAAACACCAAACTCTGAGAA

TGGAATATGTTATCCAGGAGATTTCATCGACTATGAGGAGCTGAGGGAG

CAATTGAGCTCAGTGTCATCATTCGAAAGATTCGAAATATTTCCCAAAG

AAAGCTCATGGCCCAACCACAACACAAACGGAGTAACGGCAGCATGCTC

CCATGAGGGGAAAAGCAGTTTTTACAGAAATTTGCTATGGCTGACGGAG

AAGGAGGGCTCATACCCAAAGCTGAAAAATTCTTATGTGAACAAAAAAG

GGAAAGAAGTCCTTGTACTGTGGGGTATTCATCACCCGCCTAACAGTAA

GGAACAACAGAATCTCTATCAGAATGAAAATGCTTATGTCTCTGTAGTG

ACTTCAAATTATAACAGGAGATTTACCCCGGAAATAGCAGAAAGACCCA

AAGTAAGAGATCAAGCTGGGAGGATGAACTATTACTGGACCTTGCTAAA

ACCCGGAGACACAATAATATTTGAGGCAAATGGAAATCTAATAGCACCA

ATGTATGCTTTCGCACTGAGTAGAGGCTTTGGGTCCGGCATCATCACCT

CAAACGCATCAATGCATGAGTGTAACACGAAGTGTCAAACACCCCTGGG

AGCTATAAACAGCAGTCTCCCTTACCAGAATATACACCCAGTCACAATA

GGAGAGTGCCCAAAATACGTCAGGAGTGCCAAATTGAGGATGGTTACAG

GACTAAGGAACATTCCGTCCATTCAATCCAGAGGTCTATTTGGAGCCAT

TGCCGGTTTTATTGAAGGGGGATGGACTGGAATGATAGATGGATGGTAT

GGTTATCATCATCAGAATGAACAGGGATCAGGCTATGCAGCGGATCAAA

AAAGCACACAAAATGCCATTAACGGGATTACAAACAAGGTGAACACTGT

TATCGAGAAAATGAACATTCAATTCACAGCTGTGGGTAAAGAATTCAAC

AAATTAGAAAAAAGGATGGAAAATTTAAATAAAAAAGTTGATGATGGAT

TTCTGGACATTTGGACATATAATGCAGAATTGTTAGTTCTACTGGAAAA

TGAAAGGACTCTGGATTTCCATGACTCAAATGTGAAGAATCTGTATGAG

AAAGTAAAAAGCCAATTAAAGAATAATGCCAAAGAAATCGGAAATGGAT

GTTTTGAGTTCTACCACAAGTGTGACAATGAATGCATGGAAAGTGTAAG

AAATGGGACTTATGATTATCCCAAATATTCAGAAGAGTCAAAGTTGAAC

AGGGAAAAGGTAGATGGAGTGAAATTGGAATCAATGGGGATCTATCAGA

TTCTGGCGATCTACTCAACTGTCGCCAGTTCACTGGTGCTTTTGGTCTC

CCTGGGGGCAATCAGTTTCTGGATGTGTTCTAATGGATCTTTGCAGTGC

AGAATATGCATCTGAGATTAGAATTTCAGAGATATGAGGAAAAACACCC

TTGTTTCTACT

NA (SEQ ID NO: 33)

AGCAAAAGCAGGGGTTTAAAATGAATCCAAATCAGAAAATAATAACCAT

TGGATCAATCTGTCTGGTAGTCGGACTAATTAGCCTAATATTGCAAATA

GGGAATATAATCTCAATATGGATTAGCCATTCAATTCAAACTGGAAGTC

AAAACCATACTGGAATATGCAACCAAAACATCATTACCTATAAAAATAG

CACCTGGGTAAAGGACACAACTTCAGTGATATTAACCGGCAATTCATCT

CTTTGTCCCATCCGTGGGTGGGCTATATACAGCAAAGACAATAGCATAA

GAATTGGTTCCAAAGGAGACGTTTTTGTCATAAGAGAGCCCTTTATTTC

-continued

ATGTTCTCACTTGGAATGCAGGACCTTTTTTCTGACCCAAGGTGCCTTA
CTGAATGACAAGCATTCAAGTGGGACTGTTAAGGACAGAAGCCCTTATA
GGGCCTTAATGAGCTGCCCTGTCGGTGAAGCTCCGTCCCCGTACAATTC
AAGATTTGAATCGGTTGCTTGGTCAGCAAGTGCATGTCATGATGGCATG
GGCTGGCTAACAATCGGAATTTCAGGTCCAGATAATGGAGCAGTGGCTG
TATTAAAATACAACGGCATAATAACTGAAACCATAAAAAGTTGGAGGAA
GAAAATATTGAGGACACAAGAGTCTGAATGTGCCTGTGTAAATGGTTCA
TGTTTTACTATAATGACTGATGGCCCGAGTGATGGGCTGGCCTCGTACA
AAATTTTCAAGATCGAAAAGGGGAAGGTTACTAAATCAATAGAGTTGAA
TGCACCTAATTCTCACTATGAGGAATGTTCCTGTTACCCTGATACCGGC
AAAGTGATGTGTGTGTGCAGAGACAATTGGCATGGTTCGAACCGGCCAT
GGGTGTCTTTCGATCAAAACCTGGATTATCAAATAGGATACATCTGCAG
TGGGGTTTTCGGTGACAACCCGCGTCCCGAAGATGGAACAGGCAGCTGT
GGTCCAGTGTATGTTGATGGAGCAAACGGAGTAAAGGGATTTTCATATA
GGTATGGTAATGGTGTTTGGATAGGAAGGACCAAAAGTCACAGTTCCAG
ACATGGGTTTGAGATGATTTGGGATCCTAATGGATGGACAGAGACTGAT
AGTAAGTTCTCTGTGAGGCAAGATGTTGTGGCAATGACTGATTGGTCAG
GGTATAGCGGAAGTTTCGTTCAACATCCTGAGCTGACAGGGCTAGACTG
TATGAGGCCGTGCTTCTGGGTTGAATTAATCAGGGGACGACCTAAAGAA
AAAACAATCTGGACTAGTGCGAGCAGCATTTCTTTTTGTGGCGTGAATA
GTGATACTGTAGATTGGTCTTGGCCAGACGGTGCTGAGTTGCCATTCAG
CATTGACAAGTAGTCTGTTCAAAAAACTCCTTGTTTCTACT

PA (SEQ ID NO: 34)

AGCGAAAGCA GGTACTGATC CAAAATGGAA GATTTTGTGC
GACAATGCTT CAATCCGATG ATTGTCGAGC TTGCGGAAAA
AACAATGAAA GAGTATGGGG AGGACCTGAA AATCGAAACA
AACAAATTTG CAGCAATATG CACTCACTTG GAAGTATGCT
TCATGTATTC AGATTTTCAC TTCATCAATG AGCAAGGCGA
GTCAATAATC GTAGAACTTG GTGATCCAAA TGCACTTTTG
AAGCACAGAT TTGAAATAAT CGAGGGAAGA GATCGCACAA
TGGCCTGGAC AGTAGTAAAC AGTATTTGCA ACACTACAGG
GGCTGAGAAA CCAAAGTTTC TACCAGATTT GTATGATTAC
AAGGAGAATA GATTCATCGA AATTGGAGTA ACAAGGAGAG
AAGTTCACAT ATACTATCTG GAAAAGGCCA ATAAAATTAA
ATCTGAGAAA ACACACATCC ACATTTTCTC GTTCACTGGG
GAAGAAATGG CCACAAAGGC AGACTACACT CTCGATGAAG
AAAGCAGGGC TAGGATCAAA ACCAGACTAT TCACCATAAG
ACAAGAAATG GCCAGCAGAG GCCTCTGGGA TTCCTTTCGT
CAGTCCGAGA GAGGAGAAGA GACAATTGAA GAAAGGTTTG

-continued

AAATCACAGG AACAATGCGC AAGCTTGCCG ACCAAAGTCT
CCCGCCGAAC TTCTCCAGCC TTGAAAATTT TAGAGCCTAT
GTGGATGGAT TCGAACCGAA CGGCTACATT GAGGGCAAGC
TGTCTCAAAT GTCCAAAGAA GTAAATGCTA GAATTGAACC
TTTTTTGAAA ACAACACCAC GACCACTTAG ACTTCCGAAT
GGGCCTCCCT GTTCTCAGCG GTCCAAATTC CTGCTGATGG
ATGCCTTAAA ATTAAGCATT GAGGACCCAA GTCATGAAGG
AGAGGGAATA CCGCTATATG ATGCAATCAA ATGCATGAGA
ACATTCTTTG GATGGAAGGA ACCCAATGTT GTTAAACCAC
ACGAAAAGGG AATAAATCCA AATTATCTTC TGTCATGGAA
GCAAGTACTG GCAGAACTGC AGGACATTGA GAATGAGGAG
AAAATTCCAA AGACTAAAAA TATGAAGAAA ACAAGTCAGC
TAAAGTGGGC ACTTGGTGAG AACATGGCAC CAGAAAAGGT
AGACTTTGAC GACTGTAAAG ATGTAGGTGA TTTGAAGCAA
TATGATAGTG ATGAACCAGA ATTGAGGTCG CTTGCAAGTT
GGATTCAGAA TGAGTTTAAC AAGGCATGCG AACTGACAGA
TTCAAGCTGG ATAGAGCTCG ATGAGATTGG AGAAGATGTG
GCTCCAATTG AACACATTGC AAGCATGAGA AGGAATTATT
TCACATCAGA GGTGTCTCAC TGCAGAGCCA CAGAATACAT
AATGAAGGGA GTGTACATCA ATACTGCCTT GCTTAATGCA
TCTTGTGCAG CAATGGATGA TTTCCAATTA ATTCCAATGA
TAAGCAAGTG TAGAACTAAG GAGGGAAGGC GAAAGACCAA
CTTGTATGGT TTCATCATAA AAGGAAGATC CCACTTAAGG
AATGACACCG ACGTGGTAAA CTTTGTGAGC ATGGAGTTTT
CTCTCACTGA CCCAAGACTT GAACCACATA AATGGGAGAA
GTACTGTGTT CTTGAGATAG GAGATATGCT TATAAGAAGT
GCCATAGGCC AGGTTTCAAG GCCCATGTTC TTGTATGTGA
GAACAAATGG AACCTCAAAA ATTAAAATGA AATGGGGAAT
GGAGATGAGG CGTTGCCTCC TCCAGTCACT TCAACAAATT
GAGAGTATGA TTGAAGCTGA GTCCTCTGTC AAAGAGAAAG
ACATGACCAA AGAGTTCTTT GAGAACAAAT CAGAAACATG
GCCCATTGGA GAGTCCCCCA AAGGAGTGGA GGAAAGTTCC
ATTGGGAAGG TCTGCAGGAC TTTATTAGCA AAGTCGGTAT
TCAACAGCTT GTATGCATCT CCACAACTAG AAGGATTTTC
AGCTGAATCA AGAAAACTGC TTCTTATCGT TCAGGCTCTT
AGGGACAACC TGGAACCTGG GACCTTTGAT CTTGGGGGGC
TATATGAAGC AATTGAGGAG TGCCTGATTA ATGATCCCTG
GGTTTTGCTT AATGCTTCTT GGTTCAACTC CTTCCTTACA
CATGCATTGA GTTAGTTGTG GCAGTGCTAC TATTTGCTAT
CCATACTGTC CAAAAAAGTA CCTTGTTTCT ACT

PB1

(SEQ ID NO: 35)

AGCGAAAGCAGGCAAACCATTTGAATGGATGTCAATCCGACCTTACTTT

TCTTAAAAGTGCCAGCACAAAATGCTATAAGCACAACTTTCCCTTATAC

TGGAGACCCTCCTTACAGCCATGGGACAGGAACAGGATACACCATGGAT

ACTGTCAACAGGACACATCAGTACTCAGAAAAGGGAAGATGGACAACAA

ACACCGAAACTGGAGCACCGCAACTCAACCCGATTGATGGGCCACTGCC

AGAAGACAATGAACCAAGTGGTTATGCCCAAACAGATTGTGTATTGGAG

GCGATGGCTTTCCTTGAGGAATCCCATCCTGGTATTTTTGAAAACTCGT

GTATTGAAACGATGGAGGTTGTTCAGCAAACACGAGTAGACAAGCTGAC

ACAAGGCCGACAGACCTATGACTGGACTCTAAATAGAAACCAACCTGCT

GCAACAGCATTGGCCAACACAATAGAAGTGTTCAGATCAAATGGCCTCA

CGGCCAATGAGTCTGGAAGGCTCATAGACTTCCTTAAGGATGTAATGGA

GTCAATGAACAAAGAAGAAATGGGGATCACAACTCATTTTCAGAGAAAG

AGACGGGTGAGAGACAATATGACTAAGAAAATGATAACACAGAGAACAA

TGGGTAAAAAGAAGCAGAGATTGAACAAAAGGAGTTATCTAATTAGAGC

ATTGACCCTGAACACAATGACCAAAGATGCTGAGAGAGGGAAGCTAAAA

CGGAGAGCAATTGCAACCCCAGGGATGCAAATAAGGGGGTTTGTATACT

TTGTTGAGACACTGGCAAGGAGTATATGTGAGAAACTTGAACAATCAGG

GTTGCCAGTTGGAGGCAATGAGAAGAAAGCAAAGTTGGCAAATGTTGTA

AGGAAGATGATGACCAATTCTCAGGACACCGAACTTTCTTTCACCATCA

CTGGAGATAACACCAAATGGAACGAAAATCAGAATCCTCGGATGTTTTT

GGCCATGATCACATATATGACCAGAAATCAGCCCGAATGGTTCAGAAAT

GTTCTAAGTATTGCTCCAATAATGTTCTCAAACAAAATGGCGAGACTGG

GAAAAGGGTATATGTTTGAGAGCAAGAGTATGAAACTTAGAACTCAAAT

ACCTGCAGAAATGCTAGCAAGCATCGATTTGAAATATTICAATGATTCA

ACAAGAAAGAAGATTGAAAAAATCCGACCGCTCTTAATAGAGGGGACTG

CATCATTGAGCCCTGGAATGATGATGGGCATGTTCAATATGTTAAGCAC

TGTATTAGGCGTCTCCATCCTGAATCTTGGACAAAAGAGATACACCAAG

ACTACTTACTGGTGGGATGGTCTTCAATCCTCTGACGATTTTGCTCTGA

TTGTGAATGCACCCAATCATGAAGGGATTCAAGCCGGAGTCGACAGGTT

TTATCGAACCTGTAAGCTACTTGGAATCAATATGAGCAAGAAAAAGTCT

TACATAAACAGAACAGGTACATTTGAATTCACAAGTTTTTTCTATCGTT

ATGGGTTTGTTGCCAATTTCAGCATGGAGCTTCCCAGTTTTGGGGTGTC

TGGGATCAACGAGTCAGCGGACATGAGTATTGGAGTTACTGTCATCAAA

AACAATATGATAAACAATGATCTTGGTCCAGCAACAGCTCAAATGGCCC

TTCAGTTGTTCATCAAAGATTACAGGTACACGTACCGATGCCATATAGG

TGACACACAAATACAAACCCGAAGATCATTTGAAATAAAGAAACTGTGG

GAGCAAACCCGTTCCAAAGCTGGACTGCTGGTCTCCGACGGAGGCCCAA

ATTTATACAACATTAGAAATCTCCACATTCCTGAAGTCTGCCTAAAATG

GGAATTGATGGATGAGGATTACCAGGGGCGTTTATGCAACCCACTGAAC

-continued

CCATTTGTCAGCCATAAAGAAATTGAATCAATGAACAATGCAGTGATGA

TGCCAGCACATGGTCCAGCCAAAAACATGGAGTATGATGCTGTTGCAAC

AACACACTCCTGGATCCCCAAAAGAAATCGATCCATCTTGAATACAAGT

CAAAGAGGAGTACTTGAGGATGAACAAATGTACCAAAGGTGCTGCAATT

TATTTGAAAAATTCTTCCCCAGCAGTTCATACAGAAGACCAGTCGGGAT

ATCCAGTATGGTGGAGGCTATGGTTTCCAGAGCCCGAATTGATGCACGG

ATTGATTTCGAATCTGGAAGGATAAAGAAAGAAGAGTTCACTGAGATCA

TGAAGATCTGTTCCACCATTGAAGAGCTCAGACGGCAAAAATAGTGAAT

TTAGCTTGTCCTTCATGAAAAAATGCCTTGTTTCTACT

PB2

(SEQ ID NO: 36)

AGCGAAAGCA GGTCAATTAT ATTCAATATG GAAAGAATAA

AAGAACTACG AAATCTAATG TCGCAGTCTC GCACCCGCGA

GATACTCACA AAAACCACCG TGGACCATAT GGCCATAATC

AAGAAGTACA CATCAGGAAG ACAGGAGAAG AACCCAGCAC

TTAGGATGAA ATGGATGATG GCAATGAAAT ATCCAATTAC

AGCAGACAAG AGGATAACGG AAATGATTCC TGAGAGAAAT

GAGCAAGGAC AAACTTTATG GAGTAAAATG AATGATGCCG

GATCAGACCG AGTGATGGTA TCACCTCTGG CTGTGACATG

GTGGAATAGG AATGGACCAA TAACAAATAC AGTTCATTAT

CCAAAAATCT ACAAAACTTA TTTTGAAAGA GTCGAAAGGC

TAAAGCATGG AACCTTTGGC CCTGTCCATT TTAGAAACCA

AGTCAAAATA CGTCGGAGAG TTGACATAAA TCCTGGTCAT

GCAGATCTCA GTGCCAAGGA GGCACAGGAT GTAATCATGG

AAGTTGTTTT CCCTAACGAA GTGGGAGCCA GGATACTAAC

ATCGGAATCG CAACTAACGA TAACCAAAGA GAAGAAAGAA

GAACTCCAGG ATTGCAAAAT TTCTCCTTTG ATGGTTGCAT

ACATGTTGGA GAGAGAACTG GTCCGCAAAA CGAGATTCCT

CCCAGTGGCT GGTGGAACAA GCAGTGTGTA CATTGAAGTG

TTGCATTTGA CTCAAGGAAC ATGCTGGGAA CAGATGTATA

CTCCAGGAGG GGAAGTGAGG AATGATGATG TTGATCAAAG

CTTGATTATT GCTGCTAGGA ACATAGTGAG AAGAGCTGCA

GTATCAGCAG ATCCACTAGC ATCTTTATTG GAGATGTGCC

ACAGCACACA GATTGGTGGA ATTAGGATGG TAGACATCCT

TAGGCAGAAC CCAACAGAAG AGCAAGCCGT GGATATATGC

AAGGCTGCAA TGGGACTGAG AATTAGCTCA TCCTTCAGTT

TTGGTGGATT CACATTTAAG AGAACAAGCG GATCATCAGT

CAAGAGAGAG GAAGAGGTGC TTACGGGCAA TCTTCAAACA

TTGAAGATAA GAGTGCATGA GGGATATGAA GAGTTCACAA

TGGTTGGGAG AAGAGCAACA GCCATACTCA GAAAAGCAAC

-continued

```
CAGGAGATTG ATTCAGCTGA TAGTGAGTGG GAGAGACGAA
CAGTCGATTG CCGAAGCAAT AATTGTGGCC ATGGTATTTT
CACAAGAGGA TTGTATGATA AAAGCAGTCA GAGGTGATCT
GAATTTCGTC AATAGGGCGA ATCAACGATT GAATCCTATG
CATCAACTTT TAAGACATTT TCAGAAGGAT GCGAAAGTGC
TTTTTCAAAA TTGGGGAGTT GAACCTATCG ACAATGTGAT
GGGAATGATT GGGATATTGC CCGACATGAC TCCAAGCATC
GAGATGTCAA TGAGAGGAGT GAGAATCAGC AAAATGGGTG
TAGATGAGTA CTCCAGCACG GAGAGGGTAG TGGTGAGCAT
TGACCGTTTT TTGAGAATCC GGGACCAACG AGGAAATGTA
CTACTGTCTC CCGAGGAGGT CAGTGAAACA CAGGGAACAG
AGAAACTGAC AATAACTTAC TCATCGTCAA TGATGTGGGA
GATTAATGGT CCTGAATCAG TGTTGGTCAA TACCTATCAA
TGGATCATCA GAAACTGGGA AACTGTTAAA ATTCAGTGGT
CCCAGAACCC TACAATGCTA TACAATAAAA TGGAATTTGA
ACCATTTCAG TCTTTAGTAC CTAAGGCCAT TAGAGGCCAA
TACAGTGGGT TTGTAAGAAC TCTGTTCCAA CAAATGAGGG
ATGTGCTTGG GACATTTGAT ACCGCACAGA TAATAAAACT
TCTTCCCTTC GCAGCCGCTC CACCAAAGCA AAGTAGAATG
CAGTTCTCCT CATTTACTGT GAATGTGAGG GGATCAGGAA
TGAGAATACT TGTAAGGGGC AATTCTCCTG TATTCAACTA
TAACAAGGCC ACGAAGAGAC TCACAGTTCT CGGAAAGGAT
GCTGGCACTT TAACTGAAGA CCCAGATGAA GGCACAGCTG
GAGTGGAGTC CGCTGTTCTG AGGGGATTCC TCATTCTGGG
CAAAGAAGAC AAGAGATATG GGCCAGCACT AAGCATCAAT
GAACTGAGCA ACCTTGCGAA AGGAGAGAAG GCTAATGTGC
TAATTGGGCA AGGAGACGTG GTGTTGGTAA TGAAACGGAA
ACGGGACTCT AGCATACTTA CTGACAGCCA GACAGCGACC
AAAAGAATTC GGATGGCCAT CAATTAGTGT CGAATAGTTT
AAAAACGACC TTGTTTCTAC T
```

NP (SEQ ID NO: 37)

```
AGCAAAAGCA GGGTAGATAA TCACTCACTG AGTGACATCA
AAATCATGGC GTCTCAAGGC ACCAAACGAT CTTACGAACA
GATGGAGACT GATGGAGAAC GCCAGAATGC CACTGAAATC
AGAGCATCCG TCGGAAAAAT GATTGGTGGA ATTGGACGAT
TCTACATCCA AATGTGCACC GAACTCAAAC TCAGTGATTA
TGAGGGACGG TTGATCCAAA ACAGCTTAAC AATAGAGAGA
ATGGTGCTCT CTGCTTTTGA CGAAAGGAGA AATAAATACC
TTGAAGAACA TCCCAGTGCG GGGAAAGATC CTAAGAAAAC
```

-continued

```
TGGAGGACCT ATATACAGGA GAGTAAACGG AAAGTGGATG
AGAGAACTCA TCCTTTATGA CAAAGAAGAA ATAAGGCGAA
TCTGGCGCCA AGCTAATAAT GGTGACGATG CAACGGCTGG
TCTGACTCAC ATGATGATCT GGCATTCCAA TTTGAATGAT
GCAACTTATC AGAGGACAAG AGCTCTTGTT CGCACCGGAA
TGGATCCCAG GATGTGCTCT CTGATGCAAG GTTCAACTCT
CCCTAGGAGG TCTGGAGCCG CAGGTGCTGC AGTCAAAGGA
GTTGGAACAA TGGTGATGGA ATTGGTCAGA ATGATCAAAC
GTGGGATCAA TGATCGGAAC TTCTGGAGGG GTGAGAATGG
ACGAAAAACA AGAATTGCTT ATGAAAGAAT GTGCAACATT
CTCAAAGGGA AATTTCAAAC TGCTGCACAA AAAGCAATGA
TGGATCAAGT GAGAGAGAGC CGGAACCCAG GGAATGCTGA
GTTCGAAGAT CTCACTTTTC TAGCACGGTC TGCACTCATA
TTGAGAGGGT CGGTTGCTCA CAAGTCCTGC CTGCCTGCCT
GTGTGTATGG ACCTGCCGTA GCCAGTGGGT ACGACTTTGA
AAGGGAGGGA TACTCTCTAG TCGGAATAGA CCCTTTCAGA
CTGCTTCAAA ACAGCCAAGT GTACAGCCTA ATCAGACCAA
ATGAGAATCC AGCACACAAG AGTCAACTGG TGTGGATGGC
ATGCCATTCT GCCGCATTTG AAGATCTAAG AGTATTAAGC
TTCATCAAAG GGACGAAGGT GCTCCCAAGA GGGAAGCTTT
CCACTAGAGG AGTTCAAATT GCTTCCAATG AAAATATGGA
GACTATGGAA TCAAGTACAC TTGAACTGAG AAGCAGGTAC
TGGGCCATAA GGACCAGAAG TGGAGGAAAC ACCAATCAAC
AGAGGGCATC TGCGGGCCAA ATCAGCATAC AACCTACGTT
CTCAGTACAG AGAAATCTCC CTTTTGACAG AACAACCATT
ATGGCAGCAT TCAATGGGAA TACAGAGGGG AGAACATCTG
ACATGAGGAC CGAAATCATA AGGATGATGG AAAGTGCAAG
ACCAGAAGAT GTGTCTTTCC AGGGGCGGGG AGTCTTCGAG
CTCTCGGACG AAAAGGCAGC GAGCCCGATC GTGCCTTCCT
TTGACATGAG TAATGAAGGA TCTTATTTCT TCGGAGACAA
TGCAGAGGAG TACGACAATT AAAGAAAAAT ACCCTTGTTT
CTACT
```

M (SEQ ID NO: 38)

```
AGCAAAAGCA GGTAGATATT GAAAGATGAG TCTTCTAACC
GAGGTCGAAA CGTACGTACT CTCTATCATC CCGTCAGGCC
CCCTCAAAGC CGAGATCGCA CAGAGACTTG AAGATGTCTT
TGCAGGGAAG AACACCGATC TTGAGGTTCT CATGGAATGG
CTAAAGACAA GACCAATCCT GTCACCTCTG ACTAAGGGGA
TTTTAGGATT TGTGTTCACG CTCACCGTGC CCAGTGAGCG
```

-continued

AGGACTGCAG CGTAGACGCT TTGTCCAAAA TGCCCTTAAT

GGGAACGGGG ATCCAAATAA CATGGACAAA GCAGTTAAAC

TGTATAGGAA GCTCAAGAGG GAGATAACAT TCCATGGGGC

CAAAGAAATC TCACTCAGTT ATTCTGCTGG TGCACTTGCC

AGTTGTATGG GCCTCATATA CAACAGGATG GGGGCTGTGA

CCACTGAAGT GGCATTTGGC CTGGTATGTG CAACCTGTGA

ACAGATTGCT GACTCCCAGC ATCGGTCTCA TAGGCAAATG

GTGACAACAA CCAATCCACT AATCAGACAT GAGAACAGAA

TGGTTTTAGC CAGCACTACA GCTAAGGCTA TGGAGCAAAT

GGCTGGATCG AGTGAGCAAG CAGCAGAGGC CATGGAGGTT

GCTAGTCAGG CTAGACAAAT GGTGCAAGCG ATGAGAACCA

TTGGGACTCA TCCTAGCTCC AGTGCTGGTC TGAAAAATGA

TCTTCTTGAA AATTTGCAGG CCTATCAGAA ACGAATGGGG

GTGCAGATGC AACGGTTCAA GTGATCCTCT CACTATTGCC

GCAAATATCA TTGGGATCTT GCACTTGACA TTGTGGATTC

TTGATCGTCT TTTTTTCAAA TGCATTTACC GTCGCTTTAA

ATACGGACTG AAAGGAGGGC CTTCTACGGA AGGAGTGCCA

AAGTCTATGA GGGAAGAATA TCGAAAGGAA CAGCAGAGTG

CTGTGGATGC TGACGATGGT CATTTTGTCA GCATAGAGCT

GGAGTAAAAA ACTACCTTGT TTCTACT

NS (SEQ ID NO: 39)

AGCAAAAGCA GGGTGACAAA AACATAATGG ATCCAAACAC

TGTGTCAAGC TTTCAGGTAG ATTGCTTTCT TTGGCATGTC

CGCAAACGAG TTGCAGACCA AGAACTAGGC GATGCCCCAT

TCCTTGATCG GCTTCGCCGA GATCAGAAAT CCCTAAGAGG

AAGGGGCAGT ACTCTCGGTC TGGACATCAA GACAGCCACA

CGTGCTGGAA AGCAGATAGT GGAGCGGATT CTGAAAGAAG

AATCCGATGA GGCACTTAAA ATGACCATGG CCTCTGTACC

TGCGTCGCGT TACCTAACTG ACATGACTCT TGAGGAAATG

TCAAGGGACT GGTCCATGCT CATACCCAAG CAGAAAGTGG

CAGGCCCTCT TTGTATCAGA ATGGACCAGG CGATCATGGA

TAAGAACATC ATACTGAAAG CGAACTTCAG TGTGATTTTT

GACCGGCTGG AGACTCTAAT ATTGCTAAGG GCTTTCACCG

AAGAGGGAGC AATTGTTGGC GAAATTTCAC CATTGCCTTC

TCTTCCAGGA CATACTGCTG AGGATGTCAA AAATGCAGTT

GGAGTCCTCA TCGGAGGACT TGAATGGAAT GATAACACAG

TTCGAGTCTC TGAAACTCTA CAGAGATTCG CTTGGAGAAG

CAGTAATGAG AATGGGAGAC CTCCACTCAC TCCAAAACAG

AAACGAGAAA TGGCGGGAAC AATTAGGTCA GAAGTTTGAA

-continued

GAAATAAGAT GGTTGATTGA AGAAGTGAGA CACAAACTGA

AGATAACAGA GAATAGTTTT GAGCAAATAA CATTTATGCA

AGCCTTACAT CTATTGCTTG AAGTGGAGCA AGAGATAAGA

ACTTTCTCGT TTCAGCTTAT TTAGTACTAA AAAACACCCT

TGTTTCTACT

High-titer A/PR/8/34 (H1N1, PR8(UW)) virus grows 10 times better than other NAPR/8/34 PR8 strains 45 in eggs ($10^{10}$ $EID_{50}$/mL; HA titer:1:8.000). Thus, replacement of the HA and NA genes of PR8(UW) with those of a currently circulating strain of influenza virus results in a vaccine strain that can be safely produced, and validates the use of PR8 (UW) as a master vaccine strain.

Genes that contribute to different growth properties between PR8(UW) and PR8 (Cambridge), which provides the non-HA and -NA genes of the NIBRG-14 vaccine strain (FIG. 1), were determined. Higher titers in eggs were obtained when the majority of internal genes were from PR8(UW). Highest titers were with the M viral segment of PR8(UW) and the NS gene of PR8 (Cambridge). The NS gene in PR8(UW) has a K (lysine) at residue 55 while the NS gene in PR8(Cam) has a E (glutamic acid). The polymerase subunit (PA, PB1, and PB2) and NP genes of PR8(UW) enhanced the growth of an H5N1 vaccine seed virus in chicken embryonated eggs, and the NS gene of PR8(Cambridge) enhanced the growth of an H5N1 vaccine seed virus in chicken embryonated eggs. A tyrosine (Y) at position 360 in PB2 of PR8(UW) likely contributes to the high growth rate of that virus in MDCK cells.

Example B

To develop an high-yield A/PR/8/34 (H1N1; PR8) virus backbone for growth of vaccine virus in specific host cells, random mutagenesis of the internal genes of PR8(HG) (PRBUW) was conducted. Random mutations were introduced into the UW-PR8 (Example 1) internal genes by error-prone PCR after which plasmid libraries were prepared that possessed the random mutations in an individual UW-PR8 internal gene. Then virus libraries (PR8H5N) were generated that possessed random mutations in an individual UW-PR8 internal gene, along with the other wild type internal genes and the NA and 'detoxified' HA genes of A/chicken/IndonesiaNC/09 (H5N) virus (Table 1), to generate "6+2" recombinant viruses. Consecutive passages of the virus in MDCK cells were employed to select for variants with high-growth properties.

TABLE 1

Virus libraries generated

| | Internal genes | | | Titer of virus |
|---|---|---|---|---|
| Number | Gene library | Other internal genes | HA + NA | library (pfu/ml) |
| Control | PR8 wild type | | NC/09/H5N1 | $3 \times 10^6$ |
| 1 | PB2 | 5 UW-PR8 genes | NC/09/H5N1 | $2.1 \times 10^2$ |
| 2 | PB1 | 5 UW-PR8 genes | NC/09/H5N1 | $1.6 \times 10^5$ |
| 3 | PA | 5 UW-PR8 genes | NC/09/H5N1 | $7 \times 10^3$ |
| 4 | NP | 5 UW-PR8 genes | NC/09/H5N1 | $1.5 \times 10^3$ |

TABLE 1-continued

| Virus libraries generated | | | | |
|---|---|---|---|---|
| | Internal genes | | | Titer of virus |
| Number | Gene library | Other internal genes | HA + NA | library (pfu/ml) |
| 5 | M | 5 UW-PR8 genes | NC/09/H5N1 | $1 \times 10^6$ |
| 6 | NS | 5 UW-PR8 genes | NC/09/H5N1 | $1.8 \times 10^6$ |
| 7 | PB2 + PB1 + PA | 3UW-PR8 genes | NC/09/H5N1 | 75 |
| 8 | PB2 + PB1 + PA + NP | 2UW-PR8 genes | NC/09/H5N1 | 33 |
| 9 | PB2 + NS | 4UW-PR8 genes | NC/09/H5N1 | $2 \times 10^2$ |
| 10 | M + NS | 4UW-PR8 genes | NC/09/H5N1 | $5.7 \times 10^5$ |

Virus libraries were passaged 12 times in MDCK cells or, after 2 passages, the libraries were mixed and 10 more passages were carried out (FIG. 2).

After 10 to about 12 consecutive passages in MDCK cells, plaque assays were performed and over 1,400 individual plaques were picked. FIG. 3 shows the numbers of clones with various HA titers. Growth enhancing mutations included: PB2: M202L, F323L, I504V, PB1: E1112G, V644A, NP: R74K, N417D, I116L, and NS: S161T. FIG. 4 provides the titers of recombinant viruses generated from selected mutations.

38 viruses with the highest HA titers from the random mutagenesis libraries were sequenced (Table 2)

TABLE 2

| Sequences of viruses with the highest HA titers | | | | | | | | | | |
|---|---|---|---|---|---|---|---|---|---|---|
| Clone # | Library | HA titer ($2^n$) | PB2 | PB1 | PA | HA (H3 numbering) | NP | NA | M | NS |
| WT | | 7 | | | | | | | | |
| 329 | Mix | 9 | M202L F323L | | | L182V | | | | |
| 154 | Mix | 8.5~9 | M202L F323L | | | L182V | | | | |
| 347 | Mix | 9 | M202L F323L | | | L182V | | | | |
| 94 | Mix | 8.5 | M202L F323L | | | F252I | I116L | L55S | | |
| 1045 | Mix | 9 | M202L F323L | V644A | | F252I | | | | |
| 965 | Mix | 8.5~9 | M202L F323L | | F105C | V184I | | | P90S | |
| 50 | Mix | 8.5 | M202L F323L | | | M148I (HA2) | R293M | | | |
| 1005 | Mix | 9~9.5 | M202L F323L | V644A | R401K | M148I (HA2) | | | | T49A |
| 134 | Mix | 8.5 | M202L F323L | | | | | | | A223E |
| 387 | Mix | 9 | M202L F323L | M507V V644A | | | | | | |
| 852 | Mix | 9~9.5 | M202L F323L M243I | R54I | | | | | | |
| 981 | Mix | 8.5~9 | M202L F323L | Q247H | | | | | | |
| 993 | Mix | 8.5~9 | M202L F323L | | | | N224I | | | |
| 1043 | Mix | 8.5~9 | I504V | | | L182V | R74K | | | |
| 398 | Mix | 8.5 | I504V | | | L182V | R74K, N417D | | | A30P |
| 1007 | Mix | 8.5 | I504V | V644A | | F252I | M371V | | | |
| 1042 | Mix | 8.5~9 | I504V | E75V D76G E78P P79V S80G V644A E697P F699L F700L P701H S702R Y705T | | F252I | R74K | | | |
| 999 | Mix | 8.5~9 | I504V | | | M148I (HA2) | R74K, N417D | | | |
| 1014 | Mix | 8.5 | I504V | T59I G62X A63P V644A N694K L695T | | M148I (HA2) | R74K, N417D | A265V | | |

TABLE 2-continued

Sequences of viruses with the highest HA titers

| Clone # | Library | HA titer ($2^n$) | PB2 | PB1 | PA | HA (H3 numbering) | NP | NA | M | NS |
|---|---|---|---|---|---|---|---|---|---|---|
| 1016 | Mix | 8.5~9 | I504V | | | M148I (HA2) | | | | |
| 540 | PB1 | 8.5 | | E112G | | K162E | | | | S161T |
| 548 | PB1 | 8.5~9 | | E112G L624V | | K162E | | | | S161T |
| 191 | PB1 | 8~8.5 | | E112G | | | | | | |
| 571 | PB1 | 9~9.5 | | E112G | | | | | | |
| 572 | PB1 | 8.5 | | E112G | | | | | | |
| 573 | PB1 | 8.5 | | E112G | | | | | | |
| 1404 | PB1 | 8.5 | I57V T58G A59V K61Q E677D D678E P679M | E112G S713C | | | | | | |
| 1408 | PB1 | 8.5 | | M40I G180W | | | | | | S161T |
| 582 | PB1 | 8.5~9 | | M40L, G180W | | | | | | S161T |
| 545 | PB1 | 8.5 | | M40L, G180W | | K121E (HA2) | | | | |
| 543 | PB1 | 8.5 | | I667T | | | | | | |
| 219 | PB1 | 9 | | I667T, M714T | | K162E | | | | |
| 344 | Mix | 8.5~9 | M66R | | | L182V | | | | |
| 312 | Mix | 8.5~9 | | | | L182V | I116L | | | R140Q |
| 320 | Mix | 8.5 | | | | L182V | | | | |
| 209 | PB1 | 8.5~9 | | R54I | | E136D, Q179L, A194V | | | | |

In a second approach, potentially growth-enhancing mutations described in the literature were introduced into the background of UW-PR8 virus (see Table 3 for virus stock titers) and tested for replicative ability. FIGS. 5A-D show growth curves for various viruses.

TABLE 3

UW-PR8 viruses possessing mutation(s) identified in the literature

| Gene | Mutation(s) | Virus stock titer (Pfu/ml) |
|---|---|---|
| WT | — | $2 \times 10^7$ |
| PB2 | A44S | $4.5 \times 10^7$ |
| | E158G | $3.2 \times 10^4$ |
| | E158G + NP N101G | $7.5 \times 10^4$ |
| | E158A | $8.3 \times 0^6$ |
| | D253N + Q591K | $8.3 \times 10^6$ |
| | D256G | $2.8 \times 10^7$ |
| | R368K | $3.1 \times 10^7$ |
| | E391Q | $1.4 \times 10^8$ |
| | I504V + PA I550L | $1.1 \times 10^8$ |
| | Q591K | $4.4 \times 10^7$ |
| | V613T | $1.8 \times 10^7$ |
| | A661T | $2.2 \times 10^7$ |
| | D701N + S714R + NP N319K | $1 \times 10^6$ |
| | D701N | $2.1 \times 10^7$ |
| PB1 | R327K | $1.3 \times 10^7$ |
| | V336I | $2.3 \times 10^7$ |
| | L473V + L598P | $3.9 \times 10^6$ |
| PB1F2 | F2 N66S | $1.6 \times 10^8$ |
| | F2 K73R | $1.1 \times 10^8$ |
| | F2 V76A | $4.4 \times 10^7$ |

TABLE 3-continued

UW-PR8 viruses possessing mutation(s) identified in the literature

| Gene | Mutation(s) | Virus stock titer (Pfu/ml) |
|---|---|---|
| | F2 R79Q | $6.2 \times 10^6$ |
| | F2 L82S | $2.7 \times 10^7$ |
| | F2 E87Q | $1.5 \times 10^6$ |
| PA | T97I | $1.6 \times 10^7$ |
| | K142N | $3.3 \times 10^7$ |
| | S225C | $6.7 \times 10^7$ |
| | S149P + T357K | $3.4 \times 10^8$ |
| | K356R | $8.5 \times 10^7$ |
| | A404S | $5.2 \times 10^7$ |
| | S421I | $2.7 \times 10^7$ |
| NP | R293K | $4.7 \times 10^7$ |
| | R305K | $7.2 \times 10^7$ |
| | E372D | $2.2 \times 10^7$ |
| | R422K | $1.3 \times 10^3$ |
| | T442A | $5 \times 10^7$ |
| | D455E | $2.2 \times 10^7$ |
| | I109V | $3.9 \times 10^7$ |
| M | V97A + Y100H | $1.4 \times 10^7$ |
| NS1 | K55E | $1.6 \times 10^7$ |

In a third approach, candidates from approaches 1 and 2 were combined and HA titers and PFU/mL determined (Table 4).

TABLE 4

High-growth candidates identified in approaches 1 and 2 were tested in various combinations

| | Gene origin | | | | | | | | Virus stock titer | |
|---|---|---|---|---|---|---|---|---|---|---|
| # | HA | NA | PB2 | PB1 | PA | NP | M | NS | HA ($2^n$) | Pfu/ml |
| WT | Indo/NC/09 (detoxified) | Indo/NC/09 | UW-PR8 | UW-PR8 | UW-PR8 | UW-PR8 | UW-PR8 | UW-PR8 | 7 | 3.00E+07 |
| 1 | | | M202L F323L | M507V V644A | | I116L | | K55E | 9~9.5 | 2.00E+08 |
| 2 | | | M202L F323L | R54I | | N224I | | K55E | 5 | 1.00E+05 |
| 3 | | | M202L F323L | Q247H | R401K | | | T49A | 9 | 1.00E+08 |
| 4 | | | M202L F323L | M507V V644A | K356R | T442A | V97A Y100H | K55E | 10~10.5 | 1.60E+08 |
| 5 | | | I504V | M507V V644A | I550L | R74K N417D | | K55E | 8~8.5 | 5.70E+07 |
| 6 | | | I504V | M507V V644A | I550L | R74K N417D | V97A Y100H | K55E | 9~9.5 | 4.40E+07 |
| 7 | | | I505V | E112G | I550L | R74K | | S161T | 9 | 1.60E+08 |
| 8 | | | M202L F323L | I667T M714T | | I116L | | R140Q | <1 | <1E3 |
| 9 | | | M202L F323L | E112G | | | | S161T | 8.5 | 1.30E+08 |
| 10 | | | M66R | M40I G180W | | R74K | | S161T | 8~8.5 | 2.30E+07 |
| 12 | | | R368K | PB1 F2 N66S | K356R | R422K | | K55E | 5.5 | 9.00E+02 |
| 13 | | | E391Q | R327K | S149P T357K | R293K | | | 3 | 1.60E+06 |
| 14 | | | Q591K | PB1 F2 K73R | S225C | R422K | | K55E | 7.5 | 2.00E+07 |
| 23 | | | | | | | V97A | | 8.5~9 | 1.50E+07 |
| 24 | | | | | | | Y100H | | 9~9.5 | 2.90E+07 |
| 25 | NOR 15-19 nt mut[1] | Indo/NC/09 | M202L F323L | M507V V644A | K356R | R422K | V97A Y100H | K55E | 9.5~10 | 7.50E+07 |
| 26 | Indo/NC/09 | Indo/NC/09 | | | | | | A30P | 6.5~7 | 1.00E+07 |
| 27 | (detoxified) | | | | | | | T49A | 6.5~7 | 2.00E+07 |
| 28 | | | | | | | | R140Q | 8 | 4.00E+07 |
| 29 | | | | | | | | S161T | 7~7.5 | 1.40E+07 |
| 30 | | | | | | | | A223E | 7.5 | 1.00E+07 |
| 31 | | | | I667T M714T | | | | | 3.5 | 4.00E+05 |
| 32 | NCR 15-19 nt mut | UW-PR8 | M202L F323L | V644A | K356R | T442A | Y100H | K55E | 7~7.5 | 4.30E+06 |
| 33 | Indo/NC/09 (detoxified) | Indo/NC/09 | M202L F323L | E112G | K356R | R74K | Y100H | K55E | 9~9.5 | 7.00E+07 |
| 34 | NCR 15-19 nt mut | UW-PR8 | I504V | M507V V644A | | | V97A Y100H | K55E | 7 | 2.00E+05 |
| 35 | Indo/NC/09 (detoxified) | Indo/NC/09 | M202L F323L | M507V V644A | R401K | T442A | Y100H | R140Q | 9 | 3.20E+07 |
| 36 | | | I504V | E112G | I550L | I112L | Y100H | R140Q | 9.5 | 1.30E+08 |
| 37 | | | M202L F323L | E112G | S149P T357K | T442A | Y100H | K55E | 0 | 0.00E+00 |
| 38 | | | M202L F323L | M507V V644A | | I116L | Y100H | K55E | 10.1 | 2.30E+08 |
| 39 | | | M202L F323L | M507V V644A | K356R | T442A | Y100H | K55E | 9.8 | 1.00E+08 |
| 40 | | | I504V | M507V V644A | I550L | T442A | Y100H | K55E | 9.2 | 6.00E+07 |
| 41 | | | I504V | I112G | I550L | R74K | Y100H | K55E | 9.2 | 7.50E+07 |
| P17 | | | I504V | E112G | S225C | R74K N417D | V97A Y100H | K55E | 9.5~10 | 5.80E+08 |
| P26 | | | M202L F323L | M40L G180W | S225C | R422K | V97A Y100H | K55E | 10 | 3.00E+08 |
| P61 | | Indo/NC/09 NA P263T[2] | M202L F323L | Q247H | K142N | R74K | V97A Y100H | K55E | 10~10.5 | 2.00E+08 |

[1]Mutation in the HA gene noncoding region;

[2]A P263T mutation was detected in the NA protein of this virus clone

Figure 8A:
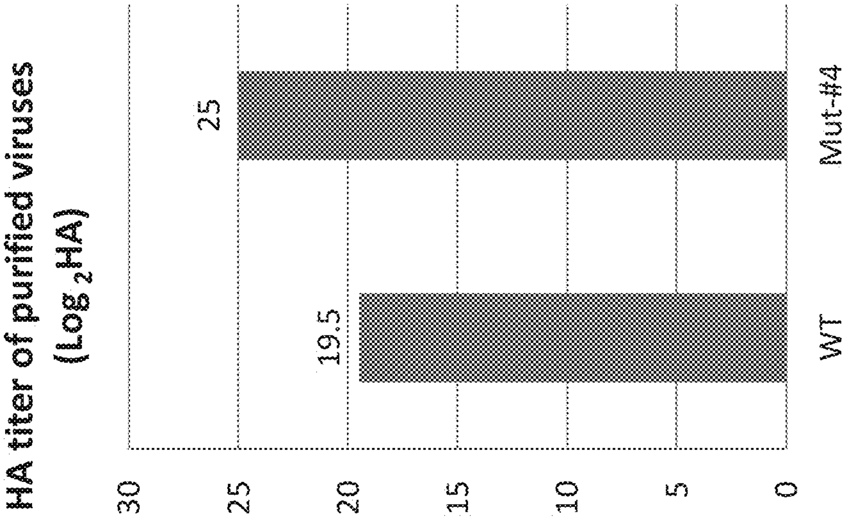
Figure 8B:
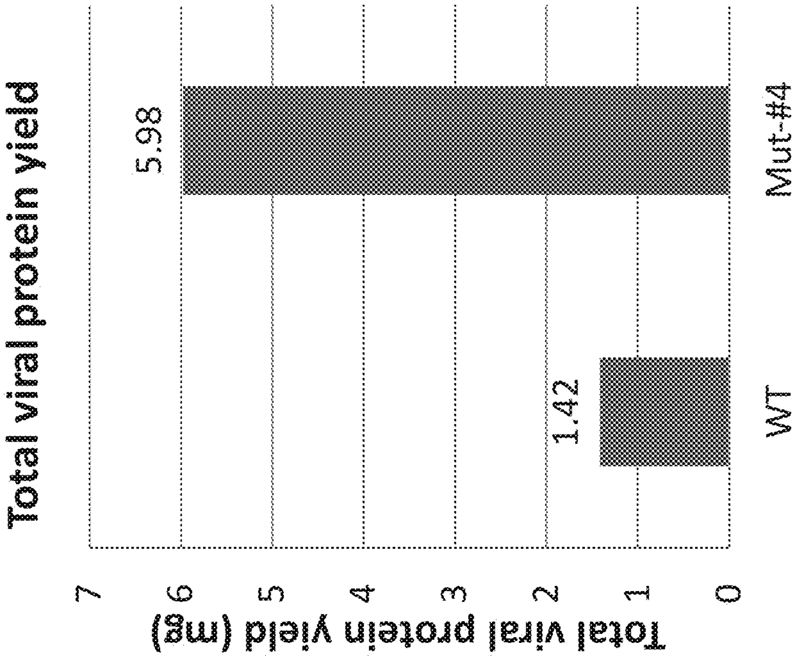

As shown in Table 4, several recombinant viruses were identified that replicated better than wild type, such as #1, #4, #36, #38, P17, P16, and P61. To identify the growth characteristics of these viruses, growth kinetics in MDCK cells were determined (FIG. 7). For one candidate, virus was purified on sucrose gradients and HA content and viral total protein evaluated. FIG. 8A shows HA titer of wild type (UW-PR8) and #4, FIG. 8B shows viral protein for wild type (UW-PR8) and #4, and FIG. 8BC is a SDS-PAGE analysis of viral proteins of wild type (UW-PR8) and #4. Further analysis demonstrated that viruses possessing the V97ANY100H mutations in M1 yielded higher HA titers than the parental virus, although the virus titer was lower (see FIGS. 9A-B). The V97A/Y100H mutations in M1 may result in particles with a larger surface into which more HA protein can be incorporated. Since inactivated influenza viruses are dosed based on their HA content, variants with high HA content are attractive vaccine candidates.

To identify mutations in the influenza promoter region that provide for enhanced replication, viruses possessing a 'U' at position 4 at the 3' end of all eight vRNA segments were prepared in the UW-PR8 PA, PB1 and PB2 internal genes (the UW-PR8 PB2, PB1, and PA segments possess a 'C' at position 4). The growth curves of the resulting viruses are shown in FIG. 11C.

Viruses possessing combinations of promoter mutations and amino acid changes were prepared and titers determined (Table 5).

TABLE 5

Virus titers of high-growth candidates.

| | Gene backbone | | | | | | | | Virus stock titer | |
|---|---|---|---|---|---|---|---|---|---|---|
| Viruses | HA | NA | PB2 | PB1 | PA | NP | M | NS | HA (2") | pfu/ml |
| Control | WT | WT | WT | WT | WT | WT | WT | WT | 7 | 3.0E+07 |
| 1 | WT | WT | 3'C4U | 3'C4U | 3'C4U | R74K | V97A | K55E | 10.5 | 2.2E+09 |
| 2 | 3' G3A U5C C8U & 5' U3C A8G | | M202L F323L | Q247H | K142N | | Y100H | | 8.5~9 | 5.6E+07 |
| 3 | NCR 15-19 nt mut | | | | | | | | 9~9.5 | 1.4E+09 |
| 4 | 3' G3A U5C C8U & 5' U3C A8G & NCR 15-19 nt mut | | | | | | | | 7 | 7.0E+07 |

Figure 10B:
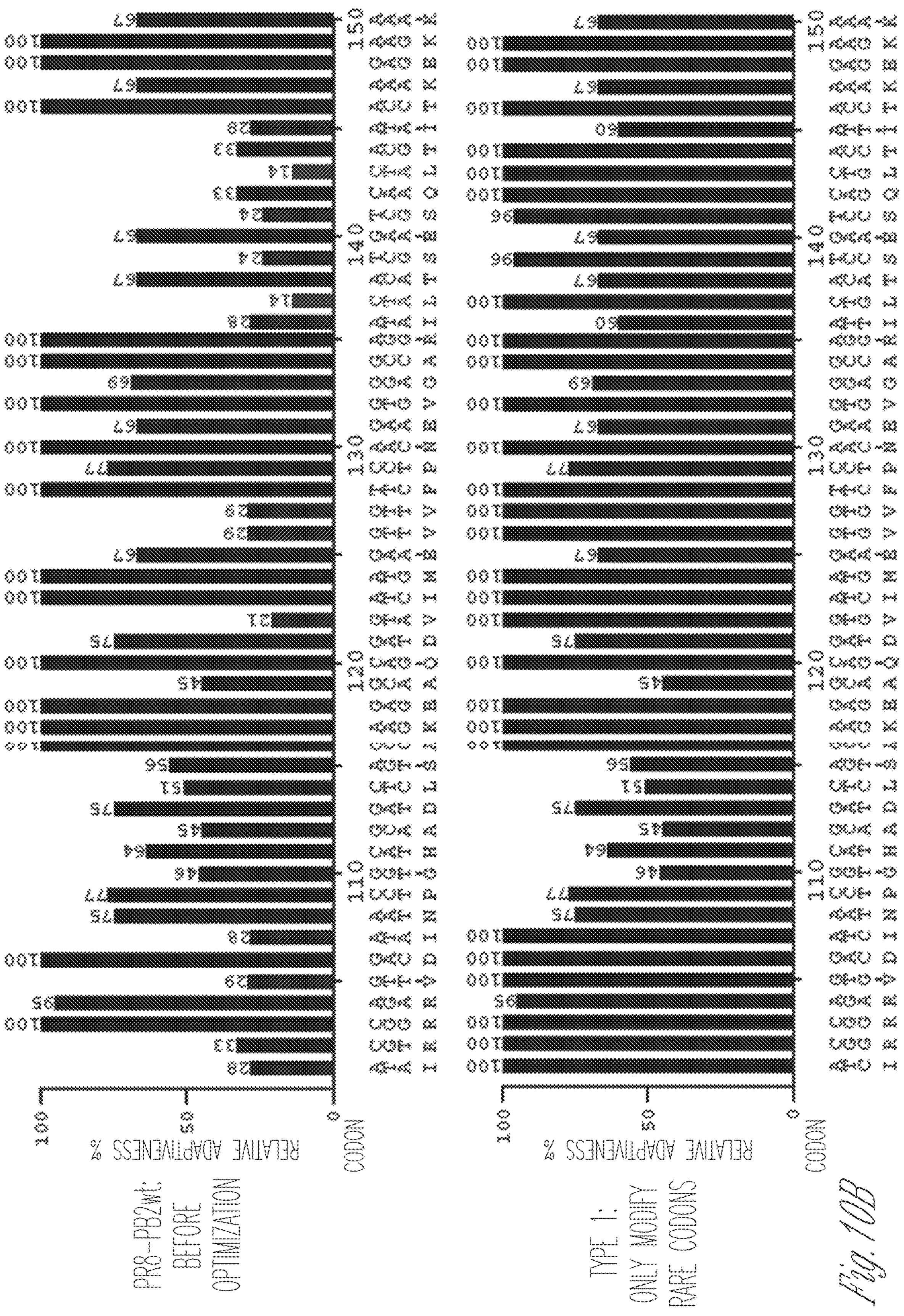
Figure 10C:
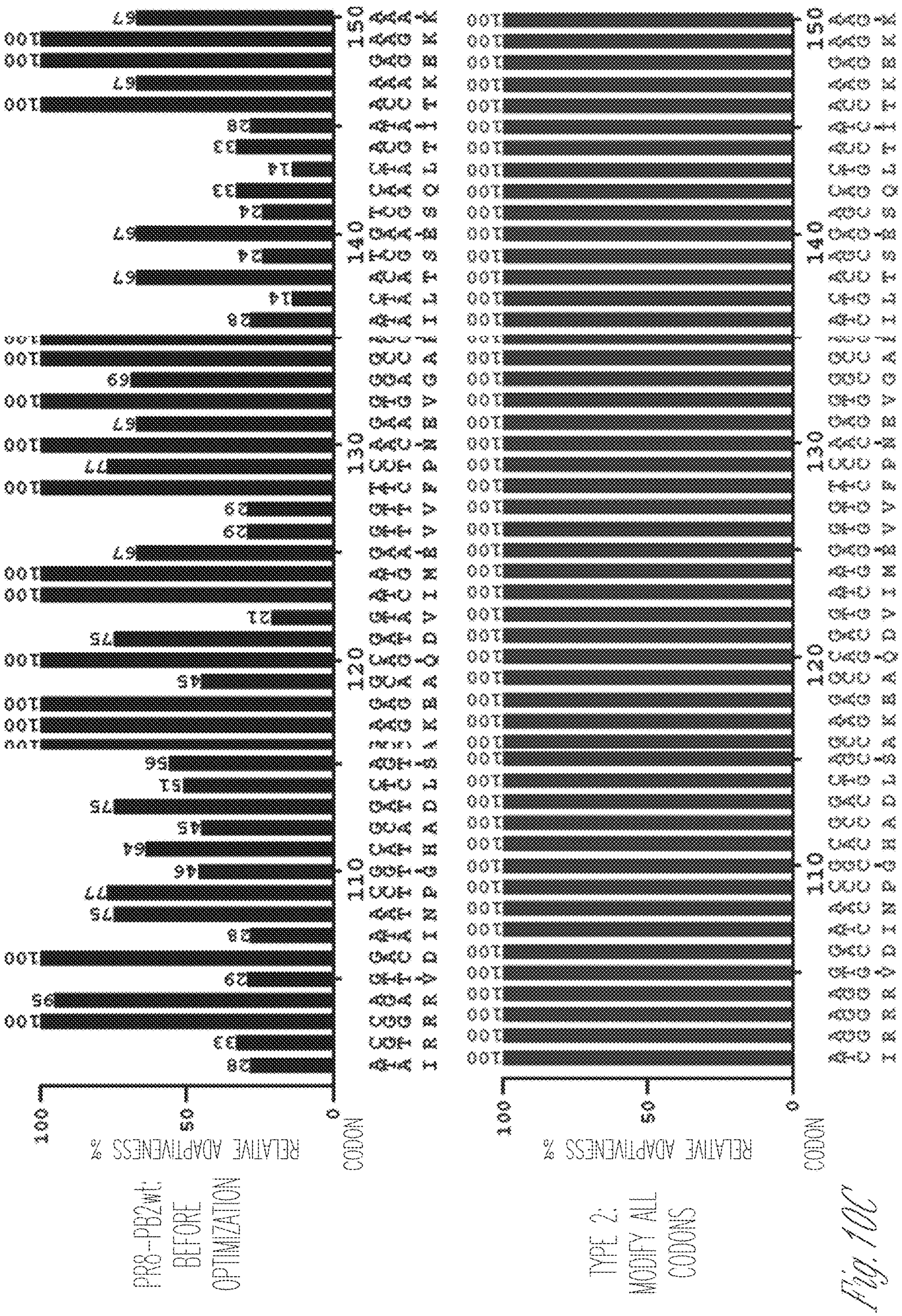

Codon usage optimization was also conducted. Alteration of codons may increase protein expression but could also alter RNA structure and stability. For example, codon usage optimization of the PB2 gene segment was performed to reflect the codon usage in canine cells (since MOCK cells are of canine origin) (FIG. 10A), while leaving the packaging signals (located at the 5' and 3' ends of the vRNA) unaltered. In one approach, codon optimization was performed for all codons in the 'internal' region of the PB2 gene (FIG. 10C) and in another approach, codon optimization was performed for so-called 'rare' codons (FIG. 10B) (used at significantly lower frequency compared to the codon used most frequently for a given amino acid) (see SEQ ID NO:25 in FIG. 10F). Analyses were carried out using the "Graphical Codon Usage Analyser" (www.gcua.de). The titers of those viruses are shown in Table 6 (see also FIGS. 10B-C).

TABLE 6

Titers of viruses encoding codon-optimized PB2 genes.

| | Gene backbone | | | | | | | | Virus stock titer | |
|---|---|---|---|---|---|---|---|---|---|---|
| Virus | HA | NA | PB2 | PB1 | PA | NP | M | NS | HA (2") | pfu/ml |
| Wild type | WT | WT | WT | WT | WT | WT | WT | WT | 7~7.5 | 3.5E+07 |
| PB2 codon optimization-1 | WT | WT | Rare codon optimized PB2 | WT | WT | WT | WT | WT | 9 | 2.1E+08 |
| PB2 codon optimization-2 | WT | WT | All Codon optimized PB2 | WT | WT | WT | WT | WT | 3 | 9.0E+05 |

Optimization of rare codons in PB2 resulted in increased titers compared to wild type virus (UW-PR8) (see FIG.

Figure 10E:
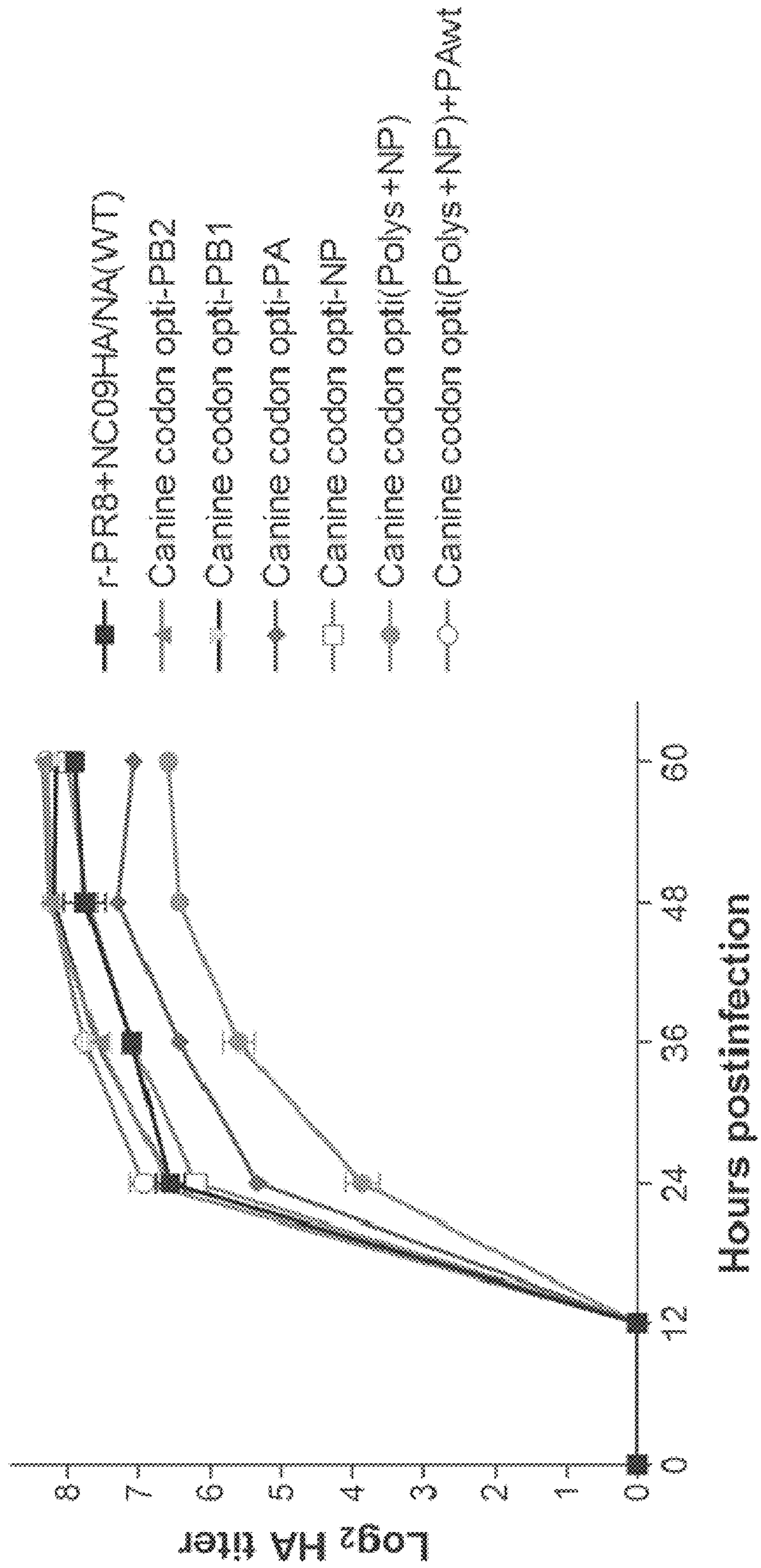

10D). Other gene segments were codon optimized and titers of viruses with those segments or combinations of optimized segments were determined (FIG. 10E).

In another approach to increase virus titer in MDCK cells, chimeric HA and NA genes were prepared (FIG. 13A) and titers of viruses having those genes were determined (FIG. 13B).

Viruses with combinations of the above-mentioned mutations (high growth backbone mutations, promoter mutations, chimeric HA and NA genes and canine codon optimization) were prepared and growth kinetics, PFU and HA titers of those viruses were determined (see FIG. 14).

An exemplary set of backbone mutations are canine codon opti-PB2+C4U+M202L, F323L; PB1: C4U+Q247H; PA: C4U+K142N; NP: Canine codon opti-NP+R74K; M: V97A, Y100H; and NS: K55E.

Figure 15:
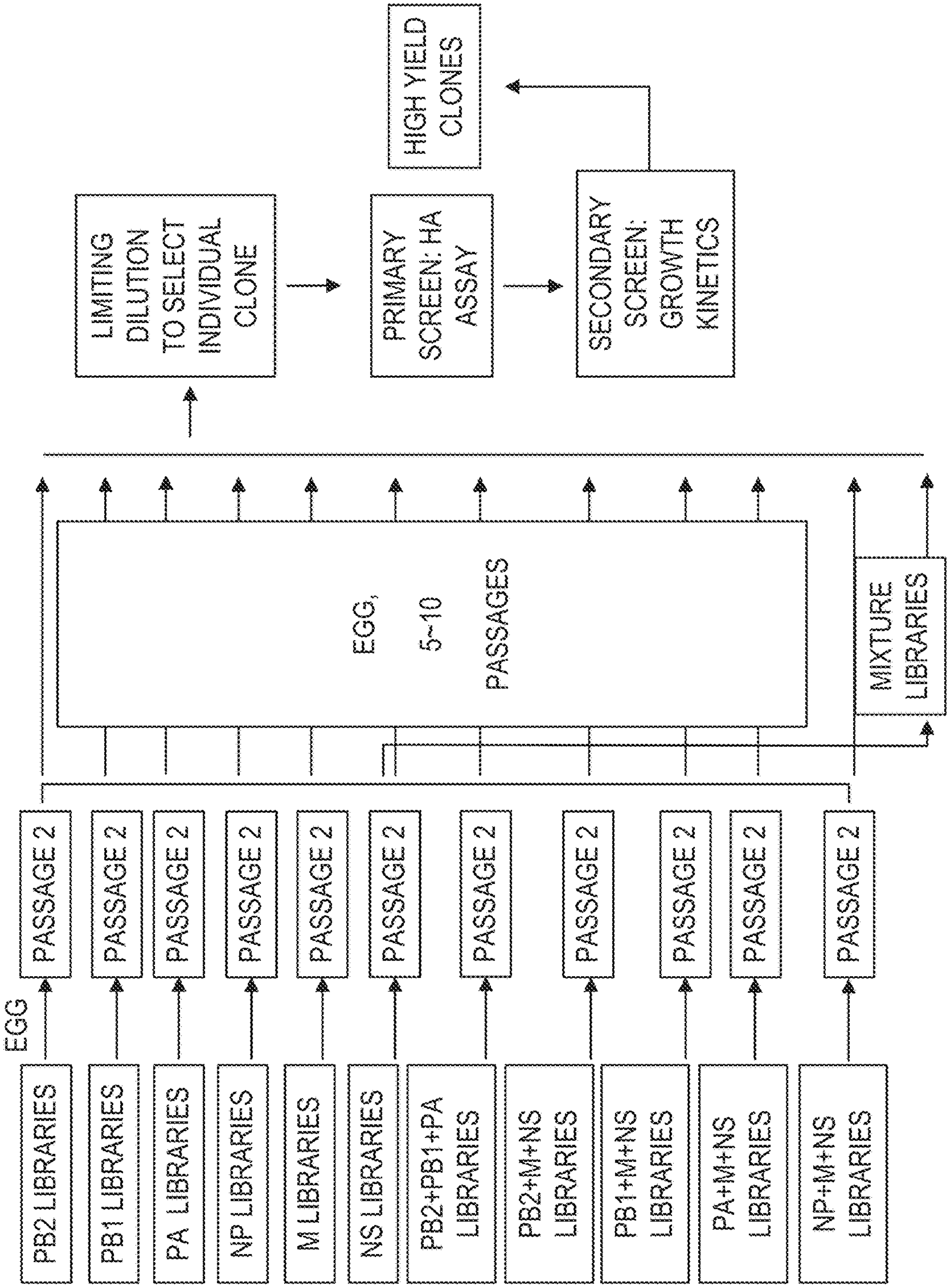
FIG. 15. Screening in eggs.
Figure 18A:
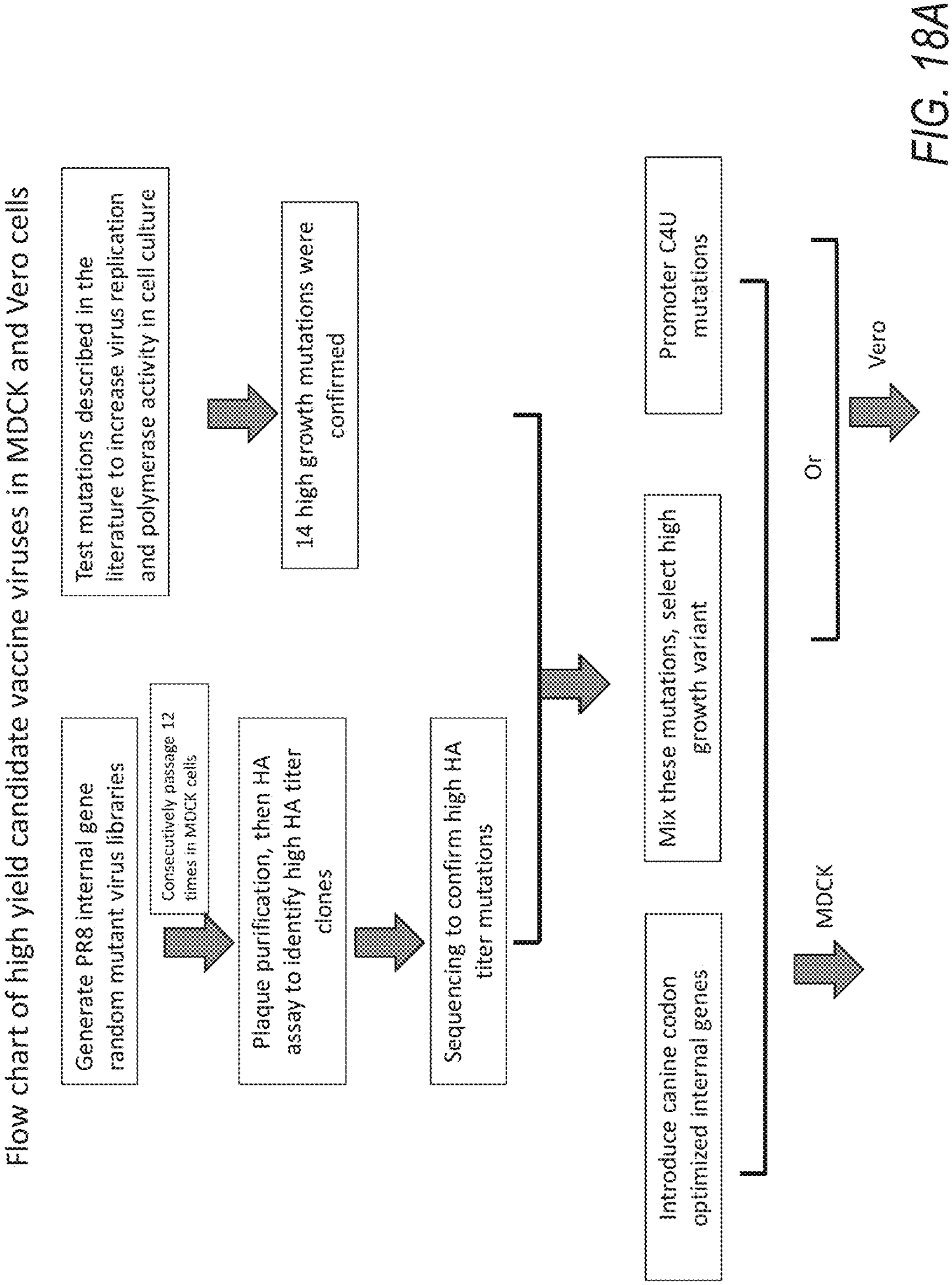
FIG. 18A-18B. Overview of generation of viruses with enhanced growth in MDCK cells and Vero cells.
Figure 18B:
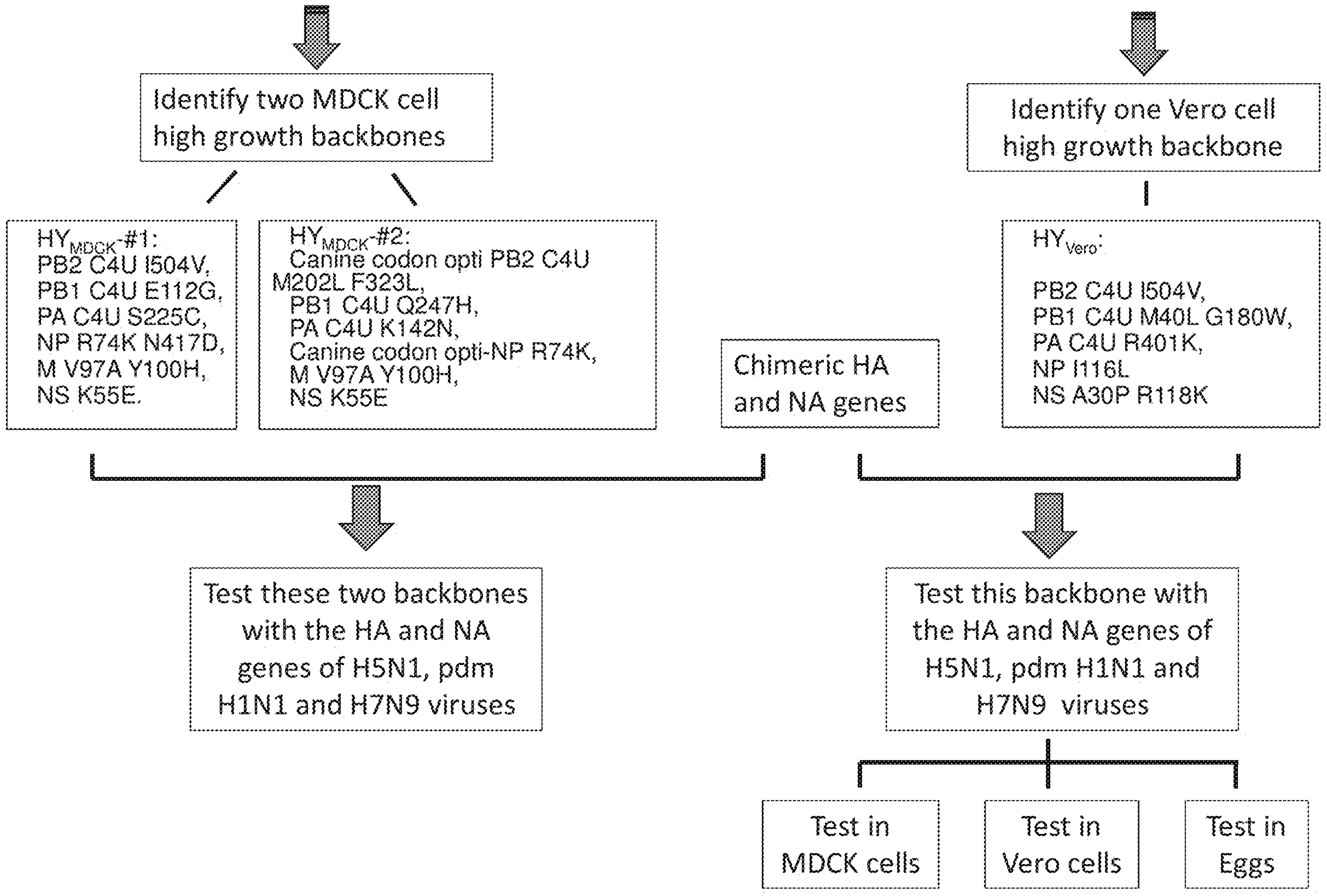

Any of the mutations described herein, or any combination thereof, may be combined with, for instance, seasonal H1N1 and H3N2, H3N2 Variant, PdmH1N1, H5N1, H7N9 or H9N2, or other clades or candidate vaccine strains. For example, HA and NA genes from A/Califoria/04/2009(pdm H1N1) were combined with the six internal genes of UW-PR/8 to generate "6+2" recombinant viruses. Eleven virus libraries were generated and passaged 10 times in eggs. Three rounds of limiting dilution were performed to screen for high growth mutants (FIG. 15). In one embodiment, a variant with high growth properties in MDCK cells has a PB2 gene segment with a promoter mutation (C4U) and a mutation that results in I504V (relative to the parental virus); a PB1 gene segment with a promoter mutation (C4U) and a mutation that results in E112G; a PA gene segment with a promoter mutation (C4U) and a mutation that results in S225C; a NP gene segment with mutations that result in R74K and N417D; a M gene segment with mutations that result in V97A and Y100H; and a NS gene segment with a mutation that results in K55E, where optionally the sequence of one or more gene segments, e.g., the NP gene segment, is modified to include canine codon optimized codons. In one embodiment, a variant with high growth properties in MDCK cells has a canine codon optimized PB2 gene segment with a promoter mutation (C4U) and mutations that result in M202L and F323L; a PB1 gene segment with a promoter mutation (C4U) and a mutation that results in Q247H; a PA gene segment with a promoter mutation (C4U) and a mutation that results in K142N; a canine codon optimized NP gene segment with a mutation that results in R74K; a M gene segment with mutations that result in V97A Y100H; and a NS gene segment with a mutation that results in K55E.

Similar experiments were conducted in Vero cells, e.g., after about 3 to 5 passages in Vero cells, using clones with high replicative properties in MDCK cells (see FIG. 16). FIG. 17 shows 5 viruses likely to have high replicative properties in Vero cells. In one embodiment, a PR8(UW) variant with high-growth properties in Vero cells has the following mutations that may be used in various combinations to increase the replicative ability of PR8(UW) virus: PB2 segment: C4U (promoter mutation), I504V (amino acid change); PB1 segment: C4U (promoter mutation); M40L (amino acid change), G180W (amino acid change); PA segment: C4U (promoter mutation), R401K (amino acid change); NP segment: I116L (amino acid change); NS segment: A30P (amino acid change in NS1), or R118K (amino acid change in NS1).

In one embodiment, a PR8(UW) variant with high-growth properties has the following residues that may be used in various combinations with each other and/or other residues, e.g., those that enhance virus replication, to increase the replicative ability of reassortants having PR8(UW) based viral segment(s): a HA segment with one or more of 136D, 162E, 179L, 182V, 184I, 252I, 449E, and/or 476I: a NA segment with 55S and/or 265V; a NS segment with NS1 having 118K; F2 with 81G; a PB1 segment with 62A, 261G, 361R, 621R, and/or 654S, and/or viral segment promoters with the growth-enhancing nucleotides described herein. e.g., having one or more of the nucleotide changes G1012C, A1013U, or U1014A in the M viral segment.

Example C

Figure 20:
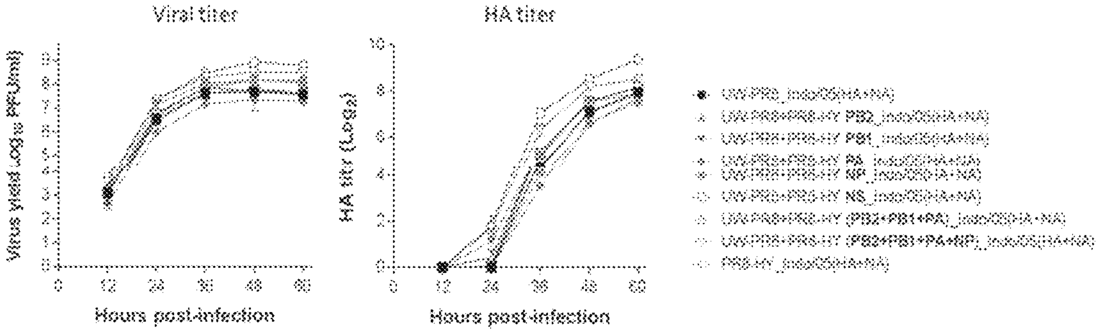
FIG. 20. Growth kinetics and HA titers of reassortant viruses possessing one or several vRNAs of PR8-HY virus.

To assess the contribution of individual viral RNA (vRNA) segments to high-yield properties, a series of reassortant viruses was generated that possessed one or several vRNA segments of a high-yield PR8 (PR8-HY) variant in the background of the parental virus [UW-PR8_Indo/05 (HA+NA)]. Vero cells were infected in triplicate with the indicated viruses at a MOI of 0.005 and incubated at 37° C. in the presence of trypsin. At the indicated time points, virus titers and HA titers were determined by performing plaque or HA assays, respectively. The results are shown in FIG. 20. These data indicated that several vRNA segments contribute to the properties of PR8-HY virus. In particular, the PB2+PB1+PA+NP vRNAs of PR8-HY virus conferred an appreciable increase in virus and HA titers, evidencing the enhanced replicative ability of this virus.

Figure 21:
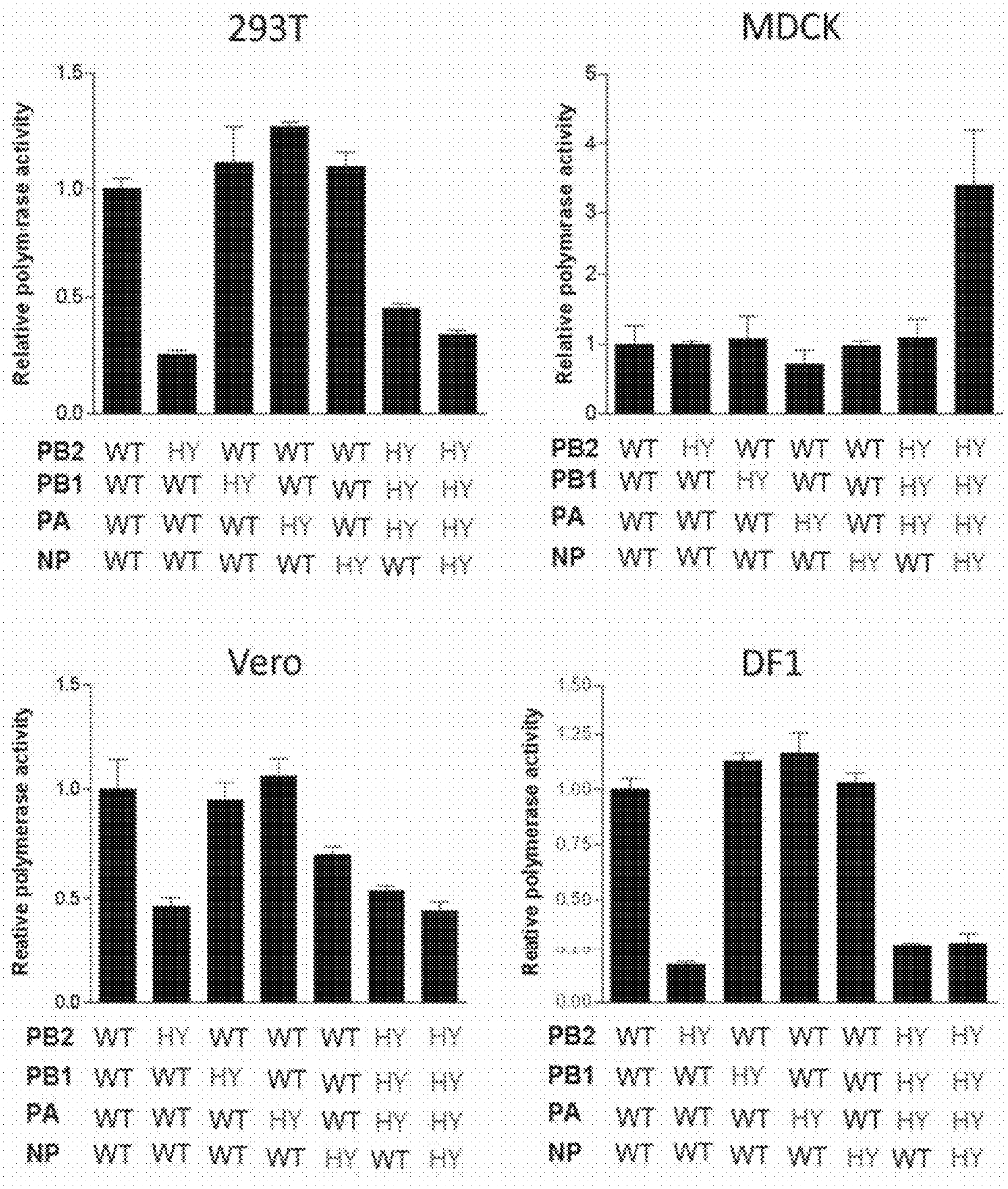
FIG. 21. Viral polymerase activity in mini-replicon assays in 293T, MDCK, Vero, and DF1 cells. The PB2, PB1, PA, and NP proteins were derived from UW-PR8 wild-type (WT) virus or from the high-yield PR8-HY (HY) variant.

To further assess which component of the viral replication complex that provides for high-yield properties, wild-type or high-yield PB2, PB1, PA, and NP proteins were tested in various combinations in minireplicon assays in human 293T, canine MDCK, African green monkey Vero, and avian DF1 cells. The results are shown in FIG. 21. Interestingly, the PB2, PB1, PA, and NP proteins of PR8-HY virus attenuated the viral replicative ability in 293T, Vero, and DF1 cells; this effect was primarily conferred by the PB2 protein. In contrast, the combination of PB2+PB1+PA+NP proteins derived from PR8-HY virus conferred a substantial increase in replicated ability in canine MDCK cells, which were used for the selection of PR8-HY virus. The findings suggested host-dependent mechanisms underlying the high yield of PR8-HY virus. For example, the combination of PB1+PA+NP proteins, or a subset thereof, derived from PR8-HY may confer enhanced viral replicative ability in 293T, Vero, and DF1 cells.

Exemplary Embodiments

An isolated, single cycle recombinant influenza virus is provided having at least seven viral segments selected from PA, PB1, PB2, NP, NS, M, HA or NA viral segments, or having at least six viral segments selected from PA, PB1, PB2, NP, NS, M, or HEF viral segments, one of which segments comprises coding sequences for an antigenic coronavirus protein or an antigenic portion thereof. In one embodiment, the antigenic coronavirus protein comprises coronavirus S (spike) sequences. In one embodiment, the antigenic coronavirus protein comprises S1 sequences. In one embodiment, the antigenic coronavirus protein comprises a soluble protein. In one embodiment, the antigenic portion comprises the receptor binding domain. In one embodiment, the antigenic coronavirus protein sequences or the portion thereof have at least 80% amino acid sequence identity to one of SEQ ID Nos. 25-28 and 50-52. In one embodiment, the virus comprises eight viral segments. In one embodiment, the virus comprises nine viral segments. In one embodiment, the virus is an influenza A or B virus. In one embodiment, the virus is an influenza C or D virus. In one embodiment, coding sequences for the antigenic coronavirus protein sequences or the portion thereof replace at least a portion of the coding sequences for one of PA, PB1, PB2, NP, NS1, NS2, M1, M2, HA, or NA. In one embodiment, coding sequences for the antigenic coronavirus protein sequences or the portion thereof are inserted into coding sequences in the viral segment of one of PA, PB1, PB2, NP, NS, M, HA or NA viral segments. In one embodiment, the virus is bivalent or trivalent. In one embodiment, the M viral segment is mutated so that upon viral replication the mutant M gene expresses a functional M1 protein and a mutant M2 protein with a deletion of the cytoplasmic tail and either lacking a transmembrane domain or having a mutated transmembrane domain. In one embodiment, the mutant M2 protein comprises the M2 extracellular domain. In one embodiment, the M2 extracellular domain comprises less than 24 residues. In one embodiment, the M2 extracellular domain comprises at least 9 residues. In one embodiment, the mutation in the transmembrane domain comprises at least one amino acid substitution. In one embodiment, the transmembrane domain is deleted. In one embodiment, the deletion in the transmembrane domain includes residues 29 to 31. In one embodiment, the deletion in the transmembrane domain comprises at least 10 residues. In one embodiment, two or more of the PA, PB1, PB2, NP, NS, and M viral segments have selected amino acid residues at positions 30, 31, 105, 142, 149, 225, 356, 357, 401, and/or 550 in PA; positions 40, 54, 59, 62, 63, 75, 76, 78, 79, 80, 112, 180, 247, 327, 507, 624, 644, 667, 694, 695, 697, 699, 700, 701, 702, 705, 713, and/or 714 in PB1; positions 57, 58, 59, 61, 66, 202, 323, 368, 391, 504, 591, 677, 678, and/or 679, in PB2; positions 74, 112, 116, 224, 293, 371, 377, 417, 422 or 442 in NP; positions 90, 97 and/or 100 in M1; or positions 30, 49, 55, 118, 140, 161 and/or 223 in NS1. In one embodiment, at least of the viral segments has a C to U promoter mutation. In one embodiment, at least one of PA, PB1, or PB2 viral segments has a C to U promoter mutation. In one embodiment, the PB2 segment has a C4U promoter mutation or 504V; the PB1 segment has one or more of C4U, 40L or 180W; the PA segment has C4U or 401K; the NP segment has 116L; or the NS segment has 30P in NS1 or 118K in NS1.

An isolated, single cycle recombinant influenza virus is provided having PA, PB1, PB2, NP, NS, M, HA or NA viral segments, or having PA, PB1, PB2, NP, NS, M, or HEF viral segments, wherein the NS or PB2 segment comprises coding sequences for an antigenic coronavirus protein or an antigenic portion thereof, and optionally the M viral segment is mutated so that upon viral replication the mutant M gene expresses a functional M1 protein and a mutant M2 protein with a deletion of the cytoplasmic tail and either lacking a transmembrane domain or having a mutated transmembrane domain. In one embodiment, the antigenic coronavirus protein comprises coronavirus S (spike) sequences. In one embodiment, the antigenic coronavirus protein comprises coronavirus S (spike) RBD sequences.

An isolated, single cycle recombinant influenza virus is provided having PA, PB1, PB2, NP, NS, M, HA or NA viral segments, or having PA, PB1, PB2, NP, NS, M, or HEF viral segments, wherein the NS segment comprises coding sequences for an antigenic coronavirus protein or an antigenic portion thereof, and optionally the M viral segment is mutated so that upon viral replication the mutant M gene expresses a functional M1 protein and a mutant M2 protein with a deletion of the cytoplasmic tail and either lacking a transmembrane domain or having a mutated transmembrane domain. In one embodiment, the antigenic coronavirus protein comprises coronavirus S (spike) sequences. In one embodiment, the antigenic coronavirus protein comprises coronavirus S (spike) RBD sequences.

Also provided is an isolated influenza virus having at least seven viral segments selected from PA, PB1, PB2, NP, NS, M, HA or NA viral segments, or having at least six viral segments selected from PA, PB1, PB2, NP, NS, M, or HEF viral segments, one of which segments comprises coding sequences for an antigenic coronavirus protein or an antigenic portion thereof. In one embodiment, the antigenic coronavirus protein comprises S1 sequences. In one embodiment, the antigenic portion comprises the receptor binding domain. In one embodiment, the antigenic coronavirus protein sequences or the portion thereof have at least 80% amino acid sequence identity to one of SEQ ID Nos. 25-28 and 50-52. In one embodiment, the virus comprises eight or nine viral segments. In one embodiment, the virus is an influenza A or B virus. In one embodiment, coding sequences for the antigenic coronavirus protein sequences or the portion thereof replace at least a portion of the coding sequences for one of PA, PB1, PB2, NP, NS1, NS2, M1, M2, HA, or NA. In one embodiment, coding sequences for the antigenic coronavirus protein sequences or the portion thereof are inserted into coding sequences in the viral segment of one of PA, PB1, PB2, NP, NS, M, HA or NA viral segments. In one embodiment, the virus is bivalent or trivalent. In one embodiment, the M viral segment is mutated so that upon viral replication the mutant M gene expresses a functional M1 protein and a mutant M2 protein with a deletion of the cytoplasmic tail and either lacking a transmembrane domain or having a mutated transmembrane domain, wherein the replication of the recombinant virus is abrogated or attenuated in vivo relative to a corresponding influenza virus with a wild-type M viral segment. In one embodiment, the mutant M2 protein comprises the M2 extracellular domain. In one embodiment, the M2 extracellular domain comprises at least 9 or 10 residues. In one embodiment, the mutation in the transmembrane domain comprises a deletion in the transmembrane domain. In one embodiment, two or more of the PA, PB1, PB2, NP, NS, and M viral segments have selected amino acid residues at positions 30, 31, 105, 142, 149, 225, 356, 357, 401, and/or 550 in PA; positions 40, 54, 59, 62, 63, 75, 76, 78, 79, 80, 112, 180, 247, 327, 507, 624, 644, 667, 694, 695, 697, 699, 700, 701, 702, 705, 713, and/or 714 in PB1; positions 57, 58, 59, 61, 66, 202, 323, 368, 391, 504, 591, 677, 678, and/or 679, in PB2; positions 74, 112, 116, 224, 293, 371, 377, 417, 422 or 442 in NP; positions 90, 97 and/or 100 in M1; or positions 30, 49, 55, 118, 140, 161 and/or 223 in NS1. In one embodiment, at least of the viral segments has a C to U promoter mutation. In one embodiment, at least one of PA, PB1, or PB2 viral segments has a C to U promoter mutation. In one embodiment, the PB2 segment has a C4U promoter mutation or 504V; the PB1 segment has one or more of C4U, 40L or 180W; the PA segment has C4U or 401K: the NP segment has 116L; or the NS segment has 30P in NS1 or 118K in NS1.

In one embodiment, a vaccine comprising an effective amount of the virus is provided. In one embodiment, the vaccine is formulated for intranasal delivery. In one embodiment, the virus is bivalent. In one embodiment, the recombinant virus comprises influenza A HA. In one embodiment, the virus comprises H1, H3, H5 or H7 HA. In one embodiment, the vaccine which further comprises a different influenza virus. In one embodiment, the vaccine further comprises at least two different influenza viruses. In one embodiment, the virus is inactivated.

Further provided is a method to immunize a vertebrate, comprising: administering to the vertebrate the vaccine disclosed herein. In one embodiment, the vertebrate is an avian. In one embodiment, the vertebrate is a mammal. In one embodiment, the vertebrate is a human. In one embodiment, the vaccine is intranasally administered. In one embodiment, the vaccine is intramuscularly administered. In one embodiment, more than one dose is administered.

The invention will be described by the following nonlimiting examples.

Example 1

In one embodiment, an eight segment single cycle recombinant influenza A virus is prepared. One of the viral RNA segments (for example, the NS segment) is modified to also express SARS-CoV-2 S (or portions thereof), e.g., a fusion of NS1 and SARS-CoV-2 S protein or a portion thereof. For fusion protein between the flu and SARS proteins, proteases that autocatalytically cleave are employed to generate functional flu and SARS proteins. The addition of heterologous protein sequences does not result in the need for a helper cell to express a protein in trans. However, if influenza virus coding sequences on one or more the viral segments are deleted (either a portion thereof or in their entirety), the corresponding influenza virus protein(s) are supplied in trans. For example, the viral M segment is modified by inserting two stop codons into M2 (downstream of the splice acceptor site), and by deleting the coding region for the transmembrane domain of M2, referred to as M2SR, which undergoes only one round of replication and requires a helper cell line for propagation That is in contrast to live-attenuated viruses which undergo several rounds of slow replication). In one embodiment, one or more of the internal viral segments are from PR8HY. In one embodiment, the HA and NA viral segments are from a heterologous strain. The M2SR having coronavirus sequences (CoroFlu M2SR) is intranasally administrated. In other embodiments, inactivated coronavirus/influenza viruses may be intramuscularly administered.

In one embodiment, a nine-segment virus is generated with eight segments expressing the flu proteins (with M2 modified as described above), and a ninth viral segment in which (part of) the flu coding region is replaced with SARS-CoV-2 S (or portions thereof).

In one embodiment, an attenuated virus is generated, e.g., one having M2 mutations that result in attenuation, e.g., M2del29-31 or M2 cytoplasmic tail deletions (see, e.g., del11 or del 22 etc. in Iwatsuki-Horimoto et al. (2006) and Watanabe et al. (2008).

Other alterations in M2 include two stop codons to prevent expression of the transmembrane domain and cytoplasmic tails and two stop codons and deletion of the coding region of the transmembrane domain (see Watanabe et al. (2009) and Sarawar et al. (2016), which are incorporated by reference herein)

Example 2

An influenza vaccine that includes coronavirus sequences and is limited to a single round of replication in vaccinated individuals, but stimulates mucosal, innate, humoral, and/or cell-mediated immune responses, was prepared. Phase I and Phase IIa clinical studies with the vaccine virus (without coronavirus sequences) have demonstrated its safety (no serious adverse events; no virus shedding) and the ability to elicit neutralizing immune responses to homologous and antigenically mismatched influenza virus strains. Importantly, this vaccine mimics the natural infection process and stimulates mucosal, innate, humoral, and cell-mediated immune responses. Thus, this platform may be employed to generate a single-cycle bivalent influenza vaccine expressing a soluble portion of the spike protein (the major antigen) of a coronavirus, e.g., the new 2019 coronavirus. The immunogenicity and protective efficacy of this vaccine is likely to be superior to that of inactivated vaccines, which stimulate B cell responses, but fail to induce other immune responses.

Figure 22:
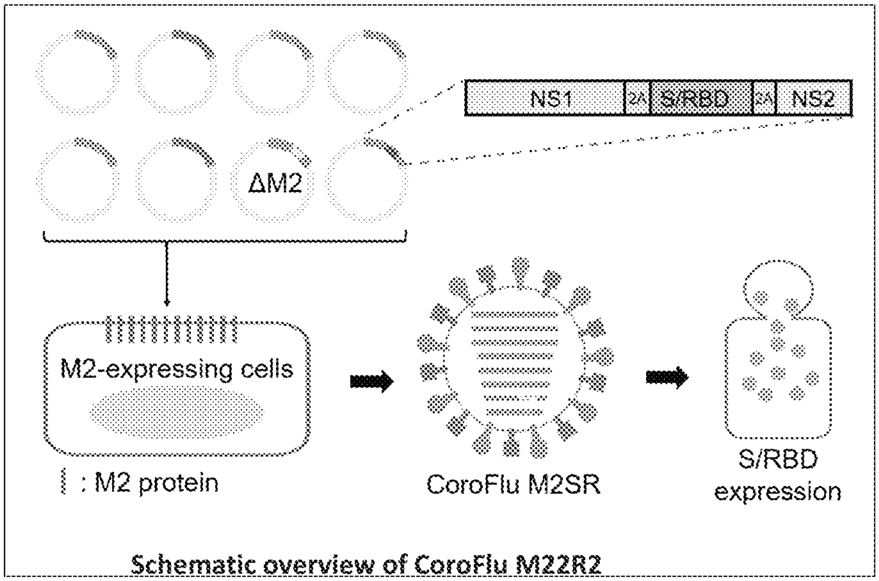
FIG. 22. Exemplary method to prepare bivalent viruses.

Generate a Bivalent Coronavirus/Influenza Virus Vaccine Candidate and Test its Protective Efficacy in Animal Models To generate the novel bivalent coronavirus/influenza virus vaccine based on the M2SR platform (called CoroFlu M2SR, FIG. 22), cells ware transfected with plasmids for influenza virus generation. One plasmid possesses a deletion of the influenza viral M2 coding region. In another plasmid, the coding region for the receptor-binding domain (RBD) of the 2019-nCoV spike (S) protein is inserted between the influenza viral NS1 and NS2 coding regions, separated by foot-and-mouse virus protease 2A autoproteolytic cleavage sites (2A). In cells expressing the M2 protein, CoroFlu M2SR vaccine virus is generated.

In one embodiment, the coronavirus S amino acid sequence, or a portion thereof, has at least 80%, e.g., 90%, 92%, 95%, 97% or 99%, including any integer between 80 and 99, contiguous amino acid sequence identity to a polypeptide having one of SEQ ID Nos. 25-28 and 50-52. In one embodiment, the S polypeptide or a portion thereof has one or more, for instance, 2, 5, 10, 15, 20 or more, conservative amino acids substitutions, e.g., conservative substitutions of up to 10% or 20% of the residues, relative to a polypeptide having one of SEQ ID Nos. 25-28 and 50-52. In one embodiment, a S polypeptide or a portion thereof has one or more, for instance, 2, 5, 10, 15, 20 or more, conservative amino acids substitutions. e.g., conservative substitutions of up to 10% or 20% of 2, 5, 10, 15, 20 or more, of a combination of conservative and non-conservative amino acids substitutions, e.g., conservative substitutions of up to 10% or 20% of the residues, or relative to a polypeptide with one of the sequences disclosed herein. In one embodiment, the coronavirus sequence in the influenza virus has 1, 2, 3, 4 or 5 substitutions relative to one of SEQ ID Nos. 25-28 and 50-52. In one embodiment, the coronavirus S1 sequence in the influenza virus has 1, 2, 3, 4 or 5 substitutions relative to the S1 sequence in one of SEQ ID Nos. 25-28 and 50-52. In one embodiment, the coronavirus RBD sequence in the influenza virus has 1, 2, 3, 4 or 5 substitutions relative to the RBD sequence in one of SEQ ID Nos. 25-28 and 50-52.

For example, the amino acid(s) can be any amino acid within these positions such as any of the amino acids listed in the table below.

| Original Residue | Exemplary Substitutions | Alternative Substitutions |
|---|---|---|
| Ala (A) | val; leu; ile | Val |
| Arg (R) | lys; gln; asn | Lys |
| Asn (N) | gln; his; lys; arg | Gln |
| Asp (D) | Glu, Asn | Glu, Asn |
| Cys (C) | Ser | Ser |
| Gln (Q) | Asn | Asn |
| Glu (E) | Asp | Asp |
| Gly (G) | Pro | Pro |

-continued

| Original Residue | Exemplary Substitutions | Alternative Substitutions |
|---|---|---|
| His (H) | asn; gln; lys; arg; gln; | Arg; Gln |
| Ile (I) | leu; val; met; ala; phe norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala | Leu |
| Pro (P) | Gly | Gly |
| Ser (S) | Thr | Thr |
| Thr (T) | Ser, Ala | Ser, Als |
| Trp (W) | Tyr | Tyr |
| Tyr (Y) | trp; phe; thr; ser | Phe |
| Val (V) | ile; leu; met; phe; ala; norleucine | Leu |

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: threonine-valine-leucine-isoleucine-alanine; phenylalanine-tyrosine; lysine-arginine; alanine-valine; glutamic-aspartic; and asparagine-glutamine.

The basic characterization of CoroFlu M2SR includes assessment of virus titers in the Vero M2 production cell line; the virus is passaged 10 consecutive times (followed by sequence analysis) in Vero M2-expressing cells to assess the genomic stability of CoroFlu M2SR.

Animal studies are carried out in Syrian hamsters (in which SARS-CoV replicates efficiently), in ferrets (an animal model that has been used for SARS-CoV research) and in transgenic mice expressing the human angiotensin-converting enzyme-2 (ACE-2) receptor, the SARS-CoV receptor to which 2019-nCoV also binds. Animals are intranasally administered with different amounts of CoroFlu M2SR (e.g., $10^5$ to $10^7$ PFU). Control animals are administered with M2SR vaccine (expressing the same HA and NA genes as CoroFlu M2SR, but not expressing S/RDB). Another control group is mock-treated. On days 1, 3, 5, and 7 after vaccination, nasal swab samples are collected to confirm the lack of virus shedding. Three weeks post-vaccination, serum samples are collected and tested for antibodies to SARS-Cov2 S/RBD and influenza HA; if the titers are low, animals are boosted.

Animals are vaccinated and challenged with live SARS-Cov2 or influenza virus three weeks after the last immunization. Control groups are mock-vaccinated, followed by live virus challenge with SARS-Cov2 and influenza virus. Groups of animals are euthanized on days 3, 6, and 9 post-infection to titrate the amounts of virus in the nasal turbinates and lungs. Other groups of animals are observed for weight changes and clinical symptoms. Nasal swabs are collected every other day (starting on day 1 post-challenge) to determine the virus load in the challenged animals.

Assess Whether the Vaccine Candidates Cause Antibody-Dependent Enhancement (ADE) of Virulence ADE (i.e., antibody-dependent enhancement of infectivity and disease severity) is a potential concern with the development of vaccines to a variety of viruses, including coronaviruses (Halsted, 2014; Huisman et al, 2009; Smatti et al., 2018; Wan et al., 2019; Wang et al., 2014; Yip et al., 2014; Takada et al., 2001; Takada et al., 2003; and Takada et al., 2007). Since ADE is most likely caused by non-neutralizing antibodies directed at sub-dominant epitopes, the use of S/RDB (instead of full-length S) may reduce the likelihood of ADE. To test this, animals are vaccinated with CoroFlu M2SR, M2SR, or mock-vaccinated, and sera will be collected three weeks later.

To assess ADE in vitro, the SARS-Cov2 is mixed with different dilutions of serum (obtained from vaccinated or control animals; see previous paragraph) and added to cells to determine virus titers. To assess ADE in vivo, two sets of experiments are carried out: In the first set of experiments, animals are administered different serum dilutions and subsequently infected with the SARS-Cov2. Control groups are treated with serum obtained from mock-vaccinated. In the other set of experiments, animals are vaccinated with CoroFlu M2SR, M2SR, or mock-vaccinated, and three weeks later infected with live SARS-Cov2. At different times post-infection, animals are euthanized to collect organs for virus titration and histopathological analysis, and sera are collected to determine antibody titers. The finding that sera obtained from CoroFlu M2SR-vaccinated animals and vaccination with CoroFlu M2SR do not increase virus titers, disease symptoms, or histopathology compared with the controls establishes the absence of ADE for CoroFlu M2SR vaccine.

REFERENCES

*Avery's Drug Treatment: Principles and Practice of Clinical Pharmacology and Therapeutics,* 3rd edition, ADIS Press, Ltd., Williams and Wilkins, Baltimore, Md. (1987).

Aymard-Henry et al., *Virology: A Practical Approach*, Oxford IRL Press, Oxford, 119-150 (1985).

Bachmeyer, *Intervirology,* 5:260 (1975).

Berkow et al., eds., *The Merck Manual,* 16th edition, Merck & Co., Rahway, N.J. (1992).

Halstead. *Microbiol. Spectr.,* 2: (2014).

Hatta et al., *Science,* 293:1840 (2001).

Horimoto et al., *J. Virol.,* 68:3120 (1994).

Horimoto et al., *Vaccine,* 24:3669 (2006).

Hsieh et al., *Science,* 369:1501 (2020).

Huisman et al., *Vaccine,* 27:505 (2009).

Itwasuki-Hormoto et al. *J. Virol.,* 80:5233 (2006).

Keitel et al., in Textbook of Influenza, eds. Nickolson, K. G., Webster, R. G., and Hay, A. (Blackwell, Oxford), pp. 373-390 (1998).

Laver & Webster, *Virology,* 6:511 (1976).

Neumann et al., *Adv. Virus Res.,* 5:265 (1999).

Neumann et al., *J. Gen. Virol.,* 83:2635 (2002).

Neumann et al., *J. Virol.,* 71:9690 (1997).

Neumann et al., *Proc. Natl. Acad. Sci. USA,* 98:9345 (1999).

Neumann et al., *Virology,* 287:243 (2001).

Osol (ed.), *Remington's Pharmaceutical Sciences*. Mack Publishing Co., Easton, Pa. 1324-1341 (1980).

Sarawar et al., *Vaccine,* 34:5090 (2016).

Smatti et al., *Front Microbiol.*, 9:2991 (2018).
Sugawara et al., *Biologicals*, 30:303 (2002).
Takada & Kawaoka, *Rev. Med. Virol.*, 13:387 (2003).
Takada et al., *J. Infect. Dis.*, 196:S347 (2007).
Takada et al., *J. Virol.*, 75:2324 (2001).
Wan et al., *J. Virol.*, doi:10.1128/JVI.02015-19 (2019).
Wang et al., *Biochem. Biophys. Res. Commun.*, 451:208 (2014).
Watanabe et al., *J. Virol.*, 82:2456 (2008).
Watanabe et al., *J. Virol.*, 83:5090 (2009).
Webby & Webster et al., *Science*, 302:1519 (2003).
Wood & Robertson, *Nat. Rev. Microbiol.*, 2:842 (2004).
World Health Organization TSR No. 673 (1982).
World Health Organization. Confirmed human cases of avian influenza A (H5N1). http://www.who.int/csr/disease/avian_influenza/country/en/index.html
Yip et al., *Virol. J.*, 11:82 (2014).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A composition for intranasal delivery comprising an amount of an isolated, single cycle, multivalent recombinant influenza virus having at least seven viral segments selected from influenza virus PA, PB1, PB2, NP, NS, M, HA or NA viral segments, or having at least six viral segments selected from PA, PB1, PB2, NP, NS, M, or HEF viral segments, wherein the NS viral segment comprises coding sequences for an antigenic coronavirus protein, or an antigenic portion thereof, flanked by protease recognition sites, wherein the coding sequences include a receptor binding domain of the coronavirus S protein, wherein the M viral segment comprises a mutant M gene that expresses a functional M1 protein and a mutant M2 protein with a deletion of the cytoplasmic tail and either lacking a transmembrane domain or having a mutated transmembrane domain, wherein the amount is effective to induce a mucosal immune response.

2. The composition of claim 1 wherein the antigenic coronavirus protein comprises S1 sequences.

3. The composition of claim 1 wherein antigenic coronavirus protein comprises a soluble protein.

4. The composition of claim 1 wherein the antigenic coronavirus protein sequences or the portion thereof have at least 80% amino acid sequence identity to one of SEQ ID Nos. 25-28 and 50-52.

5. The composition of claim 1 wherein the virus comprises eight or nine viral segments.

6. The composition of claim 1 wherein the virus is an influenza A or B virus.

7. The composition of claim 1 wherein the virus is bivalent or trivalent.

8. The composition of claim 1 wherein the M2 lacks the transmembrane domain.

9. The composition of claim 1 wherein at least one of PA, PB1, or PB2 viral segments has a C to U promoter mutation.

10. The composition of claim 1 wherein the PB2 segment has one or more of a C4U promoter mutation, 202L/323L or 504V; the PB1 segment has one or more of C4U, 40L, 112G, 180W or 247H; the PA segment has one or more of C4U, 142N, 225C or 401K; the NP segment has 74K or 116L; or the NS segment has 30P in NS1 or 118K in NS1, wherein the numbering is relative to a PB2 encoded by SEQ ID NO:3, a PB1 encoded by SEQ ID NO:2, a PA encoded by SEQ ID NO:1, a NP encoded by SEQ ID NO:4 or a NS1 encoded by SEQ ID NO:6.

11. A vaccine comprising the virus of claim 1.

12. The vaccine of claim 11 wherein the recombinant virus comprises influenza A HA.

13. A method to immunize a vertebrate, comprising: administering to the vertebrate the vaccine of claim 11.

14. The method of claim 13 wherein the vertebrate is a human.

15. The composition of claim 1 wherein the NS viral segment encodes protease recognition sites comprising T2A (EGRGSLLTCGDVEENPGP; SEQ ID NO:53), P2A (ATNFSLLKQAGDVEENPGP; SEQ ID NO:54), E2A (QCTNYALLKLAGDVESNPGP; SEQ ID NO: 55) or F2A (VKQTLNFDLLKAGDVESNPGP; SEQ ID NO:56).

16. The composition of claim 1 wherein the protease recognition sequences are autocatalytically cleaved.

* * * * *

SEQUENCE LISTING

```
<160> NUMBER OF SEQ ID NOS: 56

<210> SEQ ID NO 1
<211> LENGTH: 2233
<212> TYPE: DNA
<213> ORGANISM: Influenza virus

<400> SEQUENCE: 1

agcgaaagca ggtactgatc caaaatggaa gattttgtgc gacaatgctt caatccgatg      60

attgtcgagc ttgcggaaaa aacaatgaaa gagtatgggg aggacctgaa aatcgaaaca     120

aacaaatttg cagcaatatg cactcacttg gaagtatgct tcatgtattc agattttcac     180

ttcatcaatg agcaaggcga gtcaataatc gtagaacttg gtgatccaaa tgcacttttg     240

aagcacagat ttgaaataat cgagggaaga gatcgcacaa tggcctggac agtagtaaac     300

agtatttgca acactacagg ggctgagaaa ccaaagtttc taccagattt gtatgattac     360

aaggagaata gattcatcga aattggagta acaaggagag aagttcacat atactatctg     420

gaaaaggcca ataaaattaa atctgagaaa acacacatcc acattttctc gttcactggg     480

gaagaaatgg ccacaaaggc agactacact ctcgatgaag aaagcagggc taggatcaaa     540

accagactat tcaccataag acaagaaatg gccagcagag gcctctggga ttcctttcgt     600

cagtccgaga gaggagaaga gacaattgaa gaaaggtttg aaatcacagg aacaatgcgc     660

aagcttgccg accaaagtct cccgccgaac ttctccagcc ttgaaaattt tagagcctat     720

gtggatggat tcgaaccgaa cggctacatt gagggcaagc tgtctcaaat gtccaaagaa     780

gtaaatgcta gaattgaacc ttttttgaaa acaacaccac gaccacttag acttccgaat     840

gggcctccct gttctcagcg gtccaaattc ctgctgatgg atgccttaaa attaagcatt     900

gaggacccaa gtcatgaagg agagggaata ccgctatatg atgcaatcaa atgcatgaga     960

acattctttg gatggaagga acccaatgtt gttaaaccac acgaaaaggg aataaatcca    1020

aattatcttc tgtcatggaa gcaagtactg gcagaactgc aggacattga gaatgaggag    1080

aaaattccaa agactaaaaa tatgaagaaa acaagtcagc taaagtgggc acttggtgag    1140

aacatggcac cagaaaaggt agactttgac gactgtaaag atgtaggtga tttgaagcaa    1200

tatgatagtg atgaaccaga attgaggtcg cttgcaagtt ggattcagaa tgagtttaac    1260

aaggcatgcg aactgacaga ttcaagctgg atagagctcg atgagattgg agaagatgtg    1320

gctccaattg aacacattgc aagcatgaga aggaattatt tcacatcaga ggtgtctcac    1380

tgcagagcca cagaatacat aatgaaggga gtgtacatca atactgcctt gcttaatgca    1440

tcttgtgcag caatggatga tttccaatta attccaatga taagcaagtg tagaactaag    1500

gagggaaggc gaaagaccaa cttgtatggt ttcatcataa aaggaagatc ccacttaagg    1560
```

```
aatgacaccg acgtggtaaa ctttgtgagc atggagtttt ctctcactga cccaagactt   1620

gaaccacata aatgggagaa gtactgtgtt cttgagatag gagatatgct tataagaagt   1680

gccataggcc aggtttcaag gcccatgttc ttgtatgtga gaacaaatgg aacctcaaaa   1740

attaaaatga aatggggaat ggagatgagg cgttgcctcc tccagtcact tcaacaaatt   1800

gagagtatga ttgaagctga gtcctctgtc aaagagaaag acatgaccaa agagttcttt   1860

gagaacaaat cagaaacatg gcccattgga gagtccccca aaggagtgga ggaaagttcc   1920

attgggaagg tctgcaggac tttattagca aagtcggtat tcaacagctt gtatgcatct   1980

ccacaactag aaggattttc agctgaatca agaaaactgc ttcttatcgt tcaggctctt   2040

agggacaacc tggaacctgg gacctttgat cttgggggc tatatgaagc aattgaggag   2100

tgcctgatta atgatccctg ggttttgctt aatgcttctt ggttcaactc cttccttaca   2160

catgcattga gttagttgtg gcagtgctac tatttgctat ccatactgtc caaaaaagta   2220

ccttgtttct act                                                      2233
```

<210> SEQ ID NO 2
<211> LENGTH: 2340
<212> TYPE: DNA
<213> ORGANISM: Influenza virus

<400> SEQUENCE: 2

```
agcgaaagca ggcaaaccat ttgaatggat gtcaatccga ccttactttt cttaaaagtg     60

ccagcacaaa atgctataag cacaactttc ccttatactg gagaccctcc ttacagccat    120

gggacaggaa caggatacac catggatact gtcaacagga cacatcagta ctcagaaaag    180

ggaagatgga caacaaacac cgaaactgga gcaccgcaac tcaacccgat tgatgggcca    240

ctgccagaag acaatgaacc aagtggttat gcccaaacag attgtgtatt ggaggcgatg    300

gctttccttg aggaatccca tcctggtatt tttgaaaact cgtgtattga aacgatggag    360

gttgttcagc aaacacgagt agacaagctg acacaaggcc gacagaccta tgactggact    420

ctaaatagaa accaacctgc tgcaacagca ttggccaaca caatagaagt gttcagatca    480

aatggcctca cggccaatga gtctggaagg ctcatagact tccttaagga tgtaatggag    540

tcaatgaaca aagaagaaat ggggatcaca actcattttc agagaaagag acgggtgaga    600

gacaatatga ctaagaaaat gataacacag agaacaatgg gtaaaaagaa gcagagattg    660

aacaaaagga gttatctaat tagagcattg accctgaaca caatgaccaa agatgctgag    720

agagggaagc taaaacggag agcaattgca accccaggga tgcaaataag gggtttgta     780

tactttgttg agacactggc aaggagtata tgtgagaaac ttgaacaatc agggttgcca    840

gttggaggca atgagaagaa agcaaagttg gcaaatgttg taaggaagat gatgaccaat    900

tctcaggaca ccgaactttc tttcaccatc actggagata acaccaaatg gaacgaaaat    960

cagaatcctc ggatgttttt ggccatgatc acatatatga ccagaaatca gcccgaatgg   1020

ttcagaaatg ttctaagtat tgctccaata atgttctcaa acaaaatggc gagactggga   1080

aaagggtata tgtttgagag caagagtatg aaacttagaa ctcaaatacc tgcagaaatg   1140

ctagcaagca tcgatttgaa atatttcaat gattcaacaa gaaagaagat tgaaaaaatc   1200

cgaccgctct taatagaggg gactgcatca ttgagccctg gaatgatgat gggcatgttc   1260

aatatgttaa gcactgtatt aggcgtctcc atcctgaatc ttggacaaaa gagatacacc   1320

aagactactt actggtggga tggtcttcaa tcctctgacg attttgctct gattgtgaat   1380

gcacccaatc atgaagggat tcaagccgga gtcgacaggt tttatcgaac ctgtaagcta   1440
```

-continued cttggaatca atatgagcaa gaaaaagtct tacataaaca gaacaggtac atttgaattc 1500
acaagttttt tctatcgtta tgggtttgtt gccaatttca gcatggagct tcccagtttt 1560
ggggtgtctg ggatcaacga gtcagcggac atgagtattg gagttactgt catcaaaaac 1620
aatatgataa acaatgatct tggtccagca acagctcaaa tggcccttca gttgttcatc 1680
aaagattaca ggtacacgta ccgatgccat ataggtgaca cacaaataca aacccgaaga 1740
tcatttgaaa taaagaaact gtgggagcaa acccgttcca aagctggact gctggtctcc 1800
gacggaggcc caaatttata caacattaga aatctccaca ttcctgaagt ctgcctaaaa 1860
tgggaattga tggatgagga ttaccagggg cgtttatgca acccactgaa cccatttgtc 1920
agccataaag aaattgaatc aatgaacaat gcagtgatga tgccagcaca tggtccagcc 1980
aaaaacatgg agtatgatgc tgttgcaaca acacactcct ggatccccaa aagaaatcga 2040
tccatcttga tacaagtcaa agaggagtac ttgaggatga acaaatgtac caaaggtgct 2100
gcaatttatt tgaaaaattc ttccccagca gttcatacag aagaccagtc gggatatcca 2160
gtatggtgga ggctatggtt tccagagccc gaattgatgc acggattgat ttcgaatctg 2220
gaaggataaa gaaagaagag ttcactgaga tcatgaagat ctgttccacc attgaagagc 2280
tcagacggca aaaatagtga atttagcttg tccttcatga aaaaatgcct tgtttctact 2340

<210> SEQ ID NO 3
<211> LENGTH: 2341
<212> TYPE: DNA
<213> ORGANISM: Influenza virus

<400> SEQUENCE: 3
agcgaaagca ggtcaattat attcaatatg gaaagaataa aagaactacg aaatctaatg 60
tcgcagtctc gcacccgcga gatactcaca aaaaccaccg tggaccatat ggccataatc 120
aagaagtaca catcaggaag acaggagaag aacccagcac ttaggatgaa atggatgatg 180
gcaatgaaat atccaattac agcagacaag aggataacgg aaatgattcc tgagagaaat 240
gagcaaggac aaactttatg gagtaaaatg aatgatgccg gatcagaccg agtgatggta 300
tcacctctgg ctgtgacatg gtggaatagg aatggaccaa taacaaatac agttcattat 360
ccaaaaatct acaaaactta ttttgaaaga gtcgaaaggc taaagcatgg aacctttggc 420
cctgtccatt ttagaaacca agtcaaaata cgtcggagag ttgacataaa tcctggtcat 480
gcagatctca gtgccaagga ggcacaggat gtaatcatgg aagttgtttt ccctaacgaa 540
gtgggagcca ggatactaac atcggaatcg caactaacga taaccaaaga gaagaaagaa 600
gaactccagg attgcaaaat ttctcctttg atggttgcat acatgttgga gagagaactg 660
gtccgcaaaa cgagattcct cccagtggct ggtggaacaa gcagtgtgta cattgaagtg 720
ttgcatttga ctcaaggaac atgctgggaa cagatgtata ctccaggagg ggaagtgagg 780
aatgatgatg ttgatcaaag cttgattatt gctgctagga acatagtgag aagagctgca 840
gtatcagcag atccactagc atctttattg gagatgtgcc acagcacaca gattggtgga 900
attaggatgg tagacatcct taggcagaac ccaacagaag agcaagccgt ggatatatgc 960
aaggctgcaa tgggactgag aattagctca tccttcagtt ttggtggatt cacatttaag 1020
agaacaagcg gatcatcagt caagagagag gaagaggtgc ttacgggcaa tcttcaaaca 1080
ttgaagataa gagtgcatga gggatatgaa gagttcacaa tggttgggag aagagcaaca 1140
gccatactca gaaaagcaac caggagattg attcagctga tagtgagtgg gagagacgaa 1200

-continued

```
cagtcgattg ccgaagcaat aattgtggcc atggtatttt cacaagagga ttgtatgata   1260

aaagcagtca gaggtgatct gaatttcgtc aatagggcga atcaacgatt gaatcctatg   1320

catcaacttt taagacattt tcagaaggat gcgaaagtgc tttttcaaaa ttggggagtt   1380

gaacctatcg acaatgtgat gggaatgatt gggatattgc ccgacatgac tccaagcatc   1440

gagatgtcaa tgagaggagt gagaatcagc aaaatgggtg tagatgagta ctccagcacg   1500

gagagggtag tggtgagcat tgaccgtttt ttgagaatcc gggaccaacg aggaaatgta   1560

ctactgtctc ccgaggaggt cagtgaaaca cagggaacag agaaactgac aataacttac   1620

tcatcgtcaa tgatgtggga gattaatggt cctgaatcag tgttggtcaa tacctatcaa   1680

tggatcatca gaaactggga aactgttaaa attcagtggt cccagaaccc tacaatgcta   1740

tacaataaaa tggaatttga accatttcag tctttagtac ctaaggccat tagaggccaa   1800

tacagtgggt ttgtaagaac tctgttccaa caaatgaggg atgtgcttgg gacatttgat   1860

accgcacaga taataaaact tcttcccttc gcagccgctc caccaaagca aagtagaatg   1920

cagttctcct catttactgt gaatgtgagg ggatcaggaa tgagaatact tgtaaggggc   1980

aattctcctg tattcaacta taacaaggcc acgaagagac tcacagttct cggaaaggat   2040

gctggcactt taactgaaga cccagatgaa ggcacagctg gagtggagtc cgctgttctg   2100

aggggattcc tcattctggg caaagaagac aagagatatg ggccagcact aagcatcaat   2160

gaactgagca accttgcgaa aggagagaag gctaatgtgc taattgggca aggagacgtg   2220

gtgttggtaa tgaaacggaa acgggactct agcatactta ctgacagcca gacagcgacc   2280

aaaagaattc ggatggccat caattagtgt cgaatagttt aaaaacgacc ttgtttctac   2340

t                                                                   2341

<210> SEQ ID NO 4
<211> LENGTH: 1565
<212> TYPE: DNA
<213> ORGANISM: Influenza virus

<400> SEQUENCE: 4

agcaaaagca gggtagataa tcactcactg agtgacatca aaatcatggc gtctcaaggc     60

accaaacgat cttacgaaca gatggagact gatggagaac gccagaatgc cactgaaatc    120

agagcatccg tcggaaaaat gattggtgga attggacgat tctacatcca aatgtgcacc    180

gaactcaaac tcagtgatta tgagggacgg ttgatccaaa acagcttaac aatagagaga    240

atggtgctct ctgcttttga cgaaaggaga aataaatacc ttgaagaaca tcccagtgcg    300

gggaaagatc ctaagaaaac tggaggacct atatacagga gagtaaacgg aaagtggatg    360

agagaactca tcctttatga caaagaagaa ataaggcgaa tctggcgcca agctaataat    420

ggtgacgatg caacggctgg tctgactcac atgatgatct ggcattccaa tttgaatgat    480

gcaacttatc agaggacaag agctcttgtt cgcaccggaa tggatcccag gatgtgctct    540

ctgatgcaag gttcaactct ccctaggagg tctggagccg caggtgctgc agtcaaagga    600

gttggaacaa tggtgatgga attggtcaga atgatcaaac gtgggatcaa tgatcggaac    660

ttctggaggg gtgagaatgg acgaaaaaca agaattgctt atgaaagaat gtgcaacatt    720

ctcaaaggga aatttcaaac tgctgcacaa aaagcaatga tggatcaagt gagagagagc    780

cggaacccag ggaatgctga gttcgaagat ctcacttttc tagcacggtc tgcactcata    840

ttgagagggt cggttgctca caagtcctgc ctgcctgcct gtgtgtatgg acctgccgta    900

gccagtgggt acgactttga aagggaggga tactctctag tcggaataga ccctttcaga    960
```

-continued

```
ctgcttcaaa acagccaagt gtacagccta atcagaccaa atgagaatcc agcacacaag   1020

agtcaactgg tgtggatggc atgccattct gccgcatttg aagatctaag agtattaagc   1080

ttcatcaaag ggacgaaggt gctcccaaga gggaagcttt ccactagagg agttcaaatt   1140

gcttccaatg aaaatatgga gactatggaa tcaagtacac ttgaactgag aagcaggtac   1200

tgggccataa ggaccagaag tggaggaaac accaatcaac agagggcatc tgcgggccaa   1260

atcagcatac aacctacgtt ctcagtacag agaaatctcc cttttgacag aacaaccatt   1320

atggcagcat tcaatgggaa tacagagggg agaacatctg acatgaggac cgaaatcata   1380

aggatgatgg aaagtgcaag accagaagat gtgtctttcc aggggcgggg agtcttcgag   1440

ctctcggacg aaaaggcagc gagcccgatc gtgccttcct ttgacatgag taatgaagga   1500

tcttatttct tcggagacaa tgcagaggag tacgacaatt aaagaaaaat acccttgttt   1560

ctact                                                               1565
```

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
<211> LENGTH: 2342
<212> TYPE: DNA
<213> ORGANISM: Influenza virus

<400> SEQUENCE: 10

```
agcgaaagca ggcaaaccat ttgaatggat gtcaatccga ccttactttt cttaaaagtg     60

ccagcacaaa atgctataag cacaactttc ccttataccg gagaccctcc ttacagccat    120

gggacaggaa caggatacac catggatact gtcaacagga cacatcagta ctcagaaaag    180

ggaagatgga caacaaacac cgaaactgga gcaccgcaac tcaacccgat tgatgggcca    240

ctgccagaag acaatgaacc aagtggttat gcccaaacag attgtgtatt ggaagcaatg    300

gctttccttg aggaatccca tcctggtatt tttgaaaact cgtgtattga aacgatggag    360

gttgttcagc aaacactgag tagacaagct gacacaaggc cgacagacct atgactggac    420
```

-continued

```
tttaaataga aaccagcctg ctgcaacagc attggccaac acaatagaag tgttcagatc    480

aaatggcctc acggccaatg agtcaggaag gctcatagac ttccttaagg atgtaatgga    540

gtcaatgaaa aaagaagaaa tggggatcac aactcatttt cagagaaaga gacgggtgag    600

agacaatatg actaagaaaa tgataacaca gagaacaata ggtaaaagga aacagagatt    660

gaacaaaagg ggttatctaa ttagagcatt gaccctgaac acaatgacca aagatgctga    720

gagagggaag ctaaaacgga gagcaattgc aaccccaggg atgcaaataa gggggtttgt    780

atactttgtt gagacactgg caaggagtat atgtgagaaa cttgaacaat cagggttgcc    840

agttggaggc aatgagaaga aagcaaagtt ggcaaatgtt gtaaggaaga tgatgaccaa    900

ttctcaggac accgaacttt ctttcaccat cactggagat aacaccaaat ggaacgaaaa    960

tcagaatcct cggatgtttt tggccatgat cacatatatg accagaaatc agcccgaatg   1020

gttcagaaat gttctaagta ttgctccaat aatgttctca aacaaaatgg cgagactggg   1080

aaaagggtat atgtttgaga gcaagagtat gaaacttaga actcaaatac ctgcagaaat   1140

gctagcaagc attgatttga aatatttcaa tgattcaaca agaaagaaga ttgaaaaaat   1200

ccgaccgctc ttaatagagg ggactgcatc attgagccct ggaatgatga tgggcatgtt   1260

caatatgtta agcactgtat taggcgtctc catcctgaat cttggacaaa agagatacac   1320

caagactact tactggtggg atggtcttca atcctctgac gattttgctc tgattgtgaa   1380

tgcacccaat catgaaggga ttcaagccgg agtcgacagg ttttatcgaa cctgtaagct   1440

acttggaatc aatatgagca agaaaaagtc ttacataaac agaacaggta catttgaatt   1500

cacaagtttt ttctatcgtt atgggtttgt tgccaatttc agcatggagc ttcccagttt   1560

tggggtgtct gggatcaacg agtcagcgga catgagtatt ggagttactg tcatcaaaaa   1620

caatatgata aacaatgatc ttggtccagc aacagctcaa atggcccttc agttgttcat   1680

caaagattac aggtacacgt accgatgcca tagaggtgac acacaaatac aaacccgaag   1740

atcatttgaa ataaagaaac tgtgggagca aacccgttcc aaagctggac tgctggtctc   1800

cgacggaggc ccaaatttat acaacattag aaatctccac attcctgaag tctgcctaaa   1860

atgggaattg atggatgagg attaccaggg gcgtttatgc aacccactga acccatttgt   1920

cagccataaa gaaattgaat caatgaacaa tgcagtgatg atgccagcac atggtccagc   1980

caaaaacatg gagtatgatg ctgttgcaac aacacactcc tggatcccca aaagaaatcg   2040

atccatcttg aatacaagtc aaagaggagt acttgaagat gaacaaatgt accaaaggtg   2100

ctggaattta tttgaaaaat tcttccccag cagttcatac agaagaccag tcgggatatc   2160

cagtatggtg gaggctatgg tttccagagc ccgaattgat gcacggattg atttcgaatc   2220

tggaaggata aagaaagaag agttcactga gatcatgaag atctgttcca ccattgaaga   2280

gctcagacgg caaaaatagt gaatttagct tgtccttcat gaaaaaatgc cttgtttcta   2340

ct                                                                  2342
```

```
<210> SEQ ID NO 11
<211> LENGTH: 2341
<212> TYPE: DNA
<213> ORGANISM: Influenza virus

<400> SEQUENCE: 11

agcgaaagca ggtcaattat attcaatatg gaaagaataa aagaactaag aaatctaatg     60

tcgcagtctc gcacccgcga gatactcaca aaaaccaccg tggaccatat ggccataatc    120
```

-continued

```
aagaagtaca catcaggaag acaggagaag aacccagcac ttaggatgaa atggatgatg    180
gcaatgaaat atccaattac agcagacaag aggataacgg aaatgattcc tgagagaaat    240
gagcaaggac aaactttatg gagtaaaatg aatgatgccg gatcagaccg agtgatggta    300
tcacctctgg ctgtgacatg gtggaatagg aatggaccaa tgacaaatac agttcattat    360
ccaaaaatct acaaaactta ttttgaaaga gtcgaaaggc taaagcatgg aacctttggc    420
cctgtccatt ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
ttgcatttga ctcaaggaac atgctgggaa cagatgtata ctccaggagg ggaagtgaag    780
aatgatgatg ttgatcaaag cttgattatt gctgctagga acatagtgag aagagctgca    840
gtatcagcag acccactagc atctttattg gagatgtgcc acagcacaca gattggtgga    900
attaggatgg tagacatcct taagcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggcaa tcttcaaaca   1080
ttgaagataa gagtgcatga gggatctgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtta gaggtgatct gaatttcgtc aatagggcga atcagcgact gaatcctatg   1320
catcaacttt taagacattt tcagaaggat gcgaaagtgc tttttcaaaa ttggggagtt   1380
gaacctatcg acaatgtgat gggaatgatt gggatattgc ccgacatgac tccaagcatc   1440
gagatgtcaa tgagaggagt gagaatcagc aaaatgggtg tagatgagta ctccagcacg   1500
gagagggtag tggtgagcat tgaccggttc ttgagagtca gggaccaacg aggaaatgta   1560
ctactgtctc ccgaggaggt cagtgaaaca cagggaacag agaaactgac aataacttac   1620
tcatcgtcaa tgatgtggga gattaatggt cctgaatcag tgttggtcaa tacctatcaa   1680
tggatcatca gaaactggga aactgttaaa attcagtggt cccagaaccc tacaatgcta   1740
tacaataaaa tggaatttga accatttcag tctttagtac ctaaggccat tagaggccaa   1800
tacagtgggt ttgtaagaac tctgttccaa caaatgaggg atgtgcttgg gacatttgat   1860
accgcacaga taataaaact tcttcccttc gcagccgctc caccaaagca aagtagaatg   1920
cagttctcct catttactgt gaatgtgagg ggatcaggaa tgagaatact tgtaaggggc   1980
aattctcctg tattcaacta caacaaggcc acgaagagac tcacagttct cggaaaggat   2040
gctggcactt taaccgaaga cccagatgaa ggcacagctg gagtggagtc cgctgttctg   2100
aggggattcc tcattctggg caaagaagac aggagatatg ggccagcatt aagcatcaat   2160
gaactgagca accttgcgaa aggagagaag gctaatgtgc taattgggca aggagacgtg   2220
gtgttggtaa tgaaacgaaa acgggactct agcatactta ctgacagcca gacagcgacc   2280
aaaagaattc ggatggccat caattagtgt cgaatagttt aaaaacgacc ttgtttctac   2340
t                                                                   2341
```

<210> SEQ ID NO 12
<211> LENGTH: 2234

<212> TYPE: DNA
<213> ORGANISM: Influenza virus

<400> SEQUENCE: 12

```
agcgaaagca ggtactgatt caaaatggaa gattttgtgc gacaatgctt caatccgatg     60
attgtcgagc ttgcggaaaa aacaatgaaa gagtatgggg aggacctgaa aatcgaaaca    120
aacaaatttg cagcaatatg cactcacttg gaagtatgct tcatgtattc agatttccac    180
ttcatcaatg agcaaggcga gtcaataatc gtagaacttg gtgatcctaa tgcacttttg    240
aagcacagat ttgaaataat cgagggaaga gatcgcacaa tggcctggac agtagtaaac    300
agtatttgca acactacagg ggctgagaaa ccaaagtttc taccagattt gtatgattac    360
aaggaaaata gattcatcga aattggagta acaaggagag aagttcacat atactatctg    420
gaaaaggcca ataaaattaa atctgagaaa acacacatcc acatttttctc gttcactggg    480
gaagaaatgg ccacaagggc cgactacact ctcgatgaag aaagcagggc taggatcaaa    540
accaggctat tcaccataag acaagaaatg gccagcagag gcctctggga ttcctttcgt    600
cagtccgaga gaggagaaga gacaattgaa gaaaggtttg aaatcacagg aacaatgcgc    660
aagcttgccg accaaagtct cccgccgaac ttctccagcc ttgaaaattt tagagcctat    720
gtggatggat tcgaaccgaa cggctacatt gagggcaagc tgtctcaaat gtccaaagaa    780
gtaaatgcta gaattgaacc tttttgaaa acaacaccac gaccacttag acttccgaat    840
gggcctccct gttctcagcg gtccaaattc ctgctgatgg atgccttaaa attaagcatt    900
gaggacccaa gtcatgaagg agagggaata ccgctatatg atgcaatcaa atgcatgaga    960
acattctttg gatggaagga acccaatgtt gttaaaccac acgaaaaggg aataaatcca   1020
aattatcttc tgtcatggaa gcaagtactg gcagaactgc aggacattga gaatgaggag   1080
aaaattccaa agactaaaaa tatgaaaaaa acaagtcagc taaagtgggc acttggtgag   1140
aacatggcac cagaaaaggt agactttgac gactgtaaag atgtaggtga tttgaagcaa   1200
tatgatagtg atgaaccaga attgaggtcg cttgcaagtt ggattcagaa tgagttcaac   1260
aaggcatgcg aactgacaga ttcaagctgg atagagcttg atgagattgg agaagatgtg   1320
gctccaattg aacacattgc aagcatgaga aggaattatt tcacatcaga ggtgtctcac   1380
tgcagagcca cagaatacat aatgaagggg gtgtacatca atactgcctt acttaatgca   1440
tcttgtgcag caatggatga tttccaatta attccaatga taagcaagtg tagaactaag   1500
gagggaaggc gaaagaccaa cttgtatggt ttcatcataa aaggaagatc ccacttaagg   1560
aatgacaccg acgtggtaaa ctttgtgagc atggagtttt ctctcactga cccaagactt   1620
gaaccacaca aatgggagaa gtactgtgtt cttgagatag gagatatgct tctaagaagt   1680
gccataggcc aggtttcaag gcccatgttc ttgtatgtga ggacaaatgg aacctcaaaa   1740
attaaaatga aatggggaat ggagatgagg cgttgtctcc tccagtcact tcaacaaatt   1800
gagagtatga ttgaagctga gtcctctgtc aaagagaaag acatgaccaa agagttcttt   1860
gagaacaaat cagaaacatg gcccattgga gagtctccca aaggagtgga ggaaagttcc   1920
attggggaag gtctgcagga ctttattagc aaagtcggta tttaacagct tgtatgcatc   1980
tccacaacta gaaggatttt cagctgaatc aagaaaactg cttcttatcg ttcaggctct   2040
tagggacaat ctggaacctg ggacctttga tcttgggggg ctatatgaag caattgagga   2100
gtgcctaatt aatgatccct gggttttgct taatgcttct tggttcaact ccttccttac   2160
acatgcattg agttagttgt ggcagtgcta ctatttgcta tccatactgt ccaaaaaagt   2220
```

-continued accttgtttc tact 2234

<210> SEQ ID NO 13
<211> LENGTH: 1565
<212> TYPE: DNA
<213> ORGANISM: Influenza virus

<400> SEQUENCE: 13
agcaaaagca gggtagataa tcactcactg agtgacatca aaatcatggc gtcccaaggc 60
accaaacggt cttacgaaca gatggagact gatggagaac gccagaatgc cactgaaatc 120
agagcatccg tcggaaaaat gattggtgga attggacgat tctacatcca aatgtgcaca 180
gaacttaaac tcagtgatta tgagggacgg ttgatccaaa acagcttaac aatagagaga 240
atggtgctct ctgcttttga cgaaaggaga aataaatacc tggaagaaca tcccagtgcg 300
gggaaagatc ctaagaaaac tggaggacct atatacagaa gagtaaacgg aaagtggatg 360
agagaactca tcctttatga caaagaagaa ataaggcgaa tctggcgcca agctaataat 420
ggtgacgatg caacggctgg tctgactcac atgatgatct ggcattccaa tttgaatgat 480
gcaacttatc agaggacaag ggctcttgtt cgcaccggaa tggatcccag gatgtgctct 540
ctgatgcaag gttcaactct ccctaggagg tctggagccg caggtgctgc agtcaaagga 600
gttggaacaa tggtgatgga attggtcagg atgatcaaac gtgggatcaa tgatcggaac 660
ttctggaggg gtgagaatgg acgaaaaaca agaattgctt atgaaagaat gtgcaacatt 720
ctcaaaggga aatttcaaac tgctgcacaa aaagcaatga tggatcaagt gagagagagc 780
cggaacccag ggaatgctga gttcgaagat ctcacttttc tagcacggtc tgcactcata 840
ttgagagggt cggttgctca caagtcctgc ctgcctgcct gtgtgtatgg acctgccgta 900
gccagtgggt acgactttga aagagaggga tactctctag tcggaataga ccctttcaga 960
ctgcttcaaa acagccaagt gtacagccta atcagaccaa atgagaatcc agcacacaag 1020
agtcaactgg tgtggatggc atgccattct gccgcatttg aagatctaag agtattgagc 1080
ttcatcaaag ggacgaaggt ggtcccaaga gggaagcttt ccactagagg agttcaaatt 1140
gcttccaatg aaaatatgga gactatggaa tcaagtacac ttgaactgag aagcaggtac 1200
tgggccataa ggaccagaag tggaggaaac accaatcaac agagggcatc tgcgggccaa 1260
atcagcatac aacctacgtt ctcagtacag agaaatctcc cttttgacag aacaaccgtt 1320
atggcagcat tcactgggaa tacagagggg agaacatctg acatgaggac cgaaatcata 1380
aggatgatgg aaagtgcaag accagaagat gtgtctttcc aggggcgggg agtcttcgag 1440
ctctcggacg aaaaggcagc gagcccgatc gtgccttcct ttgacatgag taatgaagga 1500
tcttatttct tcggagacaa tgcagaggag tacgacaatt aaagaaaaat acccttgttt 1560
ctact 1565

<210> SEQ ID NO 14
<211> LENGTH: 1027
<212> TYPE: DNA
<213> ORGANISM: Influenza virus

<400> SEQUENCE: 14
agcaaaagca ggtagatatt gaaagatgag tcttctaacc gaggtcgaaa cgtacgttct 60
ctctatcatc ccgtcaggcc ccctcaaagc cgagatcgca cagagacttg aagatgtctt 120
tgcagggaag aacaccgatc ttgaggttct catggaatgg ctaaagacaa gaccaatcct 180
gtcacctctg actaagggga ttttaggatt tgtgttcacg ctcaccgtgc ccagtgagcg 240
aggactgcag cgtagacgct ttgtccaaaa tgcccttaat gggaacgggg atccaaataa 300
catggacaaa gcagttaaac tgtataggaa gctcaagagg gagataacat tccatggggc 360
caaagaaatc tcactcagtt attctgctgg tgcacttgcc agttgtatgg gcctcatata 420
caacaggatg gggctgtga ccactgaagt ggcatttggc ctggtatgtg caacctgtga 480
acagattgct gactcccagc atcggtctca taggcaaatg gtgacaacaa ccaacccact 540
aatcagacat gagaacagaa tggttttagc cagcactaca gctaaggcta tggagcaaat 600
ggctggatcg agtgagcaag cagcagaggc catggaggtt gctagtcagg ctaggcaaat 660
ggtgcaagcg atgagaacca ttgggactca tcctagctcc agtgctggtc tgaaaaatga 720
tcttcttgaa aatttgcagg cctatcagaa acgaatgggg gtgcagatgc aacggttcaa 780
gtgatcctct cgctattgcc gcaaatatca ttgggatctt gcacttgata ttgtggattc 840
ttgatcgtct ttttttcaaa tgcatttacc gtcgctttaa atacggactg aaaggagggc 900
cttctacgga aggagtgcca aagtctatga gggaagaata tcgaaaggaa cagcagagtg 960
ctgtggatgc tgacgatggt cattttgtca gcatagagct ggagtaaaaa actaccttgt 1020
ttctact 1027

<210> SEQ ID NO 15
<211> LENGTH: 890
<212> TYPE: DNA
<213> ORGANISM: Influenza virus

<400> SEQUENCE: 15
agcaaaagca gggtgacaaa gacataatgg atccaaacac tgtgtcaagc tttcaggtag 60
attgctttct ttggcatgtc cgcaaacgag ttgcagacca agaactaggt gatgccccat 120
tccttgatcg gcttcgccga gatcagaaat ccctaagagg aagggggcagc actcttggtc 180 tggacatcga gacagccaca cgtgctggaa agcagatagt ggagcggatt ctgaaagaag 240
aatccgatga ggcacttaaa atgaccatgg cctctgtacc tgcgtcgcgt tacctaaccg 300
acatgactct tgaggaaatg tcaagggaat ggtccatgct catacccaag cagaaagtgg 360
caggccctct ttgtatcaga atggaccagg cgatcatgga taaaaacatc atactgaaag 420
cgaacttcag tgtgattttt gaccggctgg agactctaat attgctaagg gctttcaccg 480
aagagggagc aattgttggc gaaatttcac cattgccttc tcttccagga catactgctg 540
aggatgtcaa aaatgcagtt ggagtcctca tcggaggact tgaatggaat gataacacag 600
ttcgagtctc tgaaactcta cagagattcg cttggagaag cagtaatgag aatgggagac 660
ctccactcac tccaaaacag aaacgagaaa tggcgggaac aattaggtca gaagtttgaa 720
gaaataagat ggttgattga agaagtgaga cacaaactga aggtaacaga gaatagtttt 780
gagcaaataa catttatgca agccttacat ctattgcttg aagtggagca agagataaga 840
actttctcat ttcagcttat ttaataataa aaaacaccct tgtttctact 890

<210> SEQ ID NO 16
<211> LENGTH: 2341
<212> TYPE: DNA
<213> ORGANISM: Influenza virus

<400> SEQUENCE: 16
agcgaaagca ggtcaattat attcaatatg gaaagaataa aagaactacg aaatctaatg 60
tcgcagtctc gcacccgcga gatactcaca aaaaccaccg tggaccatat ggccataatc 120

-continued

```
aagaagtaca catcaggaag acaggagaag aacccagcac tgaggatgaa atggatgatg    180
gcaatgaaat atccaattac agcagacaag aggatcaccg aaatgattcc tgagagaaat    240
gagcagggac agactctgtg gagtaaaatg aatgatgccg gatcagaccg agtgatggtg    300
tcacctctgg ctgtgacatg gtggaatagg aatggaccaa tcacaaatac agtgcattat    360
ccaaaaatct acaaaactta ttttgaaaga gtcgaaaggc tgaagcatgg aacctttggc    420
cctgtccatt ttagaaacca ggtcaaaatc cggcggagag tggacatcaa tcctggtcat    480
gcagatctca gtgccaagga ggcacaggat gtgatcatgg aagtggtgtt ccctaacgaa    540
gtgggagcca ggattctgac atccgaatcc cagctgacca ttaccaaaga gaagaaagaa    600
gaactccagg attgcaaaat ttctcctctg atggtggcat acatgctgga gagagaactg    660
gtccgcaaaa caagattcct cccagtggct ggtggaacaa gcagtgtgta cattgaagtg    720
ctgcatctga ctcagggaac atgctgggaa cagatgtata ctccaggagg ggaagtgagg    780
aatgatgatg tggatcagag cctgattatt gctgctagga acattgtgag aagagctgca    840
gtgtcagcag atccactggc atctctgctg gagatgtgcc acagcacaca gattggtgga    900
attaggatgg tggacatcct gaggcagaac ccaacagaag agcaggccgt ggatatttgc    960
aaggctgcaa tgggactgag aattagctca tccttcagtt ttggtggatt cacatttaag   1020
agaacaagcg gatcatcagt caagagagag gaagaggtgc tgaccggcaa tctgcagaca   1080
ctgaagatca gagtgcatga gggatatgaa gagttcacaa tggtggggag aagagcaaca   1140
gccatcctca gaaaagcaac caggagactg attcagctga tcgtgagtgg gagagacgaa   1200
cagtccattg ccgaagcaat tattgtggcc atggtgtttt cacaggagga ttgtatgatt   1260
aaagcagtca gaggtgatct gaatttcgtc aatagggcca atcagcgact gaatcctatg   1320
catcagctgc tgagacattt tcagaaggat gccaaagtgc tgtttcagaa ttggggagtg   1380
gaacctatcg acaatgtgat gggaatgatt gggatcctgc ccgacatgac tccaagcatc   1440
gagatgtcaa tgagaggagt gagaatcagc aaaatgggtg tggatgagta ctccagcacc   1500
gagagggtcg tggtgagcat tgacagattt ctgagaatcc gggaccagcg aggaaatgtg   1560
ctcctgtctc ccgaggaggt cagtgaaaca cagggaacag agaaactgac aattacttac   1620
tcatcctcaa tgatgtggga gattaatggt cctgaatcag tgctggtcaa tacctatcag   1680
tggatcatca gaaactggga aactgtgaaa attcagtggt cccagaaccc tacaatgctg   1740
tacaataaaa tggaatttga accatttcag tctctggtgc ctaaggccat tagaggccag   1800
tacagtgggt ttgtgagaac tctgttccag cagatgaggg atgtgctggg gacatttgat   1860
accgcacaga ttattaaact gctgcccttc gcagccgctc caccaaagca gagtagaatg   1920
cagttctcct catttactgt gaatgtgagg ggatcaggaa tgagaatcct ggtgaggggc   1980
aattctcctg tgttcaacta taacaaggcc accaagagac tcacagtgct cggaaaggat   2040
gctggcactc tgactgaaga cccagatgaa ggcacagctg gagtggagtc cgctgtgctg   2100
aggggattcc tcattctggg caaagaagac aagagatatg ggccagcact gagcatcaat   2160
gaactgagca acctggccaa aggagagaag gctaatgtgc taattgggca aggagacgtg   2220
gtgttggtaa tgaaacggaa acgggactct agcatactta ctgacagcca gacagcgacc   2280
aaaagaattc ggatggccat caattagtgt cgaatagttt aaaaacgacc ttgtttctac   2340
t                                                                   2341
```

<210> SEQ ID NO 17
<211> LENGTH: 2341

-continued

<212> TYPE: DNA
<213> ORGANISM: Influenza virus

<400> SEQUENCE: 17

```
agcgaaagca ggcaaaccat ttgaatggat gtcaatccga ccttactttt cttaaaagtg     60
ccagcacaaa atgctataag cacaactttc ccttatactg gagaccctcc ttacagccat    120
gggacaggaa caggatacac catggatact gtcaacagga cacatcagta ctcagaaaag    180
ggaagatgga caacaaacac cgaaactgga gcaccgcaac tcaacccgat tgatgggcca    240
ctgccagaag acaatgaacc aagtggttat gcccaaacag attgtgtatt ggaggcgatg    300
gctttccttg aggaatccca tcctggtatt tttgaaaact cgtgtattga aacgatggag    360
gttgttcagc aaacacgagt ggacaagctg acacagggcc gacagaccta tgactggact    420
ctgaatagaa accagcctgc tgcaacagca ctggccaaca caatcgaagt gttcagatca    480
aatggcctca ccgccaatga gtctggaagg ctcatcgact tcctgaagga tgtgatggag    540
tcaatgaaca aagaagaaat ggggatcaca actcattttc agagaaagag acgggtgaga    600
gacaatatga ctaagaaaat gattacacag agaacaatgg gtaaaaagaa gcagagactg    660
aacaaaagga gttatctgat tagagcactg accctgaaca caatgaccaa agatgctgag    720
agagggaagc tgaaacggag agcaattgca accccaggga tgcagattag gggtttgtg    780
tactttgtgg agacactggc aaggagtatt tgtgagaaac tggaacagtc agggctgcca    840
gtgggaggca atgagaagaa agcaaagctg gcaaatgtgg tgaggaagat gatgaccaat    900
tctcaggaca ccgaactgtc tttcaccatc actggagata acaccaaatg gaacgaaaat    960
cagaatcctc ggatgtttct ggccatgatc acatatatga ccagaaatca gcccgaatgg   1020
ttcagaaatg tgctgagtat tgctccaatt atgttctcaa acaaaatggc cagactggga   1080
aaagggtata tgtttgagag caagagtatg aaactgagaa ctcagattcc tgcagaaatg   1140
ctggcaagca tcgatctgaa atatttcaat gattcaacaa gaaagaagat tgaaaaaatc   1200
cgacccctcc tgattgaggg gactgcatca ctgagccctg gaatgatgat gggcatgttc   1260
aatatgctga gcactgtgct gggcgtctcc atcctgaatc tgggacagaa gagatacacc   1320
aagactactt actggtggga tggtctgcag tcctctgacg attttgctct gattgtgaat   1380
gcacccaatc atgaagggat tcaggccgga gtcgacaggt tttatcgaac ctgtaagctg   1440
ctgggaatca atatgagcaa gaaaaagtct tacatcaaca gaacaggtac atttgaattc   1500
acaagttttt tctatcgcta tgggtttgtg gccaatttca gcatggagct gcccagtttt   1560
ggggtgtctg ggatcaacga gtcagccgac atgagtattg gagtgactgt catcaaaaac   1620
aatatgatca acaatgatct gggtccagca acagctcaga tggccctgca gctgttcatc   1680
aaagattaca ggtacaccta ccgatgccat atcggtgaca cacagattca gacccgaaga   1740
tcatttgaaa tcaagaaact gtgggagcag acccgctcca aagctggact gctggtctcc   1800
gacggaggcc caaatctgta caacattaga aatctccaca ttcctgaagt ctgcctgaaa   1860
tgggaactga tggatgagga ttaccagggg cgcctgtgca acccactgaa cccatttgtc   1920
agccataaag aaattgaatc aatgaacaat gcagtgatga tgccagcaca tggtccagcc   1980
aaaaacatgg agtatgatgc tgtggcaaca acacactcct ggatccccaa aagaaatcga   2040
tccatcctga atacaagtca gagaggagtg ctggaggatg aacagatgta ccagaggtgc   2100
tgcaatctgt ttgaaaaatt cttccccagc agttcataca gaagaccagt cgggatctcc   2160
agtatggtgg aggctatggt gtccagagcc cgaattgatg cacggattga tttcgaatct   2220
```

-continued

```
ggaaggatca agaaagaaga gttcactgag atcatgaaga tctgttccac cattgaagag   2280

ctcagacggc aaaaatagtg aatttagctt gtccttcatg aaaaaatgcc ttgtttctac   2340

t                                                                   2341


<210> SEQ ID NO 18
<211> LENGTH: 2233
<212> TYPE: DNA
<213> ORGANISM: Influenza virus

<400> SEQUENCE: 18

agcgaaagca ggtactgatc caaaatggaa gattttgtgc gacaatgctt caatccgatg     60

attgtcgagc ttgcggaaaa aacaatgaaa gagtatgggg aggacctgaa aatcgaaaca    120

aacaaatttg cagcaatatg cactcacttg gaagtatgct tcatgtattc agattttcac    180

ttcatcaatg agcaaggcga gtcaataatc gtagaacttg gtgatccaaa tgcacttttg    240

aagcacagat ttgaaataat cgagggaaga gatcgcacaa tggcctggac agtagtaaac    300

agtatttgca acactacagg ggctgagaaa ccaaagtttc taccagattt gtatgattac    360

aaggagaata gattcatcga aattggagta acaaggagag aagttcacat atactatctg    420

gaaaaggcca ataaaattaa atctgagaaa acacacatcc acattttctc gttcactggg    480

gaagaaatgg ccacaaaggc agactacact ctcgatgaag aaagcagggc taggatcaaa    540

accagactat tcaccataag acaagaaatg gccagcagag gcctctggga ttcctttcgt    600

cagtccgaga gaggagaaga gacaattgaa gaaaggtttg aaatcacagg aacaatgcgc    660

aagcttgccg accaaagtct cccgccgaac ttctccagcc ttgaaaattt tagagcctat    720

gtggatggat tcgaaccgaa cggctacatt gagggcaagc tgtctcaaat gtccaaagaa    780

gtaaatgcta gaattgaacc ttttctgaaa acaacaccac gaccactgag actgcccaat    840

gggcctccct gttctcagcg gtccaaattc ctgctgatgg atgccctgaa actgagcatt    900

gaggacccaa gtcatgaagg agagggaatt cccctgtatg atgcaatcaa atgcatgaga    960

acattctttg gatggaagga acccaatgtg gtgaaaccac acgaaaaggg aatcaatcca   1020

aattatctgc tgtcatggaa gcaggtgctg gcagaactgc aggacattga gaatgaggag   1080

aaaattccaa agactaaaaa tatgaagaaa acaagtcagc tgaagtgggc actgggtgag   1140

aacatggcac cagaaaaggt ggactttgac gactgtaaag atgtgggtga tctgaagcag   1200

tatgatagtg atgaaccaga actgaggtcc ctggcaagtt ggattcagaa tgagtttaac   1260

aaggcatgcg aactgacaga ttcaagctgg attgagctcg atgagattgg agaagatgtg   1320

gctccaattg aacacattgc aagcatgaga aggaattatt tcacatcaga ggtgtctcac   1380

tgcagagcca cagaatacat catgaaggga gtgtacatca atactgccct gctgaatgca   1440

tcttgtgcag caatggatga tttccagctg attccaatga tcagcaagtg tagaactaag   1500

gagggaaggc gaaagaccaa cctgtatggt ttcatcatca aaggaagatc ccacctgagg   1560

aatgacaccg acgtggtgaa ctttgtgagc atggagtttt ctctcactga cccaagactg   1620

gaaccacata aatgggagaa gtactgtgtg ctggagattg gagatatgct gatcagaagt   1680

gccattggcc aggtgtcaag gcccatgttc ctgtatgtga gaacaaatgg aacctcaaaa   1740

attaaaatga aatggggaat ggagatgagg cgctgcctcc tccagtcact gcagcagatt   1800

gagagtatga ttgaagctga gtcctctgtc aaagagaaag acatgaccaa agagttcttt   1860

gagaacaaat cagaaacatg gcccattgga gagtccccca aggagtgga ggaaagttcc   1920

attgggaagg tctgcaggac tctgctggca aagtccgtgt tcaacagcct gtatgcatct   1980
```

-continued

```
ccacagctgg aaggattttc agctgaatca agaaaactgc tgctgatcgt gcaggctctg   2040

agggacaacc tggaacctgg gacctttgat ctgggggggc tgtatgaagc aattgaggag   2100

tgcctgatta atgatccctg ggtgctgctg aatgcttctt ggttcaactc cttccttaca   2160

catgcattga gttagttgtg gcagtgctac tatttgctat ccatactgtc caaaaaagta   2220

ccttgtttct act                                                      2233
```

<210> SEQ ID NO 19
<211> LENGTH: 1565
<212> TYPE: DNA
<213> ORGANISM: Influenza virus

<400> SEQUENCE: 19

```
agcaaaagca gggtagataa tcactcactg agtgacatca aaatcatggc gtctcaaggc     60

accaaacgat cttacgaaca gatggagact gatggagaac gccagaatgc cactgaaatc    120

agagcatccg tcggaaaaat gattggtgga attggacgat tctacatcca gatgtgcacc    180

gaactcaaac tcagtgatta tgagggacgg ctgatccaga acagcctgac aatcgagaga    240

atggtgctct ctgcttttga cgaaaggaga aataaatacc tggaagaaca tcccagtgcc    300

gggaaagatc ctaagaaaac tggaggacct atctacagga gagtgaacgg aaagtggatg    360

agagaactca tcctgtatga caaagaagaa atcaggcgaa tctggcgcca ggctaataat    420

ggtgacgatg caaccgctgg tctgactcac atgatgatct ggcattccaa tctgaatgat    480

gcaacttatc agaggacaag agctctggtg cgcaccggaa tggatcccag gatgtgctct    540

ctgatgcagg gttcaactct ccctaggagg tctggagccg caggtgctgc agtcaaagga    600

gtgggaacaa tggtgatgga actggtcaga atgatcaaaa gagggatcaa tgatcggaac    660

ttctggaggg gtgagaatgg acgaaaaaca agaattgctt atgaaagaat gtgcaacatt    720

ctcaaaggga aatttcagac tgctgcacag aaagcaatga tggatcaggt gagagagagc    780

cggaacccag ggaatgctga gttcgaagat ctcacttttc tggcacggtc tgcactcatc    840

ctgagagggt ccgtggctca caagtcctgc ctgcctgcct gtgtgtatgg acctgccgtg    900

gccagtgggt acgactttga aagggaggga tactctctgg tcggaattga ccctttcaga    960

ctgctgcaga acagccaggt gtacagcctg atcagaccaa atgagaatcc agcacacaag   1020

agtcagctgg tgtggatggc atgccattct gccgcatttg aagatctgag agtgctgagc   1080

ttcatcaaag ggaccaaggt gctcccaaga gggaagctgt ccactagagg agtgcagatt   1140

gcttccaatg aaaatatgga gactatggaa tcaagtacac tggaactgag aagcaggtac   1200

tgggccatca ggaccagaag tggaggaaac accaatcagc agagggcatc tgccggccag   1260

atcagcattc agcctacctt ctcagtgcag agaaatctcc cttttgacag aacaaccatt   1320

atggcagcat tcaatgggaa tacagagggg agaacatctg acatgaggac cgaaatcatc   1380

aggatgatgg aaagtgcaag accagaagat gtgtctttcc aggggcgggg agtcttcgag   1440

ctctcggacg aaaaggcagc gagcccgatc gtgccttcct ttgacatgag taatgaagga   1500

tcttatttct tcggagacaa tgcagaggag tacgacaatt aaagaaaaat acccttgttt   1560

ctact                                                               1565
```

<210> SEQ ID NO 20
<211> LENGTH: 1684
<212> TYPE: DNA
<213> ORGANISM: Influenza virus -continued

<400> SEQUENCE: 20

```
atgaacactc aaatcctggt attcgctctg attgcgatca ttccaacaaa tgcagacaaa      60
atctgcctcg gacatcatgc cgtgtcaaac ggaaccaaag taaacacatt aactgaaaga     120
ggagtggaag tcgtcaatgc aactgaaaca gtggaacgaa caaacatccc caggatctgc     180
tcaaaaggga aaaggacagt tgacctcggt caatgtggac tcctggggac aatcactgga     240
ccacctcaat gtgaccaatt cctagaattt tcagccgatt taattattga gaggcgagaa     300
ggaagtgatg tctgttatcc tgggaaattc gtgaatgaag aagctctgag gcaaattctc     360
agagaatcag gcggaattga caaggaagca atgggattca catacagtgg aataagaact     420
aatggagcaa ccagtgcatg taggagatca ggatcttcat tctatgcaga aatgaaatgg     480
ctcctgtcaa acacagataa tgctgcattc ccgccagatg actaagtcat ataaaaatac     540
aagaaaaagc ccagctctaa tagtatgggg gatccatcat tccgtatcaa ctgcagagca     600
aaccaagcta tatgggagtg gaaacaaact ggtgacagtt gggagttcta attatcaaca     660
atcttttgta ccgagtccag gagcgagacc acaagttaat ggtctatctg gaagaattga     720
ctttcattgg ctaatgctaa atcccaatga tacagtcact ttcagtttca atggggcttt     780
catagctcca gaccgtgcaa gcttcctgag aggaaaatct atgggaatcc agagtggagt     840
acaggttgat gccaattgtg aaggggactg ctatcatagt ggagggacaa taataagtaa     900
cttgccattt cagaacatag atagcagggc agttggaaaa tgtccgagat atgttaagca     960
aaggagtctg ctgctagcaa cagggatgaa gaatgttcct gagattccaa agggaagagg    1020
cctatttggt gctatagcgg gtttcattga aaatggatgg gaaggcctaa ttgatggttg    1080
gtatggtttc agacaccaga atgcacaggg agagggaact gctgcagatt acaaaagcac    1140
tcaatcggca attgatcaaa taacaggaaa attaaaccgg cttatagaaa aaaccaacca    1200
acaatttgag ttgatagaca atgaattcaa tgaggtagag aagcaaatcg gtaatgtgat    1260
aaattggacc agagattcta taacagaagt gtggtcatac aatgctgaac tcttggtagc    1320
aatggagaac cagcatacaa ttgatctggc tgattcagaa atggacaaac tgtacgaacg    1380
agtgaaaaga cagctgagag agaatgctga agaagatggc actggttgct ttgaaatatt    1440
tcacaagtgt gatgatgact gtatggccag tattagaaat aacacctatg atcacagcaa    1500
atacagggaa gaggcaatgc aaaatagaat acagattgac ccagtcaaac taagcagcgg    1560
ctacaaagat gtgatacttt ggtttagctt cggggcatca tgtttcatac ttctagccat    1620
tgtaatgggc cttgtcttca tatgtgtaaa gaatggaaac atgcggtgca ctatttgtat    1680
ataa                                                                 1684
```

<210> SEQ ID NO 21
<211> LENGTH: 560
<212> TYPE: PRT
<213> ORGANISM: Influenza virus

<400> SEQUENCE: 21

```
Met Asn Thr Gln Ile Leu Val Phe Ala Leu Ser Lys Gly Lys Arg Thr
1               5                   10                  15

Val Asp Leu Gly Ile Ala Ile Ile Pro Thr Asn Ala Asp Lys Gln Cys
            20                  25                  30

Gly Leu Leu Gly Thr Ile Thr Gly Ile Cys Leu Gly His His Ala Val
        35                  40                  45

Ser Asn Pro Pro Gln Cys Asp Gln Phe Leu Glu Phe Gly Thr Lys Val
    50                  55                  60
```

```
Asn Thr Leu Thr Glu Arg Ser Ala Asp Leu Ile Ile Glu Arg Arg Glu
65                  70                  75                  80

Gly Val Glu Val Val Asn Ala Thr Glu Thr Gly Ser Asp Val Cys Tyr
                85                  90                  95

Pro Gly Lys Phe Val Glu Arg Thr Asn Ile Pro Arg Ile Cys Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asp Lys Leu Tyr Glu Arg Val Lys Arg Gln
    450                 455                 460

Leu Arg Glu Asn Ala Glu Glu Asp Gly Thr Gly Cys Phe Glu Ile Phe
465                 470                 475                 480
```

-continued

```
His Lys Cys Asp Asp Asp Cys Met Ala Ser Ile Arg Asn Asn Thr Tyr
            485                 490                 495

Asp His Ser Lys Tyr Arg Glu Glu Ala Met Gln Asn Arg Ile Gln Ile
        500                 505                 510

Asp Pro Val Lys Leu Ser Ser Gly Tyr Lys Asp Val Ile Leu Trp Phe
    515                 520                 525

Ser Phe Gly Ala Ser Cys Phe Ile Leu Leu Ala Ile Val Met Gly Leu
530                 535                 540

Val Phe Ile Cys Val Lys Asn Gly Asn Met Arg Cys Thr Ile Cys Ile
545                 550                 555                 560
```

<210> SEQ ID NO 22
<211> LENGTH: 1398
<212> TYPE: DNA
<213> ORGANISM: Influenza virus

<400> SEQUENCE: 22

```
atgaatccaa atcagaagat tctatgcact tcagccactg ctatcataat aggcgcaatc     60

gcagtactca ttggaatagc aaacctagga ttgaacatag gactgcatct aaaaccgggc    120

tgcaattgct cacactcaca acctgaaaca accaacacaa gccaaacaat aataaacaac    180

tattataatg aaacaaacat caccaacatc caaatggaag agagaacaag caggaatttc    240

aataacttaa ctaaagggct ctgtactata aattcatggc acatatatgg gaaagacaat    300

gcagtaagaa ttggagagag ctcggatgtt ttagtcacaa gagaacccta tgtttcatgc    360

gacccagatg aatgcaggtt ctatgctctc agccaaggaa caacaatcag agggaaacac    420

tcaaacggaa caatacacga taggtcccag tatcgcgccc tgataagctg gccactatca    480

tcaccgccca cagtgtacaa cagcagggtg gaatgcattg ggtggtcaag tactagttgc    540

catgatggca aatccaggat gtcaatatgt atatcaggac caaacaacaa tgcatctgca    600

gtagtatggt acaacagaag gcctgttgca gaaattaaca catgggcccg aaacatacta    660

agaacacagg aatctgaatg tgtatgccac aacggcgtat gcccagtagt gttcaccgat    720

gggtctgcca ctggacctgc agacacaaga atatactatt ttaaagaggg gaaaatattg    780

aaatgggagt ctctgactgg aactgctaag catattgaag aatgctcatg ttacggggaa    840

cgaacaggaa ttacctgcac atgcagggac aattggcagg gctcaaatag accagtgatt    900

cagatagacc cagtagcaat gacacacact agtcaatata tatgcagtcc tgttcttaca    960

gacaatcccc gaccgaatga cccaaatata ggtaagtgta atgaccctta tccaggtaat   1020

aataacaatg gagtcaaggg attctcatac ctggatgggg ctaacacttg gctagggagg   1080

acaataagca cagcctcgag gtctggatac gagatgttaa aagtgccaaa tgcattgaca   1140

gatgatagat caaagcccat tcaaggtcag acaattgtat taaacgctga ctggagtggt   1200

tacagtggat ctttcatgga ctattgggct gaaggggact gctatcgagc gtgtttttat   1260

gtggagttga tacgtggaag acccaaggaa gataaagtgt ggtggaccag caatagtata   1320

gtatcgatgt gttccagtac agaattcctg ggacaatgga actggcctga tggggctaaa   1380

atagagtact tcctctaa                                                 1398
```

<210> SEQ ID NO 23
<211> LENGTH: 464
<212> TYPE: PRT
<213> ORGANISM: Influenza virus

<400> SEQUENCE: 23

-continued

```
Met Asn Pro Asn Gln Lys Ile Leu Cys Thr Ser Ala Thr Ala Ile Ile
1               5                   10                  15

Ile Gly Ala Ile Ala Val Leu Ile Gly Ile Ala Asn Leu Gly Leu Asn
            20                  25                  30

Ile Gly Leu His Leu Lys Pro Gly Cys Asn Cys Ser His Ser Gln Pro
        35                  40                  45

Glu Thr Thr Asn Thr Ser Gln Thr Ile Ile Asn Asn Tyr Tyr Asn Glu
    50                  55                  60

Thr Asn Ile Thr Asn Ile Gln Met Glu Glu Arg Thr Ser Arg Asn Phe
65                  70                  75                  80

Asn Asn Leu Thr Lys Gly Leu Cys Thr Ile Asn Ser Trp His Ile Tyr
                85                  90                  95

Gly Lys Asp Asn Ala Val Arg Ile Gly Glu Ser Ser Asp Val Leu Val
            100                 105                 110

Thr Arg Glu Pro Tyr Val Ser Cys Asp Pro Asp Glu Cys Arg Phe Tyr
        115                 120                 125

Ala Leu Ser Gln Gly Thr Ile Ile Arg Gly Lys His Ser Asn Gly Thr
    130                 135                 140

Ile His Asp Arg Ser Gln Tyr Arg Ala Leu Ile Ser Trp Pro Leu Ser
145                 150                 155                 160

Ser Pro Pro Thr Val Tyr Asn Ser Arg Val Glu Cys Ile Gly Trp Ser
                165                 170                 175

Ser Thr Ser Cys His Asp Gly Lys Ser Arg Met Ser Ile Cys Ile Ser
            180                 185                 190

Gly Pro Asn Asn Asn Ala Ser Ala Val Val Trp Tyr Asn Arg Arg Pro
        195                 200                 205

Val Ala Glu Ile Asn Thr Trp Ala Arg Asn Ile Leu Arg Thr Gln Glu
    210                 215                 220

Ser Glu Cys Val Cys His Asn Gly Val Cys Pro Val Val Phe Thr Asp
225                 230                 235                 240

Gly Ser Ala Thr Gly Pro Ala Asp Thr Arg Ile Tyr Phe Lys Glu Gly
                245                 250                 255

Lys Ile Leu Lys Trp Glu Ser Leu Thr Gly Thr Ala Lys His Ile Glu
            260                 265                 270

Glu Cys Ser Cys Tyr Gly Glu Arg Thr Gly Ile Thr Cys Thr Cys Arg
        275                 280                 285

Asp Asn Trp Gln Gly Ser Asn Arg Pro Val Ile Gln Ile Asp Pro Val
    290                 295                 300

Ala Met Thr His Thr Ser Gln Tyr Ile Cys Ser Pro Val Leu Thr Asp
305                 310                 315                 320

Asn Pro Arg Pro Asn Asp Pro Asn Ile Gly Lys Cys Asn Asp Pro Tyr
                325                 330                 335

Pro Gly Asn Asn Asn Asn Gly Val Lys Gly Phe Ser Tyr Leu Asp Gly
            340                 345                 350

Ala Asn Thr Trp Leu Gly Arg Thr Ile Ser Thr Ala Ser Arg Ser Gly
        355                 360                 365

Tyr Glu Met Leu Lys Val Pro Asn Ala Leu Thr Asp Asp Arg Ser Lys
    370                 375                 380

Pro Ile Gln Gly Gln Thr Ile Val Leu Asn Ala Asp Trp Ser Gly Tyr
385                 390                 395                 400

Ser Gly Ser Phe Met Asp Tyr Trp Ala Glu Gly Asp Cys Tyr Arg Ala
                405                 410                 415

Cys Phe Tyr Val Glu Leu Ile Arg Gly Arg Pro Lys Glu Asp Lys Val
```

```
            420                 425                 430

Trp Trp Thr Ser Asn Ser Ile Val Ser Met Cys Ser Ser Thr Glu Phe
        435                 440                 445

Leu Gly Gln Trp Asn Trp Pro Asp Gly Ala Lys Ile Glu Tyr Phe Leu
    450                 455                 460
```

<210> SEQ ID NO 24
<211> LENGTH: 1683
<212> TYPE: DNA
<213> ORGANISM: Influenza virus

<400> SEQUENCE: 24

```
atgaacactc aaatcctggt attcgctctg attgcgatca ttccaacaaa tgcagacaaa     60
atctgcctcg gacatcatgc tgtgtcaaac ggaaccaaag taaacacatt aactgaaaga    120
ggagtggaag tcgtcaatgc aactgaaaca gtggaacgaa caaacatccc caggatctgc    180
tcaaaaggga aaaggacagt tgacctcggt caatgtggac tcctggggac aatcactgga    240
ccacctcaat gtgaccaatt cctagaattt tcagccgatt taattattga gaggcgagaa    300
ggaagtgatg tctgttatcc tgggaaattc gtgaatgaag aagctctgag gcaaattctc    360
agagaatcag gcggaattga caaggaagca atgggattca catacagtgg aataagaact    420
aatggagcaa ccagttcatg taggagatca ggatcttcat tctatgcaga aatgaaatgg    480
ctcctgtcaa acacagataa tgctgcattc ccgcagatga ctaagtcata taaaaataca    540
agaaaaaacc cagctctaat agtatggggg atccatcatt ccggatcaac tgcagagcaa    600
accaagctat atgggagtgg aaacaaactg gtgacagttg ggagttctaa ttatcaacaa    660
tcttttgtac cgagtccggg agcgagaaca caagttaatg gtcaatctgg aagaattgac    720
tttcattggc taatgctaaa tcccaatgat acagtcactt tcagtttcaa tggggctttc    780
atagctccag accgtgcaag cttcctgaga ggaaaatcta tgggaatcca gagtggagta    840
caggttgatg ccgattgtga aggggactgc tattatagtg gagggacaat aataagtaac    900
ttgccatttc agaacataga tagcagggca gttggaaaat gtccgagata tgttaagcaa    960
aggagtctgc tgctagcaac agggatgaag aatgttcctg agattccaaa gggaagaggc   1020
ctatttggtg ctatagcggg tttcattgaa aatggatggg aaggcctaat tgatggttgg   1080
tatggtttca gacaccagaa tgcacaggga gagggaactg ctgcagatta caaaagcact   1140
caatcggcaa ttgatcaaat aacaggaaaa ttaaaccggc ttatagaaaa aaccaaccaa   1200
caatttgagt tgatagacaa tgaattcact gaggtagaga agcaaatcgg taatgtgata   1260
aattggacca gagattctat aacagaagtg tggtcataca atgctgaact cttggtagca   1320
atggagaacc agcatacaat tgatctggct gattcagaaa tggacaaact gtacgaacga   1380
gtgaaaagac agctgagaga gaatgctgaa gaagatggca ctggttgctt tgaaatattt   1440
cacaagtgtg atgatgactg tatggccagc attagaaata acacctatga tcacagcaaa   1500
tacagggaag aggcaatgca aaatagaata cagattgacc cagtcaaact aagcagcggc   1560
tacaaagatg tgatactttg gtttagcttc ggggcatcat gtttcatact tctagccatt   1620
gcaatgggcc ttgtcttcat atgtgtaaag aatggaaaca tgcggtgcac tatttgtata   1680
taa                                                                 1683
```

<210> SEQ ID NO 25
<211> LENGTH: 1273
<212> TYPE: PRT
<213> ORGANISM: Influenza virus

<400> SEQUENCE: 25

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

Tyr Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
```

-continued

```
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830
```

-continued

```
Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
        1075                1080                1085

Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
        1155                1160                1165

Ile Ser Gly Ile Asn Ala Ser Val Val Asn Ile Gln Lys Glu Ile Asp
    1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
                1205                1210                1215

Trp Leu Gly Phe Ile Ala Gly Leu Ile Ala Ile Val Met Val Thr Ile
            1220                1225                1230

Met Leu Cys Cys Met Thr Ser Cys Cys Ser Cys Leu Lys Gly Cys Cys
        1235                1240                1245
```

Ser Cys Gly Ser Cys Cys Lys Phe Asp Glu Asp Asp Ser Glu Pro Val
1250 1255 1260

Leu Lys Gly Val Lys Leu His Tyr Thr
1265 1270

<210> SEQ ID NO 26
<211> LENGTH: 1273
<212> TYPE: PRT
<213> ORGANISM: Influenza virus

<400> SEQUENCE: 26

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala
275 280 285

Val Asp Cys Ala Leu Asp Pro Leu Ser Glu Thr Lys Cys Thr Leu Lys
290 295 300

Ser Phe Thr Val Glu Lys Gly Ile Tyr Gln Thr Ser Asn Phe Arg Val
305 310 315 320

Gln Pro Thr Glu Ser Ile Val Arg Phe Pro Asn Ile Thr Asn Leu Cys
325 330 335

Pro Phe Gly Glu Val Phe Asn Ala Thr Arg Phe Ala Ser Val Tyr Ala
340 345 350

```
Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Gly Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765
```

```
Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
        1075                1080                1085

Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
        1155                1160                1165

Ile Ser Gly Ile Asn Ala Ser Val Val Asn Ile Gln Lys Glu Ile Asp
    1170                1175                1180

Arg Leu Asn Glu Val Ala Lys Asn Leu Asn Glu Ser Leu Ile Asp Leu
```

-continued 1185 1190 1195 1200

Gln Glu Leu Gly Lys Tyr Glu Gln Tyr Ile Lys Trp Pro Trp Tyr Ile
1205 1210 1215

Trp Leu Gly Phe Ile Ala Gly Leu Ile Ala Ile Val Met Val Thr Ile
1220 1225 1230

Met Leu Cys Cys Met Thr Ser Cys Cys Ser Cys Leu Lys Gly Cys Cys
1235 1240 1245

Ser Cys Gly Ser Cys Cys Lys Phe Asp Glu Asp Asp Ser Glu Pro Val
1250 1255 1260

Leu Lys Gly Val Lys Leu His Tyr Thr
1265 1270

<210> SEQ ID NO 27
<211> LENGTH: 1273
<212> TYPE: PRT
<213> ORGANISM: Influenza virus

<400> SEQUENCE: 27

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala
275 280 285

-continued

```
Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
```

-continued

```
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
        1075                1080                1085

Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135
```

Val Tyr Asp Pro Leu Gln Pro Glu Leu Asp Ser Phe Lys Glu Glu Leu
1140 1145 1150

Asp Lys Tyr Phe Lys Asn His Thr Ser Pro Asp Val Asp Leu Gly Asp
1155 1160 1165

Ile Ser Gly Ile Asn Ala Ser Val Val Asn Ile Gln Lys Glu Ile Asp
1170 1175 1180

Arg Leu Asn Glu Val Ala Lys Asn Leu Asn Glu Ser Leu Ile Asp Leu
1185 1190 1195 1200

Gln Glu Leu Gly Lys Tyr Glu Gln Tyr Ile Lys Trp Pro Trp Tyr Ile
1205 1210 1215

Trp Leu Gly Phe Ile Ala Gly Leu Ile Ala Ile Val Met Val Thr Ile
1220 1225 1230

Met Leu Cys Cys Met Thr Ser Cys Cys Ser Cys Leu Lys Gly Cys Cys
1235 1240 1245

Ser Cys Gly Ser Cys Cys Lys Phe Asp Glu Asp Asp Ser Glu Pro Val
1250 1255 1260

Leu Lys Gly Val Lys Leu His Tyr Thr
1265 1270

<210> SEQ ID NO 28
<211> LENGTH: 1273
<212> TYPE: PRT
<213> ORGANISM: Influenza virus

<400> SEQUENCE: 28

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr

-continued

```
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655
```

-continued

```
Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
            1060                1065                1070
```

-continued

Lys Asn Phe Thr Thr Ala Pro Ala Ile Cys His Asp Gly Lys Ala His
1075 1080 1085

Phe Pro Arg Glu Gly Val Phe Val Ser Asn Gly Thr His Trp Phe Val
1090 1095 1100

Thr Gln Arg Asn Phe Tyr Glu Pro Gln Ile Ile Thr Thr Asp Asn Thr
1105 1110 1115 1120

Phe Val Ser Gly Asn Cys Asp Val Val Ile Gly Ile Val Asn Asn Thr
1125 1130 1135

Val Tyr Asp Pro Leu Gln Pro Glu Leu Asp Ser Phe Lys Glu Glu Leu
1140 1145 1150

Asp Lys Tyr Phe Lys Asn His Thr Ser Pro Asp Val Asp Leu Gly Asp
1155 1160 1165

Ile Ser Gly Ile Asn Ala Ser Val Val Asn Ile Gln Lys Glu Ile Asp
1170 1175 1180

Arg Leu Asn Glu Val Ala Lys Asn Leu Asn Glu Ser Leu Ile Asp Leu
1185 1190 1195 1200

Gln Glu Leu Gly Lys Tyr Glu Gln Tyr Ile Lys Trp Pro Trp Tyr Ile
1205 1210 1215

Trp Leu Gly Phe Ile Ala Gly Leu Ile Ala Ile Val Met Val Thr Ile
1220 1225 1230

Met Leu Cys Cys Met Thr Ser Cys Cys Ser Cys Leu Lys Gly Cys Cys
1235 1240 1245

Ser Cys Gly Ser Cys Cys Lys Phe Asp Glu Asp Asp Ser Glu Pro Val
1250 1255 1260

Leu Lys Gly Val Lys Leu His Tyr Thr
1265 1270

<210> SEQ ID NO 29
<211> LENGTH: 560
<212> TYPE: PRT
<213> ORGANISM: Influenza virus

<400> SEQUENCE: 29

Met Asn Thr Gln Ile Leu Val Phe Ala Leu Ile Ala Ile Ile Pro Thr
1 5 10 15

Asn Ala Asp Lys Ile Cys Leu Gly His His Ala Val Ser Asn Gly Thr
20 25 30

Lys Val Asn Thr Leu Thr Glu Arg Gly Val Glu Val Val Asn Ala Thr
35 40 45

Glu Thr Val Glu Arg Thr Asn Ile Pro Arg Ile Cys Ser Lys Gly Lys
50 55 60

Arg Thr Val Asp Leu Gly Gln Cys Gly Leu Leu Gly Thr Ile Thr Gly
65 70 75 80

Pro Pro Gln Cys Asp Gln Phe Leu Glu Phe Ser Ala Asp Leu Ile Ile
85 90 95

Glu Arg Arg Glu Gly Ser Asp Val Cys Tyr Pro Gly Lys Phe Val Asn
100 105 110

Glu Glu Ala Leu Arg Gln Ile Leu Arg Glu Ser Gly Gly Ile Asp Lys
115 120 125

Glu Ala Met Gly Phe Thr Tyr Ser Gly Ile Arg Thr Asn Gly Ala Thr
130 135 140

Ser Ser Cys Arg Arg Ser Gly Ser Ser Phe Tyr Ala Glu Met Lys Trp
145 150 155 160

Leu Leu Ser Asn Thr Asp Asn Ala Ala Phe Pro Gln Met Thr Lys Ser
165 170 175

```
Tyr Lys Asn Thr Arg Lys Asn Pro Ala Leu Ile Val Trp Gly Ile His
            180                 185                 190

His Ser Gly Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Thr Gln Val Asn Gly Gln Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asp Cys Glu Gly
        275                 280                 285

Asp Cys Tyr Tyr Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Val Lys Ser Thr Gln Ser Ala Ile
    370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Thr Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asp Lys Leu Tyr Glu Arg Val Lys Arg Gln
    450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Ile Ala Met Gly Leu
    530                 535                 540

Val Phe Ile Cys Val Lys Asn Gly Asn Met Arg Cys Thr Ile Cys Ile
545                 550                 555                 560
```

<210> SEQ ID NO 30
<211> LENGTH: 1398
<212> TYPE: DNA
<213> ORGANISM: Influenza virus

<400> SEQUENCE: 30
atgaatccaa atcagaagat tctatgcact tcagccactg ctatcataat aggcgcaatc 60
gcagtactca ttggaatagc aaacctagga ttgaacatag gactgcatct aaaaccgagc 120
tgcaattgct cacactcaca acctgaaaca accaacacaa gccaaacaat aataaacaac 180
tattataatg aaacaaacat caccaacatc caaatggaag agagaacaag caggaatttc 240
aataacttaa ctaaagggct ctgtactata aattcatggc acatatatgg gaaagacaat 300
gcggtaagaa ttggagagag ctcggatgtt ttagtcacaa gagaacccta tgtttcatgc 360
gacccagatg aatgcaggtt ctatgctctc agccaaggaa caacaatcag aggaaaacac 420
tcaaacggaa caatacacga taggtcccag tatcgcgccc tgataagctg gccactatca 480
tcaccgccca cagtgtacaa cagcagggtg gaatgcattg ggtggtcaag tactagttgc 540
catgatggca aatccaggat gtcaatatgt atatcaggac caaacaacaa tgcatctgca 600
gtagtatggt acaacagaag gcctgttgca gaaattaaca catgggcccg aaacatacta 660
agaacacagg aatctgaatg tgtatgccac aacggcgtat gcccagtagt gttcaccgat 720
gggtctgcca ctggacctgc agacacaaga atatactatt ttaaagaggg gaaaatattg 780
aaatgggagt ctctgactgg aactgctaag catattgaag aatgctcatg ttacggggaa 840
cgaacaggaa ttacctgcac atgcaaggac aattggcagg gctcaaatag accagtgatt 900
cagatagatc cagtagcaat gacacacact agtcagtata tatgcagtcc tgttcttaca 960
gacaatcccc gaccgaatga cccaaatata ggtaagtgta atgaccctta tccaggtaat 1020
aataacaatg gagtcaaggg attctcatac ctggatgggg ctaacacttg gctagggagg 1080
acaataagca cagcctcgag gtctggatac gagatgttaa aagtgccaaa tgcattgaca 1140
gatgatagat caaagcccat tcaaggtcag acaattgtat taaacgctga ctggagtggt 1200
tacagtggat ctttcatgga ctattgggct gagggggact gctatcgagc gtgtttttat 1260
gtggaattga tacgtggaag acccaaggag gataaagtgt ggtggaccag caatagtata 1320
gtatcgatgt gttccagtac agaattcctg ggacaatgga actggcctga tggggctaaa 1380
atagagtact tcctctaa 1398

<210> SEQ ID NO 31
<211> LENGTH: 462
<212> TYPE: PRT
<213> ORGANISM: Influenza virus

<400> SEQUENCE: 31

Met Asn Pro Asn Gln Lys Ile Leu Cys Thr Ser Ala Thr Ala Ile Ile
1 5 10 15

Ile Gly Ala Ile Ala Val Leu Ile Gly Ile Ala Asn Leu Gly Leu Asn
20 25 30

Ile Gly Leu His Leu Lys Pro Ser Cys Asn Cys Ser His Ser Gln Pro
35 40 45

Glu Thr Ile Asn Thr Ser Gln Thr Ile Ile Asn Asn Tyr Tyr Asn Glu
50 55 60

Thr Asn Ile Thr Asn Ile Gln Met Glu Glu Arg Thr Ser Arg Asn Phe
65 70 75 80

Asn Asn Leu Thr Lys Gly Leu Cys Thr Ile Asn Ser Trp His Ile Tyr
85 90 95

Gly Lys Asp Asn Ala Val Arg Ile Gly Glu Ser Ser Asp Val Leu Val
100 105 110

-continued

```
Thr Arg Glu Pro Tyr Val Ser Cys Asp Pro Asp Glu Cys Arg Phe Tyr
        115                 120                 125

Ala Leu Ser Gln Gly Thr Ile Ile Arg Gly Lys His Ser Asn Gly Thr
    130                 135                 140

Ile His Asp Arg Ser Gln Tyr Arg Ala Leu Ile Ser Trp Pro Leu Ser
145                 150                 155                 160

Ser Pro Pro Thr Val Tyr Asn Ser Arg Val Glu Cys Ile Gly Trp Ser
                165                 170                 175

Ser Thr Ser Cys His Asp Gly Lys Ser Arg Met Ser Ile Cys Ile Ser
            180                 185                 190

Gly Pro Asn Asn Asn Ala Ser Ala Trp Trp Tyr Asn Arg Arg Pro Val
        195                 200                 205

Ala Glu Ile Asn Thr Trp Ala Arg Asn Ile Leu Arg Thr Gln Glu Ser
    210                 215                 220

Glu Cys Val Cys His Asn Gly Val Cys Pro Trp Phe Thr Asp Gly Ser
225                 230                 235                 240

Ala Thr Gly Pro Ala Asp Thr Arg Ile Tyr Tyr Phe Lys Glu Gly Lys
                245                 250                 255

Leu Lys Trp Glu Ser Leu Thr Gly Thr Ala Lys His Ile Glu Glu Cys
            260                 265                 270

Ser Cys Tyr Gly Glu Arg Thr Gly Ile Thr Cys Thr Cys Lys Asp Asn
        275                 280                 285

Trp Gln Gly Ser Asn Arg Pro Val Ile Gln Ile Asp Pro Val Ala Met
    290                 295                 300

Thr His Thr Ser Gln Tyr Ile Cys Ser Pro Val Leu Thr Asp Asn Pro
305                 310                 315                 320

Arg Pro Asn Asp Pro Asn Ile Gly Lys Cys Asn Asp Pro Tyr Pro Gly
                325                 330                 335

Asn Asn Asn Asn Gly Val Lys Gly Phe Ser Tyr Leu Asp Gly Ala Asn
            340                 345                 350

Thr Trp Leu Gly Arg Thr Ile Ser Thr Ala Ser Arg Ser Gly Tyr Glu
        355                 360                 365

Met Leu Lys Val Pro Asn Ala Leu Thr Asp Asp Arg Ser Lys Pro Ile
    370                 375                 380

Gln Gly Gln Thr Ile Val Leu Asn Ala Asp Trp Ser Gly Tyr Ser Gly
385                 390                 395                 400

Ser Phe Met Asp Tyr Trp Ala Glu Gly Asp Cys Tyr Arg Ala Cys Phe
                405                 410                 415

Tyr Val Glu Leu Ile Arg Gly Arg Pro Lys Glu Asp Lys Val Trp Trp
            420                 425                 430

Thr Ser Asn Ser Ile Val Ser Met Cys Ser Ser Thr Glu Phe Leu Gly
        435                 440                 445

Gln Trp Asn Trp Pro Asp Gly Ala Lys Ile Glu Tyr Phe Leu
    450                 455                 460
```

<210> SEQ ID NO 32
<211> LENGTH: 1775
<212> TYPE: DNA
<213> ORGANISM: Influenza virus

<400> SEQUENCE: 32

```
agcaaaagca ggggaaaata aaaacaacca aaatgaaggc aaacctactg gtcctgttat     60

gtgcacttgc agctgcagat gcagacacaa tatgtatagg ctaccatgcg aacaattcaa    120

ccgacactgt tgacacagta ctcgagaaga atgtgacagt gacacactct gttaacctgc    180
```

-continued tcgaagacag ccacaacgga aaactatgta gattaaaagg aatagcccca ctacaattgg 240
ggaaatgtaa catcgccgga tggctcttgg gaaacccaga atgcgaccca ctgcttccag 300
tgagatcatg gtcctacatt gtagaaacac caaactctga gaatggaata tgttatccag 360
gagatttcat cgactatgag gagctgaggg agcaattgag ctcagtgtca tcattcgaaa 420
gattcgaaat atttcccaaa gaaagctcat ggcccaacca caacacaaac ggagtaacgg 480
cagcatgctc ccatgagggg aaaagcagtt tttacagaaa tttgctatgg ctgacggaga 540
aggagggctc atacccaaag ctgaaaaatt cttatgtgaa caaaaaaggg aaagaagtcc 600
ttgtactgtg ggtattcat caccgccta acagtaagga acaacagaat ctctatcaga 660
atgaaaatgc ttatgtctct gtagtgactt caaattataa caggagattt accccggaaa 720
tagcagaaag acccaaagta agagatcaag ctgggaggat gaactattac tggaccttgc 780
taaaacccgg agacacaata atatttgagg caaatggaaa tctaatagca ccaatgtatg 840
ctttcgcact gagtagaggc tttgggtccg gcatcatcac ctcaaacgca tcaatgcatg 900
agtgtaacac gaagtgtcaa acacccctgg gagctataaa cagcagtctc ccttaccaga 960
atatacaccc agtcacaata ggagagtgcc caaaatacgt caggagtgcc aaattgagga 1020
tggttacagg actaaggaac attccgtcca ttcaatccag aggtctattt ggagccattg 1080
ccggttttat tgaagggga tggactggaa tgatagatgg atggtatggt tatcatcatc 1140
agaatgaaca gggatcaggc tatgcagcgg atcaaaaaag cacacaaaat gccattaacg 1200
ggattacaaa caaggtgaac actgttatcg agaaaatgaa cattcaattc acagctgtgg 1260
gtaaagaatt caacaaatta gaaaaaagga tggaaaattt aaataaaaaa gttgatgatg 1320
gatttctgga catttggaca tataatgcag aattgttagt tctactggaa aatgaaagga 1380
ctctggattt ccatgactca aatgtgaaga atctgtatga gaaagtaaaa agccaattaa 1440
agaataatgc caaagaaatc ggaaatggat gttttgagtt ctaccacaag tgtgacaatg 1500
aatgcatgga aagtgtaaga aatgggactt atgattatcc caaatattca gaagagtcaa 1560
agttgaacag ggaaaaggta gatggagtga aattggaatc aatggggatc tatcagattc 1620
tggcgatcta ctcaactgtc gccagttcac tggtgctttt ggtctccctg gggcaatca 1680 gtttctggat gtgttctaat ggatctttgc agtgcagaat atgcatctga gattagaatt 1740
tcagagatat gaggaaaaac acccttgttt ctact 1775

<210> SEQ ID NO 33
<211> LENGTH: 1413
<212> TYPE: DNA
<213> ORGANISM: Influenza virus

<400> SEQUENCE: 33
agcaaaagca ggggtttaaa atgaatccaa atcagaaaat aataaccatt ggatcaatct 60
gtctggtagt cggactaatt agcctaatat tgcaaatagg gaatataatc tcaatatgga 120
ttagccattc aattcaaact ggaagtcaaa accatactgg aatatgcaac caaaacatca 180
ttacctataa aaatagcacc tgggtaaagg acacaacttc agtgatatta accggcaatt 240
catctctttg tcccatccgt gggtgggcta tatacagcaa agacaatagc ataagaattg 300
gttccaaagg agacgttttt gtcataagag agccctttat ttcatgttct cacttggaat 360
gcaggacctt ttttctgacc caaggtgcct tactgaatga caagcattca agtgggactg 420
ttaaggacag aagcccttat agggccttaa tgagctgccc tgtcggtgaa gctccgtccc 480

```
cgtacaattc aagatttgaa tcggttgctt ggtcagcaag tgcatgtcat gatggcatgg    540

gctggctaac aatcggaatt tcaggtccag ataatggagc agtggctgta ttaaaataca    600

acggcataat aactgaaacc ataaaaagtt ggaggaagaa aatattgagg acacaagagt    660

ctgaatgtgc ctgtgtaaat ggttcatgtt ttactataat gactgatggc ccgagtgatg    720

ggctggcctc gtacaaaatt ttcaagatcg aaaaggggaa ggttactaaa tcaatagagt    780

tgaatgcacc taattctcac tatgaggaat gttcctgtta ccctgatacc ggcaaagtga    840

tgtgtgtgtg cagagacaat tggcatggtt cgaaccggcc atgggtgtct ttcgatcaaa    900

acctggatta tcaaatagga tacatctgca gtggggtttt cggtgacaac ccgcgtcccg    960

aagatggaac aggcagctgt ggtccagtgt atgttgatgg agcaaacgga gtaaagggat   1020

tttcatatag gtatggtaat ggtgtttgga taggaaggac caaaagtcac agttccagac   1080

atgggtttga gatgatttgg gatcctaatg gatggacaga gactgatagt aagttctctg   1140

tgaggcaaga tgttgtggca atgactgatt ggtcagggta tagcggaagt ttcgttcaac   1200

atcctgagct gacagggcta gactgtatga ggccgtgctt ctgggttgaa ttaatcaggg   1260

gacgacctaa agaaaaaaca atctggacta gtgcgagcag catttctttt tgtggcgtga   1320

atagtgatac tgtagattgg tcttggccag acggtgctga gttgccattc agcattgaca   1380

agtagtctgt tcaaaaaact ccttgtttct act                                1413
```

```
<210> SEQ ID NO 34
<211> LENGTH: 2233
<212> TYPE: DNA
<213> ORGANISM: Influenza virus

<400> SEQUENCE: 34

agcgaaagca ggtactgatc caaaatggaa gattttgtgc gacaatgctt caatccgatg     60

attgtcgagc ttgcggaaaa aacaatgaaa gagtatgggg aggacctgaa aatcgaaaca    120

aacaaatttg cagcaatatg cactcacttg gaagtatgct tcatgtattc agattttcac    180

ttcatcaatg agcaaggcga gtcaataatc gtagaacttg gtgatccaaa tgcacttttg    240

aagcacagat ttgaaataat cgagggaaga gatcgcacaa tggcctggac agtagtaaac    300

agtatttgca acactacagg ggctgagaaa ccaaagtttc taccagattt gtatgattac    360

aaggagaata gattcatcga aattggagta acaaggagag aagttcacat atactatctg    420

gaaaaggcca ataaaattaa atctgagaaa acacacatcc acattttctc gttcactggg    480

gaagaaatgg ccacaaaggc agactacact ctcgatgaag aaagcagggc taggatcaaa    540

accagactat tcaccataag acaagaaatg gccagcagag gcctctggga ttcctttcgt    600

cagtccgaga gaggagaaga gacaattgaa gaaaggtttg aaatcacagg aacaatgcgc    660

aagcttgccg accaaagtct cccgccgaac ttctccagcc ttgaaaattt tagagcctat    720

gtggatggat tcgaaccgaa cggctacatt gagggcaagc tgtctcaaat gtccaaagaa    780

gtaaatgcta gaattgaacc tttttgaaa acaacaccac gaccacttag acttccgaat    840

gggcctccct gttctcagcg gtccaaattc ctgctgatgg atgccttaaa attaagcatt    900

gaggacccaa gtcatgaagg agagggaata ccgctatatg atgcaatcaa atgcatgaga    960

acattctttg gatggaagga acccaatgtt gttaaaccac acgaaaaggg aataaatcca   1020

aattatcttc tgtcatggaa gcaagtactg gcagaactgc aggacattga gaatgaggag   1080

aaaattccaa agactaaaaa tatgaagaaa acaagtcagc taaagtgggc acttggtgag   1140

aacatggcac cagaaaaggt agactttgac gactgtaaag atgtaggtga tttgaagcaa   1200
```

```
tatgatagtg atgaaccaga attgaggtcg cttgcaagtt ggattcagaa tgagtttaac   1260

aaggcatgcg aactgacaga ttcaagctgg atagagctcg atgagattgg agaagatgtg   1320

gctccaattg aacacattgc aagcatgaga aggaattatt tcacatcaga ggtgtctcac   1380

tgcagagcca cagaatacat aatgaaggga gtgtacatca atactgcctt gcttaatgca   1440

tcttgtgcag caatggatga tttccaatta attccaatga taagcaagtg tagaactaag   1500

gagggaaggc gaaagaccaa cttgtatggt ttcatcataa aaggaagatc ccacttaagg   1560

aatgacaccg acgtggtaaa ctttgtgagc atggagtttt ctctcactga cccaagactt   1620

gaaccacata aatgggagaa gtactgtgtt cttgagatag gagatatgct tataagaagt   1680

gccataggcc aggtttcaag gcccatgttc ttgtatgtga gaacaaatgg aacctcaaaa   1740

attaaaatga aatggggaat ggagatgagg cgttgcctcc tccagtcact tcaacaaatt   1800

gagagtatga ttgaagctga gtcctctgtc aaagagaaag acatgaccaa agagttcttt   1860

gagaacaaat cagaaacatg gcccattgga gagtccccca aaggagtgga ggaaagttcc   1920

attgggaagg tctgcaggac tttattagca aagtcggtat tcaacagctt gtatgcatct   1980

ccacaactag aaggattttc agctgaatca agaaaactgc ttcttatcgt tcaggctctt   2040

agggacaacc tggaacctgg gacctttgat cttgggggc tatatgaagc aattgaggag   2100

tgcctgatta atgatccctg ggttttgctt aatgcttctt ggttcaactc cttccttaca   2160

catgcattga gttagttgtg gcagtgctac tatttgctat ccatactgtc caaaaaagta   2220

ccttgtttct act                                                      2233
```

<210> SEQ ID NO 35
<211> LENGTH: 2341
<212> TYPE: DNA
<213> ORGANISM: Influenza virus

<400> SEQUENCE: 35

```
agcgaaagca ggcaaaccat ttgaatggat gtcaatccga ccttactttt cttaaaagtg     60

ccagcacaaa atgctataag cacaactttc ccttatactg gagaccctcc ttacagccat    120

gggacaggaa caggatacac catggatact gtcaacagga cacatcagta ctcagaaaag    180

ggaagatgga caacaaacac cgaaactgga gcaccgcaac tcaacccgat tgatgggcca    240

ctgccagaag acaatgaacc aagtggttat gcccaaacag attgtgtatt ggaggcgatg    300

gctttccttg aggaatccca tcctggtatt tttgaaaact cgtgtattga aacgatggag    360

gttgttcagc aaacacgagt agacaagctg acacaaggcc gacagaccta tgactggact    420

ctaaatagaa accaacctgc tgcaacagca ttggccaaca caatagaagt gttcagatca    480

aatggcctca cggccaatga gtctggaagg ctcatagact tccttaagga tgtaatggag    540

tcaatgaaca aagaagaaat ggggatcaca actcattttc agagaaagag acgggtgaga    600

gacaatatga ctaagaaaat gataacacag agaacaatgg gtaaaaagaa gcagagattg    660

aacaaaagga gttatctaat tagagcattg accctgaaca caatgaccaa agatgctgag    720

agagggaagc taaaacggag agcaattgca accccaggga tgcaaataag gggttttgta    780

tactttgttg agacactggc aaggagtata tgtgagaaac ttgaacaatc agggttgcca    840

gttggaggca atgagaagaa agcaaagttg gcaaatgttg taaggaagat gatgaccaat    900

tctcaggaca ccgaactttc tttcaccatc actggagata acaccaaatg gaacgaaaat    960

cagaatcctc ggatgttttt ggccatgatc acatatatga ccagaaatca gcccgaatgg   1020
```

```
ttcagaaatg ttctaagtat tgctccaata atgttctcaa acaaaatggc gagactggga   1080
aaagggtata tgtttgagag caagagtatg aaacttagaa ctcaaatacc tgcagaaatg   1140
ctagcaagca tcgatttgaa atatttcaat gattcaacaa gaaagaagat tgaaaaaatc   1200
cgaccgctct taatagaggg gactgcatca ttgagccctg gaatgatgat gggcatgttc   1260
aatatgttaa gcactgtatt aggcgtctcc atcctgaatc ttggacaaaa gagatacacc   1320
aagactactt actggtggga tggtcttcaa tcctctgacg attttgctct gattgtgaat   1380
gcacccaatc atgaagggat tcaagccgga gtcgacaggt tttatcgaac ctgtaagcta   1440
cttggaatca atatgagcaa gaaaaagtct tacataaaca gaacaggtac atttgaattc   1500
acaagttttt tctatcgtta tgggtttgtt gccaatttca gcatggagct tcccagtttt   1560
ggggtgtctg ggatcaacga gtcagcggac atgagtattg gagttactgt catcaaaaac   1620
aatatgataa acaatgatct tggtccagca acagctcaaa tggcccttca gttgttcatc   1680
aaagattaca ggtacacgta ccgatgccat ataggtgaca cacaaataca aacccgaaga   1740
tcatttgaaa taaagaaact gtgggagcaa acccgttcca aagctggact gctggtctcc   1800
gacggaggcc caaatttata caacattaga aatctccaca ttcctgaagt ctgcctaaaa   1860
tgggaattga tggatgagga ttaccagggg cgtttatgca acccactgaa cccatttgtc   1920
agccataaag aaattgaatc aatgaacaat gcagtgatga tgccagcaca tggtccagcc   1980
aaaaacatgg agtatgatgc tgttgcaaca acacactcct ggatccccaa aagaaatcga   2040
tccatcttga atacaagtca aagaggagta cttgaggatg aacaaatgta ccaaaggtgc   2100
tgcaatttat ttgaaaaatt cttccccagc agttcataca gaagaccagt cgggatatcc   2160
agtatggtgg aggctatggt ttccagagcc cgaattgatg cacggattga tttcgaatct   2220
ggaaggataa agaaagaaga gttcactgag atcatgaaga tctgttccac cattgaagag   2280
ctcagacggc aaaaatagtg aatttagctt gtccttcatg aaaaaatgcc ttgtttctac   2340
t                                                                   2341
```

<210> SEQ ID NO 36
<211> LENGTH: 2341
<212> TYPE: DNA
<213> ORGANISM: Influenza virus

<400> SEQUENCE: 36

```
agcgaaagca ggtcaattat attcaatatg gaaagaataa aagaactacg aaatctaatg     60
tcgcagtctc gcacccgcga gatactcaca aaaaccaccg tggaccatat ggccataatc    120
aagaagtaca catcaggaag acaggagaag aacccagcac ttaggatgaa atggatgatg    180
gcaatgaaat atccaattac agcagacaag aggataacgg aaatgattcc tgagagaaat    240
gagcaaggac aaactttatg gagtaaaatg aatgatgccg gatcagaccg agtgatggta    300
tcacctctgg ctgtgacatg gtggaatagg aatggaccaa taacaaatac agttcattat    360
ccaaaaatct acaaaactta ttttgaaaga gtcgaaaggc taaagcatgg aacctttggc    420
cctgtccatt ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
ttgcatttga ctcaaggaac atgctgggaa cagatgtata ctccaggagg ggaagtgagg    780
```

```
aatgatgatg ttgatcaaag cttgattatt gctgctagga acatagtgag aagagctgca    840
gtatcagcag atccactagc atctttattg gagatgtgcc acagcacaca gattggtgga    900
attaggatgg tagacatcct taggcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggcaa tcttcaaaca   1080
ttgaagataa gagtgcatga gggatatgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtca gaggtgatct gaatttcgtc aatagggcga atcaacgatt gaatcctatg   1320
catcaacttt taagacattt tcagaaggat gcgaaagtgc tttttcaaaa ttggggagtt   1380
gaacctatcg acaatgtgat gggaatgatt gggatattgc ccgacatgac tccaagcatc   1440
gagatgtcaa tgagaggagt gagaatcagc aaaatgggtg tagatgagta ctccagcacg   1500
gagagggtag tggtgagcat tgaccgtttt ttgagaatcc gggaccaacg aggaaatgta   1560
ctactgtctc ccgaggaggt cagtgaaaca cagggaacag agaaactgac aataacttac   1620
tcatcgtcaa tgatgtggga gattaatggt cctgaatcag tgttggtcaa tacctatcaa   1680
tggatcatca gaaactggga aactgttaaa attcagtggt cccagaaccc tacaatgcta   1740
tacaataaaa tggaatttga accatttcag tctttagtac ctaaggccat tagaggccaa   1800
tacagtgggt ttgtaagaac tctgttccaa caaatgaggg atgtgcttgg gacatttgat   1860
accgcacaga taataaaact tcttcccttc gcagccgctc caccaaagca aagtagaatg   1920
cagttctcct catttactgt gaatgtgagg ggatcaggaa tgagaatact tgtaaggggc   1980
aattctcctg tattcaacta taacaaggcc acgaagagac tcacagttct cggaaaggat   2040
gctggcactt taactgaaga cccagatgaa ggcacagctg gagtggagtc cgctgttctg   2100
aggggattcc tcattctggg caaagaagac aagagatatg ggccagcact aagcatcaat   2160
gaactgagca accttgcgaa aggagagaag gctaatgtgc taattgggca aggagacgtg   2220
gtgttggtaa tgaaacggaa acgggactct agcatactta ctgacagcca gacagcgacc   2280
aaaagaattc ggatggccat caattagtgt cgaatagttt aaaaacgacc ttgtttctac   2340
t                                                                   2341
```

```
<210> SEQ ID NO 37
<211> LENGTH: 1565
<212> TYPE: DNA
<213> ORGANISM: Influenza virus

<400> SEQUENCE: 37

agcaaaagca gggtagataa tcactcactg agtgacatca aaatcatggc gtctcaaggc     60
accaaacgat cttacgaaca gatggagact gatggagaac gccagaatgc cactgaaatc    120
agagcatccg tcggaaaaat gattggtgga attggacgat tctacatcca aatgtgcacc    180
gaactcaaac tcagtgatta tgagggacgg ttgatccaaa acagcttaac aatagagaga    240
atggtgctct ctgcttttga cgaaaggaga aataaatacc ttgaagaaca tcccagtgcg    300
gggaaagatc ctaagaaaac tggaggacct atatacagga gagtaaacgg aaagtggatg    360
agagaactca tcctttatga caaagaagaa ataaggcgaa tctggcgcca agctaataat    420
ggtgacgatg caacggctgg tctgactcac atgatgatct ggcattccaa tttgaatgat    480
```

gcaacttatc agaggacaag agctcttgtt cgcaccggaa tggatcccag gatgtgctct 540
ctgatgcaag gttcaactct ccctaggagg tctggagccg caggtgctgc agtcaaagga 600
gttggaacaa tggtgatgga attggtcaga atgatcaaac gtgggatcaa tgatcggaac 660
ttctggaggg gtgagaatgg acgaaaaaca agaattgctt atgaaagaat gtgcaacatt 720
ctcaaaggga aatttcaaac tgctgcacaa aaagcaatga tggatcaagt gagagagagc 780
cggaacccag ggaatgctga gttcgaagat ctcacttttc tagcacggtc tgcactcata 840
ttgagagggt cggttgctca caagtcctgc ctgcctgcct gtgtgtatgg acctgccgta 900
gccagtgggt acgactttga aagggaggga tactctctag tcggaataga ccctttcaga 960
ctgcttcaaa acagccaagt gtacagccta atcagaccaa atgagaatcc agcacacaag 1020
agtcaactgg tgtggatggc atgccattct gccgcatttg aagatctaag agtattaagc 1080
ttcatcaaag ggacgaaggt gctcccaaga gggaagcttt ccactagagg agttcaaatt 1140
gcttccaatg aaaatatgga gactatggaa tcaagtacac ttgaactgag aagcaggtac 1200
tgggccataa ggaccagaag tggaggaaac accaatcaac agagggcatc tgcgggccaa 1260
atcagcatac aacctacgtt ctcagtacag agaaatctcc cttttgacag aacaaccatt 1320
atggcagcat tcaatgggaa tacagagggg agaacatctg acatgaggac cgaaatcata 1380
aggatgatgg aaagtgcaag accagaagat gtgtctttcc aggggcgggg agtcttcgag 1440
ctctcggacg aaaaggcagc gagcccgatc gtgccttcct ttgacatgag taatgaagga 1500
tcttatttct tcggagacaa tgcagaggag tacgacaatt aaagaaaaat acccttgttt 1560
ctact 1565

<210> SEQ ID NO 38
<211> LENGTH: 1027
<212> TYPE: DNA
<213> ORGANISM: Influenza virus

<400> SEQUENCE: 38
agcaaaagca ggtagatatt gaaagatgag tcttctaacc gaggtcgaaa cgtacgtact 60
ctctatcatc ccgtcaggcc ccctcaaagc cgagatcgca cagagacttg aagatgtctt 120
tgcagggaag aacaccgatc ttgaggttct catggaatgg ctaaagacaa gaccaatcct 180
gtcacctctg actaagggga ttttaggatt tgtgttcacg ctcaccgtgc ccagtgagcg 240
aggactgcag cgtagacgct ttgtccaaaa tgcccttaat gggaacgggg atccaaataa 300
catggacaaa gcagttaaac tgtataggaa gctcaagagg gagataacat tccatggggc 360
caaagaaatc tcactcagtt attctgctgg tgcacttgcc agttgtatgg gcctcatata 420
caacaggatg gggctgtga ccactgaagt ggcatttggc ctggtatgtg caacctgtga 480
acagattgct gactcccagc atcggtctca taggcaaatg gtgacaacaa ccaatccact 540
aatcagacat gagaacagaa tggttttagc cagcactaca gctaaggcta tggagcaaat 600
ggctggatcg agtgagcaag cagcagaggc catggaggtt gctagtcagg ctagacaaat 660
ggtgcaagcg atgagaacca ttgggactca tcctagctcc agtgctggtc tgaaaaatga 720
tcttcttgaa aatttgcagg cctatcagaa acgaatgggg gtgcagatgc aacggttcaa 780
gtgatcctct cactattgcc gcaaatatca ttgggatctt gcacttgaca ttgtggattc 840
ttgatcgtct ttttttcaaa tgcatttacc gtcgctttaa atacggactg aaaggagggc 900
cttctacgga aggagtgcca aagtctatga gggaagaata tcgaaaggaa cagcagagtg 960
ctgtggatgc tgacgatggt cattttgtca gcatagagct ggagtaaaaa actaccttgt 1020

```
ttctact                                                           1027

<210> SEQ ID NO 39
<211> LENGTH: 890
<212> TYPE: DNA
<213> ORGANISM: Influenza virus

<400> SEQUENCE: 39

agcaaaagca gggtgacaaa aacataatgg atccaaacac tgtgtcaagc tttcaggtag     60

attgctttct ttggcatgtc cgcaaacgag ttgcagacca agaactaggc gatgccccat    120

tccttgatcg gcttcgccga gatcagaaat ccctaagagg aaggggcagt actctcggtc    180

tggacatcaa gacagccaca cgtgctggaa agcagatagt ggagcggatt ctgaaagaag    240

aatccgatga ggcacttaaa atgaccatgg cctctgtacc tgcgtcgcgt tacctaactg    300

acatgactct tgaggaaatg tcaagggact ggtccatgct catacccaag cagaaagtgg    360

caggccctct ttgtatcaga atggaccagg cgatcatgga taagaacatc atactgaaag    420

cgaacttcag tgtgattttt gaccggctgg agactctaat attgctaagg gctttcaccg    480

aagagggagc aattgttggc gaaatttcac cattgccttc tcttccagga catactgctg    540

aggatgtcaa aaatgcagtt ggagtcctca tcggaggact tgaatggaat gataacacag    600

ttcgagtctc tgaaactcta cagagattcg cttggagaag cagtaatgag aatgggagac    660

ctccactcac tccaaaacag aaacgagaaa tggcgggaac aattaggtca gaagtttgaa    720

gaaataagat ggttgattga agaagtgaga cacaaactga agataacaga gaatagtttt    780

gagcaaataa catttatgca agccttacat ctattgcttg aagtggagca agagataaga    840

actttctcgt ttcagcttat ttagtactaa aaaacaccct tgtttctact               890

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45
```

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
<211> LENGTH: 1273
<212> TYPE: PRT
<213> ORGANISM: Influenza virus

<400> SEQUENCE: 50

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205
```

```
Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
```

```
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055
```

Pro His Gly Val Val Phe Leu His Val Thr Tyr Val Pro Ala Gln Glu
1060 1065 1070

Lys Asn Phe Thr Thr Ala Pro Ala Ile Cys His Asp Gly Lys Ala His
1075 1080 1085

Phe Pro Arg Glu Gly Val Phe Val Ser Asn Gly Thr His Trp Phe Val
1090 1095 1100

Thr Gln Arg Asn Phe Tyr Glu Pro Gln Ile Ile Thr Thr Asp Asn Thr
1105 1110 1115 1120

Phe Val Ser Gly Asn Cys Asp Val Val Ile Gly Ile Val Asn Asn Thr
1125 1130 1135

Val Tyr Asp Pro Leu Gln Pro Glu Leu Asp Ser Phe Lys Glu Glu Leu
1140 1145 1150

Asp Lys Tyr Phe Lys Asn His Thr Ser Pro Asp Val Asp Leu Gly Asp
1155 1160 1165

Ile Ser Gly Ile Asn Ala Ser Val Val Asn Ile Gln Lys Glu Ile Asp
1170 1175 1180

Arg Leu Asn Glu Val Ala Lys Asn Leu Asn Glu Ser Leu Ile Asp Leu
1185 1190 1195 1200

Gln Glu Leu Gly Lys Tyr Glu Gln Tyr Ile Lys Trp Pro Trp Tyr Ile
1205 1210 1215

Trp Leu Gly Phe Ile Ala Gly Leu Ile Ala Ile Val Met Val Thr Ile
1220 1225 1230

Met Leu Cys Cys Met Thr Ser Cys Cys Ser Cys Leu Lys Gly Cys Cys
1235 1240 1245

Ser Cys Gly Ser Cys Cys Lys Phe Asp Glu Asp Asp Ser Glu Pro Val
1250 1255 1260

Leu Lys Gly Val Lys Leu His Tyr Thr
1265 1270

<210> SEQ ID NO 51
<211> LENGTH: 1273
<212> TYPE: PRT
<213> ORGANISM: Influenza virus

<400> SEQUENCE: 51

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr

-continued

```
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575
```

-continued

```
Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990
```

```
Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
        1075                1080                1085

Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
        1155                1160                1165

Ile Ser Gly Ile Asn Ala Ser Val Val Asn Ile Gln Lys Glu Ile Asp
    1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
                1205                1210                1215

Trp Leu Gly Phe Ile Ala Gly Leu Ile Ala Ile Val Met Val Thr Ile
            1220                1225                1230

Met Leu Cys Cys Met Thr Ser Cys Cys Ser Cys Leu Lys Gly Cys Cys
        1235                1240                1245

Ser Cys Gly Ser Cys Cys Lys Phe Asp Glu Asp Asp Ser Glu Pro Val
    1250                1255                1260

Leu Lys Gly Val Lys Leu His Tyr Thr
1265                1270


<210> SEQ ID NO 52
<211> LENGTH: 1273
<212> TYPE: PRT
<213> ORGANISM: Influenza virus

<400> SEQUENCE: 52

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95
```

-continued

```
Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Val Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510
```

-continued

```
Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
```

-continued

```
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
        1075                1080                1085

Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
        1155                1160                1165

Ile Ser Gly Ile Asn Ala Ser Val Val Asn Ile Gln Lys Glu Ile Asp
    1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
                1205                1210                1215

Trp Leu Gly Phe Ile Ala Gly Leu Ile Ala Ile Val Met Val Thr Ile
            1220                1225                1230

Met Leu Cys Cys Met Thr Ser Cys Cys Ser Cys Leu Lys Gly Cys Cys
        1235                1240                1245

Ser Cys Gly Ser Cys Cys Lys Phe Asp Glu Asp Asp Ser Glu Pro Val
    1250                1255                1260

Leu Lys Gly Val Lys Leu His Tyr Thr
1265                1270


<210> SEQ ID NO 53
<211> LENGTH: 18
<212> TYPE: PRT
<213> ORGANISM: Artificial Sequence
<220> FEATURE:
<223> OTHER INFORMATION: A synthetic sequence

<400> SEQUENCE: 53

Glu Gly Arg Gly Ser Leu Leu Thr Cys Gly Asp Val Glu Glu Asn Pro
1               5                   10                  15

Gly Pro
```

-continued

```
<210> SEQ ID NO 54
<211> LENGTH: 19
<212> TYPE: PRT
<213> ORGANISM: Artificial Sequence
<220> FEATURE:
<223> OTHER INFORMATION: A synthetic sequence

<400> SEQUENCE: 54

Ala Thr Asn Phe Ser Leu Leu Lys Gln Ala Gly Asp Val Glu Glu Asn
1               5                   10                  15

Pro Gly Pro


<210> SEQ ID NO 55
<211> LENGTH: 20
<212> TYPE: PRT
<213> ORGANISM: Artificial Sequence
<220> FEATURE:
<223> OTHER INFORMATION: A synthetic sequence

<400> SEQUENCE: 55

Gln Cys Thr Asn Tyr Ala Leu Leu Lys Leu Ala Gly Asp Val Glu Ser
1               5                   10                  15

Asn Pro Gly Pro
            20


<210> SEQ ID NO 56
<211> LENGTH: 21
<212> TYPE: PRT
<213> ORGANISM: Artificial Sequence
<220> FEATURE:
<223> OTHER INFORMATION: A synthetic sequence

<400> SEQUENCE: 56

Val Lys Gln Thr Leu Asn Phe Asp Leu Leu Lys Ala Gly Asp Val Glu
1               5                   10                  15

Ser Asn Pro Gly Pro
            20
```